(12) United States Patent
Kawai

(10) Patent No.: US 11,306,106 B2
(45) Date of Patent: *Apr. 19, 2022

(54) PHARMACEUTICAL COMPOSITIONS CONTAINING SUBSTITUTED POLYCYCLIC PYRIDONE DERIVATIVES AND PRODRUG THEREOF

(71) Applicant: Shionogi & Co., Ltd., Osaka (JP)

(72) Inventor: Makoto Kawai, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/937,877

(22) Filed: Jul. 24, 2020

(65) Prior Publication Data

US 2020/0361958 A1    Nov. 19, 2020

Related U.S. Application Data

(63) Continuation of application No. 16/323,580, filed as application No. PCT/JP2017/028923 on Aug. 9, 2017, now Pat. No. 10,759,814.

(30) Foreign Application Priority Data

Aug. 10, 2016    (JP) .............................. JP2016-157732

(51) Int. Cl.
| | |
|---|---|
| C07D 498/14 | (2006.01) |
| A61P 31/16 | (2006.01) |
| A61P 31/12 | (2006.01) |
| A61P 43/00 | (2006.01) |
| A61K 31/5383 | (2006.01) |

(52) U.S. Cl.
CPC ........ C07D 498/14 (2013.01); A61K 31/5383 (2013.01); A61P 31/12 (2018.01); A61P 31/16 (2018.01); A61P 43/00 (2018.01); *C07B 2200/13* (2013.01)

(58) Field of Classification Search
CPC .. C07D 471/14; C07D 471/20; C07D 491/22; C07D 498/14; C07D 513/14; C07D 519/00; A61K 31/53; A61K 31/5383; A61K 31/542; A61K 31/553; A61K 31/675
USPC .................. 544/183, 184; 514/243
See application file for complete search history.

(56) References Cited

U.S. PATENT DOCUMENTS

| | | | |
|---|---|---|---|
| 5,475,109 A | 12/1995 | Seinick et al. | |
| 10,392,406 B2 | 8/2019 | Kawai | |
| 10,759,814 B2 * | 9/2020 | Kawai ..................... | A61P 43/00 |
| 11,040,048 B2 | 6/2021 | Shishido et al. | |
| 2013/0090300 A1 | 4/2013 | Bauman et al. | |
| 2013/0096109 A1 | 4/2013 | Hattori et al. | |
| 2013/0197219 A1 | 8/2013 | Takahashi et al. | |
| 2020/0283455 A1 | 9/2020 | Kawai et al. | |
| 2021/0230187 A1 | 7/2021 | Shibahara et al. | |

FOREIGN PATENT DOCUMENTS

| | | |
|---|---|---|
| CN | 108440564 | 8/2018 |
| EP | 1 544 199 | 6/2005 |
| EP | 1 950 212 | 7/2008 |
| EP | 2 042 502 | 4/2009 |
| EP | 2 412 709 | 2/2012 |
| EP | 2 444 400 | 4/2012 |
| EP | 2 620 436 | 7/2013 |
| EP | 3 290 424 | 3/2018 |
| EP | 3 391 888 | 10/2018 |
| EP | 3 473 629 | 4/2019 |
| GB | 2 280 435 | 2/1995 |
| JP | 5971830 B | 8/2016 |
| JP | 2017-137291 | 8/2017 |
| WO | 2006/066414 | 6/2006 |
| WO | 2013/057251 | 4/2013 |
| WO | 2013/057253 | 4/2013 |
| WO | 2013/174930 | 11/2013 |
| WO | 2013/174931 | 11/2013 |
| WO | 2014/023691 | 2/2014 |
| WO | 2014/043252 | 3/2014 |
| WO | 2014/074926 | 5/2014 |
| WO | 2014/108406 | 7/2014 |

(Continued)

OTHER PUBLICATIONS

International Search Report dated Sep. 19, 2017 in International Application No. PCT/JP2017/028923.

(Continued)

*Primary Examiner* — Deepak R Rao
(74) *Attorney, Agent, or Firm* — Wenderoth, Lind & Ponack, L.L.P.

(57) ABSTRACT

The present invention provides a pharmaceutical composition containing the following compound having antiviral action:

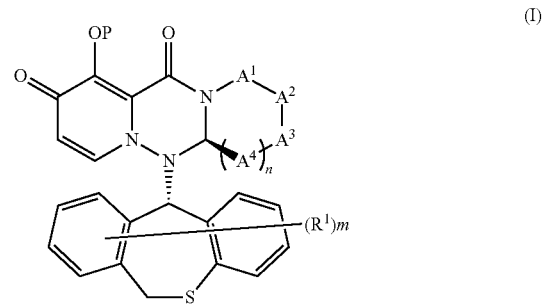

(I)

wherein each of the symbols is defined in the specification.

57 Claims, 4 Drawing Sheets

(56) References Cited

FOREIGN PATENT DOCUMENTS

| WO | 2014/108407 | 7/2014 |
|---|---|---|
| WO | 2014/108408 | 7/2014 |
| WO | 2015/038655 | 3/2015 |
| WO | 2015/038660 | 3/2015 |
| WO | 2016/005330 | 1/2016 |
| WO | 2016/005331 | 1/2016 |
| WO | 2016/175224 | 11/2016 |
| WO | 2017/046362 | 3/2017 |
| WO | 2017/072341 | 5/2017 |
| WO | 2017/104691 | 6/2017 |
| WO | 2017/109088 | 6/2017 |
| WO | 2017/153919 | 9/2017 |
| WO | 2017/153950 | 9/2017 |
| WO | 2017/156194 | 9/2017 |
| WO | 2017/158147 | 9/2017 |
| WO | 2017/158151 | 9/2017 |
| WO | 2017/221869 | 12/2017 |
| WO | 2017/223231 | 12/2017 |
| WO | 2018/042303 | 3/2018 |

OTHER PUBLICATIONS

Otto D. Hensens et al., "Isolation and Structure of Flutimide, a Novel Endonuclease Inhibitor of Influenza Virus", Tetrahedron Letters, vol. 36, No. 12, pp. 2005-2008, 1995.
Sheo B Singh, "Total Synthesis of Flutimide, A Novel Endonuclease Inhibitor of Influenza Virus", Tetrahedron Letters, vol. 36, No. 12, pp. 2009-2012, 1995.
J. Tomassini et al, "Inhibition of Cap (m$^7$GpppXm)-Dependent Endonuclease of Influenza Virus by 4-Substituted 2,4-Dioxobutanoic Acid Compounds", Antimicrobial Agents and Chemotherapy, Dec. 1994, vol. 28, No. 2, p. 2827-2837.
J.C. Hastings et al., "Anti-Influenza Virus Activities of 4-Substituted 2,4-Dioxobutanoic Acid Inhibitors", Antimicrobial Agents and Chemotherapy, May 1996, vol. 40, No. 5, p. 1304-1307.
Takashi Kojima, "Effective Solid Form Selection for the Pharmaceutical Development", Journal of Pharmaceutical Science and Technology, Japan, 2008, vol. 68, No. 5, pp. 344-349, ISSN: 0372-7629, p. 344, right col. line 14 to p. 345, left column, line 2.
Kevin E. B. Parkes, "Use of a Pharmacophore Model To Discover a New Class of Influenza Endonuclease Inhibitors", J. Med. Chem 2003, 46, p. 1153-1164.
Ajit K. Parhi et al., "Phenyl substituted 3-hydroxypyridin-2(1H)-ones: Inhibitors of influenza A endonuclease", Bioorganic & Medicinal Chemistry 21, 2013, p. 6435-6446.
Brandi M. Baughman et al., "Identification of Influenza Endonuclease Inhibitors Using a Novel Fluorescence Polarization Assay", ACS Chem. Biol., 2012, 7, p. 526-534.
Eric Chen, et al., "Computation-Guided Discovery of Influenza Endonuclease Inhibitors" ACS Medicinal Chemishy Letters, 2014, 5, p. 61-64.
Zhihui Yan et al., "Design of the influenza virus inhibitors targeting the PA endonuclease using 3D-QSAR modeling, sidechain hopping and docking", Bioorganic & Medicinal Chemistry Letters 24, 2014, p. 539-547.
Hye Yeon Sagong et al., "3-Hydroxyquinolin-2(1H)-ones As Inhibitors of Influenza A Endonuclease", ACS Medicinal Chemistry Letters, 2013, 4, p. 547-550.
Yuma Iwai et al., "Anti-influenza activity of phenethylphenylphthalimide analogs derived from thalidomide" Bioorganic & Medicinal Chemistry 18, 2010, p. 5379-5390.
Joseph D. Bauman et al., "Crystallographic Fragment Screening and Structure-Based Optimization Yields a New Class of Influenza Endonuclease Inhibitors", ACS Chem. Biol., 2013, 8, p. 2501-2508.
Hye Yeon Sagong, et al., "Phenyl Substituted 4-Hydroxypyridazin-3(2H)-ones and 5-Hydroxypyrimidin-4(3H)-ones: Inhibitors of Influenza A Endonuclease", Journal of Medicinal Chemishy, 2014, 57, p. 8086-8098.
Nicolino Pala et al., "Virtual Screening and Biological Validation of Novel Influenza Virus PA Endonuclease Inhibitors", ACS Medicinal Chemistry Letters, 2015, 6, p. 866-871.
Yuanchao Xie et al., "Caffeic acid derivatives: A new type of influenza neuraminidase inhibitors", Bioorganic & Medicinal Chemistry Letters 23, 2013, p. 3556-3560.
"Green tea catechins inhibit the endonuclease activity of influenza A virus RNA polymerase", PLos Curr 1: RRN1052, PLos Currents, Oct. 2009.
Yuma Iwai et al., "Anti-Influenza Activity of Marchantins, Macrocyclic Bisbibenzyls Contained in Liverworts", PLos One, May 2011, vol. 6, Issue 5, e19825.
Masaki Shoji et al., "Anti-influenza Activity of $C_{60}$ Fullerene Derivatives", PLos One, Jun. 2013, vol. 8, Issue 6, e66337.
Sheo B. Singh et al., "Synthesis of Natural Flutimide and Analogous Fully Substituted Pyrazine-2,6-diones, Endonuclease Inhibitors of Influenza Virus", J. Org. Chem. 2001, 66, p. 5504-5516.
Han Ju et al., "Inhibitors of Influenza Virus Polymerase Acidic (PA) Endonuclease: Contemporary Developments and Perspectives", Journal of Medicinal Chemistry, 2017, 60, p. 3533-3551.
Stella G. Muthuri et al., "Effectiveness of neuraminidase inhibitors in reducing mortality in patients admitted to hospital with influenza A H1N1pdm09 virus infection: a meta-analysis of individual participant data", Lancet Respiratory, vol. 2, May 2014, (5), p. 395-404.
International Preliminary report on Patentability dated Feb. 12, 2019 in International (PCT) Application No. PCT/JP2017/028923 with English translation.
STN Registry 1830312-72-5 (Dec. 15, 2015).
Bundgaard, Design of Prodrugs, p. 1, 1985.
Silverman, Prodrugs and Drug Delivery Systems, The Organic Chemishy of Drug Design and Drug Action, pp. 352-399, 1992.
Banker et al., Prodrugs, Modern Pharmaceutics, Third Edition, Revised and Expanded, pp. 451 and 596 (1996).
Wolff, Some consideration for prodrug design, Burger's Medicinal Chemistry and Drug Discovery, 5$^{th}$ Edition, vol. 1: Principles and Practice, pp. 975-977, 1995.
N.E. Sharpless et al., Nature Reviews Dmg Discovery 1-14, 2 (2006).
J.H. Poupaert, Drug Design: Basic Principles and Application, in 2 Encyclopedia of Pharmaceutical Technology 1362-1369, 1367 (James Swarbrick ed., 3$^{rd}$ ed 2007).
L.I. Zon et al., Nature Reviews Dmg Discovery 4, 35 (2005).
P.D. Griffiths, Cytomegalovims in, Principles and Practice of Clinical Virology 85-122 (A.J. Zuckerman et al., eds, 5$^{th}$ ed, 2001).
Sun et al., Synthesis and evaluation of a new series of substituted acyl(thio)urea and thiadiazolo[2,3-a]pyrimidine derivatives as potent inhibitors of influenza virus neuraminidase, Bioorganic & Medicinal Chemishy 14 (2006), pp. 8574-8581.
Top-Line Results for S-033188 Phase III Study in Otherwise Healthy Influenza Patients, Conference Call, Jul. 24, 2017.
Final Rejection of Korean Patent Application No. 10-2019-7000258 dated Mar. 28, 2019 (English translation).
Intellectual Property and Appeal Board decision of Korean Patent Application No. 10-2019-7000258 dated Feb. 4, 2020 (English translation).
KIPO Notice of Preliminary Rejection issued in Korean Patent Application No. 10-2019-70000258 dated Mar. 6, 2019 (English translation).
Koszalka et al., "Influenza antivirals currently in late-phase clinical trial", Influenza and Other Respiratory Viruses, vol. 11, No. 3, pp. 240-246, May 1, 2017.
Notice of Allowance dated Oct. 20, 2021 in U.S. Appl. No. 16/310,897 (corresponds with AC).

\* cited by examiner

| Time | Plasma concentration (ng/mL) | | | |
|---|---|---|---|---|
| (hr) | 0.3 mg/kg | 1 mg/kg | 3 mg/kg | 10 mg/kg |
| 0.25 | BLQ | BLQ | BLQ | BLQ |
| 0.5 | BLQ | BLQ | BLQ | BLQ |
| 1 | BLQ | BLQ | BLQ | BLQ |
| 2 | BLQ | BLQ | BLQ | BLQ |
| 4 | BLQ | BLQ | BLQ | BLQ |
| 6 | BLQ | BLQ | BLQ | BLQ |
| 8 | BLQ | BLQ | BLQ | BLQ |
| 10 | BLQ | BLQ | BLQ | BLQ |
| 24 | BLQ | BLQ | BLQ | BLQ |

BLQ : below the lower limit of quantification (< 0.500 ng/mL)

PHARMACEUTICAL COMPOSITIONS CONTAINING SUBSTITUTED POLYCYCLIC PYRIDONE DERIVATIVES AND PRODRUG THEREOF

TECHNICAL FIELD

This invention relates to substituted polycyclic pyridone derivatives having cap-dependent endonuclease inhibitory activity, prodrugs thereof, and pharmaceutical compositions including thereof.

BACKGROUND ART

Influenza is an acute respiratory infectious disease caused by infection with an influenza virus. In Japan, millions of influenza-like patients are reported every winter, and influenza is accompanied with high morbidity and mortality. Influenza is a particularly important disease in a high risk population such as baby and elderly, a complication rate with pneumonia is high in elderly, and death with influenza is occupied with elderly in many cases.

As anti-influenza drugs, Symmetrel (trade name: Amantadine) and Flumadine (trade name: Rimantadine) which inhibit the denucleation process of a virus, and Oseltamivir (trade name: Tamiflu) and Zanamivir (trade name: Relenza) which are neuraminidase inhibitors suppressing virus budding and release from a cell are known. However, since problems of appearances of resistant strains and side effects, and worldwide epidemic of a new-type influenza virus having high pathogenicity and mortality are feared, development of an anti-influenza drug having a novel mechanism has been desired.

Since a cap-dependent endonuclease which is an influenza virus-derived enzyme is essential for virus proliferation, and has the virus-specific enzymatic activity which is not possessed by a host, it is believed that the endonuclease is suitable for a target of an anti-influenza drug. The cap-dependent endonuclease of an influenza virus has a host mRNA precursor as a substrate, and has the endonuclease activity of producing a fragment of 9 to 13 bases including a cap structure (not including the number of bases of the cap structure). This fragment functions as a primer of a virus RNA polymerase, and is used in synthesizing mRNA encoding a virus protein. That is, it is believed that a substance which inhibits the cap-dependent endonuclease inhibits synthesis of a virus protein by inhibiting synthesis of virus mRNA and, as a result, inhibits virus proliferation.

As the substance which inhibits the cap-dependent endonuclease, flutimide (Patent Document 1 and Non-Patent Documents 1 and 2), 4-substituted 2,4-dioxobutanoic acid (Patent Document 2 and Non-Patent Documents 3 and 4), the compounds described in Patent Documents 3 to 12 and the like have been reported, but they have not yet led to clinical use as anti-influenza drugs. Patent Documents 9 and 12 describe compounds having a similar structure to that used in the present invention, but does not describe the compounds used in the present invention. Also, Patent Documents 13 to 15 describe compounds having a similar structure to that used in the present invention as a compound having integrase inhibitory activity, however, the documents do not describe cap-dependent endonuclease. In addition, Patent Document 16 and 17 describes an invention relating to compounds having a similar structure to that used in the present invention as a compound having cap-dependent endonuclease inhibitory activity, which has been filed by the applicants, but does not describe the compounds used in the present invention.

PRIOR ART DOCUMENTS

Patent Documents

Patent Document 1: GB2280435
Patent Document 2: U.S. Pat. No. 5,475,109
Patent Document 3: US20130090300
Patent Document 4: WO2013/057251
Patent Document 5: WO2013/174930
Patent Document 6: WO2014/023691
Patent Document 7: WO2014/043252
Patent Document 8: WO2014/074926
Patent Document 9: WO2014/108406
Patent Document 10: WO2014/108407
Patent Document 11: WO2014/108408
Patent Document 12: WO2015/038655
Patent Document 13: WO2005/016927
Patent Document 14: WO2006/066414
Patent Document 15: WO2007/049675
Patent Document 16: WO2010/147068
Patent Document 17: WO2012/039414

Non-Patent Documents

Non-Patent Document 1: Tetrahedron Lett 1995, 36(12), 2005
Non-Patent Document 2: Tetrahedron Lett 1995, 36(12), 2009
Non-Patent Document 3: Antimicrobial Agents And Chemotherapy, December 1994, p. 2827-2837
Non-Patent Document 4: Antimicrobial Agents And Chemotherapy, May 1996, p. 1304-1307

SUMMARY OF THE INVENTION

Problems to be Solved by the Invention

An object of the present invention is to provide pharmaceutical composition containing compounds having antiviral activities, especially inhibiting growth activity of influenza virus. Another object of the present invention is to provide a pharmaceutical composition containing a prodrug prepared from compounds used for in vivo administration (for example, oral administration), being efficiently absorbed into the body after administration and showing high pharmacological effect. Yet another object is to provide a pharmaceutical composition with shortening the time to alleviation of influenza symptoms.

Means for Solving the Problems

The present invention provides inventions shown below.
(1) A pharmaceutical composition comprising a compound represented by formula (I) or its pharmaceutically acceptable salt:

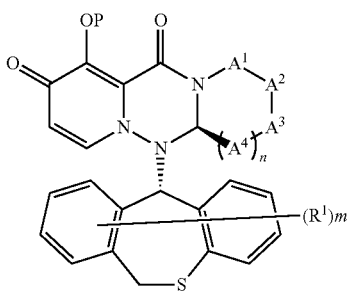

(I)

wherein
P is hydrogen or a group to form a prodrug;
$A^1$ is $CR^{1A}R^{1B}$, S or O;
$A^2$ is $CR^{2A}R^{2B}$, S or O;
$A^3$ is $CR^{3A}R^{3B}$, S or O;
$A^4$ is each independently $CR^{4A}R^{4B}$, S or O;
the number of hetero atoms among atoms constituting the ring which consists of $A^1$, $A^2$, $A^3$, $A^4$, nitrogen atom adjacent to $A^1$ and carbon atom adjacent to $A^4$ is 1 or 2;
$R^{1A}$ and $R^{1B}$ are each independently hydrogen, halogen, alkyl, haloalkyl, alkyloxy or phenyl;
$R^{2A}$ and $R^{2B}$ are each independently hydrogen, halogen, alkyl, haloalkyl, alkyloxy or phenyl;
$R^{3A}$ and $R^{3B}$ are each independently hydrogen, halogen, alkyl, haloalkyl, alkyloxy or phenyl;
$R^{4A}$ and $R^{4B}$ are each independently hydrogen, halogen, alkyl, haloalkyl, alkyloxy or phenyl;
$R^{3A}$ and $R^{3B}$ may be taken together with an adjacent carbon atom to form non-aromatic carbocycle or non-aromatic heterocycle;
$R^1$ is fluorine;
m is any integer of 1 to 2; and
n is any integer of 1 to 2.

(2) The pharmaceutical composition according to (1), comprising the compound or its pharmaceutically acceptable salt, wherein the group represented by formula:

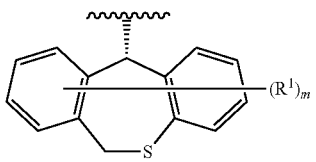

wherein each definition has the same meanings as described (1)
is a group represented by formula:

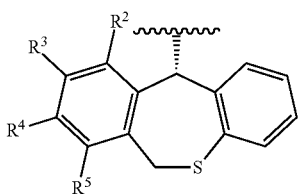

wherein $R^2$, $R^3$, $R^4$ and $R^5$ are each independently hydrogen or fluorine; the number of fluorine atoms of $R^2$, $R^3$, $R^4$ and $R^5$ is 1 or 2.

(3) The pharmaceutical composition according to (1), comprising the compound or its pharmaceutically acceptable salt, wherein the group represented by formula:

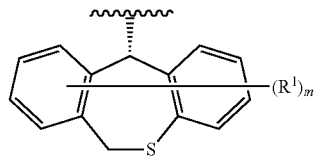

wherein each definition has the same meanings as described (1)
is a group represented by formula:

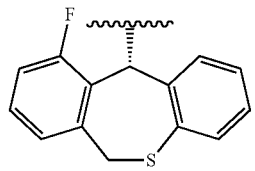

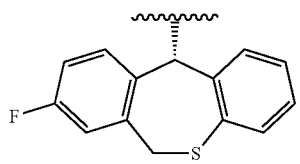

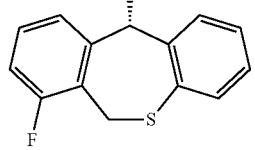

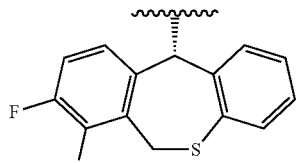

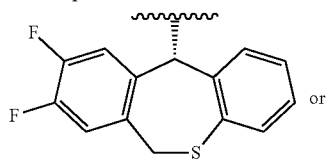

or

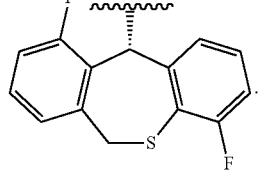

.

(4) The pharmaceutical composition according to any one of (1) to (3), comprising the compound or its pharmaceutically acceptable salt, wherein the group represented by formula:

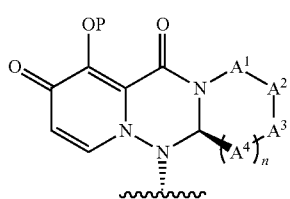
wherein each definition has the same meanings as described (1)
is a group represented by formula:
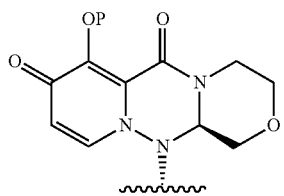
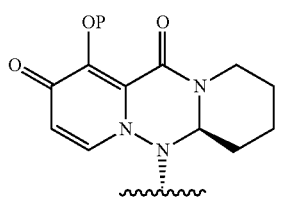
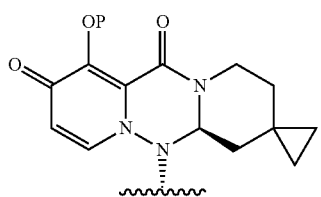
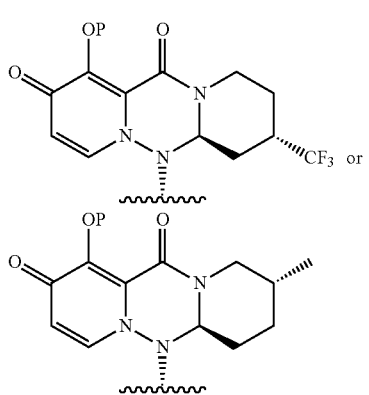
wherein each definition has the same meanings as described (1).
(5) The pharmaceutical composition according to (1), comprising the compound represented by the following formula or its pharmaceutically acceptable salt:
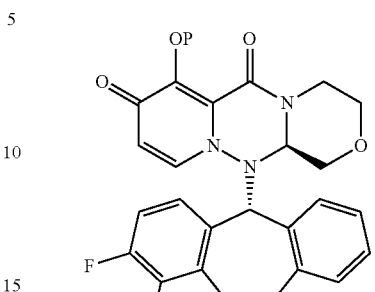
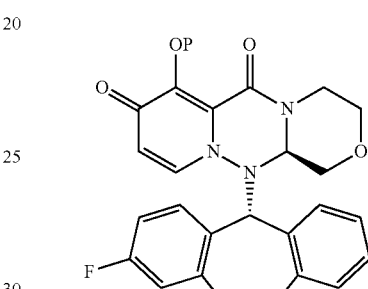
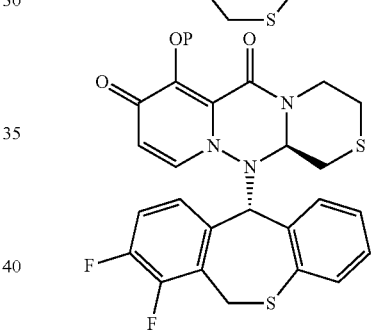
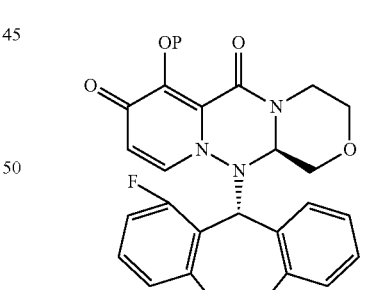
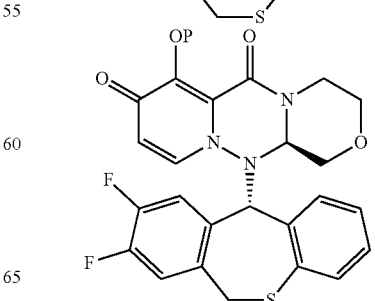

7
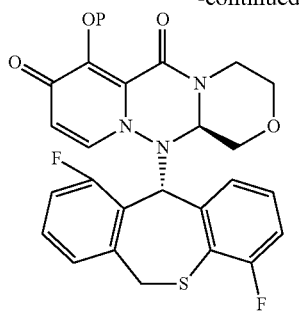
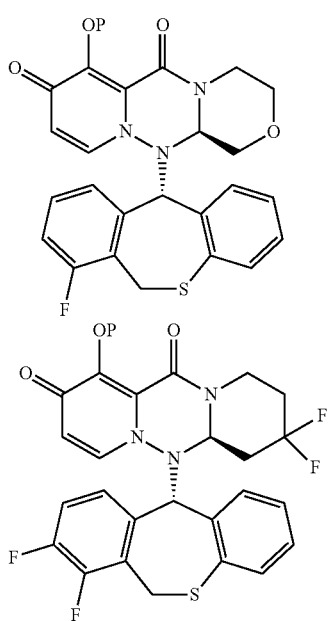
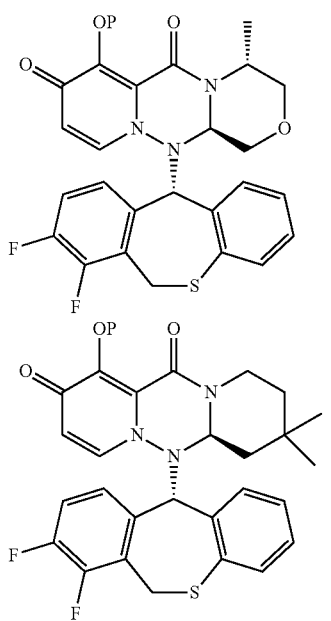
8
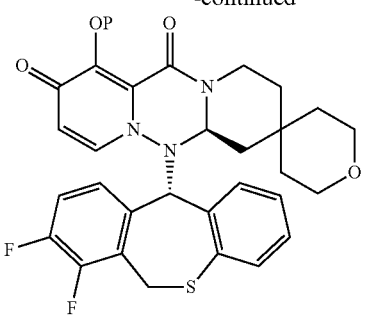
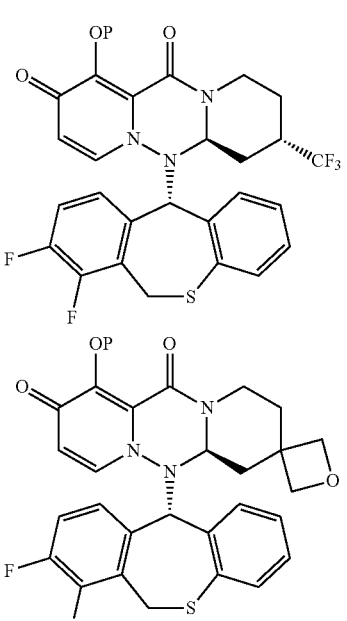
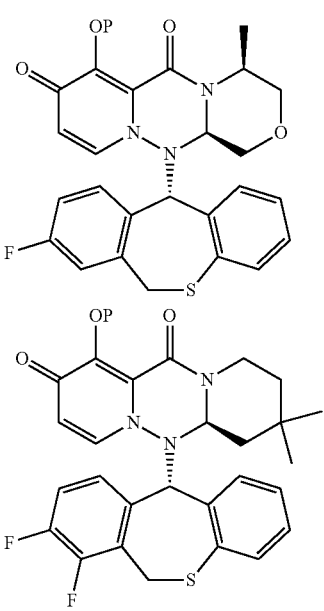

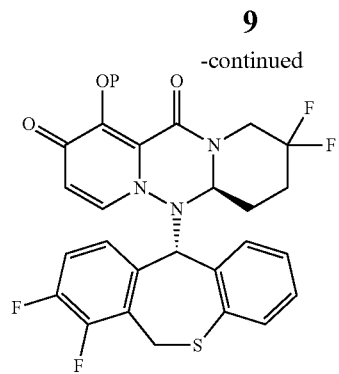
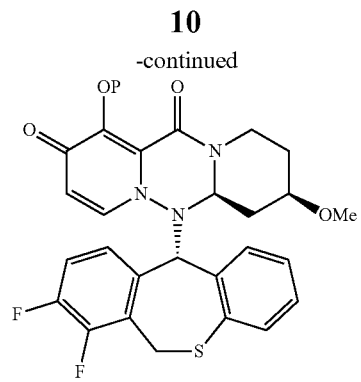
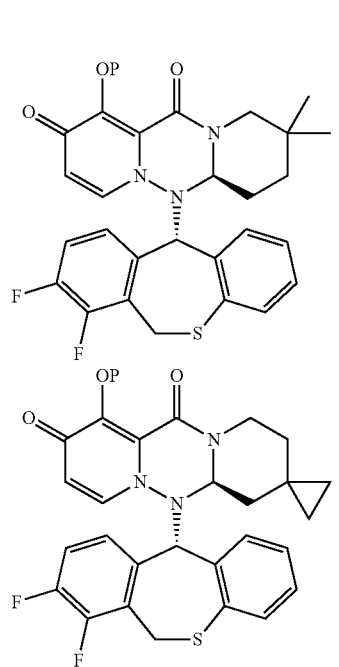
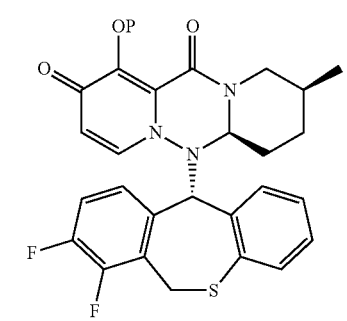
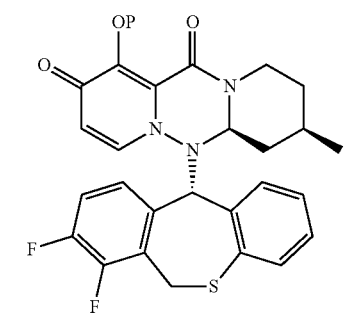
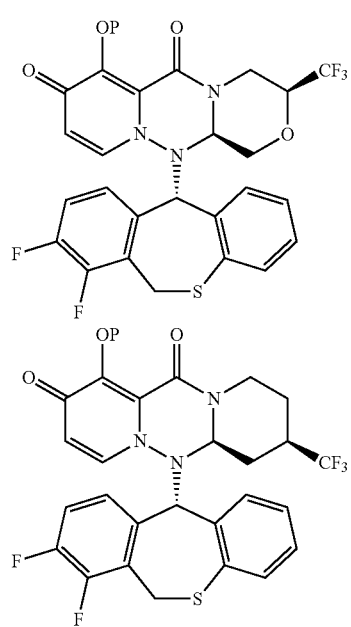
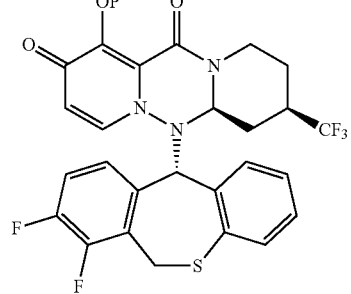
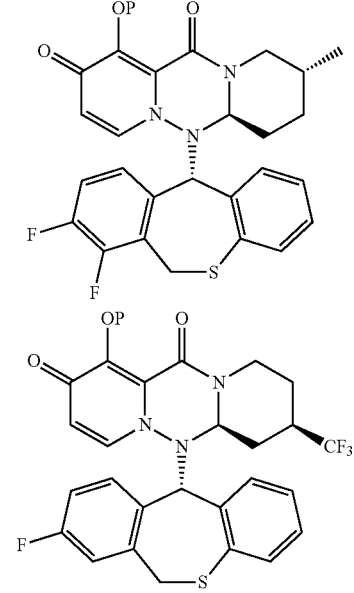

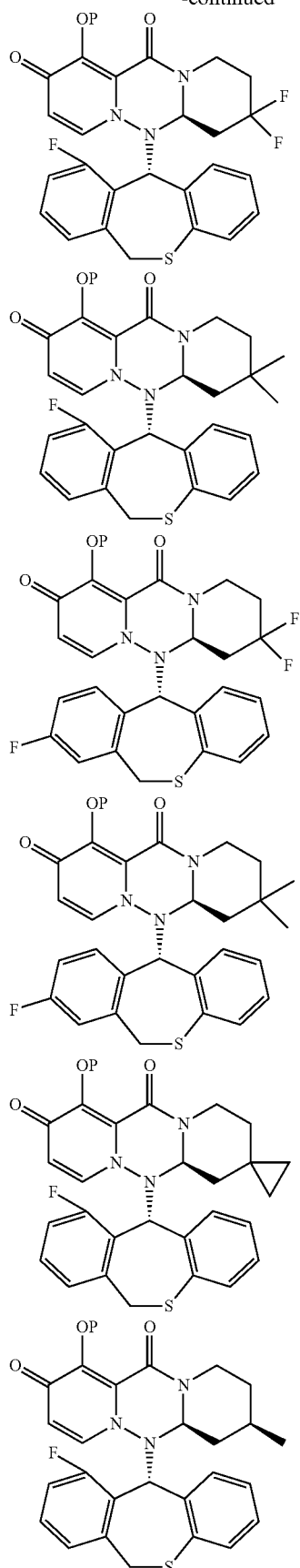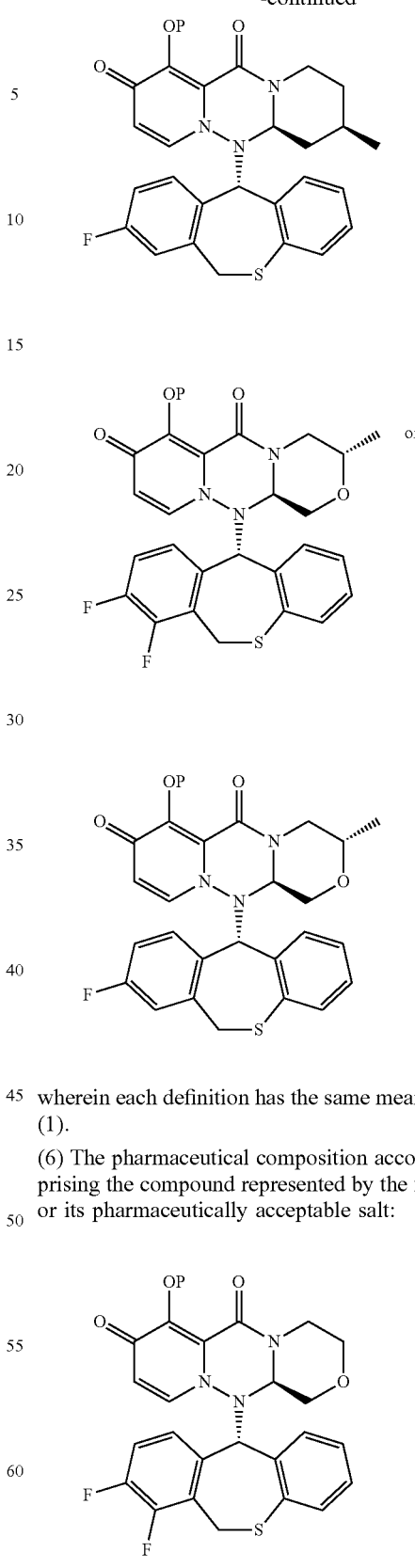
wherein each definition has the same meanings as described (1).
(6) The pharmaceutical composition according to (1), comprising the compound represented by the following formula or its pharmaceutically acceptable salt:
wherein each definition has the same meanings as described (1).

(7) The pharmaceutical composition according to (1), comprising the compound represented by the following formula or its pharmaceutically acceptable salt:

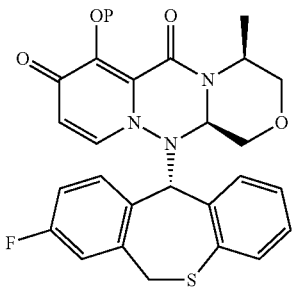

wherein each definition has the same meanings as described (1).

(8) The pharmaceutical composition according to (1), comprising the compound represented by the following formula or its pharmaceutically acceptable salt:

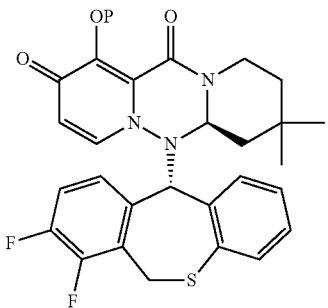

wherein each definition has the same meanings as described (1).

(9) The pharmaceutical composition according to (1), comprising the compound represented by the following formula or its pharmaceutically acceptable salt:

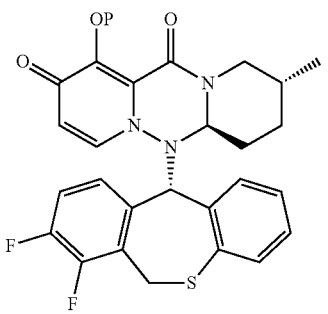

wherein each definition has the same meanings as described (1).

(10) The pharmaceutical composition according to (1), comprising the compound represented by the following formula or its pharmaceutically acceptable salt:

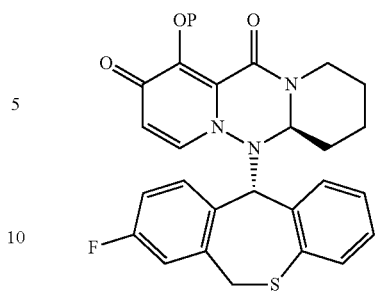

wherein each definition has the same meaning as described (1).

(11) A pharmaceutical composition comprising the compound represented by the following formula or its pharmaceutically acceptable salt:

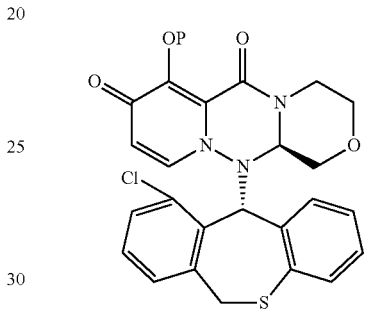

wherein each definition has the same meaning as described (1).

(12) The pharmaceutical composition according to any one of (1) to (11), comprising the compound or its pharmaceutically acceptable salt,
wherein the group to form a prodrug is a group selected from the following formula a) to ac):

| | |
|---|---|
| $-C(=O)-P^{RO}$, | a) |
| $-C(=O)-P^{R1}$, | b) |
| $-C(=O)-L-P^{R1}$, | c) |
| $-C(=O)-L-O-P^{R1}$, | d) |
| $-C(=O)-L-O-L-O-P^{R1}$, | e) |
| $-C(=O)L-O-C(=O)-P^{R1}$, | f) |
| $-C(=O)-O-P^{R2}$, | g) |
| $-C(=O)-N(-K)(P^{R2})$, | h) |
| $-C(=O)-O-L-O-P^{R2}$, | i) |
| $-C(P^{R3})_2-O-P^{R4}$, | j) |
| $-C(P^{R3})_2-O-L-O-P^{R4}$, | k) |
| $-C(P^{R3})_2-O-C(=O)-P^{R4}$, | l) |
| $-C(P^{R3})_2-O-C(=O)-O-P^{R4}$, | m) |
| $-C(P^{R3})_2-O-C(=O)-N(-K)-P^{R4}$, | n) |
| $-C(P^{R3})_2-O-C(=O)-O-L-O-P^{R4}$, | o) |

$-C(P^{R3})_2-O-C(=O)-O-L-N(P^{R4})_2,$     p)

$-C(P^{R3})_2-O-C(=O)-N(-K)-L-O-P^{R4},$     q)

$-C(P^{R3})_2-O-C(=O)-N(-K)-L-N(P^{R4})_2,$     r)

$-C(P^{R3})_2-O-C(=O)-O-L-O-L-O-P^{R4},$     s)

$-C(P^{R3})_2-O-C(=O)-O-L-N(-K)-C(=O)-P^{R4},$     t)

$-C(P^{R3})_2-O-P(=O)(-P^{R5})_2,$     u)

$-C(P^{R3})_2-P^{R6},$     v)

$-C(=N^+(P^{R7})_2)(-N(P^{R7})_2),$     w)

$-C(P^{R3})_2-C(P^{R3})_2-C(=O)-O-P^{R2},$     x)

$-C(P^{R3})_2-N(-K)-C(=O)-O-P^{R2},$     y)

$-P(=O)(-P^{R8})(-P^{R8}),$     z)

$-S(=O)_2-P^{R10},$     aa)

$-P^{R11},$ and     ab)

$-C(P^{R3})_2-C(P^{R3})_2-O-P^{R2},$     ac)

wherein L is straight or branched alkylene, or straight or branched alkenylene;
K is hydrogen, or alkyl optionally substituted by substituent group A;
$P^{R0}$ is alkyl optionally substituted by substituent group A, or alkenyl optionally substituted by substituent group A;
$P^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;
$P^{R2}$ is alkyl optionally substituted by substituent group A, carbocyclyl group optionally substituted by substituent group A, heterocyclyl group optionally substituted by substituent group A, carbocyclyl alkyl optionally substituted by substituent group A, heterocyclylalkyl optionally substituted by substituent group A or trialkylsilyl;
$P^{R3}$ is each independently hydrogen or alkyl;
$P^{R4}$ is each independently alkyl optionally substituted by substituent group A, carbocyclyl group optionally substituted by substituent group A, heterocyclyl group optionally substituted by substituent group A, alkylamino optionally substituted by substituent group A, carbocyclylalkyl optionally substituted by substituent group A, heterocyclylalkyl optionally substituted by substituent group A, or trialkylsilyl;
$P^{R5}$ is each independently hydroxy or OBn;
$P^{R6}$ is carbocyclyl group optionally substituted by substituent group A, or heterocyclyl group optionally substituted by substituent group A;
$P^{R7}$ is each independently alkyl optionally substituted by substituent group A;
$P^{R8}$ is alkyloxy optionally substituted by substituent group A;
$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclamino optionally substituted by substituent group A or heterocyclamino optionally substituted by substituent group A;

$P^{R8}$ and $P^{R9}$ may be taken together with an adjacent phosphorus atom to form heterocycle optionally substituted by substituent group A;
$P^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A; and
$P^{R11}$ is alkyl optionally substituted by substituent group A, alkenyl optionally substituted by substituent group A, carbocyclyl group optionally substituted by substituent group A, or heterocyclyl group optionally substituted by substituent group A;
Substituent group A: oxo, alkyl, hydroxyalkyl, amino, alkylamino, carbocyclyl group, heterocyclyl group, carbocyclylalkyl, alkylcarbonyl, halogen, hydroxy, carboxy, alkylcarbonylamino, alkylcarbonylaminoalkyl, alkylcarbonyloxy, alkyloxycarbonyl, aryloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho.

(13) The pharmaceutical composition according to (12), comprising the compound or its pharmaceutically acceptable salt,
wherein the group to form a prodrug is a group selected from the following formula:

$-C(=O)-P^{R0},$     a)

$-C(=O)-P^{R1},$     b)

$-C(=O)-O-P^{R2},$     g)

$-C(=O)-N(-K)(P^{R2}),$     h)

$-C(=O)-O-L-O-P^{R2},$     i)

$-C(P^{R3})_2-O-C(=O)-P^{R4},$     l)

$-C(P^{R3})_2-O-C(=O)-O-P^{R4},$     m)

$-C(P^{R3})_2-OC(=O)-O-L-O-P^{R4},$     o)

$-C(P^{R3})_2-P^{R6},$     v)

$-C(P^{R3})_2-C(P^{R3})_2-C(=O)-O-P^{R2},$     x)

$-C(P^{R3})_2-N(-K)-C(=O)-O-P^{R2},$ and     y)

$-P(=O)(-P^{R8})(-P^{R9}),$     z)

wherein L is straight or branched alkylene;
K is hydrogen or alkyl optionally substituted by substituent group A;
$P^{R0}$ is alkyl optionally substituted by substituent group A;
$P^{R1}$ is carbocyclyl group optionally substituted by substituent group A, or heterocyclyl group optionally substituted by substituent group A;
$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;
$P^{R3}$ is each independently hydrogen or alkyl;
$P^{R4}$ is alkyl optionally substituted by substituent group A, carbocyclyl group optionally substituted by substituent group A, or heterocyclyl group optionally substituted by substituent group A;

$P^{R6}$ is carbocyclyl group optionally substituted by substituent group A, or heterocyclyl group optionally substituted by substituent group A;

$P^{R8}$ is alkyloxy optionally substituted by substituent group A;

$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclyl amino optionally substituted by substituent group A or heterocyclylamino optionally substituted by substituent group A; and $P^{R8}$ and $P^{R9}$ may be taken together with an adjacent phosphorus atom to form heterocycle optionally substituted by substituent group A;

Substituent group A; oxo, alkyl, alkylamino, carbocyclyl group, heterocyclyl group, alkylcarbonyl, halogen, hydroxy, alkylcarbonylamino, alkylcarbonyloxy, alkyloxycarbonyl, aryloxycarbonylalkyl, alkylaminocarbonyloxy, alkyloxy, nitro, azido, alkylsulfonyl and trialkylsilyl.

(13-1) The pharmaceutical composition according to (12), comprising the compound or its pharmaceutically acceptable salt,
wherein the group to form a prodrug is a group selected from the following formula:

—C(=O)—$P^{R0}$, a)

—C(=O)—$P^{R1}$, b)

—C(=O)—O—$P^{R2}$, g)

—C(=O)—N(—K)($P^{R2}$), h)

—C(=O)—O-L-O—$P^{R2}$, i)

—C($P^{R3}$)$_2$—O—C(=O)—$P^{R4}$, l)

—C($P^{R3}$)$_2$—O—C(=O)—O—$P^{R4}$, m)

—C($P^{R3}$)$_2$—O—C(=O)—O-L-O—$P^{R4}$, o)

—C($P^{R3}$)$_2$—C($P^{R3}$)$_2$—C(=O)—O—$P^{R2}$, x)

—C($P^{R3}$)$_2$—N(—K)—C(=O)—O—$P^{R2}$, and y)

—P(=O)(—$P^{R8}$)(—$P^{R9}$), z)

wherein L is straight or branched alkylene;
K is hydrogen, or alkyl optionally substituted by substituent group A;
$P^{R0}$ is alkyl optionally substituted by substituent group A;
$P^{R1}$ is carbocyclyl group optionally substituted by substituent group A, or heterocyclyl group optionally substituted by substituent group A;
$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;
$P^{R3}$ is each independently hydrogen or alkyl;
$P^{R4}$ is alkyl optionally substituted by substituent group A, carbocyclyl group optionally substituted by substituent group A, or heterocyclyl group optionally substituted by substituent group A;
$P^{R6}$ is carbocyclyl group optionally substituted by substituent group A, or heterocyclyl group optionally substituted by substituent group A;

$P^{R8}$ is alkyloxy optionally substituted by substituent group A;

$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclyl amino optionally substituted by substituent group A or heterocyclylamino optionally substituted by substituent group A; and $P^{R8}$ and $P^{R9}$ may be taken together with an adjacent phosphorus atom to form heterocycle optionally substituted by substituent group A;

Substituent group A; oxo, alkyl, alkylamino, carbocyclyl, heterocyclyl, alkylcarbonyl, halogen, hydroxy, alkylcarbonylamino, alkylcarbonyloxy, alkyloxycarbonyl, aryloxycarbonylalkyl, alkylaminocarbonyloxy, alkyloxy, nitro, azido, alkylsulfonyl and trialkylsilyl.

(14) The pharmaceutical composition according to (12), comprising the compound or its pharmaceutically acceptable salt,
wherein the group to form a prodrug is a following formula:

—C($P^{R3}$)$_2$—O—C(=O)—O—$P^{R4}$ m)

wherein $P^{R3}$ is each independently hydrogen or alkyl; and $P^{R4}$ is alkyl optionally substituted by substituent group A, carbocyclyl group optionally substituted by substituent group A, or heterocyclyl group optionally substituted by substituent group A;

Substituent group A; oxo, alkyl, alkylamino, carbocyclyl group, heterocyclyl group, alkylcarbonyl, halogen, hydroxy, alkylcarbonylamino, alkylcarbonyloxy, alkyloxycarbonyl, aryloxycarbonylalkyl, alkylaminocarbonyloxy, alkyloxy, nitro, azido, alkylsulfonyl and trialkylsilyl.

(15) A pharmaceutical composition comprising a compound represented by the

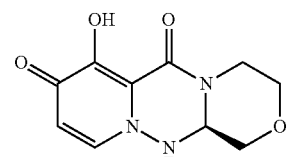

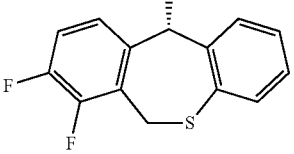

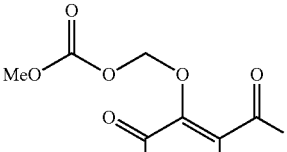

or

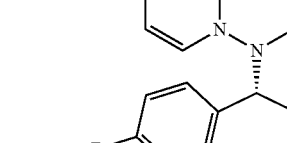

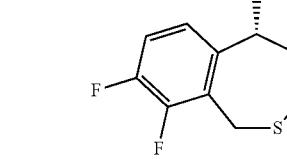

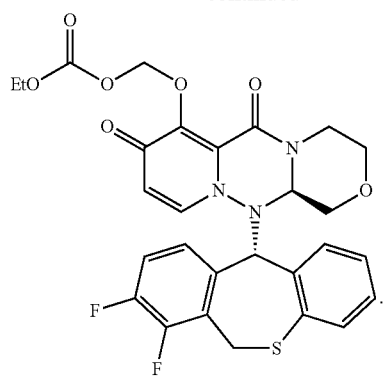

(16) A pharmaceutical composition comprising a compound represented by the following formula or its pharmaceutically acceptable salt:

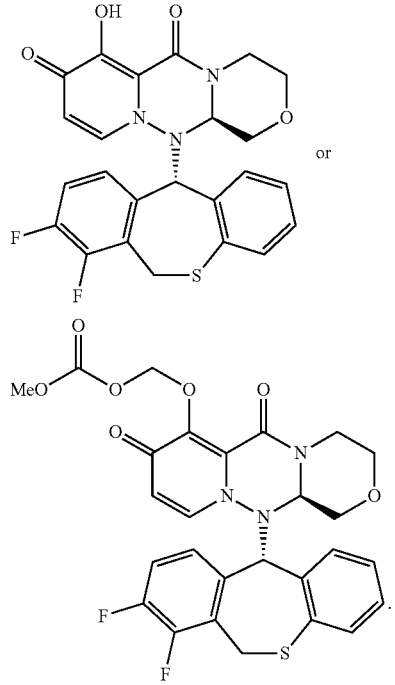

or

(17) A pharmaceutical composition comprising a compound represented by the following formula or its pharmaceutically acceptable salt:

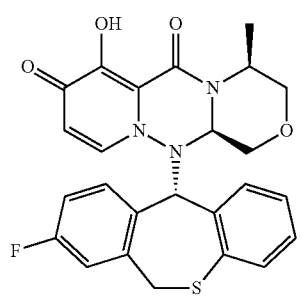

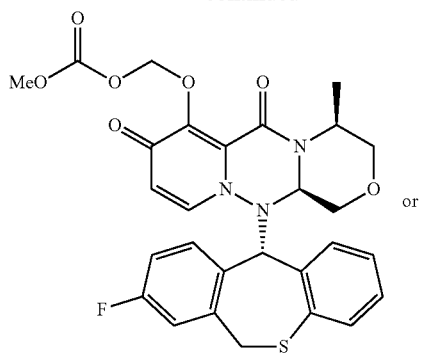

or

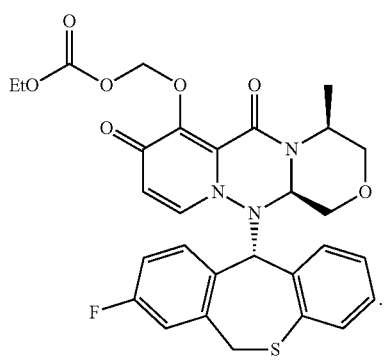

(18) A pharmaceutical composition comprising a compound represented by the following formula or its pharmaceutically acceptable salt:

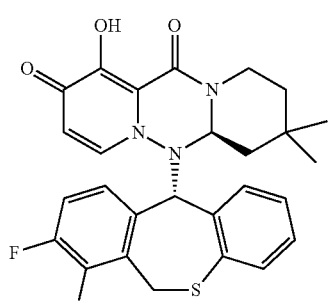

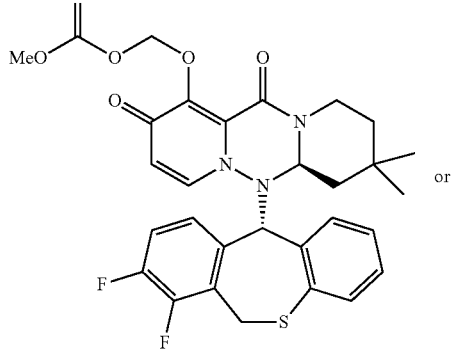

or

-continued

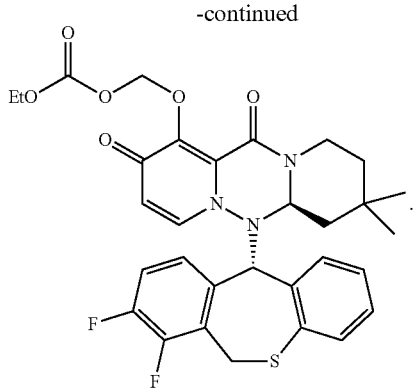

(19) A pharmaceutical composition comprising a compound represented by the following formula or its pharmaceutically acceptable salt:

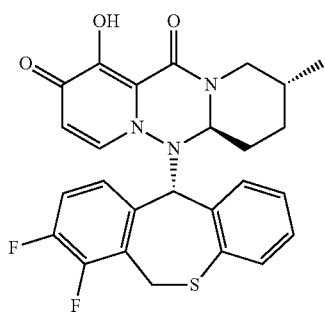

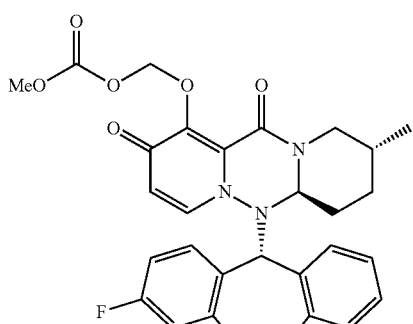

or

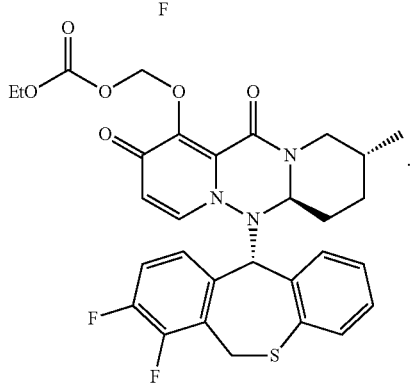

(20) A pharmaceutical composition comprising a compound represented by the following formula or its pharmaceutically acceptable salt:

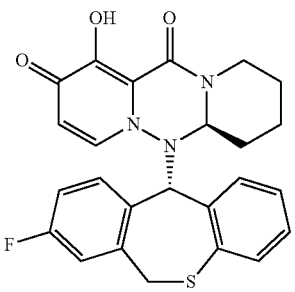

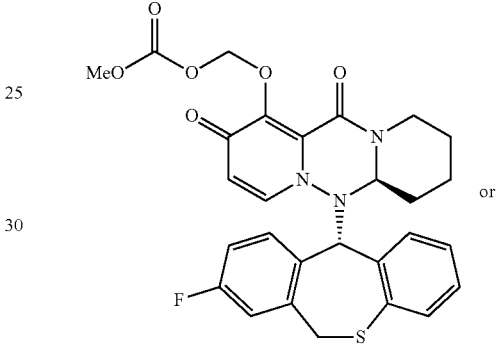

or

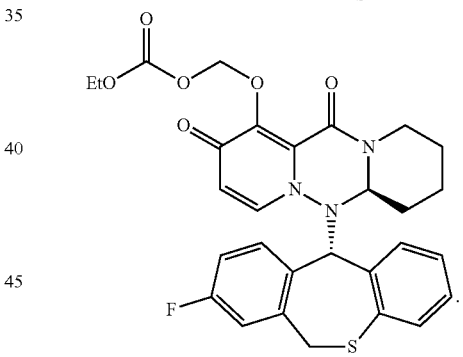

.

(21) A pharmaceutical composition comprising a compound represented by the following formula or its pharmaceutically acceptable salt:

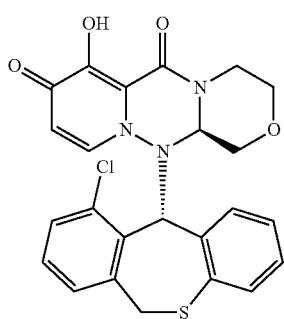

-continued

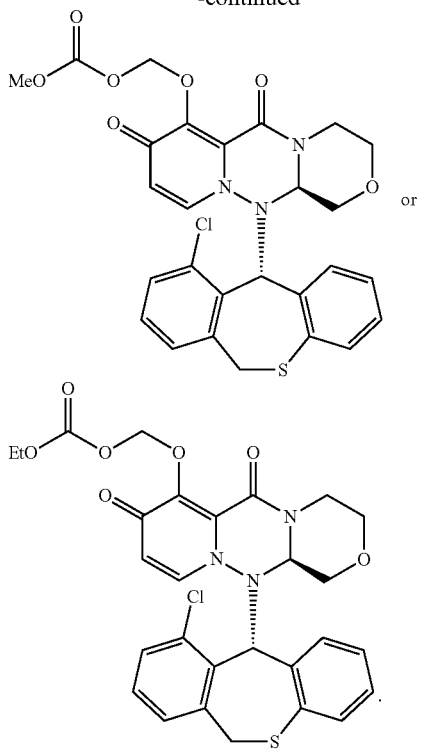

or

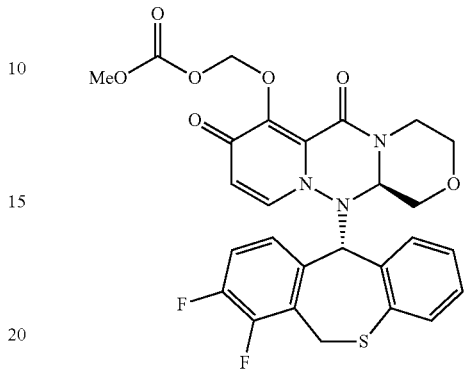

(22) The pharmaceutical composition according to any one of (1) to (21), which is an antiviral agent.
(23) The pharmaceutical composition according to any one of (1) to (21), which is a cap-dependent endonuclease inhibitor.
(24) The pharmaceutical composition according to any one of (1) to (21), which is used for shortening time to alleviation of influenza symptoms.
(24-1) A method for shortening time to alleviation of influenza symptoms, characterized in administering the compound of any one of (1) to (21) or its pharmaceutically acceptable salt.
(24-2) A method for shortening time to alleviation of influenza symptoms to treat and/or prevent an influenza virus infectious disease, characterized in administering the compound of any one of (1) to (21) or its pharmaceutically acceptable salt.
(24-3) The compound of any one of (1) to (21) or its pharmaceutically acceptable salt, for shortening time to alleviation of influenza symptoms.
(24-4) The compound of any one of (1) to (21) or its pharmaceutically acceptable salt, for shortening time to alleviation of influenza symptoms to treat and/or prevent an influenza virus infectious disease.
(25) The pharmaceutical composition according to any one of (1) to (21), which is used for reducing the influenza virus.
(25-1) A method for reducing the influenza virus, characterized in administering the compound of any one of (1) to (21) or its pharmaceutically acceptable salt.
(25-2) A method for reducing the influenza virus to treat and/or prevent an influenza virus infectious disease, characterized in administering the compound of any one of (1) to (21) or its pharmaceutically acceptable salt.
(25-3) The compound of any one of (1) to (21) or its pharmaceutically acceptable salt, for reducing the influenza virus.
(25-4) The compound of any one of (1) to (21) or its pharmaceutically acceptable salt, for reducing the influenza virus to treat and/or prevent an influenza virus infectious disease.
(26) A crystal of a compound of the following formula:

(27) The crystal according to (26), having two or more peaks in diffraction angles (2θ) selected from 8.6±0.2°, 14.1±0.2°, 17.4±0.2°, 20.0±0.2°, 24.0±0.2°, 26.3±0.2°, 29.6±0.2°, and 35.4±0.2° in an X-ray powder diffraction spectrum.
(28) The crystal according to (26), having peaks in diffraction angles (2θ) of: 8.6±0.2°, 14.1±0.2°, 17.4±0.2°, 20.0±0.2°, 24.0±0.2°, 26.3±0.2°, 29.6±0.2° and 35.4±0.2° in an X-ray powder diffraction spectrum.
(29) The crystal according to (26), wherein an X-ray powder diffraction spectrum of the crystal is substantially identical with FIG. 3.
(30) A pharmaceutical composition comprising the crystal of any one of (26) to (29).
(31) The pharmaceutical composition according to (30), which is an antiviral agent.
(32) The pharmaceutical composition according to (30), which is a cap-dependent endonuclease inhibitor.
(33) A pharmaceutical composition comprising the crystal of any one of (26) to (29), which is used for shortening time to alleviation of influenza symptoms.
(33-1) A method for shortening time to alleviation of influenza symptoms, characterized in administering the crystal of any one of (26) to (29).
(33-2) A method for shortening time to alleviation of influenza symptoms to treat and/or prevent an influenza virus infectious disease, characterized in administering the crystal of any one of (26) to (29).
(33-3) The crystal according to any one of (26) to (29), for shortening time to alleviation of influenza symptoms.
(33-4) The crystal according to any one of (26) to (29), for shortening time to alleviation of influenza symptoms to treat and/or prevent an influenza virus infectious disease.
(34) A pharmaceutical composition comprising the crystal of any one of (26) to (29), which is used for reducing the influenza virus.
(34-1) A method for reducing the influenza virus, characterized in administering the crystal of any one of (26) to (29).
(34-2) A method for reducing the influenza virus to treat and/or prevent an influenza virus infectious disease, characterized in administering the crystal of any one of (26) to (29).
(34-3) The crystal according to any one of (26) to (29), for reducing the influenza virus.

(35) The pharmaceutical composition according to any one of (1) to (21) and (30) to (34), for oral administration.
(36) The pharmaceutical composition according to (35), which is a tablet, powder, granule, capsule, pill, film, suspension, emulsion, elixir, syrup, lemonade, spirit, aromatic water, extract, decoction or tincture.
(37) The pharmaceutical composition according to (35), which is a sugar-coated tablet, film-coated tablet, enteric-coated tablet, sustained-release tablet, troche tablet, sublingual tablet, buccal tablet, chewable tablet, orally disintegrated tablet, dry syrup, soft capsule, micro capsule or sustained-release capsule.
(38) The pharmaceutical composition according to any one of (1) to (21) and (30) to (34), for parenteral administration.
(39) The pharmaceutical composition according to (38), for dermal, subcutaneous, intravenous, intraarterial, intramuscular, intraperitoneal, transmucosal, inhalation, transnasal, ophthalmic, inner ear or vaginal administration.
(40) The pharmaceutical composition according to (38) or (39), which is injection, infusion, eye drop, nose drop, ear drop, aerosol, inhalation, lotion, impregnation, liniment, mouthwash, enema, ointment, plaster, jelly, cream, patch, cataplasm, external powder or suppository.
(41) The pharmaceutical composition according to any one of (1) to (21) and (30) to (34), for a pediatric or geriatric patient.
(42) A pharmaceutical composition consisting of a combination of the pharmaceutical composition according to any one of (1) to (21) and (30) to (34) and Neuraminidase inhibitor, RNA-dependent RNA polymerase inhibitor, M2 protein inhibitor, PB2 Cap binding inhibitor, an anti-HA antibody or immunological agent.
(43) A pharmaceutical composition comprising the pharmaceutical composition according to any one of (1) to (21) and (30) to (34), for a combination therapy with Neuraminidase inhibitor, RNA-dependent RNA polymerase inhibitor, M2 protein inhibitor, PB2 Cap binding inhibitor, an anti-HA antibody or immunological agent.

Note that (13) above encompasses (13-1) above.

The present invention provides a method for treating or preventing an influenza virus infectious disease using the compounds (parent compounds and/or prodrug compounds) used in the present invention, and pharmaceutical compositions used therein. The parent compounds are effective as anti-influenza agents or intermediates of the prodrug compounds.

Effect of the Invention

The compounds (parent compounds and/or prodrugs) used in the present invention have inhibitory activity on cap-dependent endonuclease. More preferred compound is a prodrug, and the prodrug becomes a parent compound having an inhibitory activity on cap-dependent endonuclease in vivo after administration, thus is effective as a therapeutic agent and/or preventive agent for influenza virus infectious disease.

BEST MODE FOR CARRYING OUT THE INVENTION

Figures 1, 2:
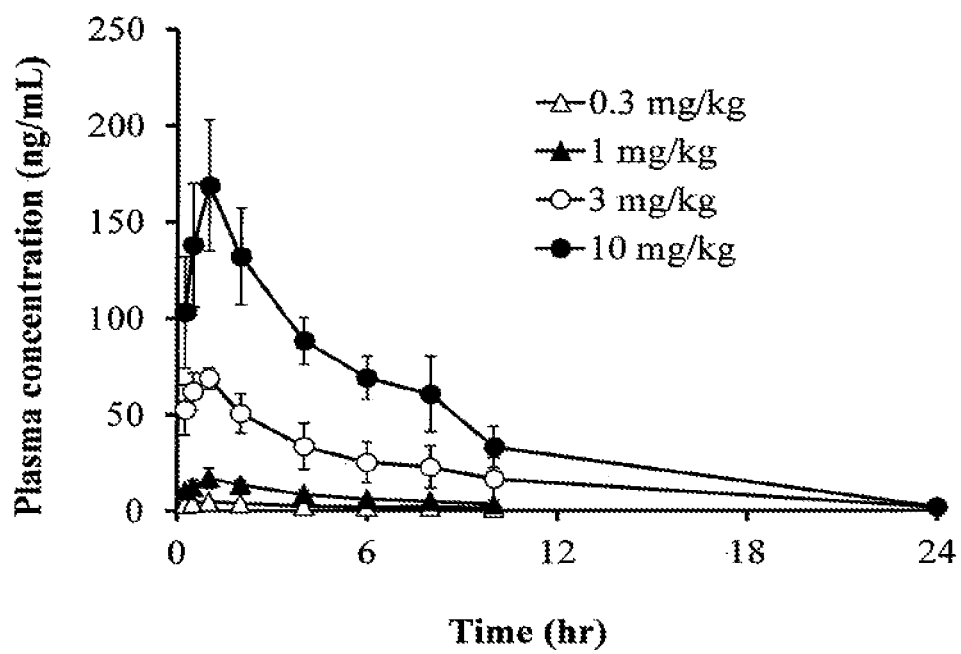
FIG. 1 is a result of measuring the plasma concentration of Compound III-2, after oral administration of prodrug Compound II-6, the parent compound of which is Compound III-2, to rat under non-fasting conditions.
FIG. 2 is a result of measuring the plasma concentration of Compound II-6, after oral administration of prodrug Compound II-6, the parent compound of which is Compound III-2, to rat under non-fasting conditions.

The meaning of each term used in the present description is explained below. Each term is used in a unified sense, and is used in the same sense when used alone, or when used in combination of other term.

The term of "consisting of" means having only components.

The term of "comprising" means not restricting with components and not excluding undescribed factors.

"Optionally substituted by substituent group A" means that an arbitrary position may be substituted by one, two or more same or different substituents selected from substituent group A.

"Prodrug" in the present description refers to a compound represented by formula (II) in the following reaction formula:

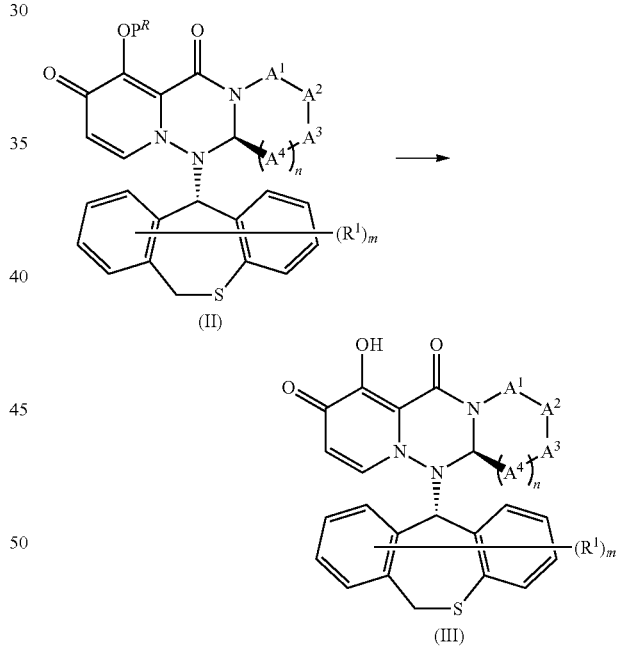

wherein each symbol is same as the above,
or its pharmaceutically acceptable salt, and means a compound showing cap-dependant endonuclease (CEN) inhibitory activity and/or CPE inhibitory effect by being converted into a compound represented by formula (III) by a decomposition reaction caused by drug-metabolizing enzymes, hydrolases, gastric acids, enterobacteria, etc. under physiological conditions in vivo.

The prodrug more preferably means a compound in which bioavailability and/or AUC (area under the blood concentration curve) in in vivo administration is improved more than those of the compound represented by formula (III).

Therefore, the prodrug is efficiently absorbed into the body in the stomach and/or intestines after in vivo administration (for example, oral administration), then converted into the compound represented by formula (III). Thus, the prodrug preferably shows an effect of treating and/or preventing influenza higher than the compound represented by formula (III).

One embodiment of the "group represented by

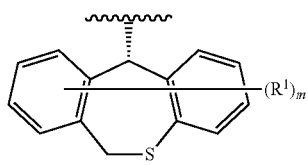

"wherein each definition has the same meaning as described (1),
is a group represented by formula:

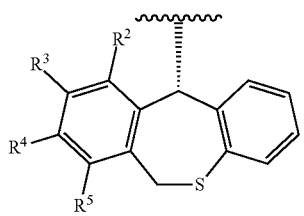

wherein $R^2$, $R^3$, $R^4$ and $R^5$ are each independently hydrogen or fluorine; the number of fluorine atoms of $R^2$, $R^3$, $R^4$ and $R^5$ is 1 or 2.

Another embodiment is a group represented by formula:

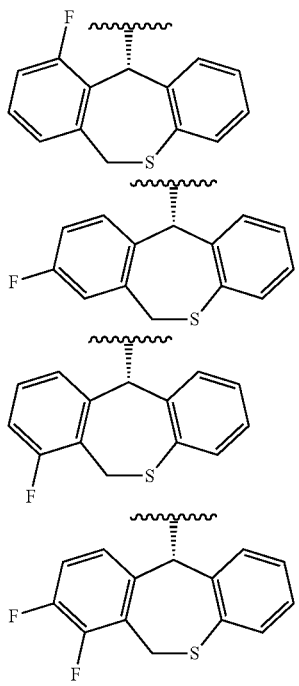

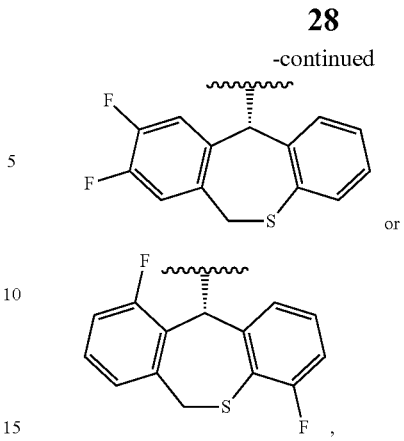

and a group represented by formula:

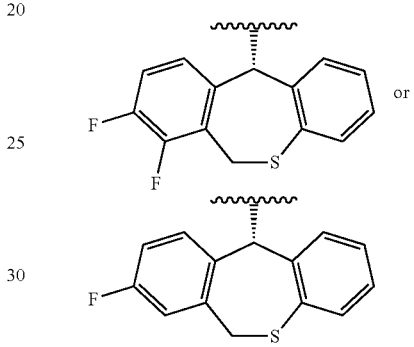

is preferable, and a group represented by formula:

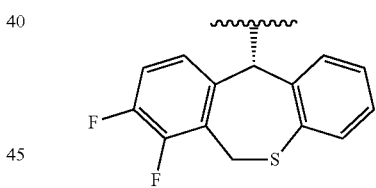

is especially preferable.

"Group to form a prodrug" in the present description refers to a "$P^R$" group in the formula (II), in the following reaction formula:

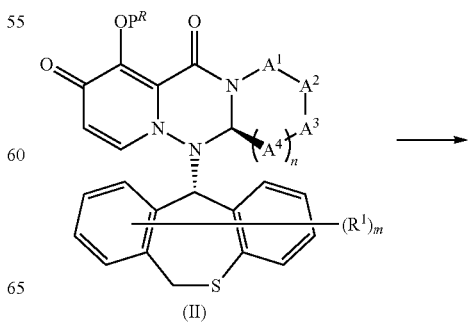

-continued

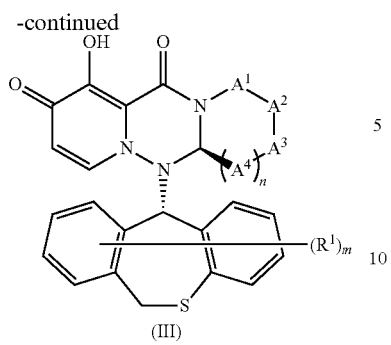

(III)

wherein each symbol is same as the above,
and —OP^R group is converted into —OH group in the formula (III) by a decomposition reaction caused by drug-metabolizing enzymes, hydrolases, gastric acids, enterobacteria, etc. under physiological conditions in vivo.

The "group to form a prodrug" more preferably means a group that improves bioavailability and/or AUC (area under the blood concentration curve) of the compound represented by formula (III) by being added to the compound represented by formula (III).

Examples of the group to form a prodrug include the groups described in Prog. Med. 5: 2157-2161 (1985) and Supplied by The British Library—"The world's Knowledge".

The "group to form a prodrug" in —OP^R group in the formula (I) or (II) may be a group converted into —OH group in vivo, and examples preferably include a group selected from the following formula a) to ac).

—C(=O)—P^{R0},  a)

—C(=O)—P^{R1},  b)

—C(=O)-L-P^{R1},  c)

—C(=O)-L-O—P^{R1},  d)

—C(=O)-L-O-L-O—P^{R1},  e)

—C(=O)-L-O—C(=O)—P^{R1},  f)

—C(=O)—O—P^{R2},  g)

—C(=O)—N(—K)(P^{R2}),  h)

—C(=O)—O-L-O—P^{R2},  i)

—C(P^{R3})_2—O—P^{R4},  j)

—C(P^{R3})_2—O-L-O—P^{R4},  k)

—C(P^{R3})_2—O—C(=O)—P^{R4},  l)

—C(P^{R3})_2—O—C(=O)—O—P^{R4},  m)

—C(P^{R3})_2—O—C(=O)—N(—K)—P^{R4},  n)

—C(P^{R3})_2O—C(=O)—O-L-O—P^{R4},  o)

—C(P^{R3})_2—O—C(=O)—O-L-N(P^{R4})_2,  p)

—C(P^{R3})_2—O—C(=O)—N(—K)-L-O—P^{R4},  q)

—C(P^{R3})_2—O—C(=O)—N(—K)-L-N(P^{R4})_2,  r)

—C(P^{R3})_2—O—C(=O)—O-L-O-L-O—P^{R4},  s)

—C(P^{R3})_2—O—C(=O)—O-L-N(—K)—C(=O)—P^{R4},  t)

—C(P^{R3})_2O—P(=O)(P^{R5})_2,  u)

—C(P^{R3})_2—P^{R6},  v)

—C(=N^+(P^{R7})_2)(—N(P^{R7})_2),  w)

—C(P^{R3})_2—C(P^{R3})_2—C(=O)—O—P^{R2},  x)

—C(P^{R3})_2—N(—K)—C(=O)—O—P^{R2},  y)

—P(=O)(—P^{R8})(—P^{R9}),  z)

—S(=O)_2—P^{R10},  aa)

—P^{R11}, and  ab)

—C(P^{R3})_2—C(P^{R3})_2—O—P^{R2},  ac)

wherein L is straight or branched alkylene, or straight or branched alkenylene;
K is hydrogen, or alkyl optionally substituted by substituent group A;
P^{R0} is alkyl optionally substituted by substituent group A, or alkenyl optionally substituted by substituent group A;
P^{R1} is carbocyclyl group optionally substituted by substituent group A, heterocyclyl group optionally substituted by substituent group A, alkylamino optionally substituted by substituent group A, or alkylsulfanyl optionally substituted by substituent group A;
P^{R2} is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl;
P^{R3} is each independently hydrogen or alkyl;
P^{R4} is each independently alkyl optionally substituted by substituent group A, carbocyclyl group optionally substituted by substituent group A, heterocyclyl group optionally substituted by substituent group A, alkylamino optionally substituted by substituent group A, carbocyclylalkyl optionally substituted by substituent group A, heterocyclylalkyl optionally substituted by substituent group A, or trialkylsilyl;
P^{R5} is each independently hydroxy or OBn;
P^{R6} is carbocyclyl group optionally substituted by substituent group A, or heterocyclyl group optionally substituted by substituent group A;
P^{R7} is each independently alkyl optionally substituted by substituent group A;
P^{R8} is alkyloxy optionally substituted by substituent group A;
P^{R9} is alkyloxy optionally substituted by substituent group A, alkylamino optionally substituted by substituent group A, carbocyclyloxy optionally substituted by substituent group A, heterocyclyloxy optionally substituted by substituent group A, carbocyclyl amino optionally substituted by substituent group A or heterocyclylamino optionally substituted by substituent group A;
P^{R8} and P^{R9} may be taken together with an adjacent phosphorus atom to form heterocycle optionally substituted by substituent group A;
P^{R10} is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A; and
P$^{R11}$ is alkyl optionally substituted by substituent group A, alkenyl optionally substituted by substituent group A, carbocyclyl group optionally substituted by substituent group A, or heterocyclyl group optionally substituted by substituent group A;

Substituent group A; oxo, alkyl, hydroxyalkyl, amino, alkylamino, carbocyclyl, heterocyclyl, carbocyclylalkyl, alkylcarbonyl, halogen, hydroxy, carboxy, alkylcarbonylamino, alkylcarbonylaminoalkyl, alkylcarbonyloxy, alkyloxycarbonyl, alkyloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho.

"Converted into a prodrug" in the present description means that, as shown in the following reaction formula:

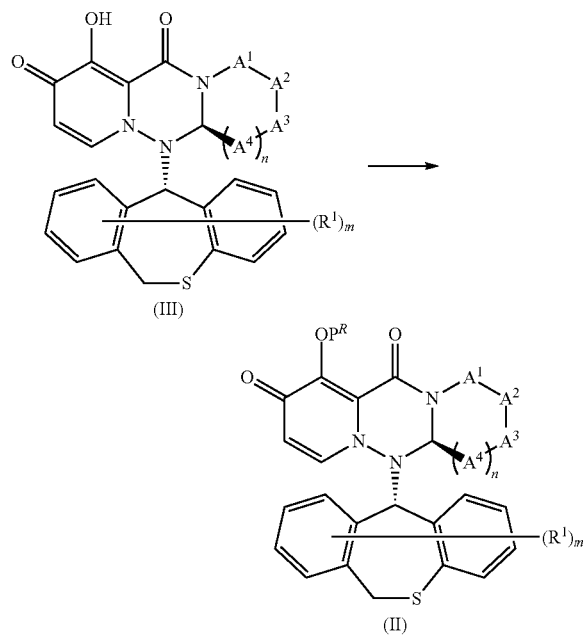

wherein each symbol is same as the above,
a hydroxy group in the formula (III) or its pharmaceutically acceptable salt is converted into —OP$^R$ group.

"Parent compound" in the present description means a compound to be a source before synthesizing the "prodrug" and/or a compound released from the "prodrug" by the reaction by enzymes, a gastric acid, and the like under physiological conditions in vivo, and specifically means a compound shown by the formula (III), or pharmaceutically acceptable salt thereof or a solvate thereof.

The term "halogen" includes a fluorine atom, a chlorine atom, a bromine atom and an iodine atom. A fluorine atom and a chlorine atom are especially preferable.

The term "alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, secbutyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, n-butyl, isobutyl, secbutyl, tert-butyl or n-pentyl. A more preferred embodiment is methyl, ethyl, n-propyl, isopropyl or tert-butyl.

The term "alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

The term "alkylene" includes a C1 to C15, preferably a C1 to C10, more preferably a C1 to C6 and further preferably a C1 to C4 liner or branched bivalent hydrocarbon group. Examples include methylene, ethylene, trimethylene, propylene, tetramethylene, pentamethylene, hexamethylene and the like.

The term "alkenylene" includes a C2 to C15, preferably a C2 to C10, more preferably a C2 to C6 and further preferably a C2 to C4 liner or branched bivalent hydrocarbon group having one or more double bond(s) at any position(s). Examples include vinylene, prenylene, butenylene, pentenylene and the like.

The term "hydroxyalkyl" means a group wherein one or more hydroxyl group(s) is replaced with hydrogen atom(s) attached to a carbon atom(s) of the above "alkyl". Examples include hydroxymethyl, 1-hydroxyethyl, 2-hydroxyethyl, 1-hydroxypropyl, 2-hydroxypropyl, 1,2-hydroxyethyl and the like.

A preferred embodiment of "hydroxyalkyl" is hydroxymethyl.

The term "alkyloxy" means a group wherein the above "alkyl" is bonded to an oxygen atom. Examples include methyloxy, ethyloxy, n-propyloxy, isopropyloxy, n-butyloxy, tert-butyloxy, isobutyloxy, sec-butyloxy, pentyloxy, isopentyloxy, hexyloxy and the like.

A preferred embodiment of "alkyloxy" is methyloxy, ethyloxy, n-propyloxy, isopropyloxy or tert-butyloxy.

The term "haloalkyl" means a group wherein one or more "halogen" described above is bonded to the above "alkyl". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like.

A preferred embodiment of "haloalkyl" is trifluoromethyl or trichloromethyl.

The term "alkylcarbonyl" means a group wherein the above "alkyl" is bonded to a carbonyl group. Examples include methylcarbonyl, ethylcarbonyl, propylcarbonyl, isopropylcarbonyl, tert-butylcarbonyl, isobutylcarbonyl, sec-butylcarbonyl, pentylcarbonyl, isopenthylcarbonyl, hexylcarbonyl and the like.

A preferred embodiment of "alkylcarbonyl" is methylcarbonyl, ethylcarbonyl or n-prop ylcarbonyl.

The term "alkylamino" means a group wherein one or two hydrogen atom(s) attached to a nitrogen atom of an amino group is replaced with the above "alkyl". Two alkyl groups may be the same or different. Examples include methylamino, ethylamino, isopropylamino, dimethylamino, diethylamino, N,N-diisopropylamino, N-methyl-N-ethylamino, N-isopropyl-N-ethylamino and the like.

A preferred embodiment of "alkylamino" is methylamino, ethylamino, dimethylamino or diethylamino.

The term "alkylaminoalkyl" means a group wherein the above "alkylamino" is bonded to the above "alkyl".

The term "alkylaminocarbonyl" means a group wherein the above "alkylamino" is bonded to a carbonyl group.

The term "alkylaminocarbonyloxy" means a group wherein the above "alkylaminocarbonyl" is bonded to an oxygen atom.

The term "alkylcarbonylamino" means a group wherein the above "alkylcarbonyl" is replaced with a hydrogen atom bonded to a nitrogen atom of an amino group. Examples include methylcarbonylamino, ethylcarbonylamino, propylcarbonylamino, isopropylcarbonylamino, tert-butylcarbonylamino, isobutylcarbonylamino, sec-butylcarbonylamino and the like.

A preferred embodiment of "alkylcarbonylamino" is methylcarbonylamino or ethylcarbonylamino.

The term "alkylcarbonyloxy" means a group wherein the above "alkylcarbonyl" is bonded to an oxygen atom. Examples include methylcarbonyloxy, ethylcarbonyloxy, propylcarbonyloxy, isopropylcarbonyloxy, tert-butylcarbonyloxy, isobutylcarbonyloxy, secbutyl carbonyloxy and the like.

A preferred embodiment of "alkylcarbonyloxy" is methylcarbonyloxy or ethylcarbonyloxy.

The term "alkylcarbonylaminoalkyl" means a group wherein the above "alkylcarbonylamino" is bonded to the above "alkyl".

The term "alkyloxycarbonyl" means a group wherein the above "alkyloxy" is bonded to a carbonyl group. Examples include methyloxycarbonyl, ethyloxycarbonyl, propyloxycarbonyl, isopropyloxycarbonyl, tert-butyloxycarbonyl, isobutyloxycarbonyl, sec-butyloxycarbonyl, penthyloxycarbonyl, isopenthyloxycarbonyl, hexyloxycarbonyl and the like.

A preferred embodiment of "alkyloxycarbonyl" is methyloxycarbonyl, ethyloxycarbonyl or propyloxycarbonyl.

The term "aryloxycarbonylalkyl" means a group wherein the above "alkyloxycarbonyl" is bonded to the above "alkyl".

The term "alkyloxycarbonyloxy" means a group wherein the above "alkyloxycarbonyl" is bonded to an oxygen atom.

The term "alkylsulfanyl" means a group wherein the above "alkyl" is replaced with a hydrogen atom bonded to a sulfur atom of a sulfanyl group. Examples include methylsulfanyl, ethylsulfanyl, n-propylsulfanyl, isopropylsulfanyl and the like.

The term "alkylsulfonyl" means a group wherein the above "alkyl" is bonded to a sulfonyl group. Examples include methylsulfonyl, ethylsulfonyl, propylsulfonyl, isopropylsulfonyl, tert-butylsulfonyl, isobutylsulfonyl, sec-butylsulfonyl and the like.

A preferred embodiment of "alkylsulfonyl" is methylsulfonyl or ethylsulfonyl.

The term "trialkylsilyl" means a group wherein three of the above "alkyl" are bonded to a silicon atom. Three alkyl groups may be the same or different. Examples include trimethylsilyl, triethylsilyl, tert-butyldimethylsilyl and the like.

The term "carbocyclyl group" means C3 to C20 preferably C3 to C16, more preferably C4 to C12 cyclic hydrocarbon group and includes aromatic carbocyclyl and non-aromatic carbocyclyl.

The term "aromatic carbocyclyl" means a cyclic aromatic hydrocarbon group which is monocyclic or polycyclic having two or more rings. Examples include phenyl, naphthyl, anthryl, phenanthryl and the like.

A preferred embodiment of "aromatic carbocyclyl" is phenyl, 1-naphthyl or 2-naphthyl. Another embodiment of "aromatic carbocyclyl" is phenyl, The term "non-aromatic carbocyclyl" means a cyclic saturated hydrocarbon group or a cyclic unsaturated non-aromatic hydrocarbon group, which is monocyclic or polycyclic having two or more rings. Examples of the "non-aromatic carbocyclyl", which is polycyclic having two or more rings, include a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge or a group to form a spiro ring as follows:

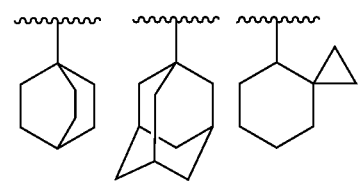

The non-aromatic carbocyclyl which is monocyclic is preferably C3 to C16, more preferably C3 to C12 and further preferably C3 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

Examples of non-aromatic carbocyclyl, which is polycyclic having two or more rings, include indanyl, indenyl, acenaphthyl, tetrahydronaphthyl, fluorenyl and the like.

The term "carbocycle" means C3 to C20 preferably C3 to C16, more preferably C4 to C12 cyclic hydrocarbon and includes aromatic carbocycle and non-aromatic carbocycle.

The term "aromatic carbocycle" means a cyclic aromatic hydrocarbon which is monocyclic or polycyclic having two or more rings. Examples include benzene ring, naphthalene ring, anthracene ring, phenanthrene ring and the like.

A preferred embodiment of "aromatic carbocycle" is benzene ring and naphthalene ring are exemplified. Another embodiment of "aromatic carbocycle" is benzene ring.

The term of "non-aromatic carbocycle" means a saturated carbocycle or an unsaturated non-aromatic carbocycle which is monocyclic or polycyclic having two or more rings. Examples of the "non-aromatic carbocycle" which is polycyclic having two or more rings, include a fused ring wherein a non-aromatic carbocycle, which is monocyclic or polycyclic having two or more rings, is fused with a ring of the above "aromatic carbocycle".

In addition, examples of the "non-aromatic carbocycle" also include a cycle having a bridge or a cycle to form a spiro ring as follows:

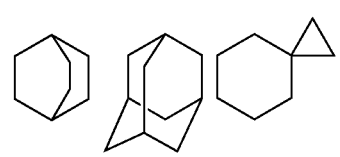

The non-aromatic carbocycle which is monocyclic is preferably C3 to C16, more preferably C3 to C12 and further preferably C3 to C8 carbocycle. Examples include cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene and the like.

Examples of non-aromatic carbocycle, which is polycyclic having two or more rings, include indane, indene, acenaphthalene, tetrahydronaphthalene, fluorine and the like are exemplified.

The term "heterocyclyl group" includes an aromatic cyclyl and a non-aromatic heterocyclyl, which is containing one or more of heteroatom(s) selected independently from O, S and N.

The term "aromatic heterocyclyl" means an aromatic cyclyl, which is monocyclic or polycyclic having two or more rings, containing one or more of heteroatom(s) selected independently from O, S and N.

Examples of "aromatic heterocyclyl", which is polycyclic having two or more rings, include a fused ring group wherein an aromatic heterocyclyl, which is monocyclic or polycyclic having two or more rings, is fused with a ring of the above "aromatic carbocyclyl".

The aromatic heterocyclyl, which is monocyclic, is preferably a 5- to 8-membered and more preferably 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

Examples of aromatic heterocyclyl, which is polycyclic having three or more rings, include carbazolyl, acridinyl, xanthenyl, phenothiazinyl, phenoxathiinyl, phenoxazinyl, dibenzofuryl and the like.

The term "non-aromatic heterocyclyl" means a non-aromatic cyclyl, which is monocyclic or polycyclic having two or more rings, containing one or more heteroatom(s) selected independently from O, S and N.

Examples of "non-aromatic heterocyclyl", which is polycyclic having two or more rings, include a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl".

In addition, examples of the "non-aromatic heterocyclyl" also include a group having a bridge or a group to form a spiro ring as follows:

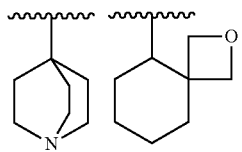

The non-aromatic heterocyclyl, which is monocyclic, is preferably a 3- to 8-membered and more preferably 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolinyl, tetrahydrothiazolinyl, tetrahydroisothiazolinyl, dihydrooxazinyl, hexahydroazepinyl, tetrahydro diazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

Examples of non-aromatic heterocyclyl, which is polycyclic having two or more rings, include indolinyl, isoindolinyl, chromanyl, isochromanyl and the like.

The term "heterocycle" includes an aromatic cycle and a non-aromatic heterocycle, which is containing one or more of heteroatom(s) selected independently from O, S and N.

The term of "aromatic heterocycle" means an aromatic cycle which is monocyclic or polycyclic having two or more rings, containing one or more of heteroatom(s) selected independently from O, S and N.

Examples of "aromatic heterocycle", which is polycyclic having two or more rings, include a fused ring wherein an aromatic heterocycle, which is monocyclic or polycyclic having two or more rings, is fused with a ring of the above "aromatic carbocycle".

The aromatic heterocycle, which is monocyclic, is preferably a 5- to 8-membered and more preferably 5- to 6-membered ring. Examples include pyrrole, imidazole, pyrazole, pyridine, pyridazine, pyrimidine, pyrazine, triazole, triazine, tetrazole, furan, thiophene, isoxazole, oxazole, oxadiazole, isothiazole, thiazole, thiadiazole and the like.

Examples of aromatic heterocycle, which is bicyclic, include indoline, isoindoline, indazorin, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, thiazolopyridine and the like.

Examples of aromatic heterocycle, which is polycyclic having three or more rings, include carbazole, acridine, xanthene, phenothiazine, phenoxathiin, phenoxazine, dibenzofuran and the like.

The term "non-aromatic heterocycle" means a non-aromatic cycle, which is monocyclic or polycyclic having two or more rings, containing one or more of heteroatom(s) selected independently from O, S and N.

Examples of "non-aromatic heterocycle", which is polycyclic having two or more rings, include a fused ling wherein a non-aromatic heterocycle, which is monocyclic or polycyclic having two or more ring(s), is fused with a ring of the above "aromatic carbocycle", "non-aromatic carbocycle" and/or "aromatic heterocycle".

In addition, examples of "non-aromatic heterocycle" also include a cycle having a bridge or a cyclo to form a spiro ring as follows:

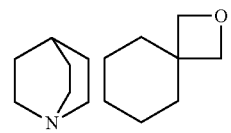

The non-aromatic heterocycle, which is monocyclic, is preferably a 3- to 8-membered and more preferably 5- to 6-membered ring. Examples include dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyran, dihydrothiazine, tetrahydrothiazoline, tetrahydroisothiazoline, dihydrooxazine, hexahydroazepine, tetrahydrodiazepine, tetrahydropyridazine, hexahydropyrimidine, dioxolane, dioxazine, aziridine, dioxoline, oxepane, thiolane, thiazine and the like.

Examples of non-aromatic heterocycle, which is polycyclic having two or more rings, include indoline, isoindoline, chroman, isochroman and the like.

The "carbocycle" part of "carbocyclylalkyl", "carbocyclyloxy" or "carbocyclylamino" is same as the above "carbocycle".

The "heterocycle" part of "heterocyclylalkyl", "heterocyclyloxy" or "heterocyclylamino" is same as the above "heterocycle".

The compounds used in the present invention are characterized in that the compounds isolated by optical resolution of tricyclic compounds substituted by the other tricyclic group improve cap-dependent endonuclease inhibitory activity.

The compounds used in the present invention are also characterized in that the compounds are efficiently absorbed into the body after administration (for example, oral administration), and showing high efficacy by introducing a group to form a prodrug.

One or more hydrogen, carbon and/or other atoms in the compounds used in the present invention may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I and $^{36}$Cl respectively. The compounds used in the present invention include compounds replaced with these isotopes. The compounds replaced with the above isotopes are useful as medicines and include all of radiolabeled compounds used in the present invention. A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound used in the present invention can be prepared using well-known methods in this field of the invention. For example, a tritium-labeled compound used in the present invention can be prepared by introducing a tritium to a certain compound used in the present invention, through a catalytic dehalogenation reaction using a tritium. This method comprises reacting with an appropriately-halogenated precursor of the compound used in the present invention with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}$C-labeled compound can be prepared by using a raw material having $^{14}$C.

The pharmaceutically acceptable salts of the compounds used in the present invention include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds used in the present invention or its pharmaceutically acceptable salts may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds used in the present invention. When the compounds used in the present invention or its pharmaceutically acceptable salts are allowed to stand in the atmosphere, the compounds may absorb water, resulting in attachment of adsorbed water or formation of hydrates. Recrystallization of the compounds used in the present invention or its pharmaceutically acceptable salts may produce crystal polymorphs.

The group to form a prodrug is preferably a group converted into OH group by action of drug-metabolizing enzymes, hydrolases, gastric acids, and/or enterobacteria, after in vivo administration (for example, oral administration).

Examples of more preferred embodiment of the group to form a prodrug include a group selected from the following formulae a) to ac).

| | |
|---|---|
| —C(=O)—P$^{R0}$, | a) |
| —C(=O)—P$^{R1}$, | b) |
| —C(=O)-L-P$^{R1}$, | c) |
| —C(=O)-L-O—P$^{R1}$, | d) |
| —C(=O)-L-O-L-O—P$^{R1}$, | e) |
| —C(=O)-L-O—C(=O)—P$^{R1}$, | f) |
| —C(=O)—O—P$^{R2}$, | g) |
| —C(=O)—N(—K)(P$^{R2}$), | h) |
| —C(=O)—O-L-O—P$^{R2}$, | i) |
| —C(P$^{R3}$)$_2$—O—P$^{R4}$, | j) |
| —C(P$^{R3}$)$_2$—O-L-O—P$^{R4}$, | k) |
| —C(P$^{R3}$)$_2$—O—C(=O)—P$^{R4}$, | l) |
| —C(P$^{R3}$)$_2$—O—C(=O)—O—P$^{R4}$, | m) |
| —C(P$^{R3}$)$_2$—O—C(=O)—N(—K)—P$^{R4}$, | n) |
| —C(P$^{R3}$)$_2$—O—C(=O)—O-L-O—P$^{R4}$, | o) |
| —C(P$^{R3}$)$_2$—O—C(=O)—O-L-N(P$^{R4}$)$_2$, | p) |
| —C(P$^{R3}$)$_2$—O—C(=O)—N(—K)-L-O—P$^{R4}$, | q) |

—C($P^{R3}$)$_2$—O—C(=O)—N(—K)-L-N($P^{R4}$)$_2$,  r)

—C($P^{R3}$)$_2$—O—C(=O)—O-L-O-L-O—$P^{R4}$,  s)

—C($P^{R3}$)$_2$—O—C(=O)—O-L-N(—K)—C(=O)—$P^{R4}$,  t)

—C($P^{R3}$)$_2$—O—P(=O)(—$P^{R5}$)$_2$,  u)

—C($P^{R3}$)$_2$—$P^{R6}$,  v)

—C(=N$^+$($P^{R7}$)$_2$)(—N($P^{R7}$)$_2$),  w)

—C($P^{R3}$)$_2$—C($P^{R3}$)$_2$—C(=O)—O—$P^{R2}$,  x)

—C($P^{R3}$)$_2$—N(—K)—C(=O)—O—$P^{R2}$,  y)

—P(=O)(—$P^{R8}$)(—$P^{R9}$),  z)

—S(=O)$_2$—$P^{R10}$,  aa)

—$P^{R11}$, and  ab)

—C($P^{R3}$)$_2$—C($P^{R3}$)$_2$—O—$P^{R2}$,  ac)

wherein L is straight or branched alkylene, or straight or branched alkenylene;
K is hydrogen, or alkyl optionally substituted by substituent group A;
$P^{R0}$ is alkyl optionally substituted by substituent group A, or alkenyl optionally substituted by substituent group A;
$P^{R1}$ is carbocyclyl group optionally substituted by substituent group A, heterocyclyl group optionally substituted by substituent group A, alkylamino optionally substituted by substituent group A, or alkylsulfanyl optionally substituted by substituent group A;
$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, heterocyclylalkyl optionally substituted by substituent group A or trialkylsilyl optionally substituted by substituent group A;
$P^{R3}$ is each independently hydrogen or alkyl;
$P^{R4}$ is each independently alkyl optionally substituted by substituent group A, carbocyclyl group optionally substituted by substituent group A, heterocyclyl group optionally substituted by substituent group A, alkyl amino optionally substituted by substituent group A, carbocyclylalkyl optionally substituted by substituent group A, heterocyclylalkyl optionally substituted by substituent group A, or trialkylsilyl;
$P^{R5}$ is each independently hydroxy or OBn;
$P^{R6}$ is carbocyclyl group optionally substituted by substituent group A, or heterocyclyl group optionally substituted by substituent group A;
$P^{R7}$ is each independently alkyl optionally substituted by substituent group A;
$P^{R8}$ is alkyloxy optionally substituted by substituent group A;
$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclyl amino optionally substituted by substituent group A or heterocyclylamino optionally substituted by substituent group A;
$P^{R8}$ and $P^{R9}$ may be taken together with an adjacent phosphorus atom to form heterocycle optionally substituted by substituent group A;

$P^{R10}$ is alkyl optionally substituted by substituent group A, carbocyclyl group optionally substituted by substituent group A, heterocyclyl group optionally substituted by substituent group A, carbocyclylalkyl optionally substituted by substituent group A or heterocyclylalkyl optionally substituted by substituent group A; and
$P^{R11}$ is alkyl optionally substituted by substituent group A, alkenyl optionally substituted by substituent group A, carbocyclyl group optionally substituted by substituent group A, or heterocyclyl group optionally substituted by substituent group A;
Substituent group A; oxo, alkyl, hydroxyalkyl, amino, alkylamino, carbocyclyl, heterocyclyl, carbocyclylalkyl, alkylcarbonyl, halogen, hydroxy, carboxy, alkylcarbonylamino, alkylcarbonylaminoalkyl, alkylcarbonyloxy, alkyloxycarbonyl, aryloxycarbonylalkyl, alkyloxycarbonyloxy, alkylaminocarbonyloxy, alkylaminoalkyl, alkyloxy, cyano, nitro, azido, alkylsulfonyl, trialkylsilyl and phospho.

Examples of further preferred embodiment of the group to form a prodrug include following groups.

—C(=O)—$P^{R0}$,  a)

—C(=O)—$P^{R1}$,  b)

—C(=O)—O—$P^{R2}$,  g)

—C(=O)—N(—K)($P^{R2}$),  h)

—C(=O)—O-L-O—$P^{R2}$,  i)

—C($P^{R3}$)$_2$—O—C(=O)—$P^{R4}$,  l)

—C($P^{R3}$)$_2$—O—C(=O)—O—$P^{R4}$,  m)

—C($P^{R3}$)$_2$—OC(=O)—O-L-O—$P^{R4}$,  o)

—C($P^{R3}$)$_2$—$P^{R6}$,  v)

—C($P^{R3}$)$_2$—C($P^{R3}$)$_2$—C(=O)—O—$P^{R2}$,  x)

—C($P^{R3}$)$_2$—N(—K)—C(=O)—O—$P^{R2}$, and  y)

—P(=O)(—$P^{R8}$)(—$P^{R9}$),  z)

wherein L is straight or branched alkylene;
K is hydrogen, or alkyl optionally substituted by substituent group A;
$P^{R0}$ is alkyl optionally substituted by substituent group A;
$P^{R1}$ is carbocyclyl group optionally substituted by substituent group A, or heterocyclyl group optionally substituted by substituent group A;
$P^{R2}$ is alkyl optionally substituted by substituent group A, carbocyclyl group optionally substituted by substituent group A, heterocyclyl group optionally substituted by substituent group A, carbocyclylalkyl optionally substituted by substituent group A, or heterocyclylalkyl optionally substituted by substituent group A;
$P^{R3}$ is each independently hydrogen or alkyl;
$P^{R4}$ is alkyl optionally substituted by substituent group A, carbocyclyl group optionally substituted by substituent group A, or heterocyclyl group optionally substituted by substituent group A;
$P^{R6}$ is carbocyclyl group optionally substituted by substituent group A, or heterocyclyl group optionally substituted by substituent group A;
$P^{R8}$ is alkyloxy optionally substituted by substituent group A;
$P^{R9}$ is alkyloxy optionally substituted by substituent group A, alkylamino optionally substituted by substituent group A, carbocyclyloxy optionally substituted by substituent group A, heterocyclyloxy optionally substituted by substituent group A, carbocyclylamino optionally substituted by substituent group A or heterocyclylamino optionally substituted by substituent group A; and
$P^{R8}$ and $P^{R9}$ may be taken together with an adjacent phosphorus atom to form heterocycle optionally substituted by substituent group A;
Substituent group A; oxo, alkyl, alkylamino, carbocyclyl, heterocyclyl, alkylcarbonyl, halogen, hydroxy, alkylcarbonylamino, alkylcarbonyloxy, alkyloxycarbonyl, aryloxycarbonylalkyl, alkylaminocarbonyloxy, alkyloxy, nitro, azido, alkylsulfonyl and trialkylsilyl.

Among the above group to form a prodrug, a) —C(=O)—$P^{R0}$, b) —C(=O)—$P^{R1}$, g) —C(=O)—O$P^{R2}$, h) —C(=O)—N(—K)($P^{R2}$), j) —C(=O)—O-L-O—$P^{R2}$, l) —C($P^{R3}$)$_2$—O—C(=O)—$P^{R4}$, m) —C($P^{R3}$)$_2$—O—C(=O)—O—$P^{R4}$, o) —C($P^{R3}$)$_2$—O—C(=O)—O-L-O—$P^{R4}$, x) —C($P^{R3}$)$_2$—C($P^{R3}$)$_2$—C(=O)—O—$P^{R2}$, and y) —C($P^{R3}$)$_2$—N(—K)—C(=O)—O—$P^{R2}$ are preferable.

In particular, a more preferable embodiment of the group to form a prodrug is the following group, $$—C(P^{R3})_2—O—C(=O)—O—P^{R4} \qquad (m)$$

wherein $P^{R3}$ is each independently hydrogen or alkyl; and $P^{R4}$ is alkyl optionally substituted by substituent group A, carbocyclyl group optionally substituted by substituent group A, or heterocyclyl group optionally substituted by substituent group A;
Substituent group A; oxo, alkyl, alkylamino, carbocyclyl, heterocyclyl, alkylcarbonyl, halogen, hydroxy, alkylcarbonylamino, alkylcarbonyloxy, alkyloxycarbonyl, aryloxycarbonylalkyl, alkylaminocarbonyloxy, alkyloxy, nitro, azido, alkylsulfonyl and trialkylsilyl.

An embodiment of $P^{R3}$ is each independently hydrogen or alkyl, and preferably hydrogen.

An embodiment of $P^{R4}$ is alkyl optionally substituted by substituent group A, carbocyclyl group optionally substituted by substituent group A, or heterocyclyl group optionally substituted by substituent group A, and preferably methyl, ethyl or the like.

An embodiment of Substituent group A includes oxo, alkyl, alkylamino, carbocyclyl, heterocyclyl, alkylcarbonyl, halogen, hydroxy, alkylcarbonylamino, alkylcarbonyloxy, alkyloxycarbonyl, aryloxycarbonylalkyl, alkylaminocarbonyloxy, alkyloxy, nitro, azido, alkylsulfonyl and trialkylsilyl, and preferably fluorine, chlorine, hydroxyl, methyl and ethyl.

Examples of another embodiment of a preferable substituent of the group to form a prodrug include following groups.

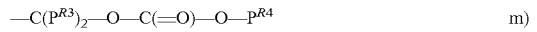

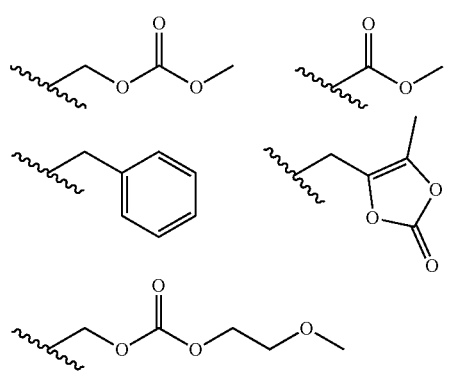

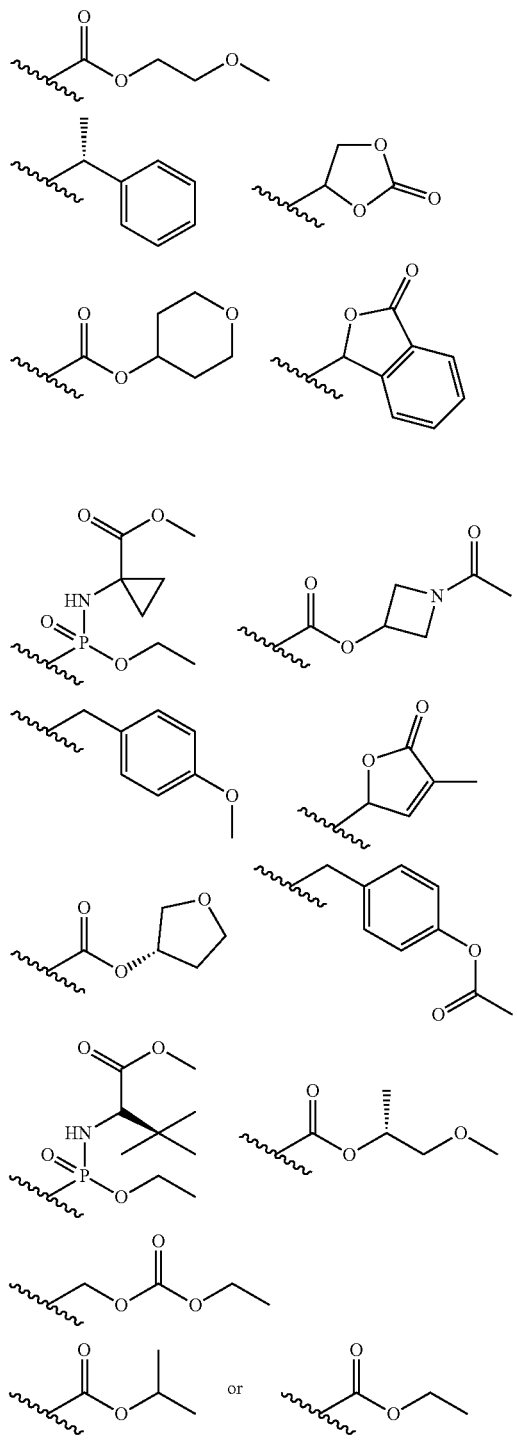

Examples of another embodiment of a preferable substituent of the group to form a prodrug include following groups.

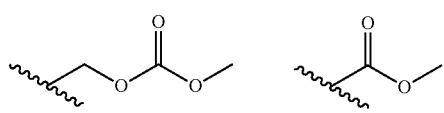

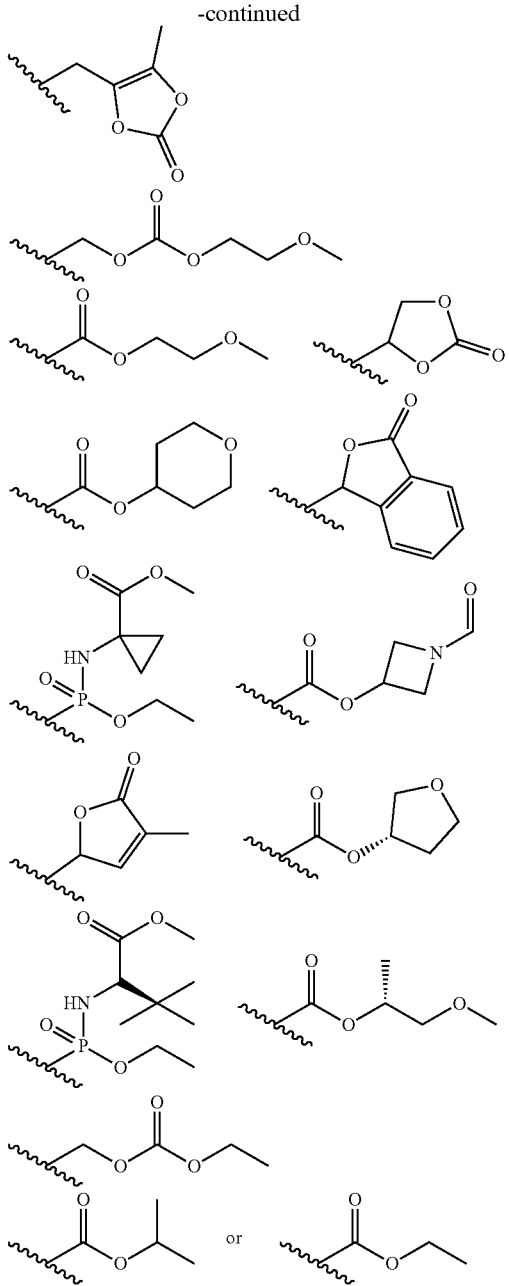

Examples of an embodiment of a particularly preferable substituent of the group to form a prodrug include following groups.

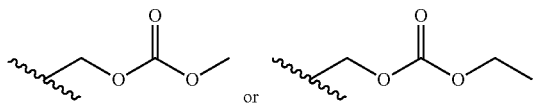

(Method for Producing Compound of the Present Invention)

A general method for producing the compound used in the present invention will be exemplified below. As to the extraction and purification, treatment which is performed in a normal experiment of organic chemistry may be conducted.

Synthesis of the compound used in the present invention can be carried out referring to the procedures known in the art.

As a raw material compound, commercially available compounds, compounds described in the present description, compounds described in the references cited in the present description, and other known compounds can be utilized.

When one wants to obtain a salt of the compound of the present invention, in the case where the compound used in the present invention is obtained in a form of a salt, it may be purified as it is and, in the case where the compound used in the present invention is obtained in a free form, a salt may be formed by a normal method by dissolving or suspending the compound in a suitable organic solvent, and adding an acid or a base.

In addition, the compound used in the present invention and a pharmaceutically acceptable salt thereof are present in a form of adducts with water or various solvents (hydrate or solvate) in some cases, and these adducts are used in the present invention.

In a general synthesis method as well as Examples and Intermediate Synthesis Examples, the meaning of each abbreviation is as follows.

Boc: tert-butoxycarbonyl
DBU: diazabicycloundecene
DMA: N,N-dimethylacetamide
DMF: N,N-dimethylformamide
HATU: O-(7-azabenzotriazol-1-yl)-N,N,N',N'-tetramethyluronium hexafluorophosphate
NMP: N-methylpyrrolidone
OBn: benzyloxy
THF: tetrahydrofuran
T3P: propyl phosphonic anhydride
WSC.HCl: N-ethyl-N'-(3-dimethylaminopropyl)carbodiimide hydrochloride The up and down of the "wedge" and "broken line wedge" indicates the absolute configuration.

(Preparation 1)

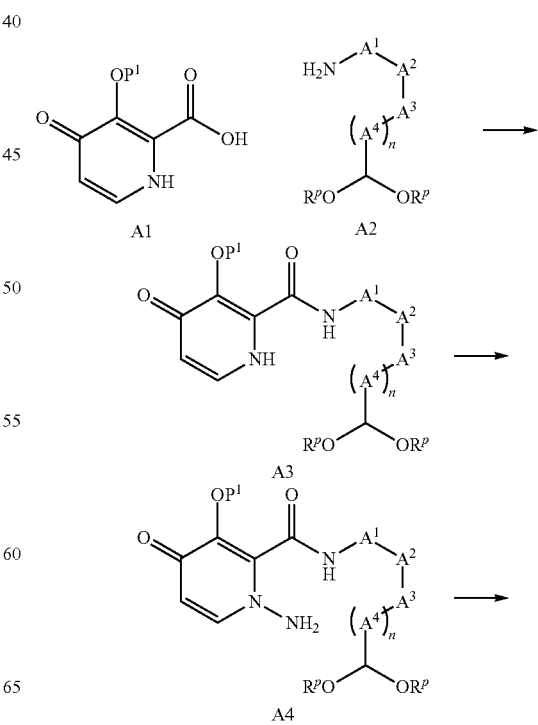

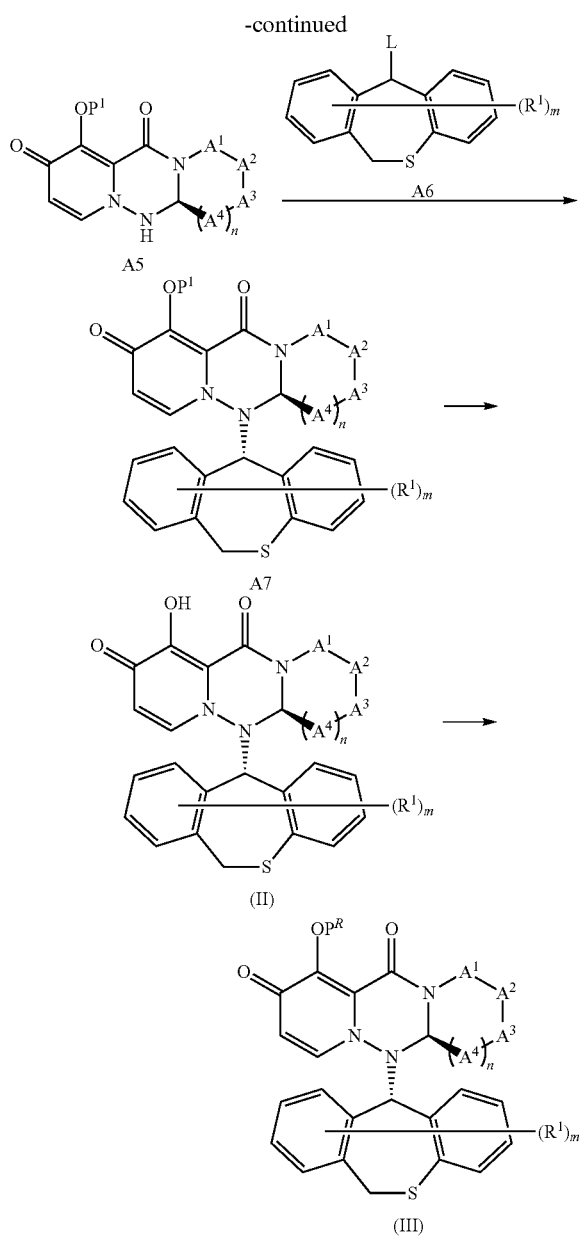

wherein P¹ is hydroxyl protective group) R^P is acetal protective group) L is leaving group) Other each symbol is same as above.

First Step

Compound A3 can be obtained by adding Compound A2 to Compound A1 in the presence of a dehydration-condensation agent such as dicyclohexylcarbodiimide, carbonyldiimidazole, dicyclohexylcarbodiimide-N-hydroxybenzotriazole, 4-(4,6-dimethoxy-1,3,5-triazin-2-yl)-4-methylmorpholinium chloride, hexafluorophosphoric acid 2-(7-aza-1H-benzotriazol-1-yl)-1,1,3,3-tetramethyluronium, WSC.HCl, HATU, etc. in a solvent such as DMF, THF, dichloromethane, acetonitrile etc. or in a mixed solvent thereof, and performing a reaction at −20° C. to 60° C., preferably −10° C. to 40° C. for 0.1 hours to 24 hours, preferably 1 hour to 12 hours.

Alternatively, Compound A3 can be obtained by adding an acylating reagent such as diphenylchlorophosphate, thionyl chloride, oxalyl chloride etc. to Compound A1 in the presence or absence of a base such as pyridine, triethylamine, diisopropylethylamine, 1-methylimidazole, etc. in the presence of a solvent such as THF, dioxane, dichloromethane, DMF etc., thereby, generating acid chloride, and adding Compound A2 having a substituent corresponding to an objective compound, and performing a reaction at −20° C. to 60° C., preferably −10° C. to 40° C. for 0.1 hours to 24 hours, preferably 0.5 hours to 12 hours.

Second Step

Compound A4 can be obtained by adding potassium carbonate, sodium carbonate, and O-(2,4-dinitrophenyl)hydroxylamine to Compound A3 in the presence of a solvent such as DMF, DMA, NMP, THF, etc., and performing a reaction at 10° C. to 60° C., preferably 20° C. to 40° C. for 0.1 hours to 48 hours, preferably 1 hour to 24 hours.

Third Step

A deprotecting reaction of an acetal protective group of Compound A4 can be performed by the general method described in Protective Groups in Organic Synthesis, Theodora W Green (John Wiley & Sons) etc. Thereafter, a generated aldehyde group is subjected to an intramolecular reaction, thereby, Compound A5 can be obtained.

For example, racemate of Compound A5 can be obtained by adding acetic acid and/or paratoluenesulfonic acid, methanesulfonic acid etc., to Compound A4 in the presence of a solvent such as DMF, toluene, THF, etc., and performing a reaction at 10° C. to 80° C., preferably 30° C. to 60° C. for 0.5 hours to 12 hours, preferably 1 hour to 6 hours. Compound A5 can be obtained by optical resolution of the racemate of Compound A5 by SFC or HPLC (chiral column).

Fourth Step

Compound A7 can be obtained by adding Compound A6, and a base such as sodium carbonate, potassium carbonate, cesium carbonate, etc. to Compound A5 in the presence of a solvent such as DMF, DMA, NMP, THF, etc. or in a mixed solvent thereof, and performing a reaction at 0° C. to 60° C., preferably 10° C. to 40° C. for 0.1 hours to 48 hours, preferably 1 hour to 24 hours.

Alternatively, Compound A7 can be obtained by adding Compound A6, and T3P, methane sulfonic acid or paratoluene sulfonic acid to Compound A5 in the presence of a solvent such as DMF, ethyl acetate, butyl acetate, 1,4-dioxane etc. or in a mixed solvent thereof, and performing a reaction at 40° C. to 150° C., preferably 60° C. to 120° C. for 0.1 hours to 48 hours, preferably 1 hour to 24 hours.

Fifth Step

A deprotecting reaction of hydroxyl protective group of Compound A7 can be performed by the general method described in Protective Groups in Organic Synthesis, Theodora W Green (John Wiley & Sons) etc.

Sixth Step

Compound (III) can be obtained by the general method including converting a hydroxyl group of Compound (II) into an ester group or ether group.

For example, the method described in Protective Groups in Organic Synthesis, Theodora W Green (John Wiley & Sons), Prog. Med. 5: 2157-2161 (1985), and Supplied by The British Library—"The world's Knowledge", etc. can be utilized.

(Preparation 2)

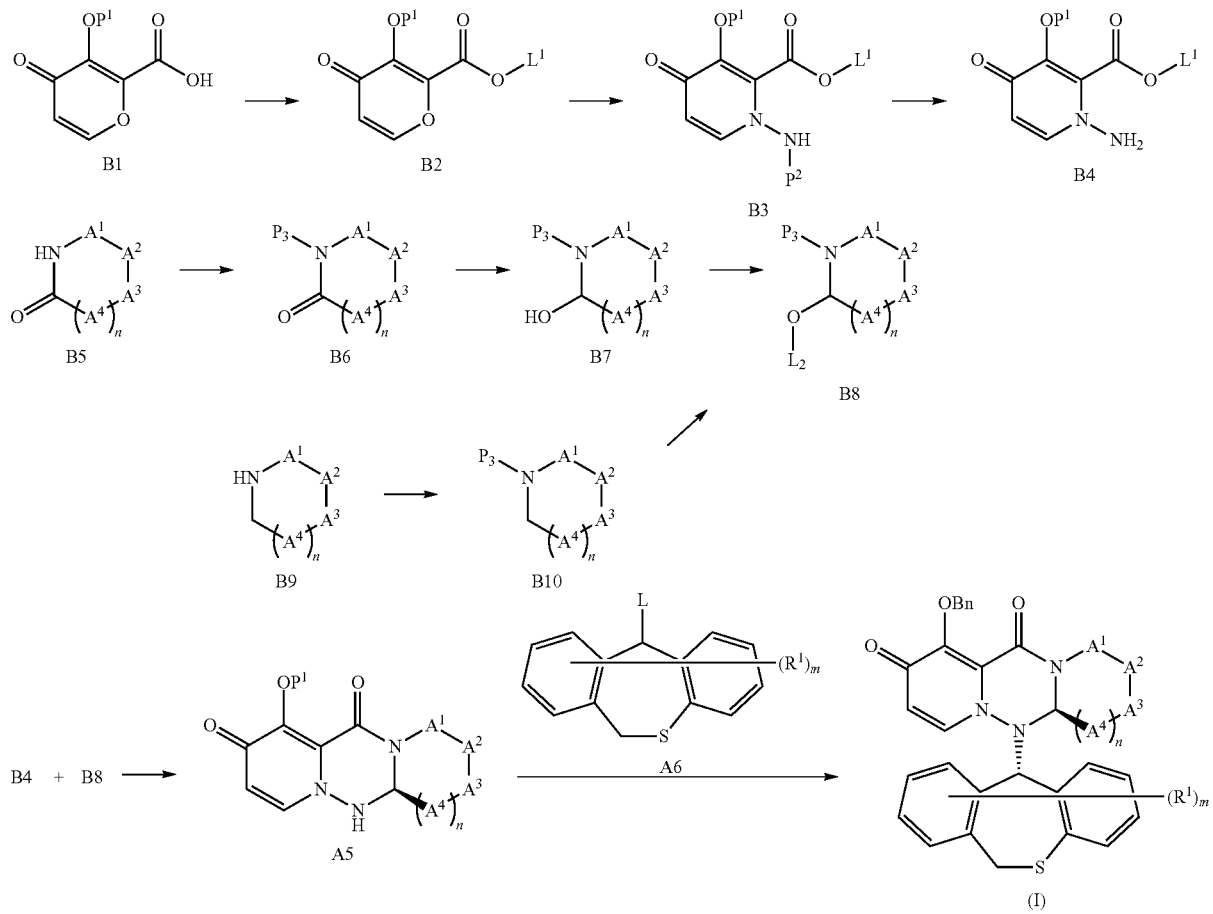

wherein P² is NH protective group; L¹ and L² is leaving group; Other each symbol is same as above.

First Step

Compound B2 can be obtained by adding Compound A2 and halogenated alkyl such as methyl iodide to Compound B1 in the presence of a base such as diazabicycloundecene in a solvent such as DMF, THF, dichloromethane, acetonitrile, etc. or in a mixed solvent thereof, and performing a reaction at −20° C. to 60° C., preferably −10° C. to 40° C. for 0.1 hours to 24 hours, preferably 1 hour to 24 hours.

Alternatively, Compound B2 can be obtained by adding acylating reagent such as diphenylchlorophosphate, thionyl chloride, oxalyl chloride, etc. to Compound B1 in a solvent such as THF, dioxane, dichloromethane, DMF, etc. or in a mixed solvent thereof, and adding alcohol in the presence of a base such as pyridine, triethylamine, diisopropylethylamine, 1-methylimidazole, etc., and performing a reaction at −20° C. to 60° C., preferably −10° C. to 40° C. for 0.1 hours to 24 hours, preferably 0.5 hours to 12 hours.

Second Step

Compound B3 can be obtained by adding para-toluene sulfonic acid pyridinium and hydrazine protected by Boc etc. to Compound B2 in a solvent such as THF, dioxane, dichloromethane, DMF etc., or in a mixed solvent thereof, and performing a reaction at 10° C. to 150° C., preferably 40° C. to 100° C. for 1 hour to 48 hours, preferably 1 hour to 24 hours.

Third Step

A deprotecting reaction of amino protective group Compound B3 can be performed by the general method described in Protective Groups in Organic Synthesis, Theodora W Green (John Wiley & Sons) etc.

Fourth Step

Compound B6 can be obtained by adding a base such as n-butyl lithium, etc. to Compound B5 in a solvent such as THF, dioxane, dichloromethane, DMF etc., or in a mixed solvent thereof, and then adding haloformic acid alkyl and performing a reaction for 0.1 hours to 48 hours, preferably 1 hour to 24 hours.

Fifth Step

Compound B7 can be obtained by adding reducing agent such as Lithium diisobutylaluminum hydride, etc. to Compound B6 in a solvent such as THF, dioxane, dichloromethane, DMF etc., or in a mixed solvent thereof, and performing a reaction for 0.1 hours to 48 hours, preferably 1 hour to 24 hours.

Sixth Step

Compound B8 can be obtained by adding para-toluene sulfonic acid or methane sulfonic acid to Compound B7 in alcohol, and performing a reaction at 0° C. to 100° C. for 0.1 hours to 48 hours, preferably 1 hour to 24 hours.

Seventh Step

Compound B10 can be obtained by adding haloformic acid alkyl to Compound B9 in the presence or absence of a base such as pyridine, triethylamine, diisopropylethylamine, 1-methylimidazole, etc., in a solvent such as THF, dioxane, dichloromethane, DMF etc., or in a mixed solvent thereof, and performing a reaction at −40° C. to 40° C. for 0.1 hours to 48 hours, preferably 1 hour to 24 hours.

Eighth Step

Compound B8 can be obtained by immersing carbon electrode (anode) and platinum electrode (cathode) to Compound B10 in a solvent such as alcohol in the presence of a base such as potassium carbonate and tetraethylaminium perchlorate, and flushing with a constant current of 0.1~1.0 A with stirring for 0.1 hours to 48 hours, preferably 1 hour to 24 hours.

Ninth to Tenth Step

Compound (I) can be obtained from Compound B4 and B8 in the same manner as in the third to sixth steps in preparation 1.

The compounds used in the present invention have cap-dependent endonuclease inhibitory activity and are useful as therapeutic or preventive agents for influenza.

The compounds (parent compounds and/or prodrugs) used in the present invention are useful for symptoms and/or diseases which are induced by influenza virus. For example, they are useful for treating, preventing, and/or improving symptoms of, cold-like symptoms accompanying fever, chill, headache, muscular or joint pain, fatigue etc., airway inflammation symptoms such as sore throat, nasal secretion, nasal congestion, cough, sputum etc., gastrointestinal symptoms such as abdominal pain, vomitus, diarrhea etc. and, further, complications accompanying secondary infection such as acute encephalopathy and pneumonia. That is to say, the compounds used in the present invention are useful for treating and/or preventing influenza virus infectious diseases.

The compounds used in the present invention are effective for shortening time to alleviation of influenza symptoms. For example, they can shorten the time to alleviation of influenza symptoms about 20 to 40 hours, preferably about 25 to 30 hours. Specifically, they can shorten the times until "cough", "sore throat", "headache", "nasal congestion", "feverishness or chills", "muscular or joint pain", and "fatigue" are alleviated. In particular, they are useful for shortening the times until "nasal congestion", "muscular or joint pain", "fatigue", "feverishness or chills", and "headache" are alleviated. Further, they are useful for shortening the times until "nasal congestion" and "muscular or joint pain" are alleviated.

Furthermore, since the compounds (parent compounds and/or prodrugs) used in the present invention reduces the influenza virus in the body in a short period of time, it can be an excellent pharmaceutical useful for treating and/or preventing influenza virus infectious diseases. After the administration of the compounds used in the present invention, the effect of decreasing the influenza virus amount in the body is observed within 72 hours, preferably within 48 hours, more preferably within 24 hours, and it is expected an earlier therapeutic effect is obtained as compared with other drugs.

Moreover, the compounds used in the present invention have usefulness as medicines.

For example, since the compounds (prodrugs) used in the present invention have advantages that oral absorbability is high, good bioavailability is exhibited, good clearance is exhibited, and pulmonary transitivity is high, they can be excellent medicaments.

Since the compounds (parent compounds) used in the present invention have the effects such as high inhibitory activity on cap structure-dependent endonuclease, and high selectivity due to a virus-specific enzyme, they can be medicaments having reduced side effects.

Further, the compounds (parent compounds and/or prodrugs) used in the present invention also have advantages that metabolism stability is high, solubility is high, oral absorbability is high, good bioavailability is exhibited, good clearance is exhibited, pulmonary transitivity is high, a half life is long, a non-protein binding rate is high, hERG channel inhibition is low, CYP inhibition is low, CPE (CytoPathic Effect) inhibiting effect is recognized, and/or negative effects are exhibited in a phototoxicity test, an Ames test and a gene toxicity test, or toxicity such as liver damage is not caused. Therefore, the pharmaceutical composition of the present invention can be an excellent medicament.

The compounds (parent compounds and/or prodrugs) used in the present invention can be administered orally or parenterally. In the case of oral administration, the compounds used in the present invention can be also used as a normal preparation, for example, as any dosage form of solid preparations such as tablets, powders, granules, capsules etc.; solutions; oleaginous suspensions; or liquid preparations such as syrups or elixirs etc. In the case of parenteral administration, the compounds used in the present invention can be used as aqueous or oleaginous suspension injectables, or nose drops. Upon preparation of them, conventional excipients, binders, lubricants, aqueous solvents, oleaginous solvents, emulsifiers, suspending agents, preservatives, stabilizers etc. can be arbitrarily used. The pharmaceutical composition of the present invention can be produced by combining (for example, mixing) a therapeutically and/or prophylactically effective amount of the compound used in the present invention with pharmaceutically acceptable carriers or diluents. The compounds used in the present invention can be suitably used as oral preparations because of their high oral absorbability.

A dose of the compounds used in the present invention is different depending on an administration method, an age, a weight and the state of a patient, and a kind of a disease and, usually, in the case of oral administration, about 0.05 mg to 3000 mg, preferably about 0.1 mg to 1000 mg, more preferably about 10 mg to 80 mg, particularly preferably about 10 to 40 mg for adult per day may be administered, if necessary, in divided doses. In another embodiment, in the case of adults, about 40 mg or 80 mg may be administered in a single dose. In the case of children, about 5 to 40 mg may be administered in a single dose depending on the body weight. In addition, in the case of parenteral administration, about 0.01 mg to 1000 mg, preferably about 0.05 mg to 500 mg, or about 1 mg to 80 mg for adult per day is administered. The dose may be administered once daily or may be divided into multiple doses per day.

The compounds used in the present invention can be used in combination with other drugs or the like (hereinafter referred to as combination drugs) to increase the activity of the compounds, reduce the dose of the compounds, or the like. In the case of treating influenza, the compounds can be used combined with or in a coupled formulation with neuraminidase inhibitor (e.g., Oseltamivir, Zanamivir, Peramivir, Inabiru and the like); RNA-dependent. RNA polymerase inhibitor (e.g., Favipiravir); M2 protein inhibitor (e.g., Amantadine); PB2 Cap binding inhibitor (e.g., VX-787); anti-HA antibody (e.g., MHAA4549A); Immune agonists (e.g., Nitazoxanide) are also possible. In this case, the timing of administration for a compound used in the present invention and the combination drug is not limited. They can be administered to the subjects to be treated, at a time or at different times. Furthermore, the combination drug with a compound used in the present invention can be administered as two or more formulations independently comprising each active ingredient or a single formulation comprising each active ingredient.

The dose for combination drugs may be appropriately selected in reference to the clinical dose. The compounding ratio of the compounds used in the present invention and co-administered drugs may be appropriately selected depending on the subject to be treated, administration route, disease to be treated, symptoms, combination of the drugs and the like. For administration in humans, for example, 1 part by weight of the compounds used in the present invention may be used in combination with 0.01 to 100 parts by weight of co-administered drugs.

The present invention will be explained in more detail below by way of Examples, Intermediate Synthesis Examples, as well as Test Examples of the present invention, but the present invention is not limited to them.

The NMR analysis obtained in each example was carried out in 300 MHz, and was measured using DMSO-$d_6$, CDCl$_3$.

The term RT represents a retention time at LC/MS: liquid chromatography/mass spectrometry, and was measured under the following conditions.
(Measurement Conditions)
(1) Column: ACQUITY UPLC (Registered trademark) BEH C18 (1.7 µm i.d. 2.1×50 mm) (Waters)
  Flow rate: 0.8 mL/min
  UV detection wavelength: 254 nm
  Mobile phase: [A]: a 0.1% formic acid-containing aqueous solution, [B]: a 0.1% formic acid-containing acetonitrile solution
  Gradient: a linear gradient of 5% to 100% solvent [B] was carried out in 3.5 minutes, and 100% solvent [B] was kept for 0.5 minutes.
(2) Column: Shim-pack XR-ODS (2.2 µm, i.d. 50×3.0 mm) (Shimadzu)
  Flow rate: 1.6 mL/min
  UV detection wavelength: 254 nm
  Mobile phase: [A]: a 0.1% formic acid-containing aqueous solution, [B]: a 0.1% formic acid-containing acetonitrile solution
  Gradient: a linear gradient of 10% to 100% solvent [B] was carried out in 3 minutes, and 100% solvent [B] was kept for 0.5 minutes.
Measurement of Powder X-Ray Diffraction Pattern The powder X-ray diffraction of crystals obtained in each example was measured in accordance with X-ray powder diffraction method described in the General Tests, Processes and Apparatus of the Japanese Pharmacopoeia. Measurement conditions are shown below.
(Apparatus)
MinFlex 600 RINT-TTR III manufactured by Rigaku Corporation
(Operation Method)
Detector: High-speed 1-dimensional detector (D/Tec Ultra 2) and variable knife edge
Measurement method: Reflection method
Type of light source: Cu tube
Wavelength used: CuKα radiation
Tube current: 10 mA or 15 mA
Tube voltage: 30 Kv or 40 Kv
Sample plate: Aluminum or glass
X-ray incidence angle (θ): 3-40°, sampling width: 0.01° or
X-ray incidence angle (θ): 4-40°, sampling width: 0.02°

In general, the diffraction angle (2θ) in powder X-ray diffraction may have a margin of error within the range of ±0.2°, and therefore the value of the diffraction angle also encompasses about ±0.2° range of the numerical value. Accordingly, the present invention encompasses not only a crystal, the peak diffraction angles of which in powder X-ray diffraction completely match, but also a crystal, the peak diffraction angles of which match within a margin of error of about ±0.2°.

Example 1-1: Method for Producing Compound i1

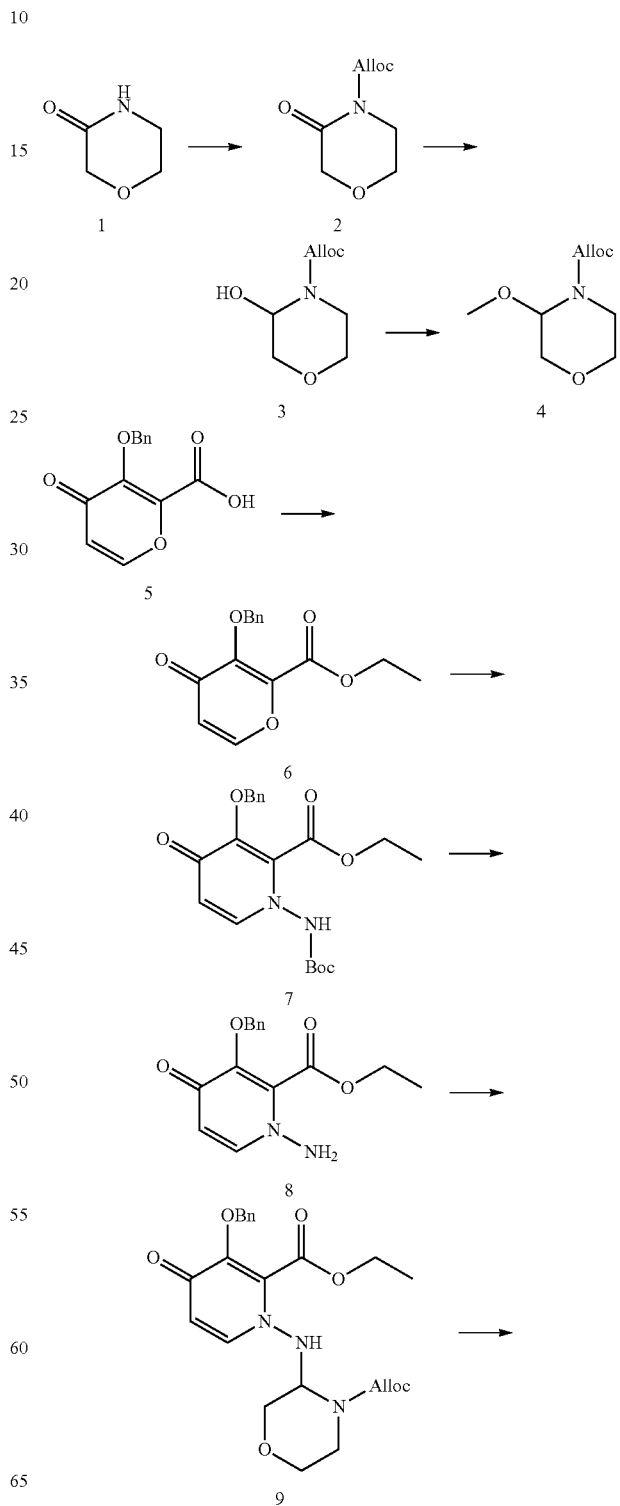

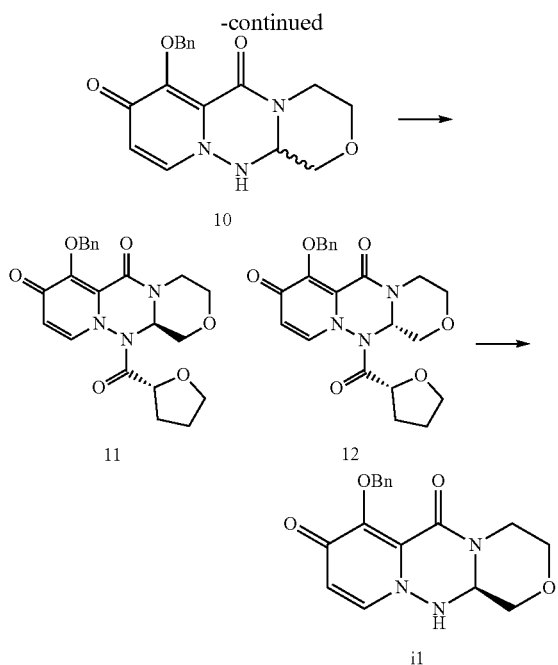

First Step

To a solution of Compound 1 (5.0 g, 49.5 mmol) in THF (100 mL) was added dropwise 1.62 mol/L n-butyllithium in hexane (90.5 mL, 49.5 mmol) at −78° C. under a nitrogen atmosphere, and the mixture was stirred at −78° C. for 2 hours. A solution of chloroformate allyl (5.96 g, 49.5 mmol) in THF (20 mL) was added dropwise thereto, and the mixture was stirred at −78° C. for 2 hours. The mixture was quenched with a saturated aqueous solution of ammonium chloride, warmed up to room temperature, and extracted with ethyl acetate. The obtained organic layer was washed with brine, dried over anhydrous magnesium sulfate, and concentrated under reduced pressure to obtain Compound 2 (5.66 g, 62%).

1H-NMR (CDCl3) δ:3.83 (t, J=8.0 Hz, 2H), 3.92 (t, J=8.0 Hz, 2H), 4.26 (s, 2H), 4.78 (d, J=8.0 Hz, 2H), 5.30 (d, J=12.0 Hz, 1H), 5.44 (d, J=16.0 Hz, 1H), 5.93-6.03 (m, 1H),

Second Step

To a solution of Compound 2 (6.6 g, 35.6 mmol) in THF (66 mL) was added dropwise 1.03 mol/L DIBAL-H in hexane (45.0 mL, 46.3 mmol), and the mixture was stirred at −78° C. for 1 hour. The mixture was quenched with acetone, an aqueous solution of Rochelle salt was added thereto. The mixture was stirred, and extracted with ethyl acetate. The obtained organic layer was washed with brine, dried over anhydrous magnesium sulfate, and concentrated under reduced pressure to obtain Compound 3 (6.21 g, 93%).

1H-NMR (CDCl3) δ: 3.44 (br, 1H), 3.50-3.64 (m, 2H), 3.71 (br, 1H), 3.95 (d, J=8.0 Hz, 2H), 4.64 (d, J=8.0 Hz, 2H), 5.24 (d, J=12.0 Hz, 1H), 5.40 (d, J=16.0 Hz, 1H), 5.47 (d, J=4 Hz, 1H), 5.87-6.00 (m, 1H)

Third Step

To a solution of Compound 3 (6.2 g, 33.1 mmol) in methanol (65 mL) was added p-Toluenesulfonic acid monohydrate (0.63 g, 3.31 mmol), and the mixture was stirred at room temperature over night. The mixture was quenched with an aqueous solution of sodium hydrogen carbonate, concentrated, and extracted with ethyl acetate. The obtained organic layer was washed with brine, dried over anhydrous magnesium sulfate, and concentrated under reduced pressure to obtain Compound 4 (5.77 g, 87%).

1H-NMR (CDCl3) δ:3.34 (s, 3H), 3.55 (br, 2H), 3.73-3.99 (m, 3H), 4.64 (d, J=8.0 Hz, 2H), 5.10-5.20 (m, 1H), 5.25 (d, J=8.0 Hz, 1H), 5.33 (d, J=16 Hz, 1H), 5.88-6.05 (m, 1H)

Fourth Step

To a solution of Compound 5 (20.0 g, 81 mmol) in DMF (100 mL) were added ethyl iodide (22.8 g, 146 mmol) and diazabicycloundecene (18.4 mL, 122 mmol), and the mixture was stirred at room temperature over night. The mixture was poured into 10% aqueous solution of ammonium chloride, and extracted with ethyl acetate. The obtained organic layer was washed with brine, dried over anhydrous magnesium sulfate, and concentrated under reduced pressure to obtain Compound 6 (22.3 g, 100%).

1H-NMR (CDCl3) δ: 1.23 (t, J=8.0 Hz, 3H), 4.28 (q, J=8.0 Hz, 2H), 5.16 (s, 2H), 6.57 (d, J=4.0 Hz, 1H), 7.28-7.48 (m, 5H), 8.21 (d, J=4.0 Hz, 1H).

Fifth Step

To a solution of Compound 6 (500 mg, 1.82 mmol) in DMA (5.0 mL) were added pyridinium p-toluenesulfonate (1.37 g, 5.47 mmol) and Boc-hydrazine (361 mg, 2.74 mmol), and the mixture was stirred at 60° C. for 14 hours. To the mixture was added water and the mixture was extracted with ethyl acetate. The obtained organic layer was washed with a saturated aqueous solution of ammonium chloride and brine, dried over anhydrous magnesium sulfate, and concentrated under reduced pressure. The obtained residue was purified by silica gel column chromatography (chloroform-methanol) to obtain Compound 7 (519 mg, 73%).

1H-NMR (CDCl3) δ:1.24 (t, J=8.0 Hz, 3H), 1.46 (s, 9H), 4.26 (q, J=8.0 Hz, 2H), 5.28 (s, 2H), 6.40 (d, J=8.0 Hz, 1H), 7.27-7.38 (m, 4H), 7.40-7.45 (m, 2H).

Sixth Step

Compound 7 (500 mg, 1.29 mmol) was dissolved in 4 mol/L hydrogen chloride in ethyl acetate (5 mL), and the mixture was stirred at room temperature for 1 hour. The mixture was concentrated under reduced pressure. To the obtained residue was added a saturated aqueous solution of sodium hydrogen carbonate, and the mixture was extracted with dichloromethane. The obtained organic layer was washed with brine, dried over anhydrous magnesium sulfate, and concentrated under reduced pressure to obtain Compound 8 (369 mg, 99%).

1H-NMR (CDCl3) δ: 1.26 (t, J=8.0 Hz, 3H), 4.31 (q, J=8.0 Hz, 2H), 5.24 (s, 2H), 6.47 (d, J=8.0, 1H), 7.28-7.44 (m, 5H), 7.64 (d, J=8.0, 1H).

Seventh Step

To a solution of Compound 8 (365 mg, 1.27 mmol) and Compound 4 (306 mg, 1.52 mmol) in acetonitrile (8 mL) was added dropwise tin chloride (0.223 mL, 1.90 mmol) at −25° C. under a nitrogen atmosphere, and the mixture was stirred at −25° C. for 45 minutes. The mixture was quenched with a saturated aqueous solution of sodium hydrogen carbonate, and dichloromethane was added thereto. The mixture was stirred at room temperature and filtered through Celite, and filtrate was extracted with dichloromethane. The obtained organic layer was washed with brine, dried over anhydrous magnesium sulfate, and concentrated under reduced pressure to obtain crude Compound 9. The obtained Compound 9 was dissolved in THF (8 mL), morpholine (1.10 mL, 12.7 mmol) and tetrakistriphenylphosphinepalladium (146 mg, 0.127 mmol) were added thereto, and the mixture was stirred at room temperature for 2 hours. To the mixture was added diethyl ether (16 mL), and the precipitated solid was filtered and dried to obtain Compound 10

(418 mg, 100%). 1H-NMR (CDCl3) δ: 2.90-2.99 (m, 1H), 3.13 (t, J=12.0 Hz, 1H), 3.40-3.46 (m, 1H), 4.00-4.08 (m, 1H), 4.14 (d, J=12.0 Hz, 1H), 5.07 (s, 2H), 6.22 (d, J=8.0 Hz, 1H), 7.29-7.40 (m, 3H), 7.56 (d, J=8.0 Hz, 2H), 7.71 (d, J=8.0 Hz, 1H)

Eighth Step

To a suspension of (R)-2-Tetrahydrofurioic Acid (855 mg, 7.36 mmol) and Compound 10 (2.00 g, 6.11 mmol) in ethyl acetate (9 ml) were added pyridine (4.00 ml, 49.6 mmol) and T3P (50% in ethyl acetate, 11.0 ml, 18.5 mmol) at room temperature, and the mixture was stirred over night. The precipitated solid was filtered and washed with ethyl acetate (4 ml) and ethanol (4 ml). The obtained solid was suspended in ethanol (6 ml) and the suspension was stirred at room temperature for 6.5 hours. The suspension was filtered and the obtained solid was washed with ethanol (2 ml) twice to obtain Compound 11 (1.18 g, 45.4%).

$^1$H-NMR (DMSO) δ: 1.80-1.94 (m, 2H), 1.95-2.14 (m, 2H), 3.21-3.35-(m, 2H), 3.50-3.60 (m, 1H), 3.70-3.82 (m, 3H), 4.00-4.05 (m, 1H), 4.32-4.38 (m, 1H), 5.14 (dd, J=10.8 Hz, 21.6 Hz, 2H), 5.76-5.81 (m, 1H), 6.29 (d; J=4.8 Hz, 1H), 7.28-7.39 (m, 3H), 7.48-7.54 (m, 2H), 7.64-7.75 (m, 1H)

Ninth Step

To a suspension of Compound 11 (500 mg, 1.18 mmol) in ethanol (3.5 ml) was added DBU (0.0035 ml, 0.023 mmol) at room temperature, and the mixture was stirred for 30 minutes. To the obtained suspension was added diisopropylether (6.5 ml), and the mixture was stirred at room temperature for 30 minutes. The precipitated solid was filtered and washed with ethyl acetate (1.5 ml) twice to obtain Compound i1 (346 mg, 89.9%).

$^1$H-NMR (DMSO) δ: 2.80-3.00 (m, 1H), 3.10-3.18 (m, 1H), 3.38-3.50 (m, 1H), 3.98-4.08 (m, 2H), 4.10-4.20 (m, 1H), 4.76-4.84 (m, 1H), 5.04-5.14 (m, 2H), 6.22 (m, J=7.6 Hz, 1H), 7.27-7.40 (m, 4H), 7.56-7.60 (m, 2H), 7.70 (d, J=7.6 Hz, 1H)

Example 1-2: Method for Producing Compound i2

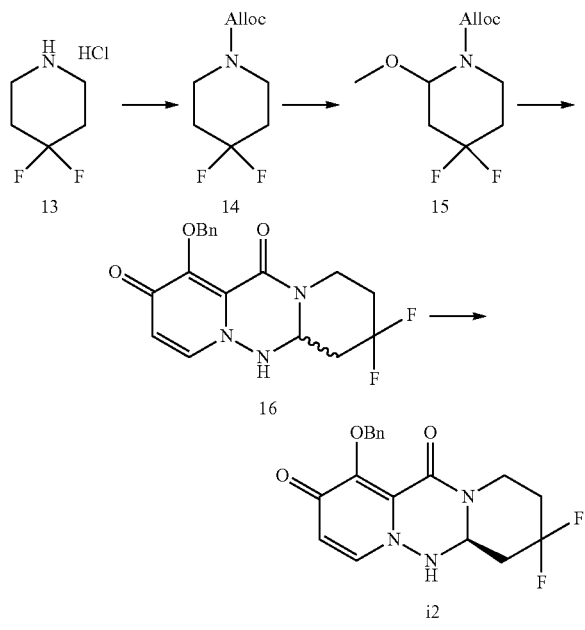

First Step

To a suspension of Compound 13 (8.0 g, 50.8 mmol) in dichloromethane (120 mL) was added triethylamine (17.6 mL, 127 mmol) under ice-water bath, and allyl chloroformate (6.44 mL, 60.9 mmol) was added dropwise thereto, and the mixture was stirred at 0° C. for 1 hour. To the mixture was added water, and the mixture was extracted with dichloromethane. The obtained organic layer was washed with 5% aqueous solution of citric acid and a saturated aqueous solution of sodium hydrogen carbonate, dried over anhydrous magnesium sulfate, and concentrated under reduced pressure to obtain Compound 14 (10.1 g, 97%).

1H-NMR (CDCl3) δ: 1.96 (br, 4H), 3.62 (s, 4H), 4.60 (s, 2H), 5.22 (d, J=12.0 Hz, 1H), 6.30 (d, J=16.0 Hz, 1H), 5.86-5.99 (m, 1H)

Second Step

To a solution of Compound 14 (0.9 g, 4.39 mmol), potassium carbonate (60 mg, 0.44 mmol) and tetraethylammonium perchlorate (50 mg, 0.22 mmol) in methanol (30 mL) were immersed carbon electrode (anode) and platinum electrode (cathode), and the mixture was flushed with a constant current of 0.1 A with stirring at room temperature for 6 hours. To the mixture were added ethyl acetate and water, and the mixture was extracted with ethyl acetate. The obtained organic layer was dried over anhydrous magnesium sulfate, and concentrated under reduced pressure to obtain Compound 15 (992 mg, 96%).

1H-NMR (CDCl3) δ: 1.81-2.15 (m, 3H), 2.39 (t, J=12.0 Hz, 1H), 3.27 (s, 3H), 3.61 (s, 1H), 4.11 (br, 1H), 4.61 (br, 2H), 5.20-5.36 (m, 2H), 5.57 (br, 1H), 5.88-5.99 (m, 1H)

Third Step

Compound 16 was obtained in the same manner as in the seventh and eighth steps in example 1-1.

Fourth Step

The optical resolution of Compound 16 (870 mg, 2.41 mmol) by Waters SFC30 System (Daicel CHIRALPAK IB, liquefied carbon dioxide-methanol) gave Compound i2 (270 mg, 31%).

Analysis Condition

<Waters SFC30 System>

Column: CHIRALPAK IB/SFC (5 μm, i.d. 250×4.6 mm) (DAICEL)

Flow rate: 8.0 mL/min; UV detection wavelength: 254 nm

Back pressure: 100 bar

Mobile phase: [A]: liquefied carbon dioxide, [B]: methanol

Gradient: 5% solvent [B] was kept for 1 minute, a linear gradient of 5% to 40% solvent [B] was carried out in 6 minutes, 40% solvent [B] was kept for 2 minutes, and 5% solvent [B] was kept for 1 minute.

Elution time: 7.3 minutes

Example 1-3: Method for Producing Compound i3

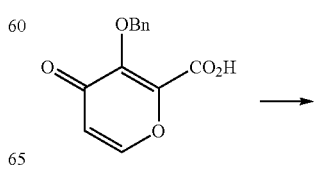

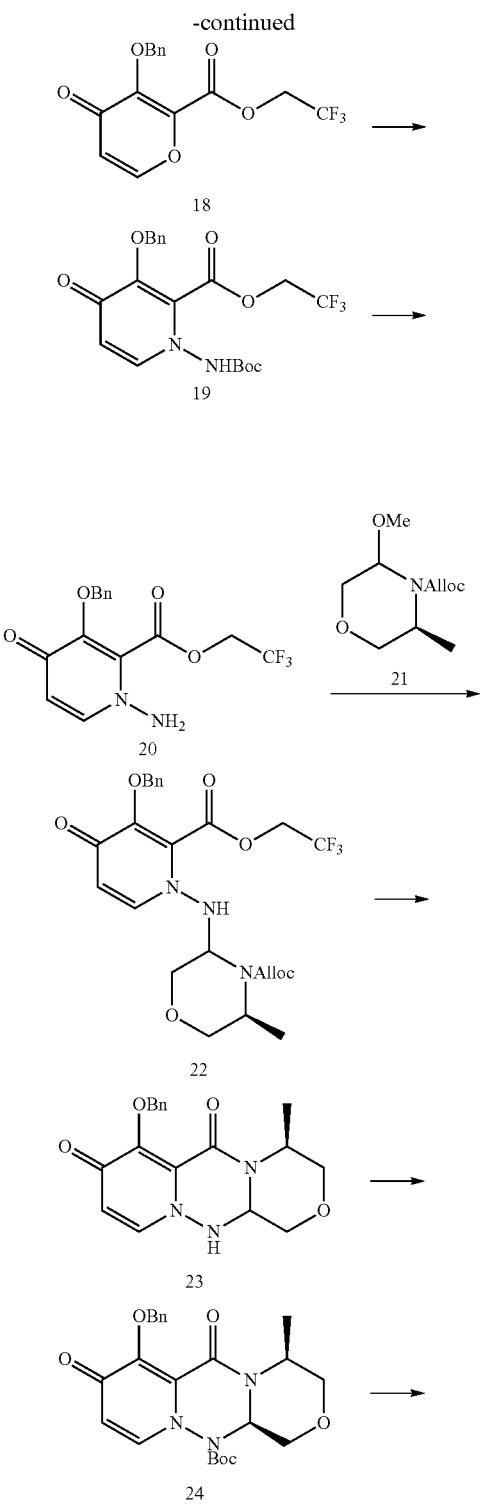

First Step

To a solution of Compound 17 (4.00 g, 16.3 mmol) in dichloromethane (40 mL) were added oxalyl dichloride (1.56 mL, 17.9 mmol) and DMF (0.013 mL, 0.162 mmol) under iced-bath, and the mixture was warmed up to room temperature and stirred for 5 hours. The mixture was concentrated under reduced pressure, and the obtained residue was dissolved in dichloromethane (40 mL), 2,2,2-trifluoroethanol (2.44 g, 24.4 mmol), triethylamine (4.50 mL, 32.5 mmol) and 4-(dimethylamino)pyridine (99.0 mg, 0.812 mmol) were added thereto under iced-bath, and the mixture was warmed up to room temperature and stirred for 1 hour. The mixture was concentrated under reduced pressure and to the obtained residue was added 1 mol/L aqueous solution of hydrochloric acid, and the mixture was extracted with ethyl acetate. The obtained organic layer was washed with 1 mol/L aqueous solution of hydrochloric acid and brine, dried over anhydrous magnesium sulfate to obtain Compound 18 (5.33 g, 100%).

1H-NMR (CDCl3) δ: 4.64 (q, J=8.2 Hz, 2H), 5.38 (s, 2H), 6.49 (d, J=5.6 Hz, 1H), 7.30-7.38 (m, 3H), 7.43-7.49 (m, 2H), 7.75 (d, J=5.6 Hz, 1H).

Second and Third Steps

Compound 20 was obtained in the same manner as in the fifth and sixth steps in example 1-1.

1H-NMR (CDCl3) δ: 4.55 (q, J=8.3 Hz, 2H), 5.18 (s, 2H), 5.29 (s, 2H), 6.37 (d, J=7.8 Hz, 1H), 7.30-7.42 (m, 6H).

Fourth and Fifth Steps

Compound 23 was obtained in the same manner as in the seventh step in example 1-1.

LC/MS (ESI): m/z=342.1 [M+H]+, RT=1.00, 1.09 min, method (1)

Sixth Step

To a solution of Compound 23 (820 mg, 2.40 mmol) in dichloromethane (16.5 mL) were added Boc$_2$O (0.837 mL, 3.60 mmol), triethylamine (0.499 mL, 3.60 mmol) and 4-(dimethylamino)pyridine (44.0 mg, 0.360 mmol), and the mixture was stirred at room temperature for 3.5 hours. To the mixture was added 1 mol/L aqueous solution of hydrochloric acid and the mixture was extracted with ethyl acetate. The obtained organic layer was washed with 1 mol/L aqueous solution of hydrochloric acid and brine, dried over anhydrous sodium sulfate, and concentrated under reduced pressure. The obtained residue was purified by silica gel column chromatography (chloroform-methanol) to obtain Compound 24 (593 mg, 56%) and Compound i3 (170 mg, 16%).

Compound 24: LC/MS (ESI): m/z=441.9 [M+H]+, RT=1.67 min, method (1)

Seventh Step

Compound 24 (547 mg, 1.24 mmol) was dissolved in acetic acid (5.5 mL) and the mixture was stirred at 80° C. for 5 hours. The mixture was concentrated under reduced pressure and the obtained residue was purified by silica gel column chromatography (chloroform-methanol) to obtain Compound i3 (454 mg, 100%). 1H-NMR (CDCl3) δ: 1.46 (d, J=6.4 Hz, 3H), 3.45 (dd, J=10.5, 10.5 Hz, 1H), 3.55 (dd, J=11.7, 4.3 Hz, 1H), 3.92 (dd, J=11.7, 3.6 Hz, 1H), 3.95-4.01 (m, 2H), 4.76 (dq, J=13.9, 4.3 Hz, 1H), 5.19 (d, J=10.2 Hz, 1H), 5.22 (d, J=10.2 Hz, 1H), 5.36 (d, J=12.9 Hz, 1H), 6.28 (d, J=7.8 Hz, 1H), 7.25 (d, J=7.8 Hz, 1H), 7.28-7.36 (m, 3H), 7.56-7.61 (m, 2H).

Example 1-4: Method for Producing Compound III-2

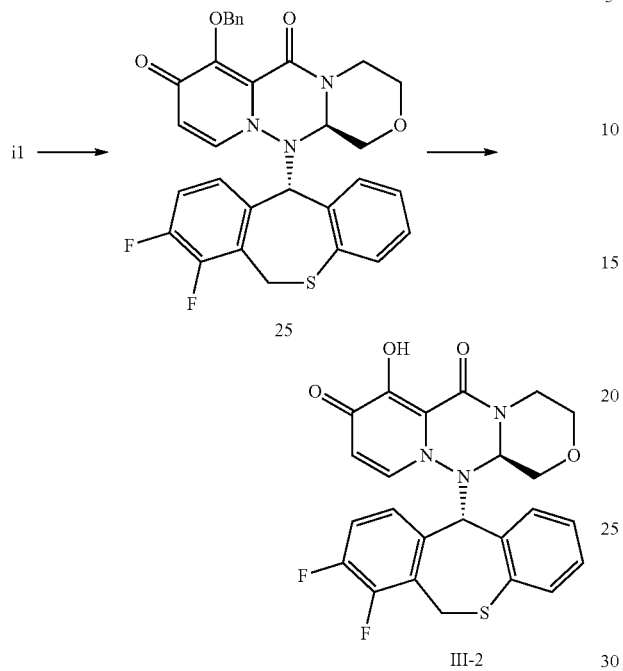

First Step

Compound i1 (1100 g, 3360 mmol) and 7,8-difluoro-6,11-dihydrodibenzothiepine-11-ol (977 g, 3697 mmol) were suspended in 50 wt % T3P in ethyl acetate (3208 g, 5041 mmol) and ethyl acetate (1.1 L). To the mixture was added methanesulfonic acid (436 ml, 6721 mmol) at room temperature and the mixture was stirred at 70° C. for 5.5 hours. To the mixture was added water under ice-water bath and the mixture was stirred at room temperature for 1 hour. THF was added thereto and the mixture was extracted with ethyl acetate. The obtained organic layer was washed with water and 8% aqueous solution of sodium hydrogen carbonate, dried over anhydrous sodium sulfate, and concentrated under reduced pressure. The obtained residue was dissolved in THF (5.5 L) and potassium carbonate (790 g, 5713 mmol) was added thereto. The mixture was warmed up to 50° C., benzyl bromide (240 ml, 2016 mmol) was added dropwise thereto, and the mixture was stirred al 60° C. for 8.5 hours. To the mixture was added dropwise 2 mol/L aqueous solution of hydrochloric acid under ice-water bath, and the mixture was stirred at room temperature for 10 minutes and extracted with ethyl acetate. The obtained organic layer was washed with water and 8% aqueous solution of sodium hydrogen carbonate and dried over anhydrous magnesium sulfate. An activated carbon (Norit SX-2, 240 g) was added thereto, the mixture was filtered through Celite, and the filtrate was concentrated under reduced pressure. To the obtained residue was added ethyl acetate and hexane and the precipitated solid was filtered to obtain Compound 25 (1019 g, 1776 mmol, 53%).

$^1$H-NMR (CDCl$_3$) δ: 2.88 (1H, t, J=11.2 Hz), 3.28-3.39 (2H, m), 3.72 (1H, d, J=12.6 Hz), 3.86 (1H, d, J=9.6 Hz), 4.03 (1H, d, J=13.9 Hz), 4.45 (1H, d, J=8.6 Hz), 4.67 (1H, d, J=13.1 Hz), 5.19-5.26 (2H, m), 5.45 (1H, d, J=10.9 Hz), 5.63 (1H, d, J=10.9 Hz), 5.77 (1H, d, J=7.6 Hz), 6.40 (1H, d, J=7.8 Hz), 6.68 (1H, t, J=6.9 Hz), 6.94-7.01 (2H, m), 7.03-7.12 (3H, m), 7.29-7.38 (3H, m), 7.61 (2H, d, J=7.1 Hz).

Second Step

To a solution of Compound 25 (1200 g, 2092 mmol) in DMA (3.6 L) was added lithium chloride (443 g, 10.5 mol) at room temperature, and the mixture was stirred at 80° C. for 3 hours. To the mixture were added acetone (1.2 L), 0.5 mol/L aqueous solution of hydrochloric acid (6.0 L) and water (2.4 L) under ice-water bath, and the mixture was stirred for 1 hour. The precipitated solid was filtered. The obtained solid was dissolved in chloroform, isopropyl ether was added thereto, and the precipitated solid was filtered to obtain Compound III-2 (950 g, 1965 mmol, 94%).

$^1$H-NMR (CDCl$_3$) δ: 2.99 (1H, dt, J=17.5, 6.8 Hz), 3.47 (1H, td, J=11.9, 2.5 Hz), 3.60 (1H, t, J=10.6 Hz), 3.81 (1H, dd, J=11.9, 3.3 Hz), 3.96 (1H, dd, J=11.0, 2.9 Hz), 4.07 (1H, d, J=13.8 Hz), 4.58 (1H, dd, J=10.0, 2.9 Hz), 4.67 (1H, dd, J=13.5, 1.9 Hz), 5.26-5.30 (2H, m), 5.75 (1H, d, J=7.8 Hz), 6.69 (1H, d, J=7.7 Hz), 6.83-6.87 (1H, m). 6.99-7.04 (2H, m). 7.07-7.15 (3H, m).

Example 2: Method for Producing Compound III-42

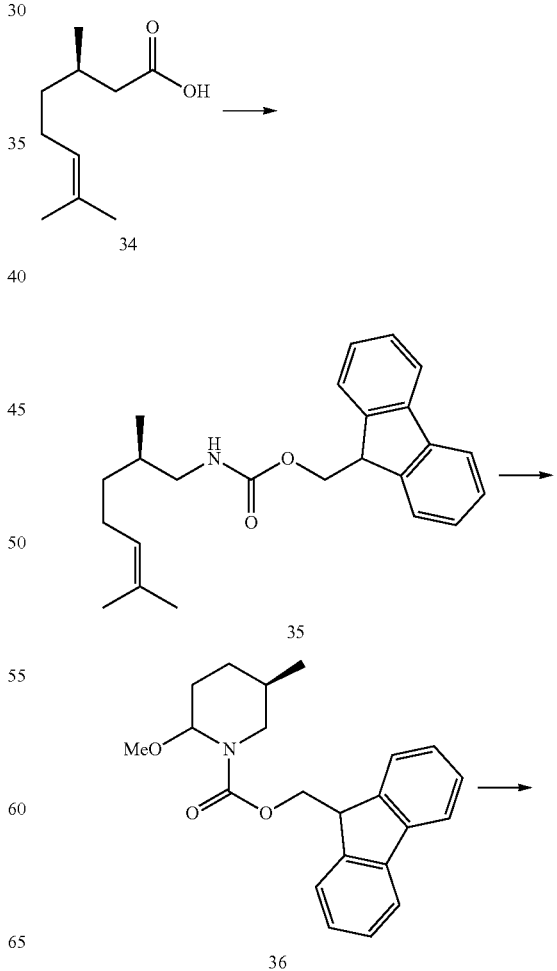

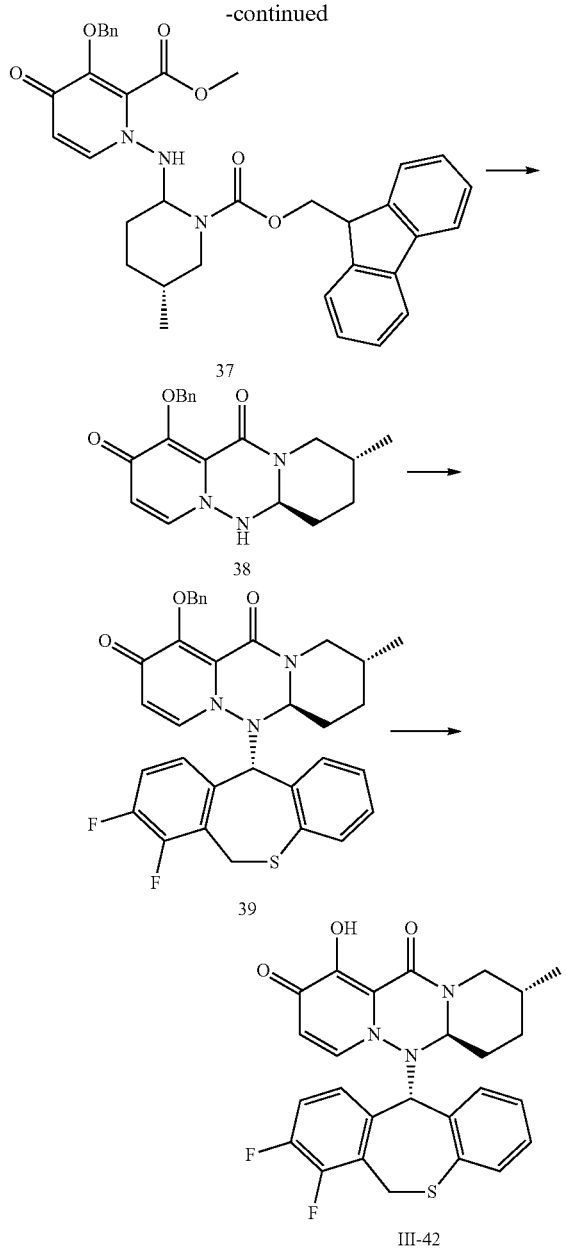

First Step

Compound 34 (947 mg, 5.56 mmol) was dissolved in toluene (8 ml), triethylamine (0.848 ml, 6.12 mmol) was added thereto, and the mixture was stirred at room temperature for 30 minutes. Diphenylphosphonoazide (1.32 ml, 6.12 mmol) was added thereto, the mixture was stirred at 80° C. for 1 hour, (9H-fluoren-9-yl) methanol (5.46 g, 27.8 mmol) was added thereto, and the mixture was heated to reflux at 120° C. for 1 hour. The mixture was cooled to room temperature, and a saturated aqueous solution of sodium hydrogen carbonate was added thereto to stop the reaction. The reaction solution was extracted with ethyl acetate, and the obtained organic layer was washed with brine, dried over anhydrous sodium sulfate, and concentrated under reduced pressure. The obtained residue was purified by silica gel column chromatography (ethyl acetate-hexane) to obtain Compound 35 (1.5 g, 74%).

1H-NMR (CDCl3) δ:7.77 (2H, d, J=7.3 Hz), 7.60 (2H, d, J=7.3 Hz), 7.41-7.39 (2H, m), 7.32-7.30 (2H, m), 5.10-5.07 (1H, m), 4.75 (1H, brs), 4.41 (2H, d, J=6.6 Hz), 4.22 (1H, t, J=6.6 Hz), 3.15-3.12 (1H, m), 3.04-3.01 (1H, m), 2.04-1.96 (2H, m), 1.68 (3H, s), 1.62 (3H, s), 1.39-1.37 (1H, m), 1.17-1.16 (1H, m), 0.90 (3H, d, J=6.6 Hz), 0.87-0.83 (1H, m)

Second Step

Compound 35 (204 mg, 0.561 mmol) was dissolved in a mixed solution of dioxane (3 ml) and water (1.5 ml), then potassium osmate(VI) dihydrate (10.3 mg, 0.028 mmol) and sodium periodate (360 mg, 1.68 mmol) were added thereto, and the mixture was stirred at room temperature overnight. The reaction was stopped with a 10% aqueous solution of sodium thiosulphate, the reaction solution was extracted with ethyl acetate, and the obtained organic layer was washed with brine, dried over anhydrous sodium sulfate, and concentrated under reduced pressure to obtain a crude product. The crude product was dissolved in methanol (4 ml), tosic acid monohydrate (13.8 mg, 0.072 mmol) was added thereto, and the mixture was stirred at room temperature for 2 hours. The reaction was stopped by adding a saturated aqueous solution of sodium hydrogen carbonate, the reaction solution was extracted with ethyl acetate, and the obtained organic layer was washed with brine, dried over anhydrous sodium sulfate, and concentrated under reduced pressure. The obtained residue was purified by silica gel column chromatography (hexane-ethyl acetate) to obtain a diastereomeric mixture of Compound 36 (115 mg, 58%).

1H-NMR (CDCl3) δ:7.80-7.73 (2H, m), 7.60-7.54 (2H, m), 7.45-7.28 (4H, m), 5.36 (0.5H, s), 4.95 (0.5H, s), 4.62-4.55 (1H, m), 4.48 (1H, d, J=6.6 Hz), 4.30-4.20 (1H, m), 3.90-3.82 (0.5H, m), 3.74-3.65 (m, 0.5H), 3.20 (1.5H, s), 2.90 (1.5H, s), 2.57 (0.5H, t, J=11.4 Hz), 2.47 (0.5H, t, J=11.4 Hz), 1.90-1.70 (1H, m), 1.60-1.30 (2.5H, m), 0.93-0.80 (3.5H, m)

Third Step

Compound 36 (115 mg, 0.33 mmol) and methyl 1-amino-3-(benzyloxy)-4-oxo-1,4-dihydropyridine-2-carboxylate (50 mg, 0.182 mmol) were dissolved in acetonitrile (3 ml), and the mixture was cooled to −30° C. Tin tetrachloride (0.032 ml, 0.27 mmol) was added thereto, and the mixture was stirred for 4 hours. Saturated sodium hydrogen carbonate was added to the reaction solution, and the reaction solution was extracted with methylene chloride. The obtained organic layer was washed with a saturated aqueous solution of sodium chloride, dried over sodium sulfate, filtered, and concentrated under reduced pressure. The obtained residue was purified by silica gel column chromatography (chloroform-methanol) to obtain a diastereomeric mixture of Compound 37 (115 mg, 59%).

LC/MS (ESI): m/z=595 [M+H]+, RT=2.49, 2.63 min, method (1)

Fourth Step

Compound 37 (20.5 g, 34.5 mmol) was dissolved in THF (400 ml), piperidine (68.4 ml, 691 mmol) was added thereto, and the mixture was stirred at room temperature for 2 hours. The reaction solution was diluted with diethyl ether (500 ml), and the produced precipitates were filtered to obtain a crude product.

The crude product was dissolved in ethanol (200 ml), DBU (5.06 ml, 33.6 mmol) was added thereto, and the mixture was stirred at 80° C. for 2 hours. The reaction solution was concentrated, and the obtained solids were recrystallized with THF to obtain Compound 38 (6.5 g, 57%).

LC/MS (ESI): m/z=340 [M+H]+, RT=1.29 min, method (1)

Fifth Step

Compound 38 (2.0 g, 5.89 mmol) and 7,8-difluoro-6,11-dihydrodibenzo[b,e]thiepin-11-ol (2.34 g, 8.84 mmol) were dissolved in a solution of T3P in ethyl acetate (18 mL), and the mixture was stirred in a sealed tube at 110° C. for 1.5 hours. The reaction was stopped by adding water, the reaction solution was extracted with ethyl acetate, and the obtained organic layer was washed with brine, dried over anhydrous sodium sulfate, and concentrated under reduced pressure. The obtained residue was recrystallized with chloroform-hexane to obtain Compound 39 (1.1 g, 32%).

LC/MS (ESI): m/z=586 [M+H]$^+$, RT=2.46 min, method (1)

Sixth Step

Compound 39 (1.1 g, 1.89 mmol) was dissolved in dimethylacetamide (10 ml), lithium chloride (398 mg, 9.39 mmol) was added thereto, and the mixture was stirred at 120° C. The reaction solution was diluted with ethyl acetate, and the obtained organic layer was washed with 2 mol/L hydrochloric acid, dried over anhydrous sodium sulfate, and concentrated under reduced pressure to obtain Compound III-42 (556 mg, 59.6%).

1H-NMR (CDCl3) δ: 7.15-7.03 (4H, m), 7.01-6.94 (1H, m), 6.86-6.82 (1H, m), 6.68 (1H, d, J=7.8 Hz), 5.78 (1H, d, J=7.6 Hz), 5.35 (1H, dd, J=13.8, 2.4 Hz), 5.22 (1H, s), 4.65-4.57 (1H, m), 4.25 (1H, dd, J=11.4, 2.5 Hz), 4.05 (1H, d, J=13.9 Hz), 2.18 (1H, t, J=12.4 Hz), 1.96 (1H, d, J=13.6 Hz), 1.87-1.57 (5H, m), 1.29-1.22 (2H, m), 0.91 (3H, d, J=6.6 Hz).

LC/MS (ESI): m/z=497 [M+H]$^+$, RT=2.16 min, method (1)

Example 3: Method for Producing Compound 42

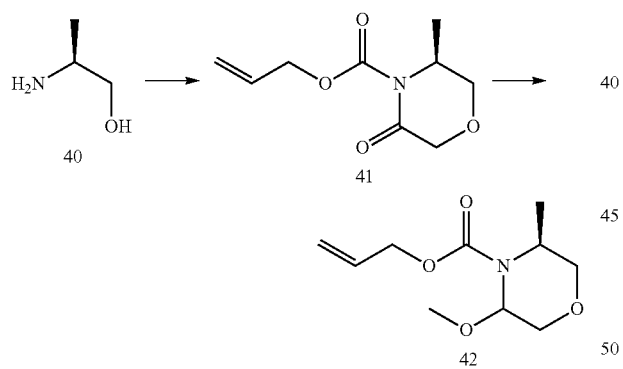

First Step

Compound 40 (1.00 g, 13.3 mmol) was dissolved in THF (100 mL), 60% sodium hydride (0.69 g, 14.7 mmol) was added thereto at room temperature, and the mixture was stirred under a nitrogen stream at room temperature for 30 minutes. Ethyl chloroacetate (1.4 mL, 13.3 mmol) was added thereto, and the mixture was stirred under a nitrogen stream at room temperature for 30 minutes and at 90° C. for 3 hours. After concentration under reduced pressure, THF (40 mL) was added to the residue, further, 60% sodium hydride (0.59 g, 14.7 mmol) was added thereto, and the mixture was stirred under a nitrogen stream at room temperature for 30 minutes. Allyl chloroformate was added dropwise thereto, and the mixture was stirred at room temperature for 3 hours. A saturated aqueous solution of ammonium chloride (30 mL) was added thereto, and the reaction solution was extracted with ethyl acetate (150 mL). The obtained organic layer was washed with water (50 mL) and brine (100 mL) and dried over anhydrous magnesium sulfate, and the obtained residue was purified by silica gel column chromatography (hexane-ethyl acetate) to obtain Compound 41 (0.96 g, 36%).

$^1$H-NMR (CDCl$_3$) δ: 1.42 (d, J=6.5 Hz, 3H), 3.77-3.89 (m, 2H), 4.19 (d, J=17.4 Hz, 1H), 4.27-4.36 (m, 2H), 4.74-4.83 (m, 2H), 5.31 (dd, J=10.4, 1.4 Hz, 1H), 5.46 (dd, J=17.2, 1.4 Hz, 1H), 5.98 (dddd, J=17.2, 10.4, 5.6, 5.6 Hz, 1H).

LC/MS (ESI): m/z=199.8 [M+H]$^+$, method (1)

Second Step

Compound 41 (2.69 g, 13.5 mmol) was dissolved in THF (30 mL) under a nitrogen atmosphere and cooled to −78° C. with dry ice-acetone. A 1.02 mol/L solution of DIBAL-H in hexane (17.2 mL, 17.6 mmol) was added dropwise thereto, and the mixture was stirred at −78° C. for 1 hour. An aqueous solution of Rochelle salt was added thereto, and the mixture was stirred, and extracted with ethyl acetate. The obtained organic layer was washed with brine, dried over anhydrous magnesium sulfate, and concentrated under reduced pressure. The obtained residue was dissolved in methanol (30 mL), p-toluenesulfonic acid monohydrate (0.244 g, 1.28 mmol) was added thereto, and the mixture was stirred at room temperature for 7 hours. The mixture was quenched with an aqueous solution of sodium hydrogen carbonate and extracted with ethyl acetate. The obtained organic layer was washed with brine, dried over anhydrous magnesium sulfate, and concentrated under reduced pressure. The residue was purified by silica gel column chromatography (ethyl acetate-hexane) to obtain Compound 42 (2.43 g, 88%).

$^1$H-NMR (CDCl$_3$) δ: 1.42 (d, J=7.0 Hz, 3H), 3.34 (s, 3H), 3.53 (dd, J=12.0, 2.3 Hz, 1H), 3.64 (dd, J=11.5, 3.8 Hz, 1H), 3.76 (d, J=11.4 Hz, 1H), 4.01 (d, J=12.0 Hz, 1H), 4.06-4.12 (m, 1H), 4.65 (d, J=5.4 Hz, 2H), 5.14 (br s, 1H), 5.24 (dd, J=10.4, 1.3 Hz, 2H), 5.33 (dd, J=17.3, 1.4 Hz, 2H), 5.95 (ddd, J=22.6, 10.7, 5.5 Hz, 1H).

Example 4: Method for Producing Compound 50

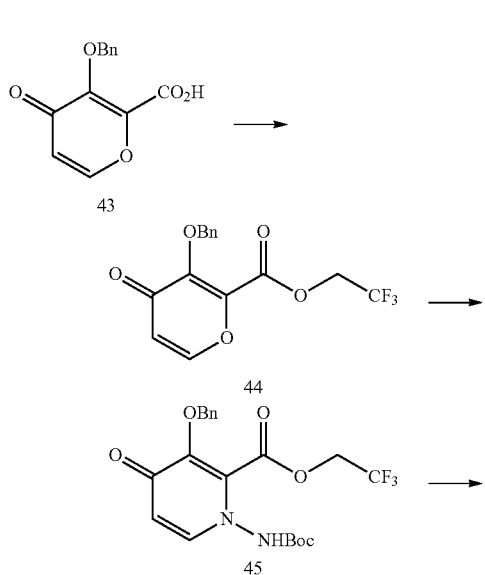

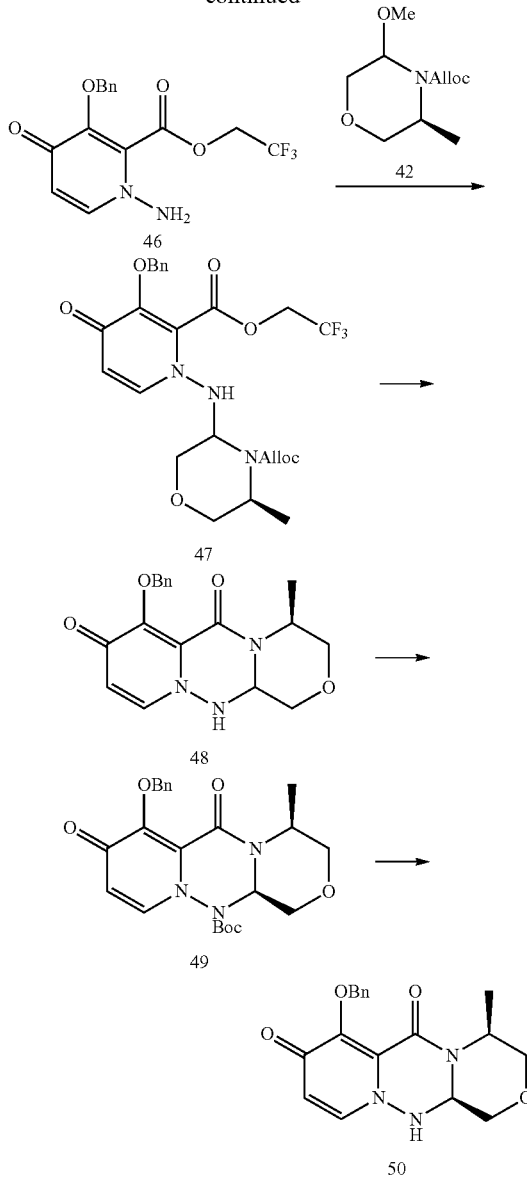

First Step

Compound 43 (4.00 g, 16.3 mmol) was dissolved in dichloromethane (40 mL), then oxalyl dichloride (1.56 mL, 17.9 mmol) and DMF (0.013 mL, 0.162 mmol) were added dropwise thereto under iced-bath, and the mixture was warmed up to room temperature and stirred for 5 hours. The mixture was concentrated under reduced pressure, and the obtained residue was dissolved in dichloromethane (40 mL), then 2,2,2-trifluoroethanol (2.44 g, 24.4 mmol), triethylamine (4.50 mL, 32.5 mmol) and 4-(dimethylamino)pyridine (99.0 mg, 0.812 mmol) were added thereto under iced-bath, and the mixture was warmed up to room temperature and stirred for 1 hour. The mixture was concentrated under reduced pressure, a 1 mol/L aqueous solution of hydrochloric acid (100 mL) was added to the obtained residue, and the mixture was extracted with ethyl acetate (200 mL). The obtained organic layer was washed with a 1 mol/L aqueous solution of hydrochloric acid (100 mL) and brine (100 mL), dried over anhydrous magnesium sulfate to obtain Compound 44 (5.33 g, 100%).

1H-NMR (CDCl3) δ: 4.64 (q, J=8.2 Hz, 2H), 5.38 (s, 2H), 6.49 (d, J=5.6 Hz, 1H), 7.30-7.38 (m, 3H), 7.43-7.49 (m, 2H), 7.75 (d, J=5.6 Hz, 1H).

Second Step

Compound 44 (5.33 g, 16.2 mmol) was dissolved in DMF (55 mL), then Boc hydrazine (1.93 g, 14.6 mmol) and PPTS (12.2 g, 0.162 mmol) were added thereto, and the mixture was stirred at 60° C. for 16 hours. Water (100 mL) was added to the reaction solution, and the reaction solution was extracted with ethyl acetate (300 mL). The obtained organic layer was washed with water (100 mL) and brine (100 mL), and dried over anhydrous sodium sulfate. The obtained organic layer was concentrated under reduced pressure, and the obtained residue was purified by silica gel column chromatography (hexane-ethyl acetate) to obtain Compound 45 (1.69 g, 22%).

1H-NMR (CDCl3) δ: 1.45 (s, 9H), 4.51 (q, J=8.2 Hz, 2H), 5.29 (s, 2H), 6.42 (d, J=7.9 Hz, 1H), 7.28-7.37 (m, 4H), 7.39-7.43 (m, 2H), 7.68 (brs, 1H).

Third Step

Compound 45 (1.59 g, 3.59 mmol) was dissolved in 4 mol/L hydrogen chloride in ethyl acetate (16 mL), and the mixture was stirred at room temperature for 1.5 hours. A saturated aqueous solution of sodium hydrogen carbonate (100 mL) was added to the reaction solution, and the reaction solution was extracted with dichloromethane (200 mL) and dried over anhydrous magnesium sulfate to obtain Compound 46 (1.18 g, 96%).

1H-NMR (CDCl3) δ: 4.55 (q, J=8.3 Hz, 2H), 5.18 (s, 2H), 5.29 (s, 2H), 6.37 (d, J=7.8 Hz, 1H), 7.30-7.42 (m, 6H).

Fourth Step

Compound 46 (1.18 g, 3.45 mmol) and Compound 42 (890 mg, 4.14 mmol) were dissolved in acetonitrile (24 mL), tin tetrachloride (0.607 mL, 5.17 mmol) was added dropwise thereto at −30° C., and the mixture was stirred at −30° C. for 1 hour. A saturated aqueous solution of sodium hydrogen carbonate (200 mL) and dichloromethane (200 mL) were added to the reaction solution, and unwanted matter was filtered off. The obtained organic layer was washed with brine (100 mL) and dried over anhydrous sodium sulfate. The obtained organic layer was concentrated under reduced pressure, and the obtained residue was purified by silica gel column chromatography (chloroform-methanol) to obtain Compound 47 (1.22 g, 67%). LC/MS (ESI): m/z=525.9 [M+H]+, RT=2.02 min, method (1)

Fifth Step

Compound 47 (1.15 g, 2.19 mmol) was dissolved in THF (23 mL), then morpholine (0.953 mL, 10.9 mmol) and tetrakistriphenylphosphinepalladium (126 mg, 0.109 mmol) were added thereto under nitrogen atmosphere, and the mixture was stirred at room temperature for 7.5 hours. The mixture was concentrated under reduced pressure, and the obtained residue was purified by silica gel column chromatography (chloroform-methanol) to obtain Compound 48 (890 mg, quant.).

LC/MS (ESI): m/z=342.1 [M+H]+, RT=1.00, 1.09 min, method (1)

Sixth Step

Compound 48 (820 mg, 2.40 mmol) was dissolved in dichloromethane (16.5 mL), then Boc2O (0.837 mL, 3.60 mmol), triethylamine (0.499 mL, 3.60 mmol) and 4-(dimethylamino)pyridine (44.0 mg, 0.360 mmol) were added thereto, and the mixture was stirred at room temperature for 3.5 hours. A 1 mol/L aqueous solution of hydrochloric acid (50 mL) was added to the reaction solution, and the mixture was extracted with ethyl acetate (125 mL). The obtained organic layer was washed with a 1 mol/L aqueous solution of hydrochloric acid (50 mL) and brine (50 mL), and dried over anhydrous sodium sulfate. The obtained organic layer was concentrated under reduced pressure, and the obtained residue was purified by silica gel column chromatography (chloroform-methanol) to obtain Compound 49 (593 mg, 56%) and Compound 50 (170 mg, 16%).

LC/MS (ESI): m/z=441.9 [M+H]$^+$, RT=1.67 min, method (1)

Seventh Step

Compound 49 (547 mg, 1.24 mmol) was dissolved in acetic acid (5.5 mL), and the mixture was stirred at 80° C. for 5 hours. The mixture was concentrated under reduced pressure, and the obtained residue was purified by silica gel column chromatography (chloroform-methanol) to obtain Compound 50 (454 mg, quant.).

1H-NMR (CDCl3) δ: 1.46 (d, J=6.4 Hz, 3H), 3.45 (dd, J=10.5, 10.5 Hz, 1H), 3.55 (dd, J=11.7, 4.3 Hz, 1H), 3.92 (dd, J=11.7, 3.6 Hz, 1H), 3.95-4.01 (m, 2H), 4.76 (dq, J=13.9, 4.3 Hz, 1H), 5.19 (d, J=10.2 Hz, 1H), 5.22 (d, J=10.2 Hz, 1H), 5.36 (d, J=12.9 Hz, 1H), 6.28 (d, J=7.8 Hz, 1H), 7.25 (d, J=7.8 Hz, 1H), 7.28-7.36 (m, 3H), 7.56-7.61 (m, 2H).

Example 5: Method for Producing Compound 55

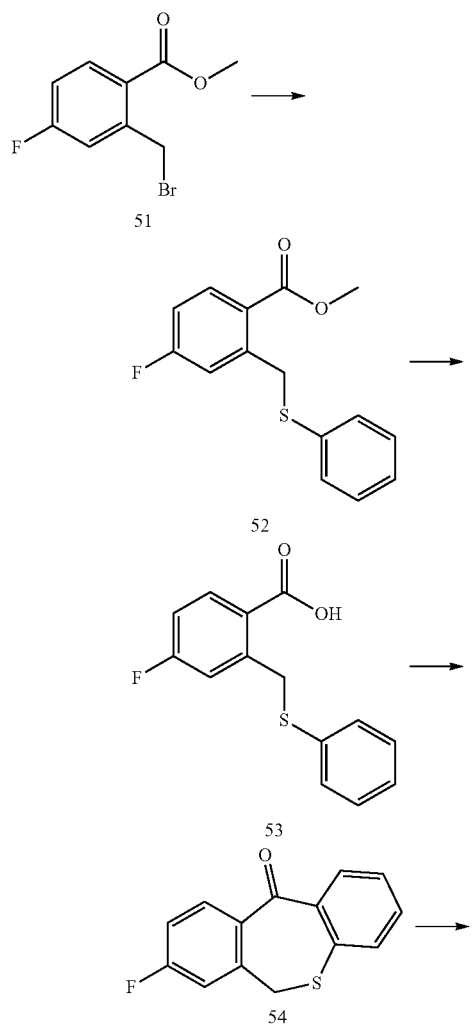

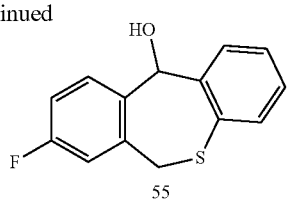

First Step

To a suspension of Compound 51 (19.2 g, 77.8 mmol) and potassium carbonate (16.13 g, 117 mmol) in acetone (190 mL) was added thiophenol (8.01 mL, 78 mmol), and the mixture was stirred at 40° C. for 1 hour. The reaction solution was cooled to 25° C. and ethyl acetate and water were added thereto. The mixture was extracted with ethyl acetate, and the obtained organic layer was washed twice with water and concentrated under reduced pressure to obtain Compound 52.

$^1$H-NMR (CDCl$_3$) δ: 3.93 (3H, s), 4.93 (2H, s), 7.03-7.07 (1H, m), 7.18-7.35 (6H, m), 7.93-8.06 (1H, m).

Second Step

To a solution of Compound 52 (21.5 g, 77.8 mmol) in methanol (60 mL) and THF (40 mL) was added dropwise 2 mol/L sodium hydroxide (97.0 mL, 195 mmol) under ice bath, and the reaction solution was left to stand still all night. The reaction solution was concentrated under reduced pressure and water was added thereto. The obtained aqueous layer was washed twice with hexane. The aqueous layer was made acidic with 6 mol/L hydrochloric acid and extracted twice with ethyl acetate. The obtained organic layer was dried with sodium sulfate and concentrated under reduced pressure. The obtained residue was crystallized with ethyl acetate/hexane to obtain Compound 53 as crystals (7.7 g).

$^1$H-NMR (CDCl$_3$) δ: 4.40 (2H, s), 6.81-6.84 (1H, m), 7.07-7.32 (6H, m), 7.86-7.90 (1H, m).

Third Step

To polyphosphoric acid (200 g, 29.4 mmol) was added Compound 53 (7.70 g, 29.4 mmol) at 60° C., and the reaction mixture was warmed up to 140° C. and stirred for 1 hour. The reaction solution was cooled to 40° C., and water was added thereto under iced-bath. The slurry was filtered, and the filtrate was washed with water. Ethyl acetate was added to the filtrate, and the obtained organic layer was washed with water and brine, dried over sodium sulfate, and concentrated under reduced pressure. The obtained residue was crystallized with ethyl acetate/hexane to obtain Compound 54 as crystals (3.6 g).

$^1$H-NMR (CDCl$_3$) δ: 4.03 (2H, s), 6.92-7.06 (2H, m), 7.26-7.40 (4H, m), 7.67 (1H, dd, J=5.5 Hz, J=8.0 Hz), 8.25 (1H, d, J=8.0 Hz).

Fourth Step

To a solution of Compound 54 (3.60 g, 14.7 mmol) in methanol (14 mL) and THF (28 mL) was added sodium hydrogen borate (613 mg, 16.2 mmol) under ice-bath. The reaction solution was stirred at room temperature for 30 minutes. Water was added thereto, and the reaction solution was left to stand still all night. The reaction solution was concentrated under reduced pressure, and ethyl acetate and water were added to the concentrate. The mixture was extracted. The obtained organic layer was washed with brine, dried over sodium sulfate, and concentrated under reduced pressure. The obtained residue was purified by silica gel column chromatography (methylene chloride) to obtain Compound 55 (1.7 g) as crystals.

¹H-NMR (CDCl₃) δ: 4.15 (1H, d, J=14.0 Hz), 4.57 (1H, d, J=14.0 Hz), 6.09 (1H, s), 6.91-6.93 (2H, m), 7.10-7.17 (3H, m), 7.39 (1H, dd, J=5.5 Hz, J=8.0 Hz), 7.48 (1H, d, J=8.0 Hz).

Example 6: Method for Producing Compound III-30

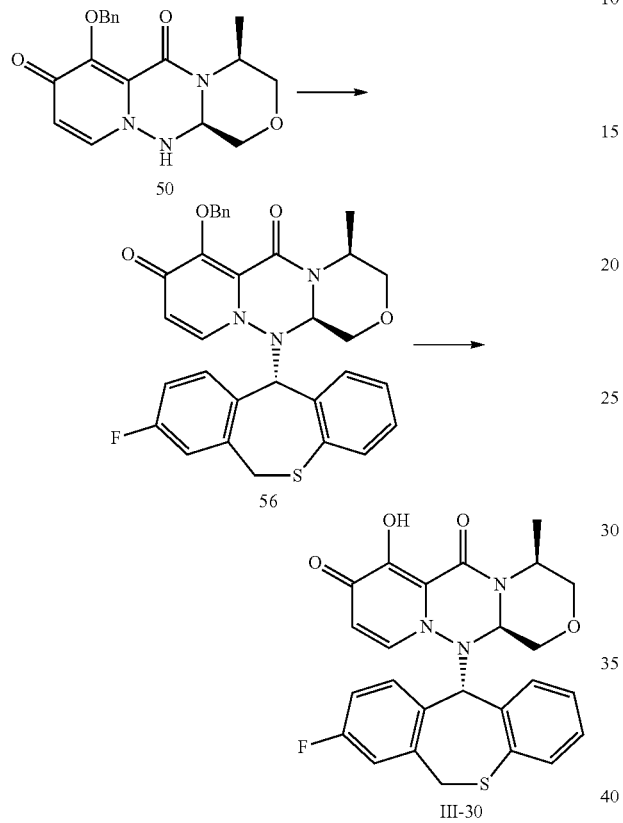

First Step

Compound 50 (154.0 mg, 0.451 mmol) and Compound 55 (117 mg, 0.474 mmol) were dissolved in a solution of T3P in ethyl acetate (1.5 mL), and the mixture was stirred in a sealed tube at 100° C. for 4 hours. The reaction was stopped by adding water, the reaction solution was extracted with ethyl acetate, and the obtained organic layer was washed with brine, dried over anhydrous magnesium sulfate, and concentrated under reduced pressure. The obtained residue was recrystallized with chloroform-hexane to obtain Compound 56 (70.2 mg, 27%).

LC/MS (ESI): m/z=570 [M+H]⁺, RT=2.18 min, method (1)

Second Step

Compound 56 (70.2 mg, 0.123 mmol) was dissolved in DMA (1 mL), lithium chloride (52.2 g, 1.23 mmol) was added thereto, and the mixture was stirred at 100° C. for 4 hours. The mixture was cooled to room temperature, and a 1 mol/L aqueous solution of hydrochloric acid was added thereto to stop the reaction. The reaction solution was extracted with ethyl acetate, the obtained organic layer was washed with 1 mol/L hydrochloric acid and brine, dried over anhydrous sodium sulfate, and concentrated under reduced pressure. The obtained solids were washed with ethyl acetate to obtain Compound III-30 (28.6 mg, 48%).

1H-NMR (CDCl3) δ: 1.78 (d, J=7.2 Hz, 3H), 3.26-3.32 (m, 1H), 3.44-3.60 (m, 3H), 3.72 (dd, J=11.7, 2.6 Hz, 1H), 3.94 (dd, J=11.2, 2.9 Hz, 1H), 4.42 (dd, J=9.9, 2.8 Hz, 1H), 5.29 (s, 1H), 5.54 (d, J=13.6 Hz, 1H), 5.76 (d, J=7.8 Hz, 1H), 6.71 (d, J=7.7 Hz, 1H), 6.81-6.86 (m, 1H), 6.96-7.04 (m, 2H), 7.07-7.11 (m, 3H), 7.23-7.25 (m, 1H).

LC/MS (ESI): m/z=480 [M+H]⁺, RT=1.87 min, method (1)

Example 7: Method for Producing Compound III-54

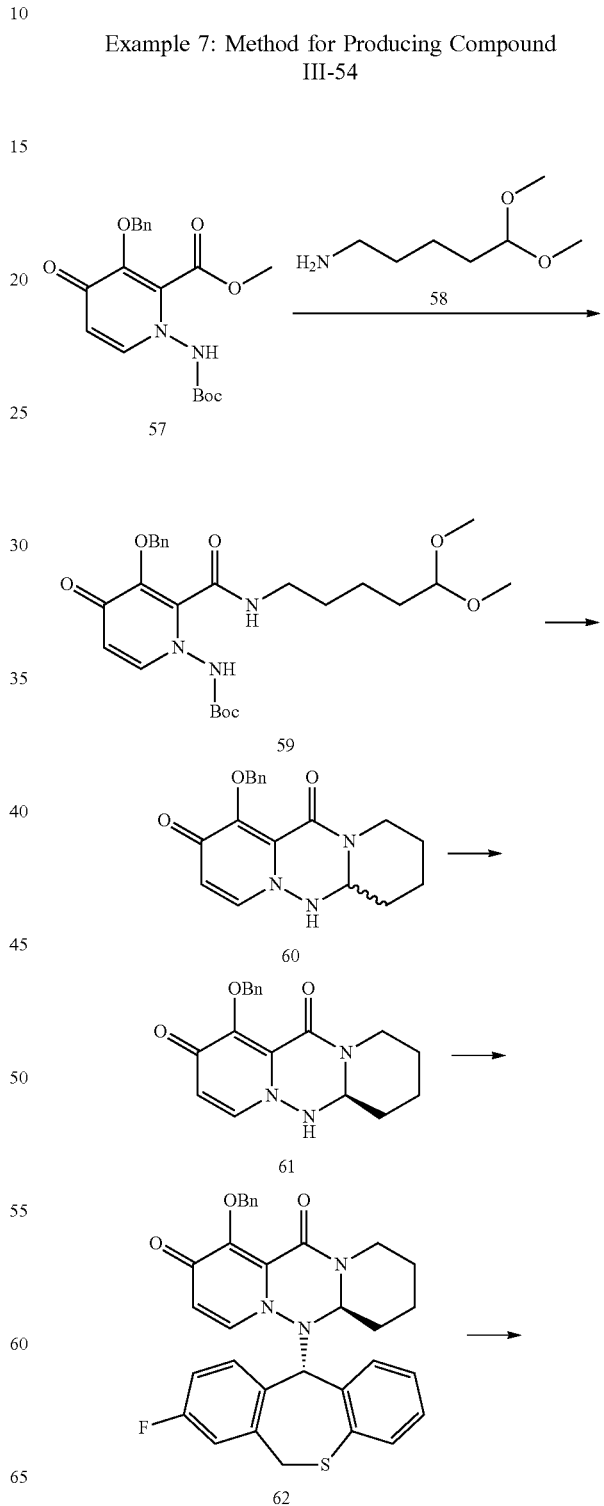

-continued

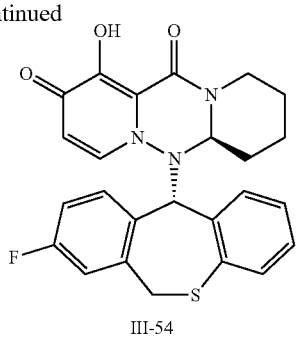

III-54

First Step

Compound 57 (60.6 g, 0.162 mol) was dissolved in THF (122 ml), then Compound 58 (Journal of Organic Chemistry, 80(20), 9868-9880; 2015) (50 g, 0.34 mol) and DBU (2.6 g, 17 mmol) were added thereto, and the mixture was stirred at 60° C. for 48 hours. The reaction solution was concentrated, and purified by silica gel column chromatography (dichloromethane-methanol) to obtain Compound 59 (73.2 g, 93.3%).

Second Step

Compound 59 (73.2 g, 0.15 mol) was dissolved in a mixed solvent of acetonitrile (580 ml) and water (145 ml), methanesulfonic acid (43.1 g, 0.45 mol) was added thereto, and the mixture was stirred at 60° C. for 20 hours. The mixture was concentrated under reduced pressure until the residue was about 300 ml. Ethyl acetate (250 ml) and an aqueous solution of sodium carbonate (500 ml) were added thereto, the pH of the mixture was regulated to 8, and the mixture was stirred for 30 minutes. Precipitates were filtered, and washed with a mixed solvent of ethyl acetate-hexane and water, and dried to obtain Compound 60 (33 g, 68%).

1H NMR (400 MHz, d-DMSO) δ:7.70 (d, J=7.6 Hz, 1H), 7.55 (d, J=7.1 Hz, 2H), 7.40-7.22 (m, 4H), 6.21 (d, J=7.6 Hz, 1H), 5.05 (s, 2H), 4.59 (d, J=3.6 Hz, 1H), 4.39-4.27 (m, 1H), 2.80-2.65 (m, 1H), 1.99-1.87 (m, 1H), 1.78 (s, 2H), 1.51-1.15 (m, 3H).

Third Step

The optical resolution of Compound 60 (4.0 g, 12.3 mmol) by Waters SFC30 System (Daicel CHIRALPAK IB, liquefied carbon dioxide-methanol) gave Compound 61 (1.79 g, 45%).

Analysis Condition
<Waters SFC30 System>
Column: CHIRALPAK IB/SFC (5 μm, i.d. 250×4.6 mm) (DAICEL)
Flow rate: 8.0 mL/mini UV detection wavelength: 254 nm
Back pressure: 100 bar
Mobile phase: [A]: liquefied carbon dioxide, [B]: methanol
Gradient: 5% solvent. [B] was kept, for 1 minute, a linear gradient, of 5% to 40% solvent [B] was carried out in 6 minutes, 40% solvent [B] was kept for 2 minutes, and 5% solvent [B] was kept for 1 minute.
Elution time: 7.9 minutes Fourth Step Compound 61 (1.76 g, 5.41 mmol) and 8-fluoro-6,11-dihydrodibenzo[b,e]thiepin-11-ol (1.99 g, 8.11 mmol) were dissolved in T3P (50%, ethyl acetate solution, 16 ml), and the mixture was stirred in a sealed tube at 100° C. for 3 hours. Ethyl acetate and water were added thereto, the mixture was neutralized with a saturated aqueous solution of sodium hydrogen carbonate, and the aqueous layer was extracted with ethyl acetate. The obtained organic layer was washed with brine, dried over anhydrous sodium sulfate, and concentrated under reduced pressure. The obtained residue was dissolved in THF (15 ml), then potassium carbonate (1.49 g, 10.8 mmol) and benzyl bromide (0.321 ml) were added thereto, and the mixture was heated to reflux for 6 hours. Further, 1-methylpiperazine (0.30 ml) was added thereto, and the mixture was heated to reflux for 1 hour. The reaction solution was extracted with ethyl acetate. The obtained organic layer was washed with 2 mol/L hydrochloric acid and brine, dried over anhydrous magnesium sulfate, and concentrated under reduced pressure. The obtained residue was purified by silica gel column chromatography (chloroform-acetone) to obtain Compound 62 (1.15 g, 38.4%).

LC/MS (ESI): m/z=554 [M+H]$^+$, RT=2.24 min. method (1)

Fifth Step

Compound 62 (1.0 g, 1.81 mol) and lithium chloride (383 mg, 9.03 mmol) were dissolved in DMA, and the mixture was stirred at 100° C. for 3 hours. The reaction solution was cooled to room temperature, acetone (5 ml) was added thereto, a 1 mol/L aqueous solution of hydrochloric acid (40 ml) was added dropwise thereto, and the mixture was stirred at room temperature for 15 minutes. The produced white solids were filtered, washed with a 50% aqueous solution of acetone, and dried to obtain Compound III-54 (760 mg, 91%).

$^1$H-NMR (CDCl$_3$) δ: 1.47-2.05 (m, 6H), 2.50-2.58 (m, 1H), 3.51 (d, J=12.0 Hz, 1H), 4.26-4.31 (m, 1H), 4.68-4.74 (m, 1H), 5.22 (s, 1H), 5.62 (d, J=13.6 Hz, 1H), 5.77 (d, J=7.6 Hz, 1H), 6.68 (d, J=7.6 Hz, 1H), 6.80-6.82 (m, 1H), 6.88-7.02 (m, 1H), 7.03-7.15 (m, 5H) LC/MS (ESI): m/z=464.2 [M+H]$^+$, RT=1.92 min, method (1)

Example 8: Method for Producing Compound III-20

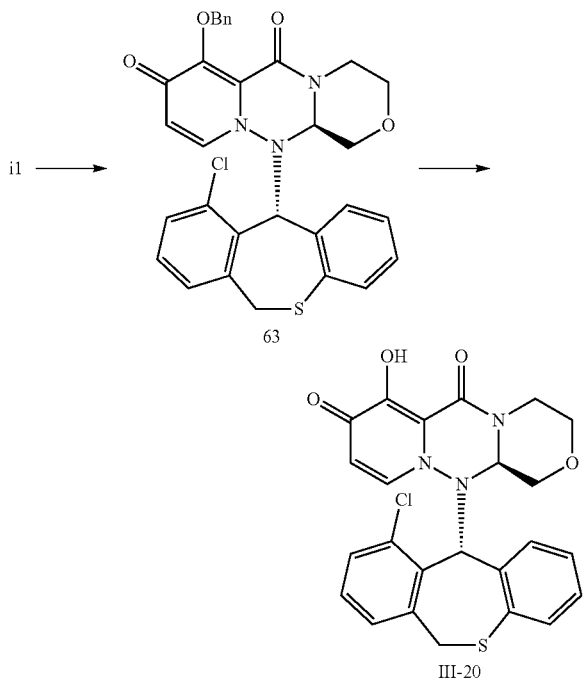

73

First Step

Compound i1 (500 mg, 1.53 mmol) and 10-chloro-6,11-dihydrodibenzo[b,e]thiepin-11-ol (602 mg, 2.29 mmol) were dissolved in T3P (50%, ethyl acetate solution, 5 ml), and the mixture was stirred in a sealed tube at 105° C. for 1.5 hours. The reaction solution was extracted with ethyl acetate, the obtained organic layer was washed with water and brine, dried over anhydrous magnesium sulfate, and concentrated under reduced pressure. The obtained residue was purified by silica gel column chromatography (chloroform-ethyl acetate-methanol) to obtain Compound 63 (210 mg, 24%).

1H-NMR (CDCl3) δ: 2.96 (t, J=12.0 Hz, 1H), 3.30-3.43 (m, 2H), 3.53 (d, J=13.2 Hz, 1H), 3.73 (d, J=11.6 Hz, 1H), 3.86 (d, J=10.8 Hz, 1H), 4.42 (d, J=7.2 Hz, 1H), 4.71 (d, J=13.6 Hz, 1H), 5.42 (d, J=10.8 Hz, 1H), 5.57-5.65 (m, 2H), 5.79 (d, J=7.6 Hz, 1H), 6.18 (s, 1H), 6.47 (d, J=7.2 Hz, 1H), 6.67 (t, J=6.8 Hz, 1H), 7.00-7.14 (m, 3H), 7.22-7.40 (m, 6H), 7.64 (d, J=7.2 Hz, 2H).

Second Step

Compound 63 (210 mg, 0.368 mmol) was dissolved in DMA (3 ml), lithium chloride (78 mg, 1.84 mmol) was added thereto, and the mixture was stirred at 100° C. for 4 hours. The reaction solution was extracted with ethyl acetate, the obtained organic layer was washed with 1 mol/L hydrochloric acid and brine, dried over anhydrous sodium sulfate, and concentrated under reduced pressure. The obtained residue was recrystallized with dichloromethane-diethyl ether to obtain Compound III-20 (124 mg, 70%).

1H-NMR (CDCl3) δ: 3.09 (t, J=12.8 Hz, 1H), 3.48 (t, J=11.6 Hz, 1H), 3.55-3.62 (m, 2H), 3.81 (d, J=11.6 Hz, 1H), 3.93 (d, J=10.8 Hz, 1H), 4.53 (d, J=9.6 Hz, 1H), 4.69 (d, J=13.2 Hz, 1H), 5.68 (d, J=12.8 Hz, 1H), 5.76 (d, J=6.8 Hz, 1H), 6.26 (s, 1H), 6.80-6.88 (m, 2H), 7.05-7.15 (m, 3H), 7.24-7.28 (m, 1H), 7.34 (t, J=7.6 Hz, 1H), 7.39 (d, J=8.0 Hz, 1H).

Example 9: Method for Producing Compound III-33

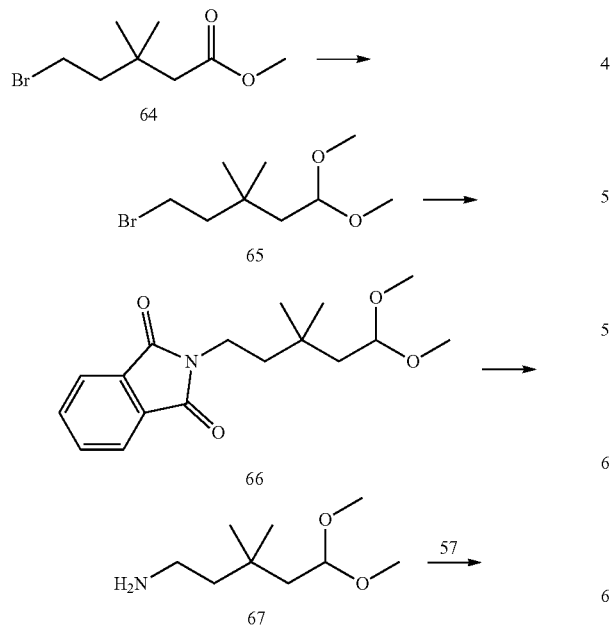

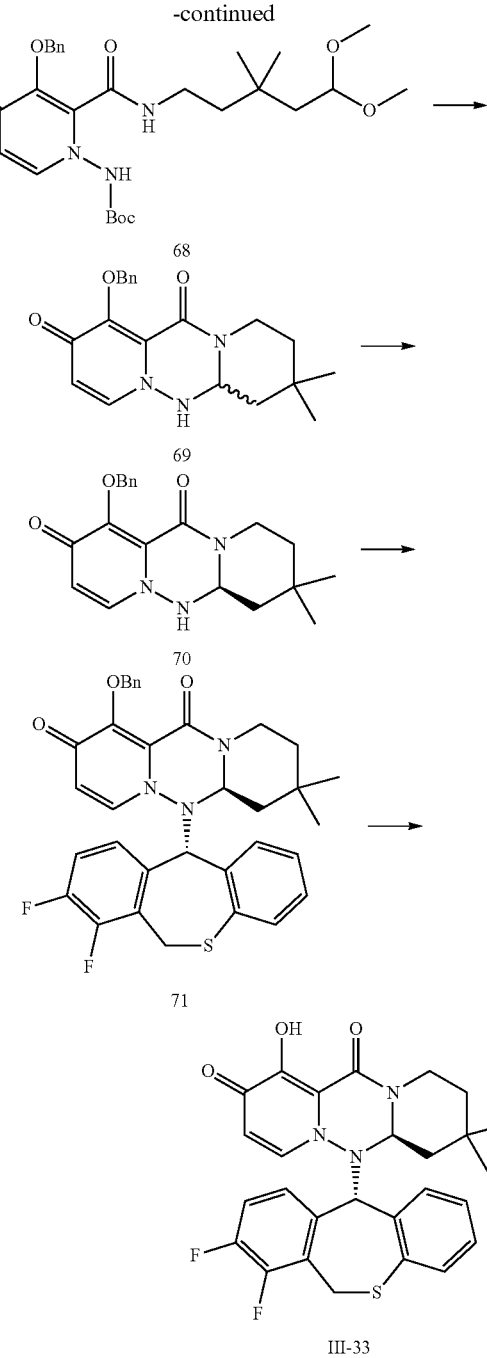

First Step

Compound 64 (3.54 g, 14.9 mmol) was dissolved in dichloromethane (70 ml), and DIBAL-H (1 mol/L, 16.4 ml, 16.4 mmol) was added dropwise thereto at −78° C. The mixture was stirred at −78° C. for 1 hour, the reaction was quenched with methanol, and the temperature of the mixture was increased to room temperature. The reaction mixture was extracted with dichloromethane, the obtained organic layer was washed with 2 mol/L hydrochloric acid and brine, dried over anhydrous magnesium sulfate, and concentrated under reduced pressure. The obtained residue was dissolved in methanol (35 ml), ammonium chloride (80 mg, 1.49 mmol) was added thereto, and the mixture was heated to reflux for 1 hour. The reaction mixture was extracted with diethyl ether, and the obtained organic layer was washed with a saturated aqueous solution of sodium hydrogen carbonate and brine, dried over anhydrous magnesium sulfate, and concentrated under reduced pressure to obtain Compound 65 (2.73 g, 76%).

$^1$H-NMR (CDCl3) δ: 0.96 (s, 6H), 1.53 (d, J=5.2 Hz, 2H), 1.85-1.90 (m, 2H), 3.31 (s, 6H), 3.38-3.43 (m, 2H), 4.44 (t, J=5.2 Hz, 1H)

Second Step

Compound 65 (2.7 g, 11.3 mmol) was dissolved in acetone (50 ml), then potassium carbonate (5.46 g), isoindoline-1,3-dione (2.49 g, 16.9 mmol) and tetrabutylammonium bromide (1.09 g, 3.39 mmol) were added thereto, and the mixture was healed to reflux for 6 hours. The reaction solution was filtered and concentrated under reduced pressure. The obtained residue was purified by silica gel column chromatography (hexane-ethyl acetate) to obtain Compound 66 (1.1 g, 32%).

$^1$H-NMR (CDCl$_3$) δ: 1.04 (s, 6H), 1.58-1.65 (m, 4H), 3.32 (s, 6H), 3.65-3.75 (m, 2H), 4.52 (t, J=5.2 Hz, 1H), 7.65-7.75 (m, 2H), 7.80-7.90 (m, 2H)

Third Step

Compound 66 (1.14 g, 3.73 mmol) was dissolved in ethanol-water (VI, 4 ml), hydrazine monohydrate (374 mg, 7.47 mmol) was added thereto, and the mixture was stirred at 60° C. for 5 hours. The reaction solution was extracted with dichloromethane, and the obtained organic layer was washed with a 1 mol/L aqueous solution of sodium hydroxide and brine, dried over anhydrous magnesium sulfate, and concentrated under reduced pressure to obtain Compound 67 (750 mg, 100%).

$^1$H-NMR (CDCl$_3$) δ: 0.93 (s, 6H), 1.38-1.45 (m, 2H), 1.52 (d, J=5.2 Hz, 2H), 2.65-2.75 (m, 2H), 3.30 (s, 6H), 4.46 (t, J=5.2 Hz, 1H), 5.30 (s, 2H)

Fourth Step

Compound 57 (300 mg, 0.80 mmol) was dissolved in THF (0.6 ml), then Compound 67 (351 mg, 2.00 mmol) and DBU (12 μl, 0.08 mmol) were added thereto, and the mixture was stirred at 60° C. for 18 hours. The reaction solution was concentrated under reduced pressure, and the obtained residue was purified by silica gel column chromatography (chloroform-methanol) to obtain Compound 68 (440 mg, 80%).

$^1$H-NMR (CDCl$_3$) δ: 0.90 (s, 6H), 1.20-1.32 (m, 2H), 1.44 (s, 9H), 1.47 (d, J=5.2 Hz, 2H), 3.11-3.25 (m, 2H), 3.26 (s, 6H), 4.41 (t, J=5.21 Hz, 1H), 5.28 (s, 2H), 6.38 (d, J=8.0, 1H), 6.87 (br, 1H), 7.29-7.40 (m, 6H), 8.49 (br, 1H)

Fifth Step

Compound 68 (210 mg, 0.41 mmol) was dissolved in a mixed solvent of acetonitrile (1.8 ml) and water (310 μl), methanesulfonic acid (79 μl, 1.22 mmol) was added thereto, and the mixture was stirred at 60° C. for 6 hours. The mixture was cooled to room temperature, the pH of the mixture was regulated to 7 with a 2 mol/L aqueous solution of sodium hydroxide, and the reaction solution was extracted with dichloromethane. The obtained organic layer was washed with brine, dried over anhydrous magnesium sulfate, and concentrated under reduced pressure. The obtained residue was purified by silica gel column chromatography (chloroform-methanol) to obtain Compound 69 (55 mg, 49%).

$^1$H-NMR (CDCl$_3$) δ: 0.95 (s, 3H), 0.98 (s, 3H), 1.40-1.45 (m, 2H), 1.53-1.65 (m, 2H), 2.80-2.89 (m, 1H), 4.05-4.15 (m, 1H), 4.40-4.48 (m, 1H), 5.14-5.31 (m, 2H), 5.48 (d, J=12.4 Hz, 1H), 6.32 (d, J=7.6 Hz, 1H), 7.25-7.40 (m, 4H), 7.59 (d, J=6.8 Hz, 2H)

Sixth Step

The optical resolution of Compound 69 (6.69 g, 18.9 mmol) by Waters SFC30 System (Daicel CHIRALPAK IB, liquefied carbon dioxide-methanol) gave Compound 70 (3.40 g, 50%).

Analysis Condition

<Waters SFC30 System>

Column: CHIRALPAK IB/SFC (5 μm, i.d. 250×4.6 mm) (DAICEL)

Flow rate: 8.0 mL/min; UV detection wavelength: 254 nm

Back pressure: 100 bar

Mobile phase: [A]: liquefied carbon dioxide, [B]: methanol

Gradient: 5% solvent [B] was kept for 1 minute, a linear gradient of 5% to 40% solvent [B] was carried out in 6 minutes, 40% solvent [b] was kept for 2 minutes, and 5% solvent [B] was kept for 1 minute.

Elution time: 7.67 minutes

Seventh Step

Compound 70 (2.0 g, 5.66 mmol) and 7,8-difluoro-6,11-dihydrodibenzo[b,e]thiepin-11-ol (1.94 g, 7.36 mmol) were dissolved in T3P (50% ethyl acetate, 20 ml), and the mixture was stirred in a sealed tube at 105° C. for 2.5 hours. The reaction solution was extracted with ethyl acetate, and the obtained organic layer was washed with water and brine, dried over anhydrous magnesium sulfate, and concentrated under reduced pressure. The obtained residue was purified by silica gel column chromatography (chloroform-acetone) to obtain a diastereomeric mixture (2.84 g). This was recrystallized with ethyl acetate to obtain Compound 71 (1.26 g, 37%).

$^1$H-NMR (CDCl3) δ: 0.80 (s, 3H), 0.91 (s, 3H), 1.20-1.45 (m, 4H), 2.49-2.58 (m, 1H), 4.02 (d, J=13.6 Hz, 1H), 4.25-4.33 (m, 1H), 4.55-4.65 (m, 1H), 5.19 (s, 1H), 5.24-5.30 (m, 1H), 5.47-5.59 (m, 2H), 5.80 (d, J=7.6 Hz, 1H), 6.42 (d, J=8.0 Hz, 1H), 6.65-6.71 (m, 1H), 6.95-7.12 (m, 5H), 7.27-7.39 (m, 3H), 7.61 (d, J=6.8 Hz, 2H)

Eighth Step

Compound 71 (980 mg, 1.63 mmol) was dissolved in DMA (8 ml), lithium chloride (346 mg, 8.17 mmol) was added thereto, and the mixture was stirred at 100° C. for 3 hours. The reaction solution was extracted with ethyl acetate, the obtained organic layer was washed with 2 mol/L hydrochloric acid and brine, dried over anhydrous sodium sulfate, and concentrated under reduced pressure. The obtained residue was crystallized with ethyl acetate to obtain Compound III-33 (780 mg, 94%).

$^1$H-NMR (CDCl$_3$) δ: 0.85 (s, 3H), 0.97 (s, 3H), 1.34-2.00 (m, 4H), 2.62-2.66 (m, 1H), 4.05 (d, J=13.6 Hz, 1H), 4.40-4.48 (m, 1H), 4.56-4.63 (m, 1H), 5.24 (s, 1H), 5.30-5.35 (m, 1H), 5.80 (d, J=7.6 Hz, 1H), 6.68 (d, J=7.6 Hz, 1H), 6.78-6.90 (m, 1H), 6.95-7.15 (m, 4H), 7.16-7.22 (m, 1H)

LC/MS (ESI): m/z=510.2 [M+H]$^+$, RT=2.25 min, method (1)

The following example compounds were synthesized from commercially available compounds or intermediates suitably synthesized from commercially available compounds according to the above examples.

TABLE 1

| No. | Structure | H-NMR or LC/MS |
|---|---|---|
| III-3 | 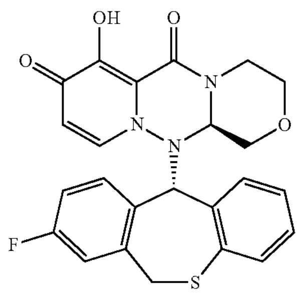 [SMILES: O=C1c2c(O)c(=O)ccn2N([C@H]2c3ccc(F)cc3CSc3ccccc32)[C@@H]2COCCN12] | 1H-NMR (CDCl3) δ: 2.99 (t, J = 12.4 Hz, 1H), 3.43-3.61 (m, 3H), 3.81 (d, J = 12.0 Hz, 1H), 3.96 (d, J = 11.0 Hz, 1H), 4.59 (d, J = 9.8 Hz, 1H), 4.66 (d, J = 13.2 Hz, 1H), 5.26 (s, 1H), 5.54 (d, J = 13.4 Hz, 1H), 5.75 (d, J = 8.2 Hz, 1H), 6.69 (d, J = 7.7 Hz, 1H), 6.84 (t, J = 7.0 Hz, 1H), 6.98-7.05 (m, 2H), 7.07-7.12 (m, 3H), 7.22 (t, J = 7.0 Hz, 1H). |
| III-9 | 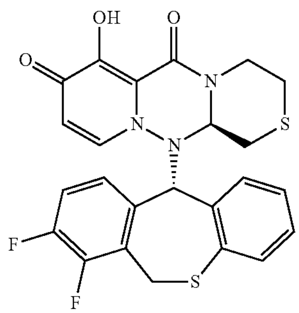 | 1H-NMR(CDCl3) δ: 2.37 (d, J = 13.2 Hz, 1H), 2.57 (d, J = 12.4 Hz, 1H), 2.79-2.87 (m, 1H), 2.90-3.03 (m, 2H), 4.08 (d, J = 13.6 Hz, 1H), 4.64 (d, J = 10.8 Hz, 1H), 5.05 (d, J = 12.0 Hz, 1H), 5.19 (s, 1H), 5.25-5.32 (m, 1H), 5.78 (d, J = 7.6 Hz, 1H), 6.66 (d, J = 7.6 Hz, 1H), 6.84 (t, J = 7.6 Hz, 1H), 6.90-7.20 (m, 5H). |
| III-10 | 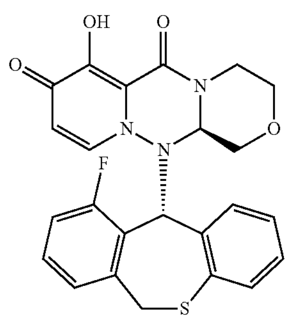 | 1H-NMR(CDCl3) δ: 3.06 (t, J = 11.6 Hz, 1H), 3.47 (t, J = 11.2 Hz, 1H), 3.50-3.63 (m, 2H), 3.80 (d, J = 11.6 Hz, 1H), 3.94 (d, J = 11.2 Hz, 1H), 4.58 (d, J = 9.6 Hz, 1H), 4.69 (d, J = 13.6 Hz, 1H), 5.57 (d, J = 13.6 Hz, 1H), 5.75 (d, J = 7.6 Hz, 1H), 5.90 (s, 1H), 6.78 (d, J = 7.6 Hz, 1H), 6.85 (t, J = 7.6 Hz, 1H), 7.04-7.17 (m, 5H), 7.35-7.42 (m, 1H). |
| III-11 | 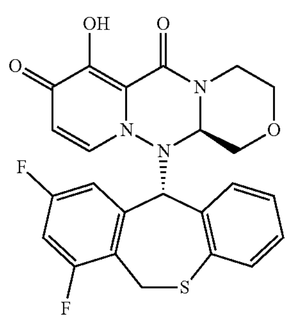 [SMILES: O=C1c2c(O)c(=O)ccn2N([C@@H]2c3ccccc3SCc3c(F)cc(F)cc32)[C@@H]2COCCN12] | 1H-NMR(CDCl3) δ: 3.04 (t, J = 12.0 Hz, 1H), 3.47 (t, J = 11.6 Hz, 1H), 3.59 (t, J = 11.2 Hz, 1H), 3.82 (d, J = 12.0 Hz, 1H), 3.97 (d, J = 10.8 Hz, 1H), 4.03 (d, J = 14.0 Hz, 1H), 4.56 (d, J = 11.6 Hz, 1H), 4.68 (d, J = 13.6 Hz, 1H), 5.17 (d, J = 14.0 Hz, 1H), 5.24 (s, 1H), 5.75 (d, J = 8.0 Hz, 1H), 6.69 (d, J = 7.6 Hz, 1H), 6.80-6.88 (m, 2H), 6.98 (t, J = 8.8 Hz, 1H), 7.04-7.16 (m, 3H). |
| III-12 | 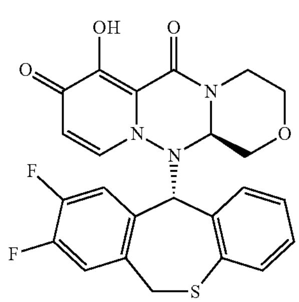 [SMILES: O=C1c2c(O)c(=O)ccn2N([C@H]2c3cc(F)c(F)cc3CSc3ccccc32)[C@@H]2COCCN12] | 1H-NMR(CDCl3) δ: 3.04 (t, J = 12.8 Hz, 1H), 3.40-3.62 (m, 3H), 3.82 (d, J = 12.0 Hz, 1H), 3.96 (d, J = 11.2 Hz, 1H), 4.58 (d, J = 9.6 Hz, 1H), 4.68 (d, J = 13.6 Hz, 1H), 5.19 (s, 1H), 5.49 (d, J = 13.6 Hz, 1H), 5.74 (d, J = 7.6 Hz, 1H), 6.68 (d, J = 7.2 Hz, 1H), 6.85 (t, J = 7.6 Hz, 1H), 7.03 (d, J = 7.6 Hz, 1H), 7.06-7.16 (m, 3H), 7.21 (t, J = 8.8 Hz, 1H). |

TABLE 1-continued

| No. | Structure | H-NMR or LC/MS |
|---|---|---|
| III-13 | 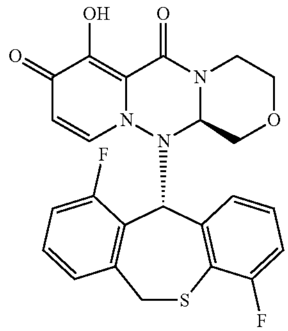 [SMILES: O=C1c2c(O)c(=O)ccn2N([C@@H]2c3cccc(F)c3SCc3cccc(F)c32)[C@@H]2COCCN12] | 1H-NMR(CDCl3) δ: 3.04 (t, J = 12.0 Hz, 1H), 3.47 (t, J = 12.0 Hz, 1H), 3.58 (t, J = 10.8 Hz, 1H), 3.69 (d, J = 13.6 Hz, 1H), 3.81 (d, J = 12.0 Hz, 1H), 3.94 (d, J = 11.2 Hz, 1H), 4.57 (d, J = 13.6 Hz, 1H), 4.69 (d, J = 14.0 Hz, 1H), 5.59 (d, J = 13.6 Hz, 1H), 5.79 (d, J = 7.6 Hz, 1H), 5.96 (s, 1H), 6.63 (d, J = 7.6 Hz, 1H), 6.81-6.88 (m, 1H), 6.96 (t, J = 9.6 Hz, 1H), 7.04-7.13 (m, 2H), 7.17 (d, J = 7.6 Hz, 1H), 7.38-7.45 (m, 1H). |

TABLE 2

| III-14 | | 1H-NMR (CDCl3) δ: 3.00-3.07 (m, 1H), 3.47 (td, J = 12.0, 2.6 Hz, 1H), 3.57-3.62 (m, 2H), 3.82 (dd, J = 11.9, 3.3 Hz, 1H), 3.97 (dd, J = 11.1, 2.9 Hz, 1H), 4.60 (dd, J = 10.0, 3.0 Hz, 1H), 4.68 (dd, J = 13.6, 2.0 Hz, 1H), 5.20 (s, 1H), 5.47 (d, J = 13.4 Hz, 1H), 5.76 (d, J = 7.8 Hz, 1H), 6.70 (d, J = 7.8 Hz, 1H), 6.82-6.86 (m, 1H), 6.98 (dd, J = 8.7, 2.5 Hz, 1H), 7.07-7.16 (m, 4H), 7.35 (dd, J = 8.3, 5.5 Hz, 1H). |
|---|---|---|
| III-21 | | 1H-NMR(CDCl3) δ:1.85-1.98 (m, 1H), 2.10-2.23 (m, 2H), 2.31-2.43 (m, 1H), 2.69 (t, J = 10.8 Hz, 1H), 4.09 (d, J = 13.2 Hz, 1H), 4.51 (d, J = 12.4 Hz, 1H), 4.77 (d, J = 13.6 Hz, 1H), 5.20-5.30 (m, 1H), 5.78 (d, J = 7.2 Hz, 1H), 5.77 (d, J = 7.6 Hz, 1H), 6.68 (d, J = 7.2 Hz, 1H), 6.81-6.88 (m, 1H), 6.96-7.02 (m, 1H), 7.05-7.17 (m, 4H). |
| III-22 | | 1H-NMR(CDCl3) δ: 1.22 (d, J = 7.2 Hz, 3H), 3.49-3.58 (m, 4H), 3.95 (dd, J = 10.8, 2.8 Hz, 1H), 4.08 (d, J = 13.8 Hz, 1H), 4.74 (dd, J = 10.0, 2.8 Hz, 1H), 4.99-5.05 (m, 1H), 5.22 (s, 1H), 5.30 (dd, J = 13.8, 2.3 Hz, 1H), 5.75 (d, J = 7.8 Hz, 1H), 6.69 (d, J = 7.7 Hz, 1H), 6.84 (t, J = 7.0 Hz, 1H), 6.97-7.02 (m, 2H), 7.08-7.14 (m, 3H). |

TABLE 2-continued
| | | |
|---|---|---|
| III-23 | 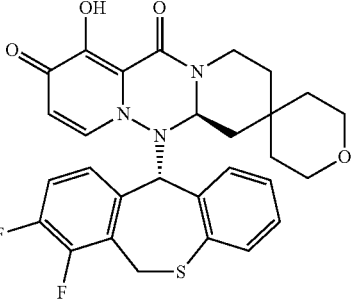 | 1H-NMR(CDCl3) δ: 1.29-1.87 (m, 8H), 2.67 (td, J = 13.5, 2.6 Hz, 1H), 3.54-3.66 (m, 5H), 4.08 (d, J = 13.7 Hz, 1H), 4.47 (dd, J = 12.0, 2.3 Hz, 1H), 4.61 (dd, J = 13.8, 3.1 Hz, 1H), 5.24-5.33 (m, 2H), 5.79 (d, J = 7.8 Hz, 1H), 6.68 (d, J = 7.5 Hz, 1H), 6.83-6.87 (m, 1H), 6.98-7.15 (m, 5H). |
| III-26 | 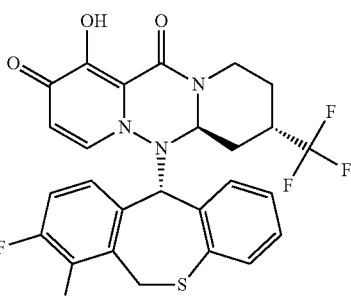 | 1H-NMR (CDCl3) δ: 1.82-2.17 (5H, m), 2.59-2.76 (1H, m), 2.84 (1H, t, J = 11.5 Hz) 4.09 (1H, d, J = 13.8 Hz), 4.63-4.69 (2H, m), 5.22 (1H, s), 5.27 (1H, dd, J = 13.9, 2.4 Hz), 5.79 (1H, d, J = 7.7 Hz), 6.68 (1H, d, J = 7.7 Hz), 6.83-6.87 (1H, m), 7.15-6.96 (5H, m). |
| III-28 | 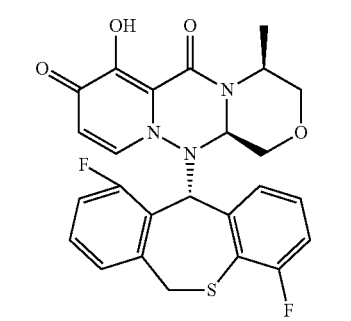 [SMILES: C[C@H]1COC[C@@H]2N1C(=O)c1c(O)c(=O)ccn1N2[C@@H]1c2cccc(F)c2SCc2cccc(F)c21] | 1H-NMR (CDCl3) δ: 1.79 (d, J = 7.2 Hz, 3H), 3.33-3.40 (m, 1H), 3.46-3.75 (m, 5H), 3.94 (dd, J = 11.0, 2.9 Hz, 1H), 4.43 (dd, J = 9.7, 2.7 Hz, 1H), 5.58 (d, J = 13.6 Hz, 1H), 5.81 (d, J = 7.7 Hz, 1H), 6.00 (s, 1H), 6.65 (d, J = 7.7 Hz, 1H), 6.82-6.88 (m, 1H), 6.94-7.01 (m, 2H), 7.11 (t, J = 9.2 Hz, 1H), 7.17 (d, J = 7.5 Hz, 1H), 7.39-7.44 (m, 1H) |
| III-29 | 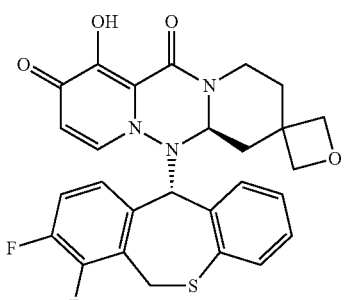 | 1H-NMR (CDCl3) δ: 1.62-1.69 (m, 1H), 1.90 (t, J = 12.4 Hz, 1H), 2.13 (d, J = 13.7 Hz, 1H), 2.38-2.46 (m, 2H), 4.09-4.20 (m, 3H), 4.32 (d, J = 6.3 Hz, 1H), 4.37-4.41 (m, 2H), 4.71 (dd, J = 13.7, 3.4 Hz, 1H), 5.23 (s, 1H), 5.36 (dd, J = 13.7, 2.6 Hz, 1H), 5.79 (d, J = 7.8 Hz, 1H), 6.68 (d, J = 7.8 Hz, 1H), 6.82-6.87 (m, 1H), 6.94-6.99 (m, 1H), 7.05-7.15 (m, 4H). |

TABLE 3
| | | |
|---|---|---|
| III-31 | 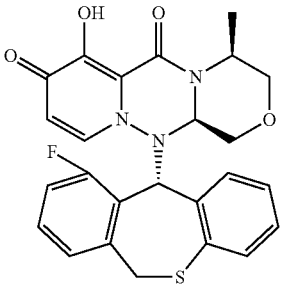 [SMILES: C[C@H]1COC[C@@H]2N1C(=O)c1c(O)c(=O)ccn1N2[C@@H]1c2ccccc2SCc2cccc(F)c21] | LC/MS (ESI): m/z = 480 [M + H]⁺. RT = 1.81 min. method (1) |
| III-34 | 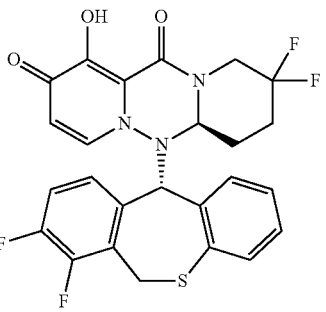 | 1H-NMR (CDCl3) δ: 1.86-2.18 (4H, m), 2.30-2.46 (1H, m), 2.90 (1H, dd, J = 30.0, 13.9 Hz), 4.07 (1H, d, J = 13.7 Hz), 4.41-4.48 (1H, m), 4.99-5.06 (1H, m), 5.20 (1H, s), 5.30 (1H, dd, J = 13.7, 2.4 Hz), 5.78 (1H, d, J = 7.8 Hz), 6.68 (1H, d, J = 7.8 Hz), 6.83-6.87 (1H, m), 7.00 (1H, dd, J = 8.3, 4.1 Hz), 7.06-7.17 (4H, m). |
| III-35 | 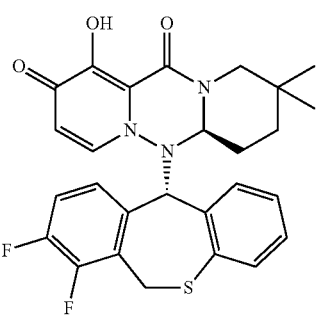 [SMILES: CC1(C)CC[C@@H]2N(C1)C(=O)c1c(O)c(=O)ccn1N2[C@@H]1c2ccccc2SCc2c1ccc(F)c2F] | 1H-NMR(CDCl3) δ: 0.89 (s, 3H), 0.95 (s, 3H), 1.25-2.20 (m, 4H), 2.39 (d, J = 12.4 Hz, 1H), 4.05 (d, J = 12.4 Hz, 1H), 4.20-4.28 (m, 1H), 4.39-4.44 (m, 1H), 5.20 (1H, s), 5.33-5.38 (m, 1H), 5.78 (d, J = 7.6 Hz, 1H), 6.68 (d, J = 7.6 Hz, 1H), 6.80-6.83 (m, 1H), 6.88-7.18 (m, 5H) |
| III-36 | 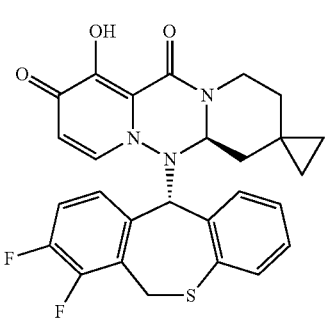 [SMILES: O=C1c2c(O)c(=O)ccn2N([C@@H]2c3ccccc3SCc3c2ccc(F)c3F)[C@@H]2CC3(CCN12)CC3] | 1H-NMR(CDCl3) δ: 0.18-0.25 (m, 1H), 0.26-0.35 (m, 1H), 0.36-0.50 (m, 2H), 0.76-0.83 (m, 1H), 0.98-1.40 (m, 1H), 1.60-2.24 (m, 4H), 2.60-2.70 (m, 1H), 4.04 (d, J = 13.6 Hz, 1H), 4.32-4.48 (m, 1H), 4.69-4.75 (m, 1H), 5.26 (s, 1H), 5.77 (d, J = 8.0 Hz, 1H), 6.69 (d, J = 8.0 Hz, 1H), 6.80-6.90 (m, 1H), 7.00-7.18 (m, 5H). |

TABLE 4

| | | |
|---|---|---|
| III-37 | 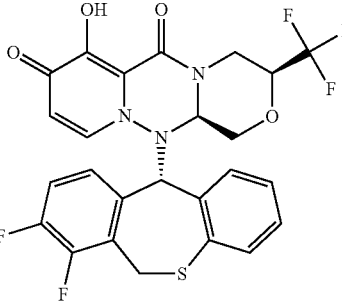 | 1H-NMR (CDCl3) δ: 3.26 (dd, J = 14.6, 5.7 Hz, 1H), 3.85-4.11 (m, 4H), 4.68 (dd, J = 10.4, 3.6 Hz, 1H), 5.07 (d, J = 14.7 Hz, 1H), 5.22-5.27 (m, 2H), 5.74 (d, J = 7.7 Hz, 1H), 6.69 (d, J = 7.5 Hz, 1H), 6.85 (t, J = 6.9 Hz, 1H), 6.97-7.15 (m, 5H). |
| III-38 | 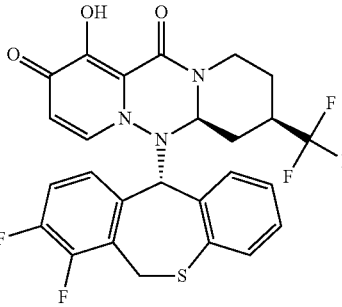 | 1H-NMR (CDCl3) δ: 1.49-1.79 (m, 2H), 1.91 (d, J = 11.9 Hz, 1H), 2.08-2.13 (m, 1H), 2.47-2.62 (m, 2H), 4.07-4.10 (m, 1H), 4.35 (dd, J = 11.9. 2.3 Hz, 1H), 4.84 (dd, J = 13.4, 4.0 Hz, 1H), 5.25 (s, 1H), 5.31 (dd, J = 13.9, 2.4 Hz, 1H), 5.79 (d, J = 7.7 Hz, 1H), 6.69 (d, J = 7.9 Hz, 1H), 6.83-6.87 (m, 1H), 6.97-7.00 (m, 1H), 7.06-7.15 (m, 4H). |
| III-39 | 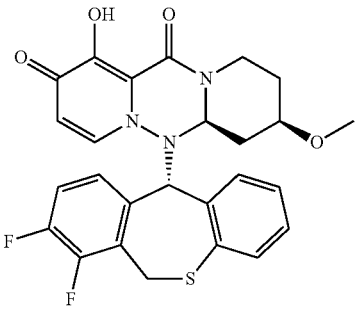 [SMILES: CO[C@@H]1CCN2C(=O)c3c(O)c(=O)ccn3N([C@@H]3c4ccccc4SCc4c3ccc(F)c4F)[C@@H]2C1] | 1H-NMR(CDCl3) δ: 1.31-1.44 (m, 1H), 1.58 (q, J = 11.6 Hz, 1H), 2.05 (d, J = 10.8 Hz, 1H), 2.26 (d, J = 11.6 Hz, 1H), 2.47 (t, J = 11.2 Hz, 1H), 3.31 (s, 3H), 3.40-3.48 (m, 1H), 4.06 (d, J = 13.6 Hz, 1H), 4.24 (d, J = 10.0 Hz, 1H), 4.68-4.76 (m, 1H), 5.23 (s, 1H), 5.34 (d, J = 13.6 Hz, 1H), 5.78 (d, J = 7.6 Hz, 1H), 6.68 (d, J = 7.6 Hz, 1H), 6.84 (t, J = 7.6 Hz, 1H), 6.95-7.00 (m, 1H), 7.03-7.15 (m, 4H). |
| III-40 | 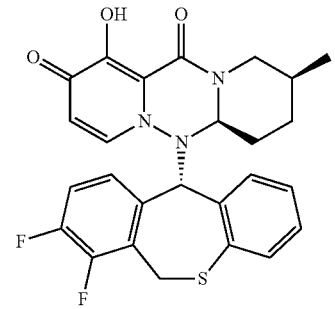 [SMILES: C[C@H]1CC[C@@H]2N(C1)C(=O)c1c(O)c(=O)ccn1N2[C@@H]1c2ccccc2SCc2c1ccc(F)c2F] | 1H-NMR (CDCl3) δ: 0.94 (3H, d, J = 7.2 Hz), 1.45-1.86 (5H, m), 1.86-2.12 (1H, m), 2.79 (1H, dd, J = 13.3, 3.5 Hz), 4.05 (1H, d, J = 13.7 Hz), 4.27 (1H, dd, J = 11.6, 2.4 Hz), 4.56 (1H, d, J = 13.2 Hz), 5.36 (1H, dd, J = 13.6, 2.4 Hz), 5.20 (1H, s), 5.79 (1H, d, J = 7.7 Hz), 6.69 (1H, d, J = 7.4 Hz), 6.81-6.87 (1H, m), 6.95-7.01 (1H, m), 7.05-7.14 (4H, m). |
| III-41 | 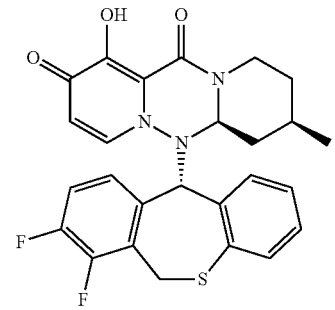 [SMILES: C[C@@H]1CCN2C(=O)c3c(O)c(=O)ccn3N([C@@H]3c4ccccc4SCc4c3ccc(F)c4F)[C@@H]2C1] | 1H-NMR (CDCl3) δ: 0.96 (3H, d, J = 6.5 Hz), 1.16-1.20 (1H, m), 1.34-1.40 (1H, m), 1.64-1.79 (3H, m), 1.85-1.89 (1H, m), 2.52 (1H, td, J = 13.1, 2.6 Hz), 4.05 (1H, d, J = 13.8 Hz), 4.28 (1H, dd, J = 11.5, 2.2 Hz), 4.70 (1H, dd, J = 13.3. 3.6 Hz), 5.23 (1H, s), 5.36 (1H, dd, J = 13.7, 2.4 Hz), 5.79 (1H, d, J = 7.8 Hz), 6.68 (1H, d, J = 7.5 Hz), 6.82-6.86 (1H, m), 6.98 (1H, dd, J = 8.3, 5.3 Hz), 7.02-7.15 (4H, m). |

TABLE 5

| | | |
|---|---|---|
| III-43 | (structure) | 1H-NMR (CDCl3) δ: 1.55 (1H, ddd, J = 26.3, 13.0, 4.6 Hz), 1.74 (1H, q, J = 12.3 Hz), 1.89 (1H, d, J = 13.1 Hz), 2.09 (1H, d, J = 12.7 Hz), 2.58 (1H, td, J = 13.2, 2.6 Hz), 2.40-2.52 (1H, m), 3.54 (1H, d, J = 13.4 Hz), 4.35 (1H, dd, J = 11.7, 2.3 Hz), 4.84 (1H, dd, J = 13.4, 3.8 Hz), 5.23 (1H, s), 5.57 (1H, d, J = 13.4 Hz), 5.80 (1H, d, J = 7.7 Hz), 6.69 (1H, d, J = 7.7 Hz), 6.82-6.86 (1H, m), 6.98 (1H, td, J = 8.2, 2.6 Hz), 7.07-7.14 (4H, m), 7.20 (1H, dd, J = 8.3, 5.5 Hz). |
| III-44 | (structure) | 1H-NMR(CDCl3) δ: 1.83-2.00 (m, 1H), 2.08-2.23 (m, 2H), 2.37 (t, J = 13.6 Hz, 1H), 2.74 (t, J = 13.2 Hz, 1H), 3.63 (d, J = 13.6 Hz, 1H), 4.51 (d, J = 11.6 Hz, 1H), 4.76-4.84 (m, 1H), 5.54 (d, J = 13.2 Hz, 1H), 5.79 (d, J = 8.0 Hz, 1H), 5.87 (s, 1H), 6.77 (d, J = 7.2 Hz, 1H), 6.85 (t, J = 7.2 Hz, 1H), 7.04-7.18 (m, 5H), 7.35-7.43 (m, 1H). |
| III-45 | (structure) | 1H-NMR(CDCl3) δ: 0.82 (s, 3H), 0.96 (s, 3H), 1.30-1.61 (m, 4H), 2.71 (t, J = 13.2 Hz, 1H), 1.99 (d, J = 12.8 Hz, 1H), 2.54 (t, J = 12.8 Hz, 1H), 4.04 (d, J = 13.6 Hz, 1H), 4.27 (dd, J = 2.0 Hz, 11.2 Hz, 1H), 4.69-4.74 (m, 1H), 5.23 (s, 1H), 5.35 (dd, J = 2.4 Hz, 13.6 Hz, 1H), 5.77 (d, J = 7.6 Hz, 1H), 6.68 (d, J = 7.6 Hz, 1H), 6.80-6.86 (m, 1H), 6.95-7.00 (m, 1H), 7.03-7.14 (m, 4H). |
| III-46 | (structure) | 1H-NMR(CDCl3) δ: 1.83-2.00 (m, 1H), 2.07-2.27 (m, 2H), 2.37 (t, J = 13.2 Hz, 1H), 2.67 (t, J = 13.2 Hz, 1H), 3.54 (d, J = 13.2 Hz, 1H), 4.51 (d, J = 11.2 Hz, 1H), 4.75-4.82 (m, 1H), 5.24 (s, 1H), 5.50 (d, J = 13.2 Hz, 1H), 5.77 (d, J = 7.2 Hz, 1H), 6.68 (d, J = 7.6 Hz, 1H), 6.80-6.86 (m, 1H), 6.95-7.02 (m, 1H), 7.05-7.14 (m, 4H), 7.16-7.23 (m, 1H) |
| III-47 | (structure) | 1H-NMR(CDCl3) δ: 0.82 (s, 3H), 0.97 (s, 3H), 1.24-1.44 (m, 2H), 1.46-1.60 (m, 2H), 2.58-2.68 (m, 1H), 3.50 (d, J = 13.2 Hz, 1H), 4.44 (dd, J = 2.8 Hz, 11.6 Hz, 1H), 4.57 (dd, J = 2.8 Hz, 13.2 Hz, 1H), 5.23 (s, 1H), 5.58 (d, J = 13.6 Hz, 1H), 5.78 (d, J = 7.6 Hz, 1H), 6.68 (d, J = 7.6 Hz, 1H), 6.80-6.86 (m, 1H), 6.95-7.03 (m, 2H), 7.05-7.13 (m, 3H), 7.18-7.24 (m, 1H). |

TABLE 5-continued

| | | |
|---|---|---|
| III-48 | *(structure)* | 1H-NMR(CDCl3) δ: 0.10-0.16 (m, 1H), 0.25-0.31 (m, 1H), 0.36-0.49 (m, 2H), 0.79 (d, J = 14.0 Hz, 1H), 0.99 (d, J = 12.8 Hz, 1H), 1.92-2.03 (m, 1H), 2.18 (t, J = 12.0 Hz, 1H), 2.65-2.77 (m, 1H), 3.58 (d, J = 13.6 Hz, 1H), 4.45 (dd, J = 2.4 Hz, 11.6 Hz, 1H), 4.73 (dd, J = 3.6 Hz, 13.2 Hz, 1H), 5.58 (d, J = 13.6 Hz, 1H), 5.81 (d, J = 7.6 Hz, 1H), 5.88 (s, 1H), 6.78 (d, J = 7.2 Hz, 1H), 6.81-6.88 (m, 1H), 7.05-7.16 (m, 5H), 7.34-7.43 (m, 1 H). |

TABLE 6

| | | |
|---|---|---|
| III-49 | *(structure)* | 1H-NMR (CDCl3) δ: 0.95 (d, J = 6.5 Hz, 3H), 1.12-1.24 (m, 1H), 1.36 (dd, J = 24.1, 11.7 Hz, 1H), 1.48-1.75 (m, 2H), 1.86 (d, J = 12.7 Hz, 1H), 2.59 (td, J = 13.1, 2.8 Hz, 1H), 3.59 (d, J = 13.3 Hz, 1H), 4.28 (dd, J = 11.5, 2.4 Hz, 1H), 4.73 (dd, J = 13.6, 3.0 Hz, 1H), 5.66 (d, J = 13.3 Hz, 1H), 5.79 (d, J = 7.7 Hz, 1H), 5.85 (s, 1H), 6.77-6.79 (m, 1H), 6.82-6.86 (m, 1H), 7.03-7.11 (m, 3H), 7.14 (d, J = 7.7 Hz, 2H), 7.36 (td, J = 8.0, 5.5 Hz, 1H). |
| III-50 | *(structure)* | 1H-NMR (CDCl3) δ: 0.95 (d, J = 6.5 Hz, 3H), 1.12-1.28 (m, 1H), 1.36 (q, J = 12.0 Hz, 1H), 1.63-1.78 (m, 3H), 1.86 (d, J = 12.8 Hz, 1H), 2.52 (td, J = 13.1, 2.8 Hz, 1H), 3.51 (d, J = 13.4 Hz, 1H), 4.28 (dd, J = 11.6, 2.3 Hz, 1H), 4.69 (dd, J = 13.5, 3.3 Hz, 1H), 5.22 (s. 1H), 5.62 (d, J = 13.4 Hz, 1H), 5.78 (d, J = 7.7 Hz, 1H), 6.68 (d, J = 7.7 Hz, 1H), 6.81-6.85 (m, 1H), 6.97 (td, J = 8.3, 2.6 Hz, 1H), 7.05-7.10 (m, 4H), 7.20 (dd, J = 8.4, 5.4 Hz, 1H). |
| III-51 | *(structure)* | 1H-NMR (CDCl3) δ: 1.17 (d, J = 6.1 Hz, 3H), 2.61 (dd, J = 13.3, 10.7 Hz, 1H), 3.54-3.59 (m, 1H), 3.64 (t, J = 10.6 Hz, 1H), 3.96 (dd, J = 11.1, 2.9 Hz, 1H), 4.07 (d, J = 13.8 Hz, 1H), 4.54 (dd, J = 10.0, 2.9 Hz, 1H), 4.64 (dd, J = 13.4, 2.3 Hz, 1H), 5.26-5.30 (m, 2H), 5.75 (d, J = 7.7 Hz, 1H), 6.68 (d, J = 7.7 Hz, 1H), 6.85 (t, J = 7.2 Hz, 1H), 6.98-7.03 (m, 2H), 7.07-7.15 (m, 3H). |
| III-52 | *(structure)* | 1H-NMR (CDCl3) δ: 1.16 (d, J = 6.0 Hz, 3H), 2.55-2.65 (m, 1H), 3.48-3.60 (m, 2H), 3.64 (t, J = 10.4 Hz, 1H), 3.94 (dd, J = 2.8 Hz, 11.2 Hz, 1H), 4.54 (dd, J = 2.8 Hz, 10.0 Hz, 1H), 4.62 (dd, J = 2.0 Hz, 13.6 Hz, 1 H), 5.25 (s, 1H), 5.54 (d, J = 13.2 Hz, 1H), 5.74 (d, J = 7.2 Hz, 1H), 6.68 (d, J = 7.2 Hz, 1H), 6.79-6.86 (m, 1H), 6.96-7.05 (m, 2H), 7.05-7.15 (m, 3H), 7.17-7.24 (m, 1H). |

TABLE 7

| ID | Structure | 1H-NMR |
|---|---|---|
| III-53 | 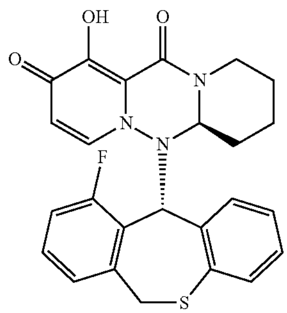 [SMILES: O=C1c2c(O)c(=O)ccn2N([C@@H]2c3ccccc3SCc3cccc(F)c32)[C@@H]2CCCCN12] | 1H-NMR (CDCl3) δ: 1.45-1.74 (m, 4H), 1.85 (d, J = 12.0 Hz, 1H), 1.95-2.02 (m, 1H), 2.61 (t, J = 12.4 Hz, 1H), 3.58 (d, J = 14.0 Hz, 1H), 4.27 (d, J = 10.8 Hz, 1H), 4.74 (d, J = 12.4 Hz, 1H), 5.65 (d, J = 14.0 Hz, 1H), 5.78 (d, J = 6.8 Hz, 1H), 5.85 (s, 1H), 6.75-6.88 (m, 2H), 7.02-7.15 (m, 5H), 7.34-7.40 (m, 1H). |
| III-55 | 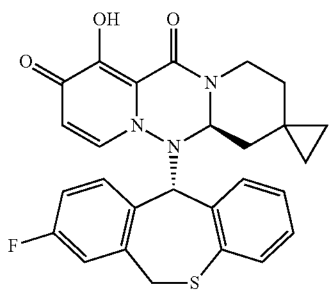 [SMILES: O=C1c2c(O)c(=O)ccn2N([C@H]2c3ccc(F)cc3CSc3ccccc32)[C@@H]2CC3(CCN12)CC3] | 1H-NMR (CDCl3) δ: 0.12-0.18 (m, 1H), 0.25-0.31 (m, 1H), 0.36-0.49 (m, 2H), 0.78 d, J = 14.0 Hz, 1H), 0.99 (d, J = 12.4 Hz, 1H), 1.92-2.00 (m, 1H), 2.18 (t, J = 11.6 Hz, 1H), 2.58-2.68 (m, 1H), 3.48 (d, J = 13.2 Hz, 1H), 4.44 (dd, J = 2.0 Hz, 11.6 Hz, 1H), 4.70 (dd, J = 3.2 Hz, 12.8 Hz, 1H), 5.24 (s, 1H), 5.53 (d, J = 13.6 Hz, 1H), 5.77 (d, J = 8.0 Hz, 1H), 6.89 (d, J = 7.2 Hz, 1H), 6.80-6.87 (m, 1H), 6.95-7.02 (m, 2H), 7.03-7.14 (m, 3H), 7.20-7.26 (m, 1H). |
| III-57 | 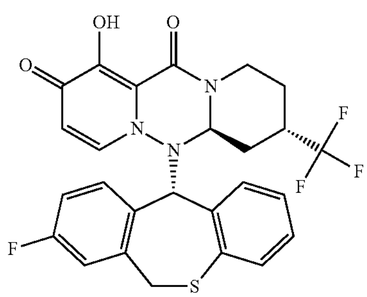 [SMILES: O=C1c2c(O)c(=O)ccn2N([C@H]2c3ccc(F)cc3CSc3ccccc32)[C@@H]2C[C@@H](C(F)(F)F)CCN12] | 1H-NMR δ: 7.20 (dd, J = 8.6, 5.5 Hz, 1H), 7.14-7.08 (m, 3H), 7.03-6.97 (m, 2H), 6.85-6.82 (m, 1H), 6.68 (d, J = 7.7 Hz, 1H), 5.81 (d, J = 7.5 Hz, 1H), 5.53 (d, J = 13.6 Hz, 1H), 5.21 (s, 1H), 4.69-4.63 (m, 1H), 3.54 (d, J = 13.6 Hz, 1H), 2.85-2.80 (m, 1H), 2.66 (brs, 1H), 2.15-2.00 (m, 2H), 1.95-1.80 (m, 2H) |
| III-58 | 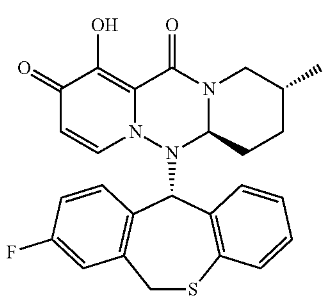 [SMILES: C[C@@H]1CC[C@@H]2N(C1)C(=O)c1c(O)c(=O)ccn1N2[C@H]1c2ccc(F)cc2CSc2ccccc21] | 1H-NMR (CDCl3) δ: 0.90 (d, J = 6.5 Hz, 3H), 1.23 (ddd, J = 25.6, 12.8, 4.1 Hz, 1H), 1.63-1.86 (m, 3H), 1.95 (d, J = 13.7 Hz, 1H), 2.17 (t, J = 12.3 Hz, 1H), 3.51 (d, J = 13.4 Hz, 1H), 4.25 (d, J = 11.0 Hz, 1H), 4.60 (d, J = 12.0 Hz, 1H), 5.21 (s, 1H), 5.61 (d, J = 13.3 Hz, 1H), 5.78 (d, J = 7.7 Hz, 1H), 6.68 (d, J = 7.8 Hz, 1H), 6.83 (t, J = 6.7 Hz, 1H), 6.99 (t, J = 8.2 Hz, 1H), 7.05-7.09 (m, 4H), 7.20 (dd, J = 8.1, 5.7 Hz, 1H). |
| III-59 | 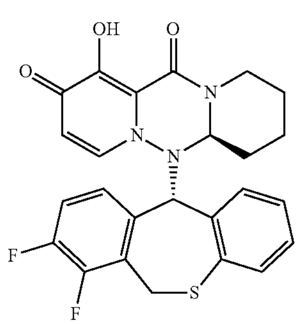 | 1H-NMR (CDCl3) δ: 1.45-1.79 (m, 4H), 1.87 (d, J = 10.8 Hz, 1H), 1.99 (d, J = 12.8 Hz, 1H), 2.54 (t, J = 12.8 Hz, 1H), 4.04 (d, J = 13.6 Hz, 1H), 4.27 (dd, J = 2.0 Hz, 11.2 Hz, 1H), 4.69-4.74 (m, 1H), 5.23 (s, 1H), 5.35 (dd, J = 2.4 Hz, 13.6 Hz, 1H), 5.77 (d, J = 7.6 Hz, 1H), 6.68 (d, J = 7.6 Hz, 1H), 6.80-6.86 (m, 1H), 6.95-7.00 (m, 1H), 7.03-7.14 (m, 4H). |

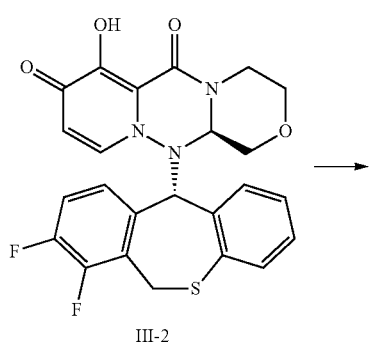

III-2

↓

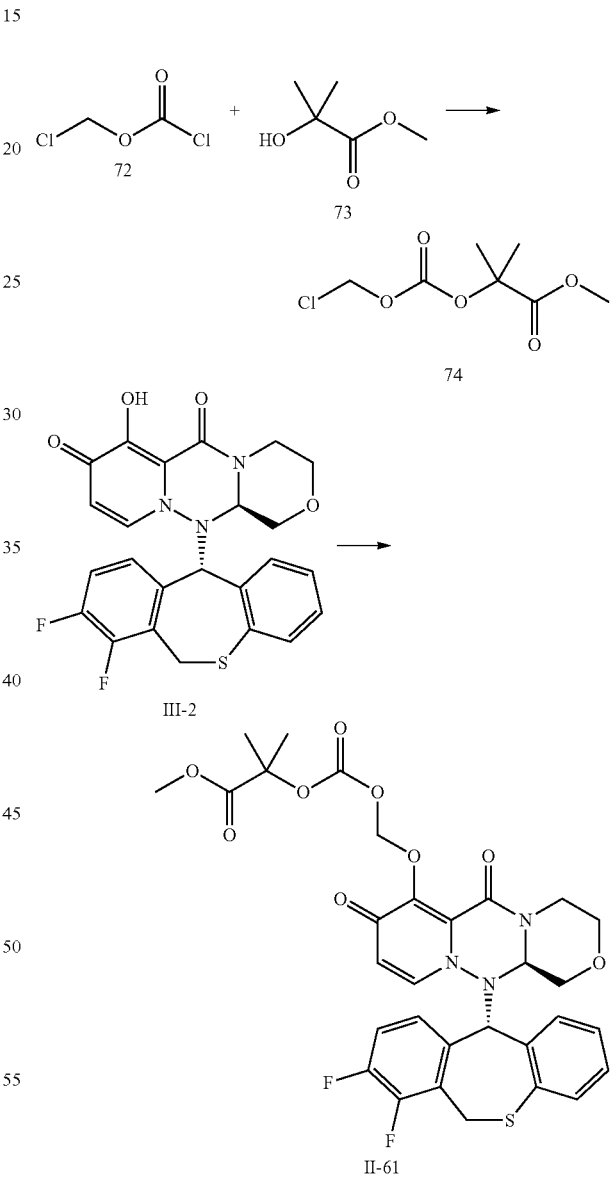

To Compound III-2 (4.0 g, 8.3 mmol) were added potassium carbonate (1483.4 mg, 10.7 mmol), potassium iodide (549.5 mg, 3.3 mmol), tetrahydrofuran (33.1 g), N,N-dimethylacetamide (3.8 g), and water (80.3 mg), and the mixture was stirred. The temperature was increased to 60° C., and chloromethyl methyl carbonate (1758.9 mg, 14.2 mmol) was added. The mixture was stirred at 60° C. for 9 hours and cooled to 20° C. Acetic acid (822.0 mg), 2-propanol (3.1 g), and water (20.0 g) were added, and the mixture was extracted twice with tetrahydrofuran (1.8 g, 8.9 g). The obtained organic layer was concentrated under reduced pressure to a liquid weight of about 32 g by distilling off the solvent. The temperature was increased to 45° C., 2-propanol (1.6 g) was added, and the mixture was cooled to 20° C. An aqueous solution of sodium acetate prepared from sodium acetate (339.0 mg) and water (46.0 g) was added, and the mixture was cooled to 5° C. The mixture was stirred at 5° C. for 3 hours, and the produced pale yellowish white precipitates were filtered. The obtained solids were washed with a mixed solution of 2-propanol (4.7 g) and water (6.0 g), and the solids were washed with 2-propanol (6.3 g) again. Dimethylsulfoxide (30.9 g) was added to the obtained pale yellowish white solids, and the mixture was stirred. The temperature was increased to 60° C., and a mixed solution of dimethylsulfoxide (2.2 g) and water (4.8 g) was added. Further, a mixed solution of dimethylsulfoxide (19.9 g) and water (28.4 g) was added, and the mixture was cooled to 20° C. The mixture was stirred at 20° C. for 3 hours, and the produced white precipitates were filtered. The obtained solids were washed with a mixed solution of dimethylsulfoxide (8.0 g) and water (4.8 g), and the solids were washed with water (12.0 g) again. The obtained solids were dried to obtain white crystals (1-form) of Compound II-6 (4.21 g).

$^1$H-NMR (DMSO-D6) δ: 2.91-2.98 (1H, m), 3.24-3.31 (1H, m), 3.44 (1H, t, J=10.4 Hz), 3.69 (1H, dd, J=11.5, 2.8 Hz), 3.73 (3H, s), 4.00 (1H, dd, J=10.8, 2.9 Hz), 4.06 (1H, d, J=14.3 Hz), 4.40 (1H, d, J=11.8 Hz), 4.45 (1H, dd, J=9.9, 2.9 Hz), 5.42 (1H, dd, J=14.4, 1.8 Hz), 5.67 (1H, d, J=6.5 Hz), 5.72-5.75 (3H, m), 6.83-6.87 (1H, m), 7.01 (1H, d, J=6.9 Hz), 7.09 (1H, dd, J=8.0, 1.1 Hz), 7.14-7.18 (1H, m), 7.23 (1H, d, J=7.8 Hz), 7.37-7.44 (2H, m).

Powder X-ray diffraction 2θ(°): 8.6±0.2°, 14.1±0.2°, 17.4±0.2°, 20.0±0.2°, 24.0±0.2°, 26.3±0.2°, 29.6±0.2°, and 35.4±0.2°.

Figure 3:
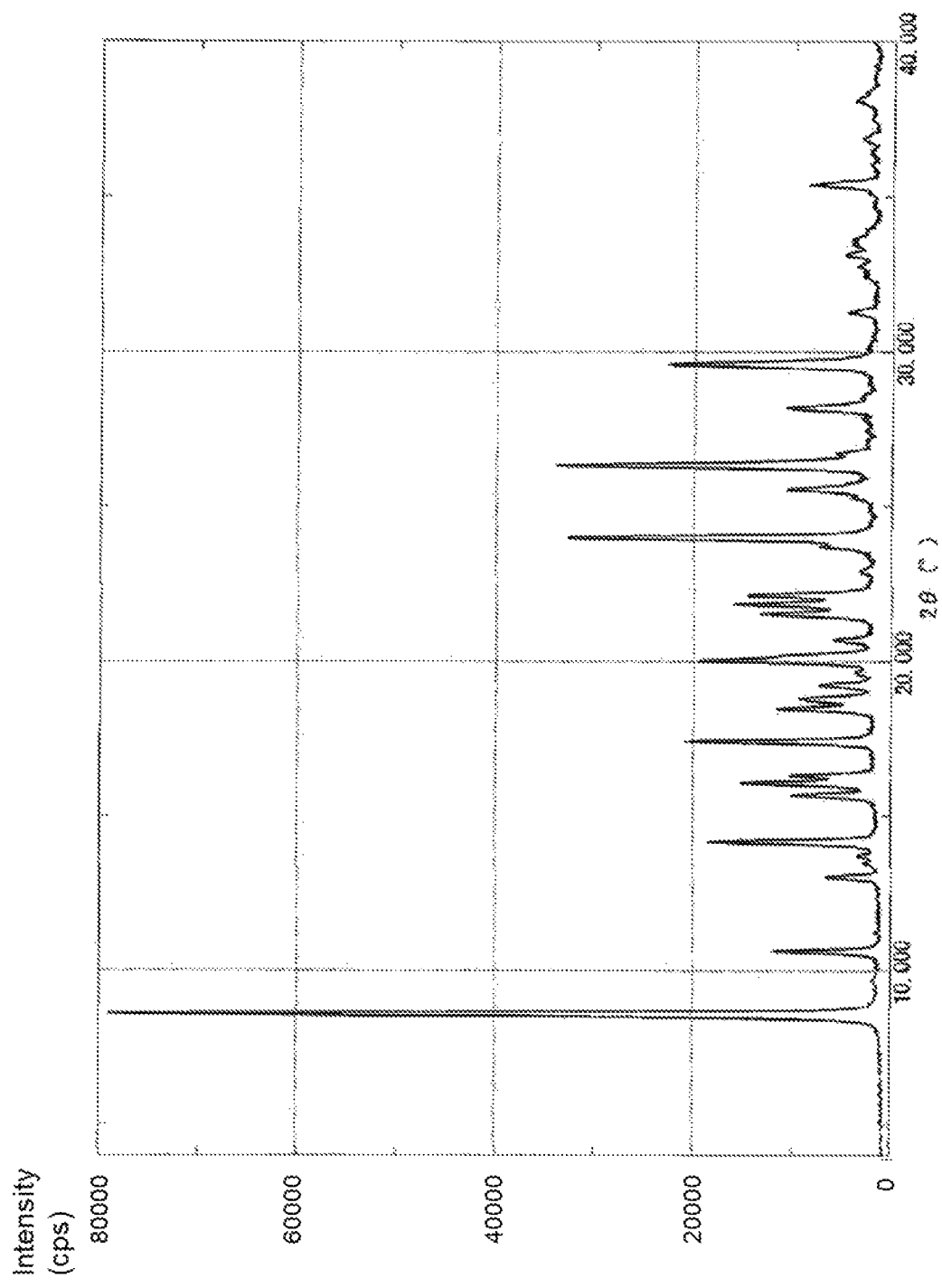
FIG. 3 is powder X-ray diffraction data of I-form crystals of Compound II-6. The horizontal axis indicates 2θ, and the vertical axis indicates intensity.

FIG. 3 shows powder X-ray diffraction results of I-form crystals of Compound II-6.

Example 11: Method for Producing Compound II-61

First Step

To a solution of chloromethyl chloroformate (300 mg, 2.33 mmol) and Compound 73 (330 mg, 2.79 mmol) in dichloromethane (6.0 mL) was added pyridine (207 μL, 2.56 mmol) at 0° C. under nitrogen atmosphere, and the mixture was stirred at 0° C. for 30 minutes, was warmed up to room temperature and was stirred for 1 hour. To the mixture was added 2 mol/L aqueous solution of hydrochloric acid and the mixture was extracted with dichloromethane. The obtained organic layer was washed with brine, dried over anhydrous magnesium sulfate, and concentrated under reduced pressure to obtain Compound 74 (440 mg, 90%).

1H-NMR (CDCl3) δ:1.65 (s, 6H), 3.77 (s, 3H), 5.71 (s, 2H).

Second Step

Compound III-2 (300 mg, 0.62 mmol), potassium carbonate (172 mg, 1.24 mmol), potassium iodide (103 mg, 0.62 mmol) and Compound 74 (261 mg, 1.24 mmol) were dissolved in DMA (3.0 mL) and the mixture was stirred at 80° C. for 3 hours. To the mixture was added 2 mol/L aqueous solution of hydrochloric acid and the mixture was extracted with ethyl acetate. The obtained organic layer was washed with brine, dried over anhydrous magnesium sulfate, and concentrated under reduced pressure. The obtained residue was purified by silica gel column chromatography (chloroform-methanol) to obtain Compound II-61 (360 mg, 86%).

1H-NMR (CDCl3) δ: 1.63 (s, 3H), 1.67 (s, 3H), 2.86-2.93 (m, 1H), 3.38-3.61 (m, 2H), 3.68-3.78 (m, 4H), 3.90-3.96 (m, 1H), 4.06 (d, J=14.0 Hz, 1H), 4.51 (dd, J=2.0 Hz, 9.6 Hz, 1H), 4.65 (d, J=12.4 Hz, 1H), 5.21 (d, J=14.4 Hz, 1H), 5.36 (s, 1H), 5.80-5.95 (m. 3H), 6.85-6.92 (m, 2H), 7.03-7.22 (m, 6H).

Example 12: Method for Producing Compound II-4

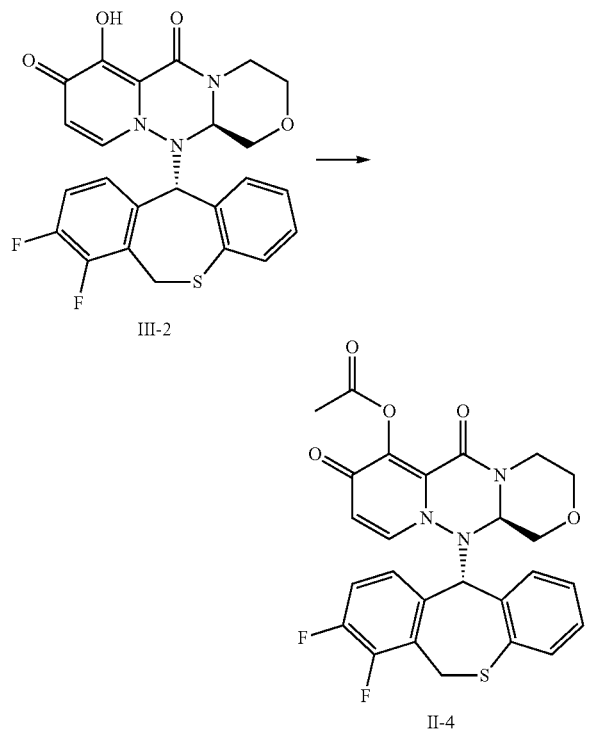

To a solution of Compound III-2 (90 mg, 0.186 mmol) in dichloromethane (2 mL) were added acetic anhydride (0.053 mL, 0.558 mmol), triethylamine (0.077 mL, 0.558 mmol) and a catalytic amount of DMAP, and the mixture was stirred at room temperature for 2 hours. The mixture was concentrated under reduced pressure and the obtained residue was purified by silica gel column chromatography (chloroform-methanol). To the obtained solution was added ether and the precipitated solid was filtered to obtain Compound II-4 (71 mg, 73%).

1H-NMR (CDCl3) δ:2.46 (s, 3H), 2.88-2.99 (m, 1H), 3.35-3.50 (m, 1H), 3.60-3.65 (m, 1H), 3.75-3.83 (m, 1H), 3.90-4.00 (m, 1H), 4.05 (d, J=14.0 Hz, 1H), 4.52-4.57 (m, 1H), 4.60-4.70 (m, 1H), 5.24-5.34 (m, 1H), 5.35 (s, 1H), 5.88 (d, J=7.6 Hz, 1H), 6.85-6.82 (m, 1H), 6.90-7.05 (m, 2H), 7.06-7.20 (m, 4H)

LC/MS (ESI): m/z=526.2 [M+H]+, RT=1.87 min, method (1)

Example 13: Method for Producing Compound II-65

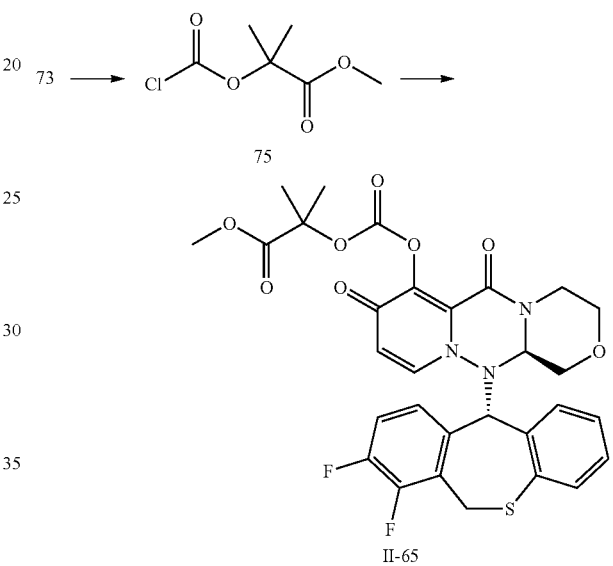

First Step

To a solution of triphosgene (300 mg, 2.54 mmol) in dichloromethane (6.0 mL) was added pyridine (257 μL, 3.17 mmol) at 0° C. under nitrogen atmosphere and the mixture was stirred for 15 minutes. To the mixture was added a solution of Compound 73 (377 mg, 1.27 mmol) in dichloromethane (1.0 mL), and the mixture was stirred at 0° C. for 15 minutes, warmed up to room temperature and stirred for 15 minutes. The mixture was concentrated under reduced pressure, ethyl acetate (4.0 mL) was added thereto, and the mixture was filtered. The filtrate was concentrated under reduced pressure to obtain Compound 75 (380 mg).

Second Step

To a solution of Compound III-2 (350 mg, 0.724 mmol) in dichloromethane (3.5 mL) were added Compound 75 (196 mg, 1.09 mmol) and triethylamine (301 μL, 2.17 mmol) at 0° C. and the mixture was stirred at 0° C. for 30 minutes. To the mixture was added 2 mol/L aqueous solution of hydrochloric acid and the mixture was extracted with dichloromethane. The obtained organic layer was washed with brine, dried over anhydrous magnesium sulfate, and concentrated under reduced pressure. The obtained residue was purified by silica gel column chromatography (chloroform-methanol) to obtain Compound II-65 (380 mg, 84%).

1H-NMR (CDCl3) δ:1.73 (s, 3H), 1.77 (s, 3H), 2.90-2.99 (m, 1H), 3.37-3.43 (m, 1H), 3.57 (t, J=8.8 Hz, 1H), 3.76 (dd, J=2.8 Hz, 12.0 Hz, 1H), 3.81 (s, 3H), 3.94 (dd, J=2.8 Hz, 10.8 Hz, 1H), 4.05 (d, J=14.0 Hz, 1H), 4.55 (dd, J=2.8 Hz, 9.6 Hz, 1H), 4.65 (d, J=12.0 Hz, 1H), 5.28 (d, J=12.0 Hz, 1H), 5.34 (s, 1H), 5.89 (d, J=8.0 Hz, 1H), 6.86-6.95 (m, 2H), 7.03-7.15 (m, 5H).

Example 14: Method for Producing Compound II-129

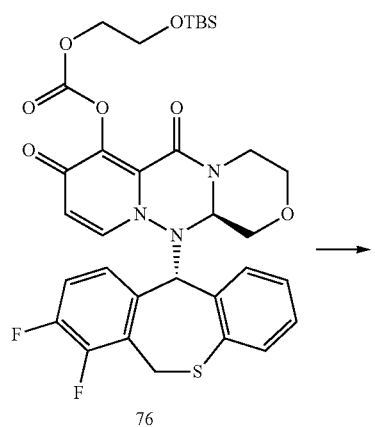

76

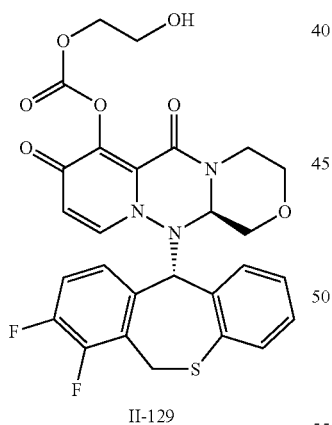

II-129

To a solution of Compound 76 (276 mg, 0.402 mmol) in THF (1 mL) were added acetic acid (121 mg, 2.01 mmol) and 1 mol/L TBAF in THF (1.21 mL, 1.21 mmol) under ice-water bath and the mixture was stirred at room temperature for 4 hours. The mixture was concentrated under reduced pressure. The obtained residue was purified by silica gel column chromatography (ethyl acetate-methanol) to obtain Compound II-129 (179 mg, 78%).

LC/MS (ESI): m/z=572.0 [M+H]$^+$, RT=1.74 min, method (2)

Example 15: Method for Producing Compound II-115

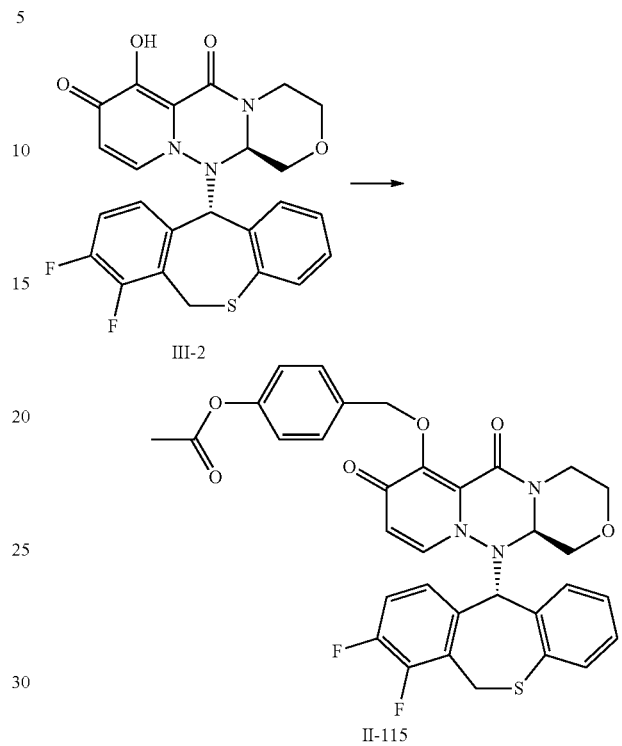

III-2

II-115

To a solution of Compound III-2 (300 mg, 0.62 mmol) in DMF (4 mL) were added potassium carbonate (258 mg, 1.87 mmol), 4-(chloromethyl)phenyl acetate (344 mg, 1.87 mmol) and sodium iodide (139 mg, 1.87 mmol) at room temperature and the mixture was stirred at 65° C. for 1 hour. To the mixture was added water and the mixture was extracted with ethyl acetate. The obtained organic layer was washed with water, dried over anhydrous sodium sulfate, and concentrated under reduced pressure. The obtained residue was purified by silica gel column chromatography (ethyl acetate-methanol) to obtain Compound II-115 (120 mg, 31%).

LC/MS (ESI): m/z=631.95 [M+H]$^+$, RT=2.07 min, method (2)

Example 16: Method for Producing Compound II-143

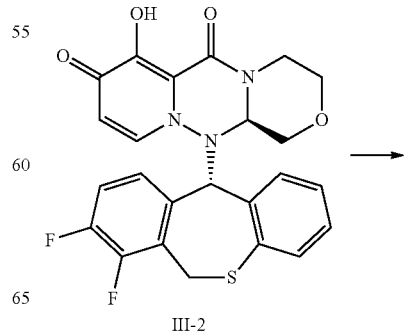

III-2

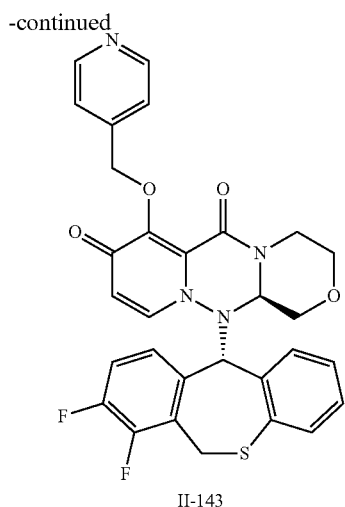

II-143

To a solution of Compound III-2 (150 mg, 0.31 mmol) in dichloromethane (2 mL) 3 mmol/g triphenylphosphine supported on polymer (310 mg, 0.93 mmol), pyridin-4-ylmethanol (68 mg, 0.62 mmol) and 40% DEAD in toluene (270 mg, 0.62 mmol) at room temperature and the mixture was stirred at room temperature for 30 minutes. The mixture was purified by amino column chromatography (ethyl acetate-methanol) to obtain Compound II-143 (63 mg, 35%).

LC/MS (ESI): m/z=575.00 [M+H]$^+$, RT=1.43 min, method (2)

Example 17: Method for Producing Compound II-27

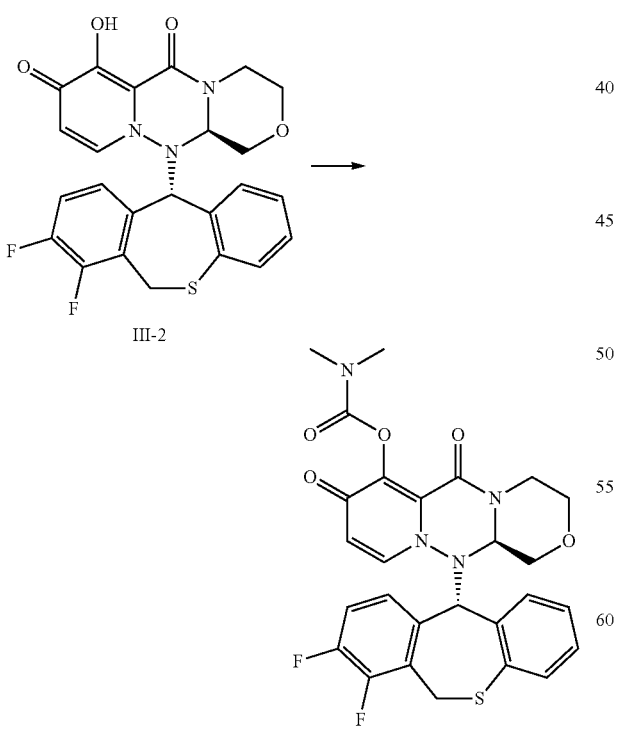

III-2

II-27

To a solution of Compound III-2 (65 mg, 0.134 mmol) in pyridine (0.8 mL) was added dimethylcarbamoyl chloride (21.7 mg, 0.202 mmol) and the mixture was stirred at 80° C. over night. To the mixture was added 1 mol/L aqueous solution of hydrochloric acid and the mixture was extracted with ethyl acetate. The obtained organic layer was washed with brine, dried over anhydrous magnesium sulfate, and concentrated under reduced pressure. The obtained residue was solidified with ethyl acetate-hexane to obtain Compound II-27 (65 mg, 87%).

1H-NMR (CDCl3) δ:2.89 (t, J=11.2 Hz, 1H), 2.99 (s, 1H), 3.01 (s, 3H), 3.18-3.26 (m, 4H), 3.45 (t, J=10.8 Hz, 1H), 3.59 (t, J=10.8 Hz, 1H), 3.70-3.80 (m, 1H), 3.90-3.98 (m, 1H), 4.03 (d, J=13.6 Hz, 1H), 4.50-4.70 (m, 2H), 5.21-5.35 (m, 2H), 5.82 (d, J=7.6 Hz, 1H), 6.91 (t, J=7.6 Hz, 1H), 7.00-7.20 (m, 6H).

Example 18: Method for Producing Compound II-55

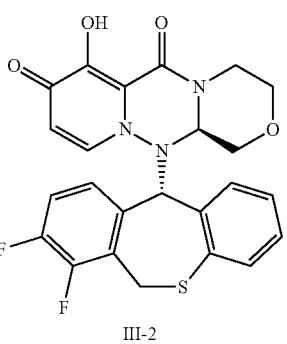

III-2

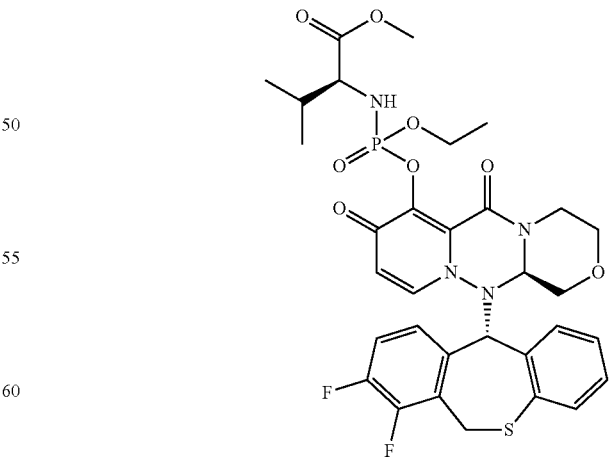

II-55

To a solution of ethyl phosphorodichloridate (135 mg, 0.829 mmol) in dichloromethane (3 mL) was added L-valine methyl ester hydrochloride (139 mg, 0.829 mmol) and then added dropwise a solution of triethylamine (168 mg, 1.66 mmol) in dichloromethane (2 mL) at −78° C. The mixture was stirred at room temperature for 1 hour. Compound III-2 (200 mg, 0.414 mmol) and triethylamine (126 mg, 1.25 mmol) were added thereto, and the mixture was stirred at same temperature for 6 hours. The mixture was concentrated and the obtained residue was purified by silica gel column chromatography (ethyl acetate-methanol) to obtain Compound II-55 (112 mg, 38%).

LC/MS (ESI): m/z=705.05 [M+H]$^+$, RT=2.18 min, method (2)

Example 19: Method for Producing Compound II-57

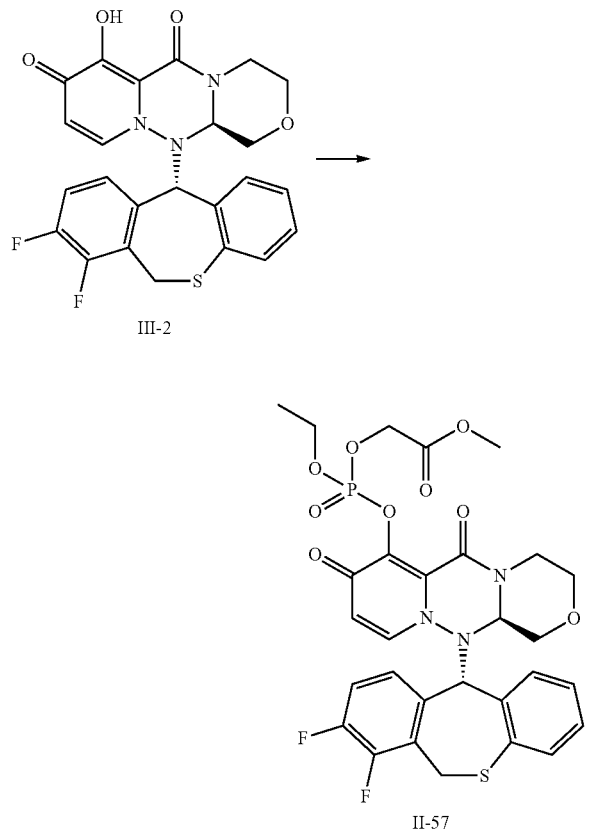

III-2

II-57

To a solution of ethyl phosphorodichloridate (202 mg, 1.24 mmol) in dichloromethane (3 mL) was added dropwise a mixture of triethylamine (126 mg, 1.24 mmol) and methyl glycolate (112 mg, 1.24 mmol) in dichloromethane (2 mL). The mixture was stirred at room temperature for 2 hours. Compound III-2 (200 mg, 0.414 mmol) and triethylamine (126 mg, 1.25 mmol) were added thereto and the mixture was stirred at same temperature for 1 hour. The mixture was concentrated and the obtained residue was purified by silica gel column chromatography (ethyl acetate-methanol) to obtain Compound II-57 (143 mg, 52%).

LC/MS (ESI): m/z=664.00 [M+H]$^+$, RT=1.93 min, method (2)

Example 20: Method for Producing Compound II-58

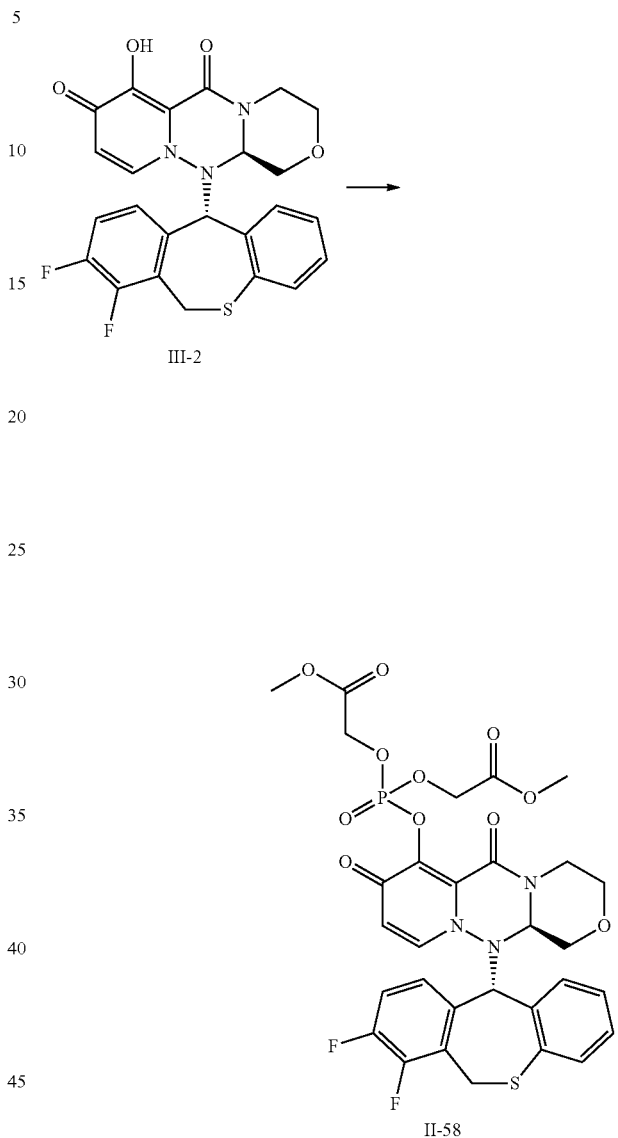

III-2

II-58

To a solution of phosphoryl chloride (1.53 g, 10 mmol) in dichloromethane (10 mL) was added dropwise the mixture of triethylamine (2.12 g, 20.95 mmol) and methyl glycolate (1.89 mg, 21 mmol) in dichloromethane (5 mL). The mixture was stirred at room temperature for 2 hours. To the mixture (2 mL) were added Compound III-2 (200 mg, 0.414 mmol) and triethylamine (126 mg, 1.25 mmol) and the mixture was stirred at same temperature for 1 hour. The mixture was concentrated and the obtained residue was purified by silica gel column chromatography (ethyl acetate-methanol) to obtain Compound II-58 (166 mg, 57%).

LC/MS (ESI): m/z=707.90 [M+H]$^+$, RT=1.93 min, method (2)

The following example compounds were synthesized from commercially available compounds or intermediates suitably synthesized from commercially available compounds according to the above examples.

TABLE 8

| No. | Structure | NMR or LC/MS |
|---|---|---|
| II-5 | 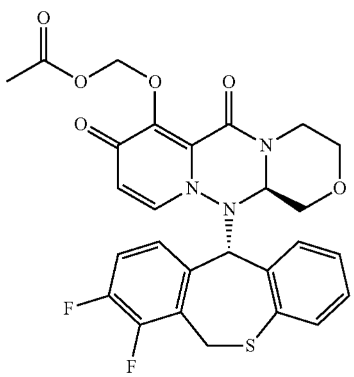 [SMILES: CC(=O)OCOc1c2n(ccc1=O)N([C@@H]1c3ccccc3SCc3c1ccc(F)c3F)[C@@H]1COCCN1C2=O] | 1H-NMR (DMSO-d6) δ: 2.04 (s, 3H), 2.90-3.00 (m, 1H), 3.44-3.50 (m, 2H), 3.64-3.72 (m, 1H), 3.95-4.00 (m, 1H), 4.11-4.10 (m, 1H), 4.20-4.30 (m, 2H), 5.40-5.5.46 (m, 1H), 6.62-5.75 (m, 4H), 6.80-6.90 (m, 1H), 6.98-7.10 (m, 1H), 7.11-7.20 (m, 2H), 7.21-7.30 (m, 1H), 7.45-7.50 (m, 2H) |
| II-7 | 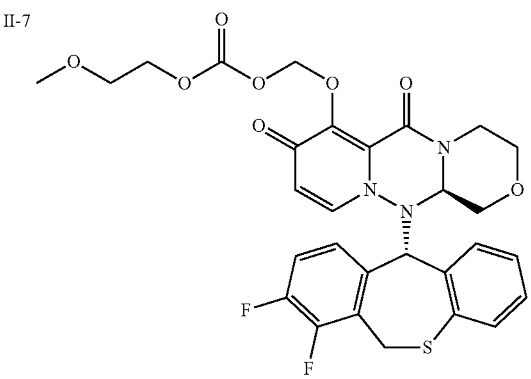 | 1H-NMR (CDCl3) δ: 2.85-2.97 (m, 1H), 3.38 (s, 3H), 3.39-3.48 (m, 1H), 3.54 (t, J = 10.4 Hz, 1H), 3.68 (t, J = 4.4 Hz, 2H), 3.74 (dd, J = 2.8 Hz, 12.0 Hz, 1H), 3.92 (dd, J = 2.8 Hz, 10.8 Hz, 1H), 4.05 (d, J = 13.6 Hz, 1H), 4.36 (q, J = 4.4 Hz, 2H), 4.51 (dd, J = 2.8 Hz, 9.6 Hz, 1H), 4.65 (d, J = 12.0 Hz, 1H), 5.27 (dd, J = 2.0 Hz, 13.6 Hz, 1H), 5.34 (s, 1H), 5.86 (d, J = 8.0 Hz, 1H), 5.93 (s, 2H), 6.81-6.89 (m, 2H), 6.98-7.15 (m, 5H). |
| II-8 | 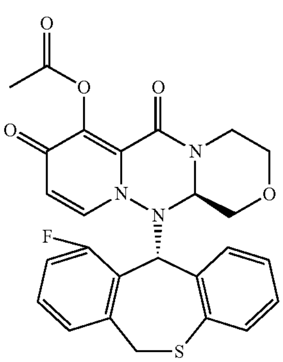 [SMILES: CC(=O)Oc1c2n(ccc1=O)N([C@@H]1c3ccccc3SCc3cccc(F)c31)[C@@H]1COCCN1C2=O] | LC/MS (ESI): m/z = 508 [M + H]+, RT = 1.76 min, method (2) |
| II-9 | 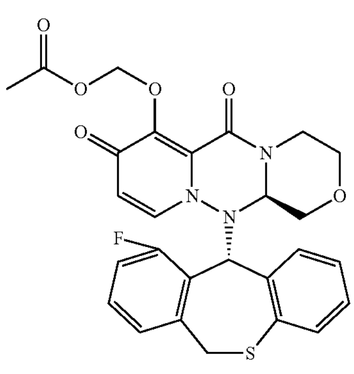 [SMILES: CC(=O)OCOc1c2n(ccc1=O)N([C@@H]1c3ccccc3SCc3cccc(F)c31)[C@@H]1COCCN1C2=O] | 1H-NMR (CDCl3) δ: 2.05 (s, 3H), 2.92-3.02 (m, 1H), 3.40-3.48 (m, 1H), 3.51-3.62 (m, 2H), 3.72-3.80 (m, 1H), 3.88-3.92 (m, 1H), 4.50-4.56 (m, 1H), 4.64-4.72 (m, 1H), 5.55 (d, J = 13.6 Hz, 1H), 5.78-5.82 (m, 1H), 5.84-5.88 (m, 1H), 5.90-5.98 (m, 2H), 6.82-7.00 (m, 2H), 7.00-7.20 (m, 5H), 7.35-7.42 (m, 1H) |

TABLE 8-continued

| No. | Structure | NMR or LC/MS |
|---|---|---|
| II-10 | 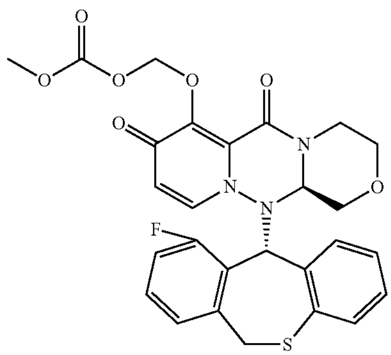 [SMILES: COC(=O)OCOc1c2n(ccc1=O)N([C@@H]1c3ccccc3SCc3cccc(F)c31)[C@@H]1COCCN1C2=O] | LC/MS (ESI): m/z = 554 [M + H]+, RT = 1.76 min, method (1) |
| II-11 | 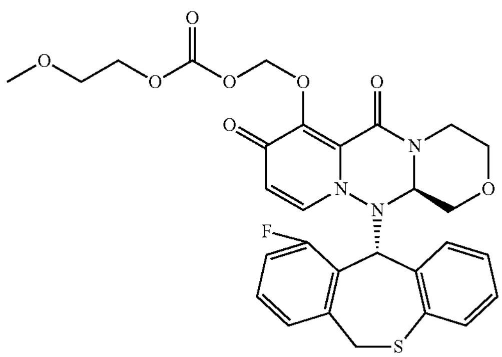 [SMILES: COCCOC(=O)OCOc1c2n(ccc1=O)N([C@@H]1c3ccccc3SCc3cccc(F)c31)[C@@H]1COCCN1C2=O] | LC/MS (ESI): m/z = 598 [M + H]+, RT = 1.80 min, method (2) |

TABLE 9

| No. | Structure | NMR or LC/MS |
|---|---|---|
| II-16 | 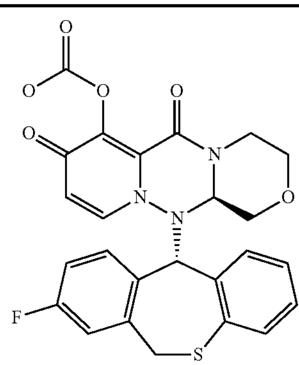 | LC/MS (ESI): m/z = 508 [M + H]+, RT = 1.76 min, method (2) |
| II-17 | 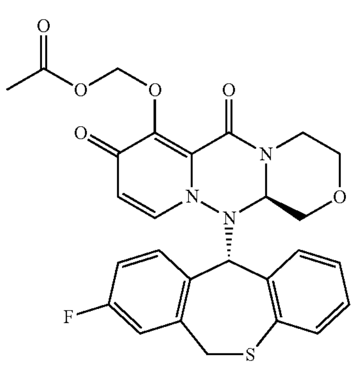 [SMILES: CC(=O)OCOc1c2n(ccc1=O)N([C@H]1c3ccc(F)cc3CSc3ccccc31)[C@@H]1COCCN1C2=O] | LC/MS (ESI): m/z = 538 [M + H]+, RT = 1.78 min, method (2) |

TABLE 9-continued

| No. | Structure | NMR or LC/MS |
| --- | --- | --- |
| II-18 | 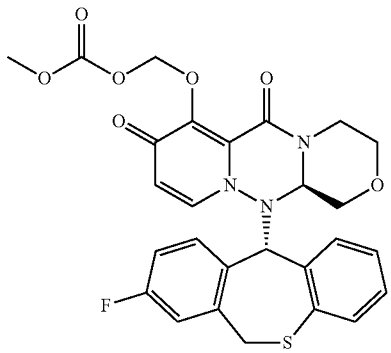 [SMILES: COC(=O)OCOc1c2n(ccc1=O)N([C@H]1c3ccc(F)cc3CSc3ccccc31)[C@@H]1COCCN1C2=O] | LC/MS (ESI): m/z = 554 [M + H]+, RT = 1.81 min, method (2) |
| II-19 | 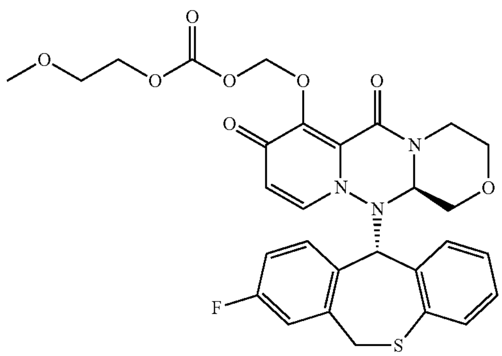 [SMILES: COCCOC(=O)OCOc1c2n(ccc1=O)N([C@H]1c3ccc(F)cc3CSc3ccccc31)[C@@H]1COCCN1C2=O] | LC/MS (ESI): m/z = 598 [M + H]+, RT = 1.85 min, method (2) |
| II-24 | 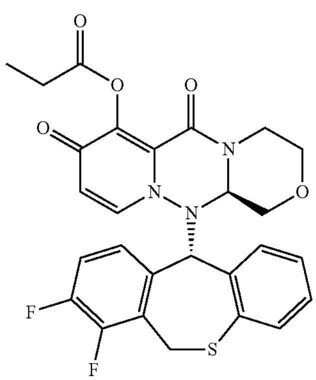 [SMILES: CCC(=O)Oc1c2n(ccc1=O)N([C@@H]1c3ccccc3SCc3c1ccc(F)c3F)[C@@H]1COCCN1C2=O] | 1H-NMR (CDCl3) δ: 1.33 (3H, t, J = 7.0 Hz), 2.82 (2H, d, J = 6.1 Hz), 2.93 (1H, t, J = 11.2 Hz), 3.42 (1H, t, J =11.4 Hz), 3.59 (1H, t, J = 10.2 Hz), 3.78 (1H, d, J = 11.2 Hz), 3.96 (1H, d, J = 10.3 Hz), 4.06 (1H, d, J = 13.8 Hz), 4.55 (1H, d, J = 8.9 Hz), 4.63 (1H. d, J = 13.6 Hz), 5.29 (1H, d, J = 13.9 Hz), 5.36 (1H, s), 5.88 (1H, d, J = 7.4 Hz), 6.90 (1H, s), 7.03-7.12 (6H, m). |
| II-25 | 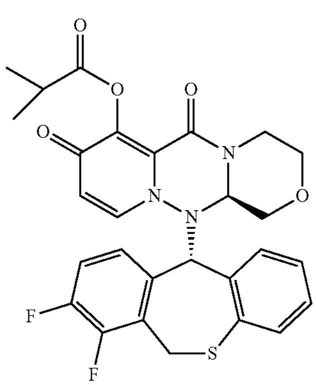 [SMILES: CC(C)C(=O)Oc1c2n(ccc1=O)N([C@@H]1c3ccccc3SCc3c1ccc(F)c3F)[C@@H]1COCCN1C2=O] | 1H-NMR (CDCl3) δ: 1.42 (d, J = 6.8 Hz, 6H), 2.85-3.05 (m, 2H), 3.40-3.49 (m, 1H), 3.59 (t, J = 10.4 Hz, 1H), 3.76 (d, J = 11.4 Hz, 1H), 3.94 (d, J = 10.4 Hz, 1H), 4.06 (d, J = 14.1 Hz, 1H), 4.51-4.57 (m, 1H), 4.59-4.70 (m, 1H), 5.25-5.32 (m, 1H), 5.35-5.39 (m, 1H), 5.80-5.89 (m, 1H), 6.85-7.15 (m, 7H). |

TABLE 10

| No. | Structure | NMR or LC/MS |
| --- | --- | --- |
| II-26 | 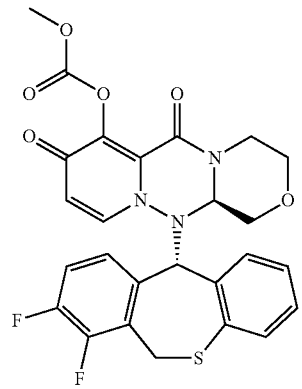 [SMILES: COC(=O)Oc1c2n(ccc1=O)N([C@@H]1c3ccccc3SCc3c1ccc(F)c3F)[C@@H]1COCCN1C2=O] | LC/MS (ESI): m/z = 542 [M + H]+, RT = 1.92 min, method (1) |
| II-28 | 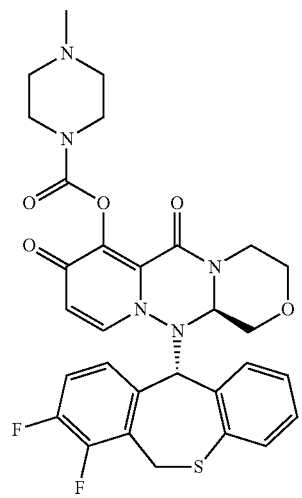 [SMILES: CN1CCN(C(=O)Oc2c3n(ccc2=O)N([C@@H]2c4ccccc4SCc4c2ccc(F)c4F)[C@@H]2COCCN2C3=O)CC1] | LC/MS (ESI): m/z = 610 [M + H]+, RT = 1.57 min, method (1) |
| II-29 | 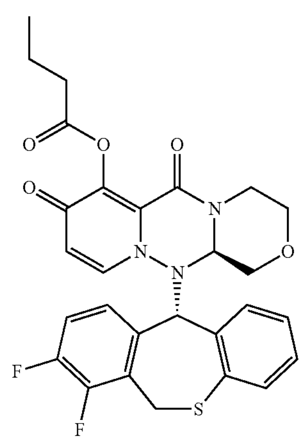 [SMILES: CCCC(=O)Oc1c2n(ccc1=O)N([C@@H]1c3ccccc3SCc3c1ccc(F)c3F)[C@@H]1COCCN1C2=O] | LC/MS (ESI): m/z = 554 [M + H]+, RT = 2.10 min, method (1) |

TABLE 10-continued

| No. | Structure | NMR or LC/MS |
|-----|-----------|--------------|
| II-30 | 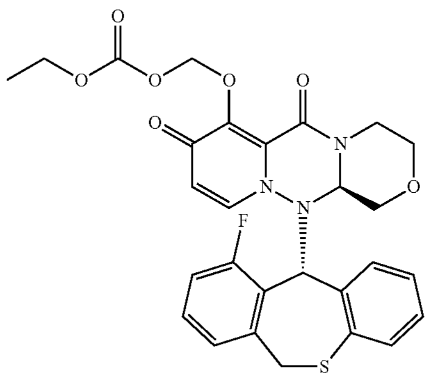 [SMILES: CCOC(=O)OCOc1c2n(ccc1=O)N([C@@H]1c3ccccc3SCc3cccc(F)c31)[C@@H]1COCCN1C2=O] | LC/MS (ESI): m/z = 568 [M + H]+, RT = 1.91 min, method (1) |
| II-31 | 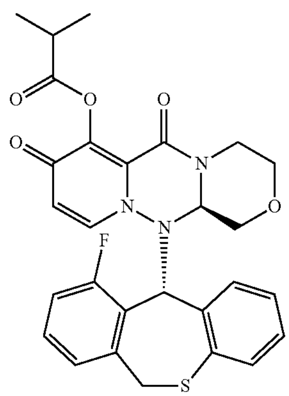 [SMILES: CC(C)C(=O)Oc1c2n(ccc1=O)N([C@@H]1c3ccccc3SCc3cccc(F)c31)[C@@H]1COCCN1C2=O] | 1H-NMR (CDCl3) δ: 1.42 (d, J = 6.8 Hz, 6H), 2.90-3.07 (m, 2H), 3.44 (t, J = 10.8 Hz, 1H), 3.60 (d, J = 12.8 Hz, 2H), 3.77 (d, J = 10.8 Hz, 1H), 3.93 (dd, J = 10.8, 2.8 Hz, 1H), 4.56 (dd, J = 9.6, 2.8 Hz, 1H), 4.67 (m, 1H), 5.59 (m, 1H), 5.87 (m, 1H), 5.59 (s, 1H), 6.91-7.21 (m, 7H), 7.38 (m, 1H). |

TABLE 11

| No. | Structure | NMR or LC/MS |
|-----|-----------|--------------|
| II-32 | 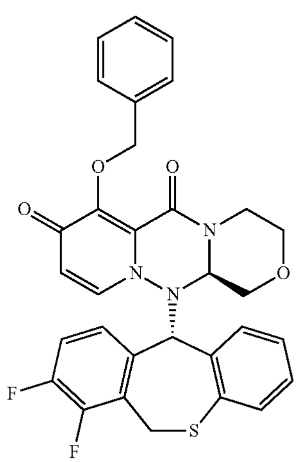 [SMILES: O=C1c2c(OCc3ccccc3)c(=O)ccn2N([C@@H]2c3ccccc3SCc3c2ccc(F)c3F)[C@@H]2COCCN12] | 1H-NMR (CDCl3) δ: 2.88 (1H, t, J = 11.2 Hz), 3.28-3.39 (2H, m), 3.72 (1H, d, J = 12.6 Hz), 3.86 (1H, d, J = 9.6 Hz), 4.03 (1H, d, J = 13.9 Hz), 4.45 (1H, d, J = 8.6 Hz), 4.67 (1H, d, J = 13.1 Hz), 5.19-5.26 (2H, m), 5.45 (1H, d, J = 10.9 Hz), 5.63 (1H, d, J = 10.9 Hz), 5.77 (1H, d, J = 7.6 Hz), 6.40 (1H, d, J = 7.8 Hz), 6.68 (1H, t, J = 6.9 Hz), 6.94-7.01 (2H, m), 7.03-7.12 (3H, m), 7.29-7.38 (3H, m), 7.61 (2H, d, J = 7.1 Hz). |

TABLE 11-continued
| No. | Structure | NMR or LC/MS |
|---|---|---|
| II-33 | 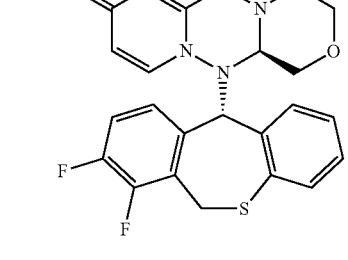 | 1H-NMR (CDCl3) δ: 1.46 (t, J = 7.2 Hz, 3H), 2.95 (m, 1H), 3.42 (td, J = 12.0, 2.4 Hz, 1H), 3.58 (t, J = 10.4 Hz, 1H), 3.78 (dd, J = 12.0, 2.8 Hz, 1H), 3.95 (dd, J = 11.2, 2.8 Hz, 1H), 4.07 (d, J = 13.6 Hz, 1H), 4.41 (m, 2H), 4.56 (dd, J = 10.0, 2.8 Hz, 1H), 4.67 (dd, J = 10.0, 2.4 Hz, 1H), 5.29 (dd, J = 2.0 Hz, 1H), 5.36 (s, 1H), 5.91 (d, J = 8.0 Hz, 1H), 6.88-7.15 (m, 7H). |
| II-34 | 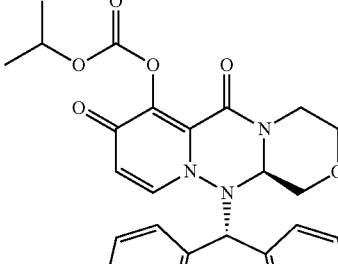 | 1H-NMR (CDCl3) δ: 1.46 (m, 6H), 2.95 (m, 1H), 3.41 (td, J = 12.0, 2.0 Hz, 1H), 3.58 (t, J = 10.8 Hz, 1H), 3.77 (dd, J = 12.0, 3.2 Hz, 1H), 3.95 (dd, J = 10.8, 2.4 Hz, 1H), 4.06 (d, J = 14.0 Hz, 1H), 4.55 (dd, J = 9.6, 2.8 Hz, 1H), 4.67 (d, J = 13.6 Hz, 1H), 5.04 (m, 1H), 5.29 (d, J = 13.6 Hz, 1H), 5.36 (s, 1H), 5.90 (d, J = 8.0 Hz, 1H), 6.90-7.13 (m, 7H). |
| II-36 | 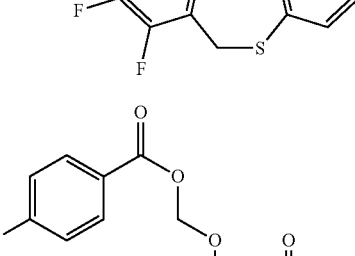 | LC/MS (ESI): m/z = 663 [M + H]+, RT = 2.29 min, method (1) |
| II-37 | 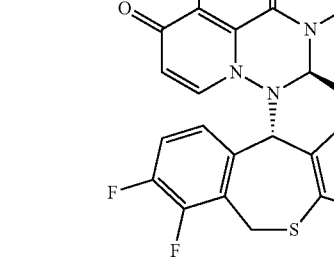 | LC/MS (ESI): m/z = 626 [M + H]+, RT = 2.18 min, method (1) |

TABLE 12

| No. | Structure | NMR or LC/MS |
|---|---|---|
| II-38 | 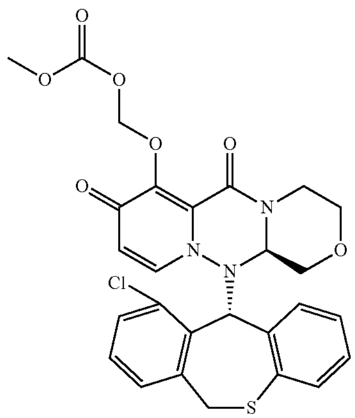 [SMILES: COC(=O)OCOc1c2n(ccc1=O)N([C@@H]1c3ccccc3SCc3cccc(Cl)c31)[C@@H]1COCCN1C2=O] | LC/MS (ESI): m/z = 570 [M + H]+, RT = 1.85 min, method (2) |
| II-39 | 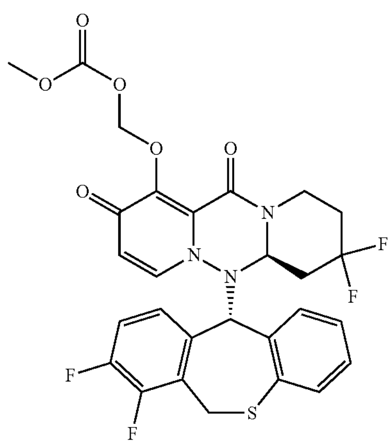 [SMILES: COC(=O)OCOc1c2n(ccc1=O)N([C@@H]1c3ccccc3SCc3c1ccc(F)c3F)[C@@H]1CC(F)(F)CCN1C2=O] | LC/MS (ESI): m/z = 606 [M + H]+, RT = 2.12 min, method (2) |
| II-40 | 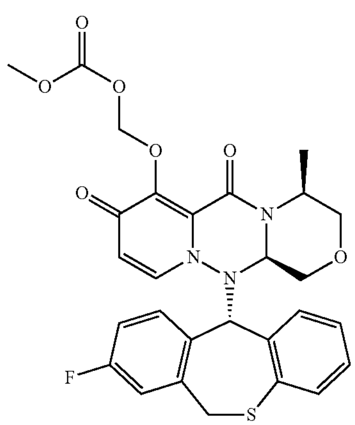 [SMILES: COC(=O)OCOc1c2n(ccc1=O)N([C@H]1c3ccc(F)cc3CSc3ccccc31)[C@@H]1COC[C@H](C)N1C2=O] | LC/MS (ESI): m/z = 568 [M + H]+, RT = 1.92 min, method (2) |

TABLE 12-continued

| No. | Structure | NMR or LC/MS |
| --- | --- | --- |
| II-41 | 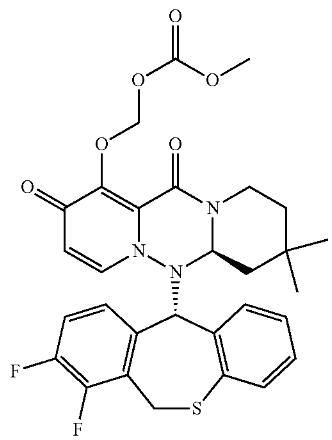 [SMILES: COC(=O)OCOc1c2n(ccc1=O)N([C@@H]1c3ccccc3SCc3c1ccc(F)c3F)[C@@H]1CC(C)(C)CCN1C2=O] | LC/MS (ESI): m/z = 598 [M + H]+, RT = 2.27 min, method (2) |
| II-42 | 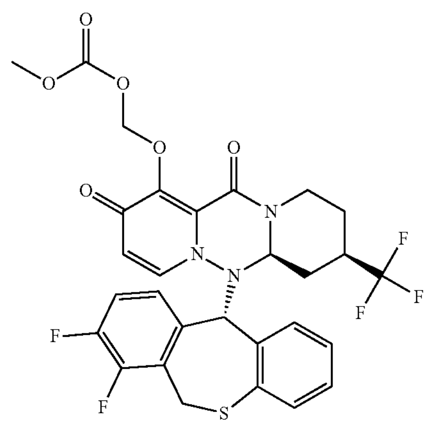 [SMILES: COC(=O)OCOc1c2n(ccc1=O)N([C@@H]1c3ccccc3SCc3c1ccc(F)c3F)[C@@H]1C[C@H](C(F)(F)F)CCN1C2=O] | LC/MS (ESI): m/z = 638 [M + H]+, RT = 2.17 min, method (2) |

TABLE 13

| No. | Structure | NMR or LC/MS |
| --- | --- | --- |
| II-43 | 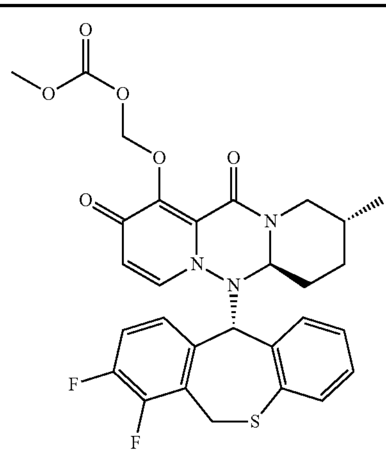 | LC/MS (ESI): m/z = 584 [M + H]+, RT = 2.18 min, method (2) |

TABLE 13-continued
| No. | Structure | NMR or LC/MS |
|---|---|---|
| II-44 | 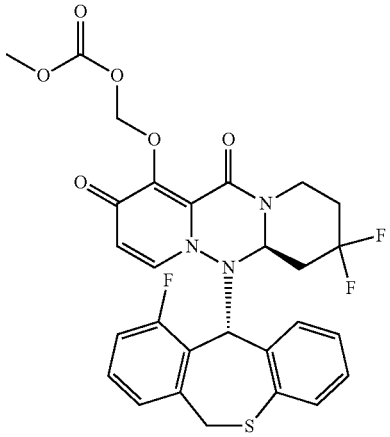 [SMILES: COC(=O)OCOc1c2n(ccc1=O)N([C@@H]1c3ccccc3SCc3cccc(F)c31)[C@@H]1CC(F)(F)CCN1C2=O] | LC/MS (ESI): m/z = 588 [M + H]+, RT = 2.00 min, method (2) |
| II-45 | 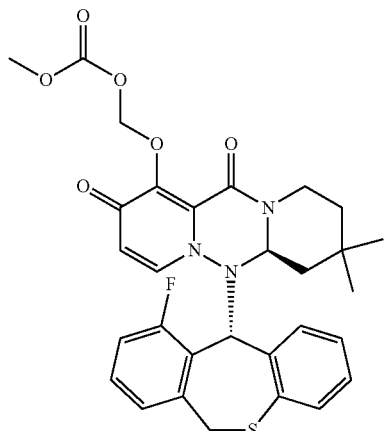 | LC/MS (ESI): m/z = 580 [M + H]+, RT = 2.14 min, method (2) |
| II-46 | 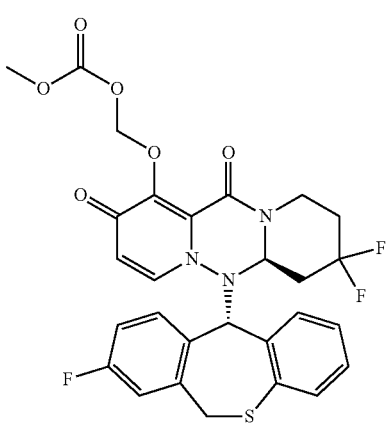 [SMILES: COC(=O)OCOc1c2n(ccc1=O)N([C@H]1c3ccc(F)cc3CSc3ccccc31)[C@@H]1CC(F)(F)CCN1C2=O] | LC/MS (ESI): m/z = 588 [M + H]+, RT = 2.04 min, method (2) |

TABLE 13-continued

| No. | Structure | NMR or LC/MS |
|---|---|---|
| II-47 | (structure) | LC/MS (ESI): m/z = 580 [M + H]+, RT = 2.17 min, method (2) |

TABLE 14

| No. | Structure | NMR or LC/MS |
|---|---|---|
| II-48 | (structure) | LC/MS (ESI): m/z = 586 [M + H]+, RT = 2.03 min, method (2) |
| II-49 | (structure) | LC/MS (ESI): m/z = 596 [M + H]+, RT = 2.18 min, method (2) |

TABLE 14-continued

| No. | Structure | NMR or LC/MS |
| --- | --- | --- |
| II-50 | 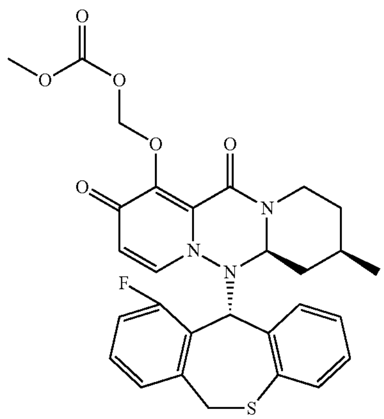 | LC/MS (ESI): m/z = 566 [M + H]+, RT = 2.02 min, method (2) |
| II-51 | 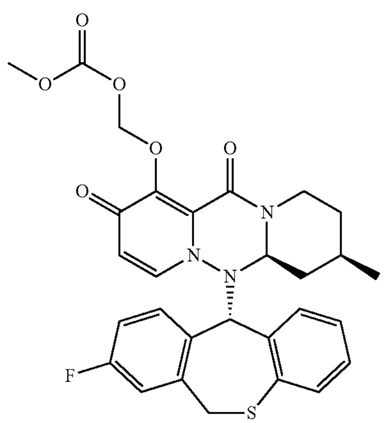 | LC/MS (ESI): m/z = 566 [M + H]+, RT = 2.08 min, method (2) |
| II-52 | 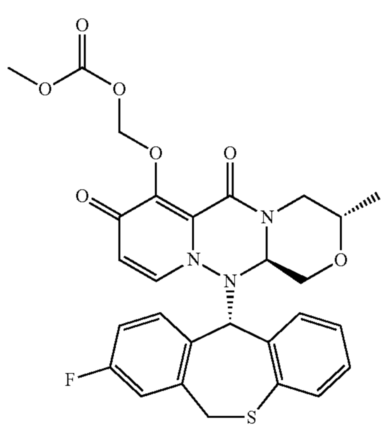 | LC/MS (ESI): m/z = 568 [M + H]+, RT = 1.93 min, method (2) |

TABLE 15
| No. | Structure | NMR or LC/MS |
| --- | --- | --- |
| II-53 | 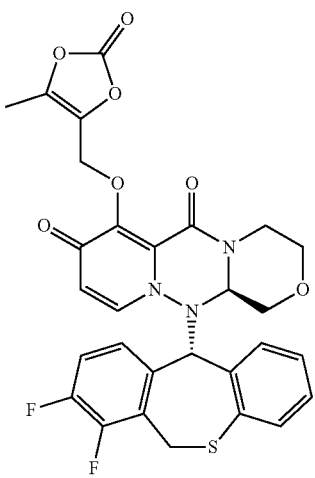 | LC/MS (ESI): m/z = 598.1 [M + H]+, RT = 1.96 min, method (2) |
| II-54 | 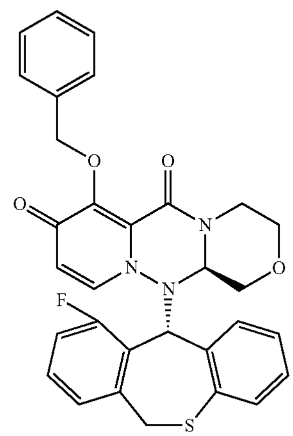 [SMILES: O=C1c2c(OCc3ccccc3)c(=O)ccn2N([C@@H]2c3ccccc3SCc3cccc(F)c32)[C@@H]2COCCN12] | 1H-NMR (CDCl3) δ: 2.89-2.98 (m, 1H), 3.30-3.43 (m, 2H), 3.57 (d, J = 13.4 Hz, 1H), 3.73 (dd, J = 11.6, 2.8 Hz, 1H), 3.87 (dd, J = 10.7, 2.4 Hz, 1H), 4.49 (dd, J = 9.9, 2.5 Hz, 1H), 4.72 (d, J = 12.9 Hz, 1H), 5.43 (d, J = 10.8 Hz, 1H), 5.51 (d, J = 13.4 Hz, 1H), 5.64 (d, J = 10.9 Hz, 1H), 5.78 (d, J = 7.7 Hz, 1H), 5.84 (s, 1H), 6.44 (d, J = 7.8 Hz, 1H), 6.67 (t, J = 7.0 Hz, 1H), 7.02-7.13 (m, 5H), 7.29-7.40 (m, 4H), 7.64 (d, J = 7.7 Hz, 2H). |
| II-56 | 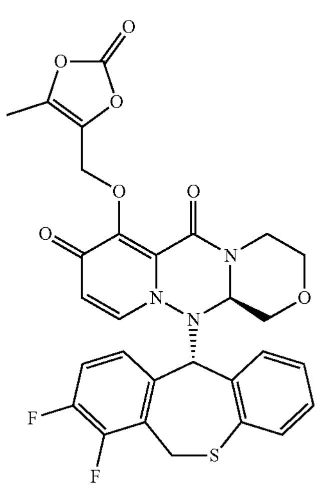 [SMILES: Cc1oc(=O)oc1COc1c2n(ccc1=O)N([C@@H]1c3ccccc3SCc3c1ccc(F)c3F)[C@@H]1COCCN1C2=O] | LC/MS (ESI): m/z = 595.90 [M + H]+, RT = 1.93 min, method (2) |

TABLE 15-continued
| No. | Structure | NMR or LC/MS |
|-----|-----------|--------------|
| II-59 | 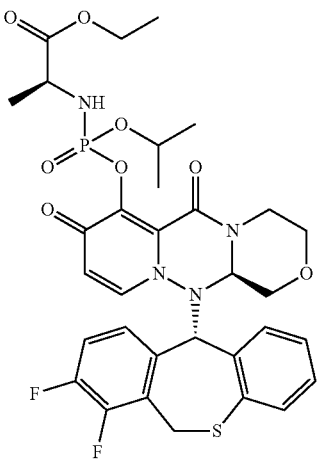 [SMILES: CCOC(=O)[C@H](C)NP(=O)(Oc1c2n(ccc1=O)N([C@@H]1c3ccccc3SCc3c1ccc(F)c3F)[C@@H]1COCCN1C2=O)OC(C)C] | LC/MS (ESI): m/z = 705.05 [M + H]+, RT = 2.16 min, method (2) |
TABLE 16
| No. | Structure | NMR or LC/MS |
|-----|-----------|--------------|
| II-60 | 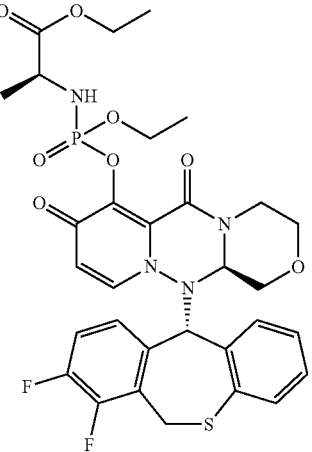 | LC/MS (ESI): m/z = 691.00 [M + H]+, RT = 2.08 min, method (2) |
| II-62 | 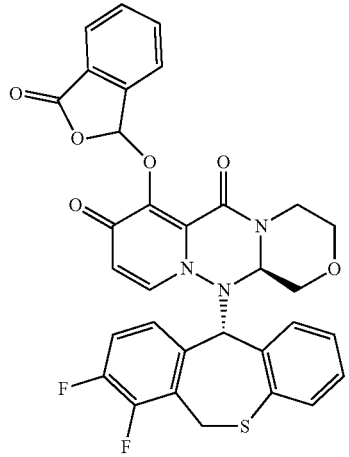 [SMILES: O=C1OC(Oc2c3n(ccc2=O)N([C@@H]2c4ccccc4SCc4c2ccc(F)c4F)[C@@H]2COCCN2C3=O)c2ccccc21] | LC/MS (ESI): m/z = 615.95 [M + H]+, RT = 2.07 min, method (2) |

TABLE 16-continued

| No. | Structure | NMR or LC/MS |
| --- | --- | --- |
| II-63 | 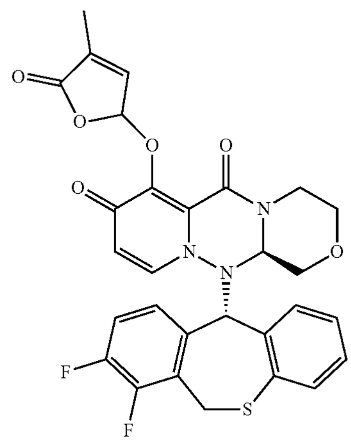 [SMILES: CC1=CC(Oc2c3n(ccc2=O)N([C@@H]2c4ccccc4SCc4c2ccc(F)c4F)[C@@H]2COCCN2C3=O)OC1=O] | LC/MS (ESI): m/z = 579.95 [M + H]+, RT = 1.92 min, method (2) |
| II-64 | | LC/MS (ESI): m/z = 642.35 [M + H]+, RT = 2.05 min, method (2) |
| II-66 | 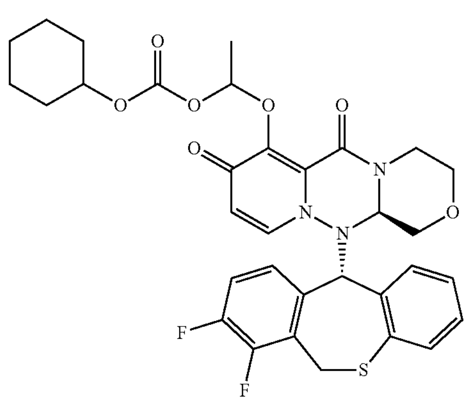 [SMILES: CC(OC(=O)OC1CCCCC1)Oc1c2n(ccc1=O)N([C@@H]1c3ccccc3SCc3c1ccc(F)c3F)[C@@H]1COCCN1C2=O] | LC/MS (ESI): m/z = 654.05 [M + H]+, RT = 2.43, 2.51 min, method (2) |

TABLE 17
| No. | Structure | NMR or LC/MS |
| --- | --- | --- |
| II-67 | 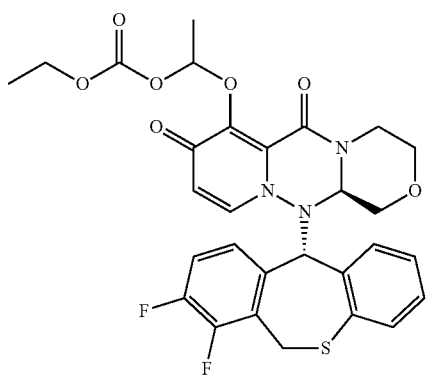 [SMILES: CCOC(=O)OC(C)Oc1c2n(ccc1=O)N([C@@H]1c3ccccc3SCc3c1ccc(F)c3F)[C@@H]1COCCN1C2=O] | LC/MS (ESI): m/z = 600.00 [M + H]+, RT = 2.05, 2.11 min, method (2) |
| II-68 | 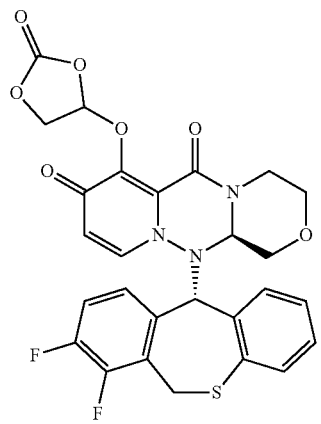 [SMILES: O=C1OCC(Oc2c3n(ccc2=O)N([C@@H]2c4ccccc4SCc4c2ccc(F)c4F)[C@@H]2COCCN2C3=O)O1] | LC/MS (ESI): m/z = 569.95 [M + H]+, RT = 1.84 min, method (2) |
| II-69 | 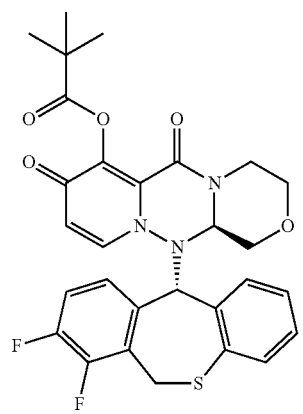 [SMILES: CC(C)(C)C(=O)Oc1c2n(ccc1=O)N([C@@H]1c3ccccc3SCc3c1ccc(F)c3F)[C@@H]1COCCN1C2=O] | LC/MS (ESI): m/z = 568.00 [M + H]+, RT = 2.17 min, method (2) |

TABLE 17-continued

| No. | Structure | NMR or LC/MS |
|---|---|---|
| II-70 | 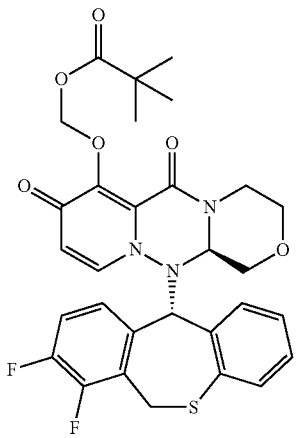 [SMILES: CC(C)(C)C(=O)OCOc1c2n(ccc1=O)N([C@@H]1c3ccccc3SCc3c1ccc(F)c3F)[C@@H]1COCCN1C2=O] | LC/MS (ESI): m/z = 598.00 [M + H]+, RT = 2.23 min, method (2) |
| II-71 | 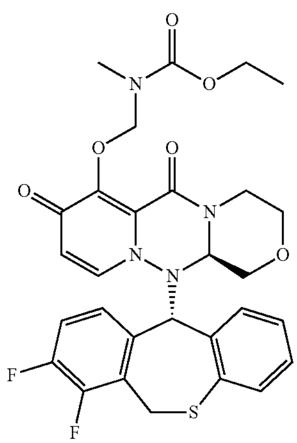 [SMILES: CCOC(=O)N(C)COc1c2n(ccc1=O)N([C@@H]1c3ccccc3SCc3c1ccc(F)c3F)[C@@H]1COCCN1C2=O] | LC/MS (ESI): m/z = 599.05 [M + H]+, RT = 1.99 min, method (2) |

TABLE 18

| No. | Structure | NMR or LC/MS |
|---|---|---|
| II-72 | 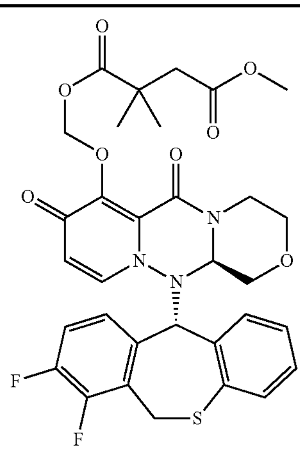 | LC/MS (ESI): m/z = 656.00 [M + H]+, RT = 2.13 min, method (2) |

TABLE 18-continued

| No. | Structure | NMR or LC/MS |
|---|---|---|
| II-73 | 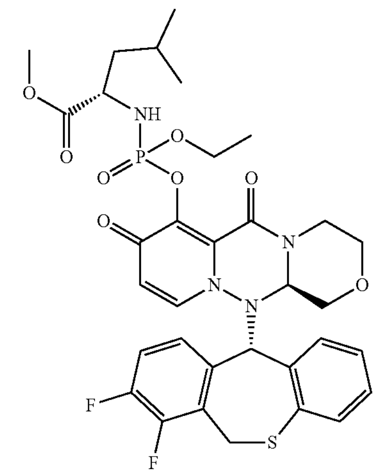 [SMILES: CCOP(=O)(N[C@@H](CC(C)C)C(=O)OC)Oc1c2n(ccc1=O)N([C@@H]1c3ccccc3SCc3c1ccc(F)c3F)[C@@H]1COCCN1C2=O] | LC/MS (ESI): m/z = 719.05 [M + H]+, RT = 2.28 min, method (2) |
| II-74 | 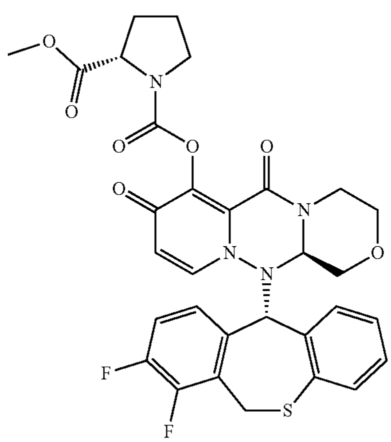 [SMILES: COC(=O)[C@@H]1CCCN1C(=O)Oc1c2n(ccc1=O)N([C@@H]1c3ccccc3SCc3c1ccc(F)c3F)[C@@H]1COCCN1C2=O] | LC/MS (ESI): m/z = 638.95 [M + H]+, RT = 1.89 min, method (2) |
| II-75 | 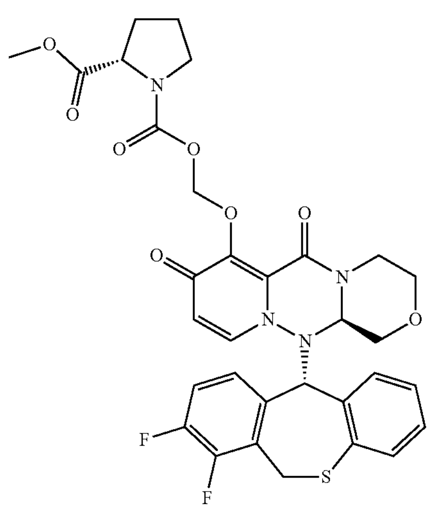 [SMILES: COC(=O)[C@@H]1CCCN1C(=O)OCOc1c2n(ccc1=O)N([C@@H]1c3ccccc3SCc3c1ccc(F)c3F)[C@@H]1COCCN1C2=O] | LC/MS (ESI): m/z = 668.95 [M + H]+, RT = 1.97 min, method (2) |

TABLE 19
| No. | Structure | NMR or LC/MS |
|---|---|---|
| II-76 | 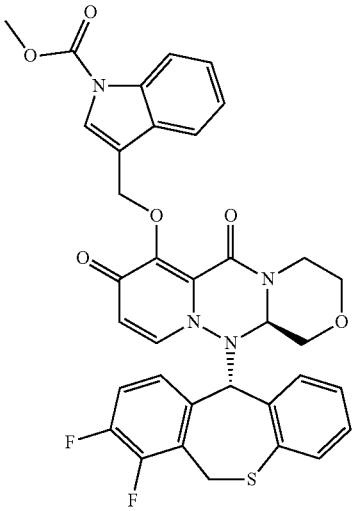 [SMILES: COC(=O)n1cc(COc2c3n(ccc2=O)N([C@@H]2c4ccccc4SCc4c2ccc(F)c4F)[C@@H]2COCCN2C3=O)c2ccccc21] | LC/MS (ESI): m/z = 671.00 [M + H]+, RT = 2.24 min, method (2) |
| II-77 | 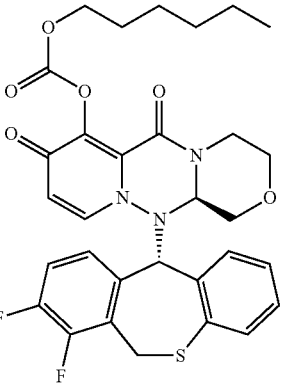 | LC/MS (ESI): m/z = 612.10 [M + H]+, RT = 2.45 min, method (2) |
| II-78 | 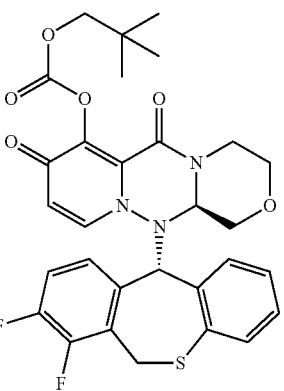 | LC/MS (ESI): m/z = 598.00 [M + H]+, RT = 2.29 min, method (2) |

TABLE 19-continued
| No. | Structure | NMR or LC/MS |
|---|---|---|
| II-79 | 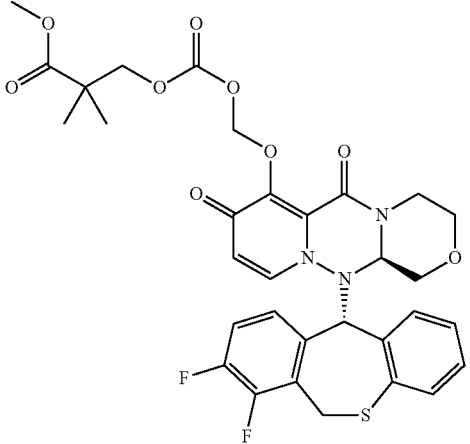 [SMILES: COC(=O)C(C)(C)COC(=O)OCOc1c2n(ccc1=O)N([C@@H]1c3ccccc3SCc3c1ccc(F)c3F)[C@@H]1COCCN1C2=O] | LC/MS (ESI): m/z = 672 [M + H]+, RT = 2.27 min, method (1) |
TABLE 20
| No. | Structure | NMR or LC/MS |
|---|---|---|
| II-80 | 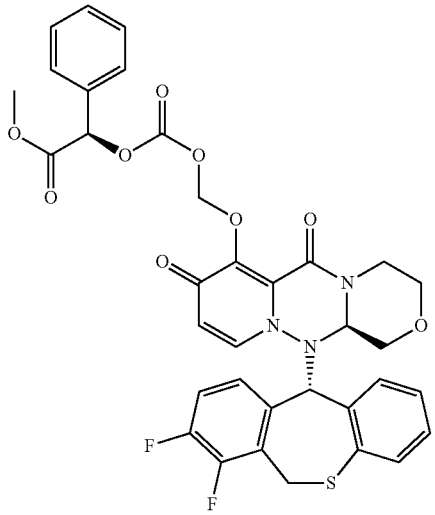 [SMILES: COC(=O)[C@H](OC(=O)OCOc1c2n(ccc1=O)N([C@@H]1c3ccccc3SCc3c1ccc(F)c3F)[C@@H]1COCCN1C2=O)c1ccccc1] | LC/MS (ESI): m/z = 706 [M + H]+, RT = 2.39 min, method (1) |
| II-81 | 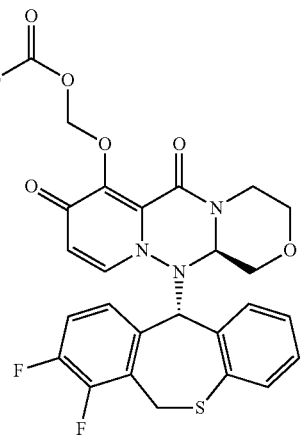 | LC/MS (ESI): m/z = 644 [M + H]+, RT = 2.13 min, method (1) |

TABLE 20-continued
| No. | Structure | NMR or LC/MS |
|---|---|---|
| II-82 | 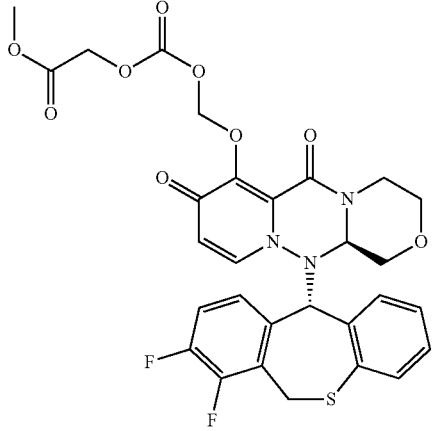 [SMILES: COC(=O)COC(=O)OCOc1c2n(ccc1=O)N([C@@H]1c3ccccc3SCc3c1ccc(F)c3F)[C@@H]1COCCN1C2=O] | LC/MS (ESI): m/z = 630 [M + H]+, RT = 2.03 min, method (1) |
| II-83 | 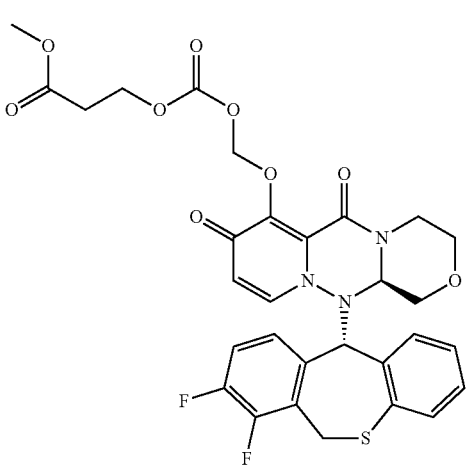 [SMILES: COC(=O)CCOC(=O)OCOc1c2n(ccc1=O)N([C@@H]1c3ccccc3SCc3c1ccc(F)c3F)[C@@H]1COCCN1C2=O] | LC/MS (ESI): m/z = 644 [M + H]+, RT = 2.06 min, method (1) |
TABLE 21
| No. | Structure | NMR or LC/MS |
|---|---|---|
| II-84 | 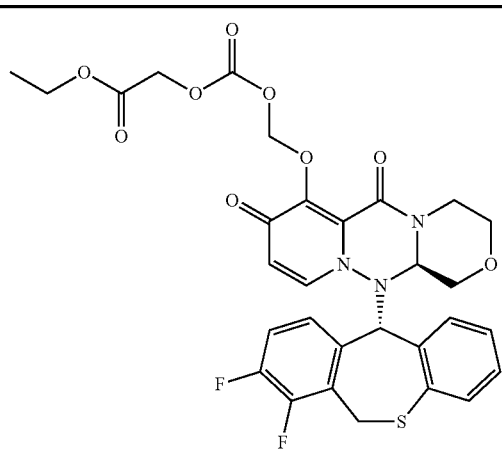 | LC/MS (ESI): m/z = 644 [M + H]+, RT = 2.15 min, method (1) |

TABLE 21-continued

| No. | Structure | NMR or LC/MS |
|---|---|---|
| II-85 | 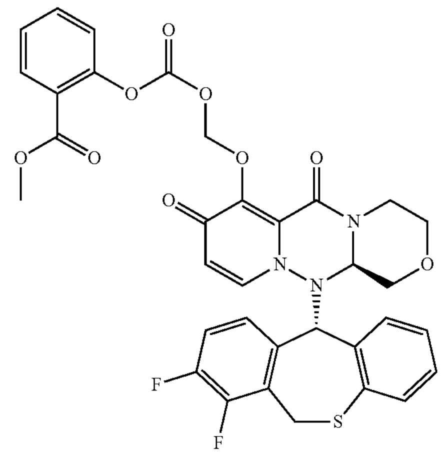 [SMILES: COC(=O)c1ccccc1OC(=O)OCOc1c2n(ccc1=O)N([C@@H]1c3ccccc3SCc3c1ccc(F)c3F)[C@@H]1COCCN1C2=O] | LC/MS (ESI): m/z = 692 [M + H]+, RT = 2.31 min, method (1) |
| II-86 | 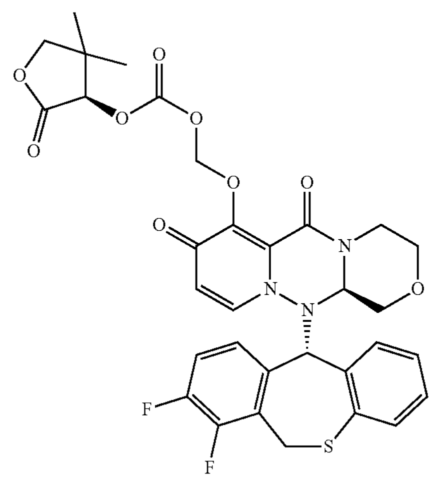 [SMILES: CC1(C)COC(=O)[C@@H]1OC(=O)OCOc1c2n(ccc1=O)N([C@@H]1c3ccccc3SCc3c1ccc(F)c3F)[C@@H]1COCCN1C2=O] | LC/MS (ESI): m/z = 670 [M + H]+, RT = 2.20 min, method (1) |
| II-87 | 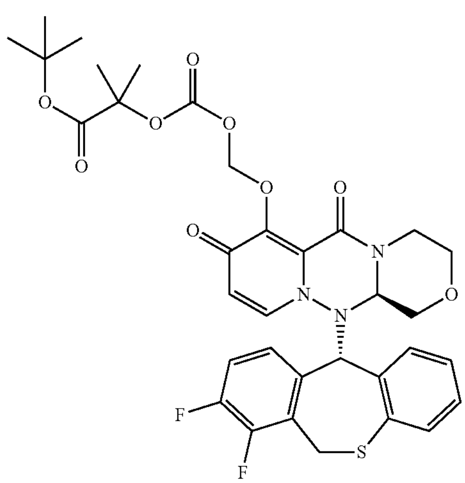 [SMILES: CC(C)(C)OC(=O)C(C)(C)OC(=O)OCOc1c2n(ccc1=O)N([C@@H]1c3ccccc3SCc3c1ccc(F)c3F)[C@@H]1COCCN1C2=O] | LC/MS (ESI): m/z = 700 [M + H]+, RT = 2.45 min, method (1) |

TABLE 22
| No. | Structure | NMR or LC/MS |
|---|---|---|
| II-88 | 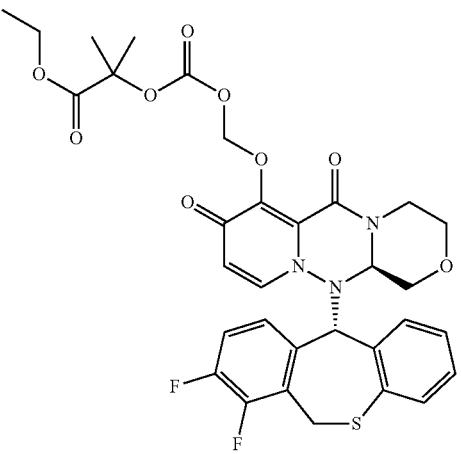 [SMILES: CCOC(=O)C(C)(C)OC(=O)OCOc1c2n(ccc1=O)N([C@@H]1c3ccccc3SCc3c1ccc(F)c3F)[C@@H]1COCCN1C2=O] | LC/MS (ESI): m/z = 672 [M + H]+, RT = 2.31 min, method (1) |
| II-89 | 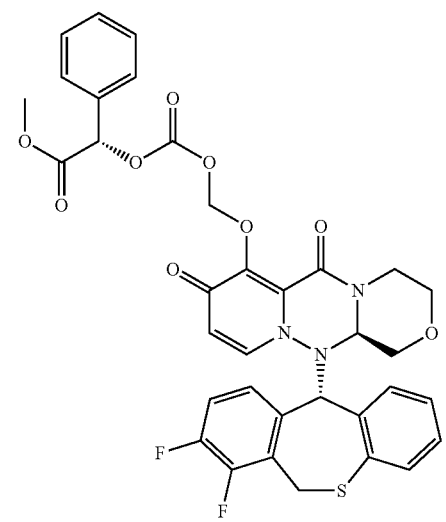 [SMILES: COC(=O)[C@@H](OC(=O)OCOc1c2n(ccc1=O)N([C@@H]1c3ccccc3SCc3c1ccc(F)c3F)[C@@H]1COCCN1C2=O)c1ccccc1] | LC/MS (ESI): m/z = 706 [M + H]+, RT = 2.37 min, method (1) |
| II-90 | 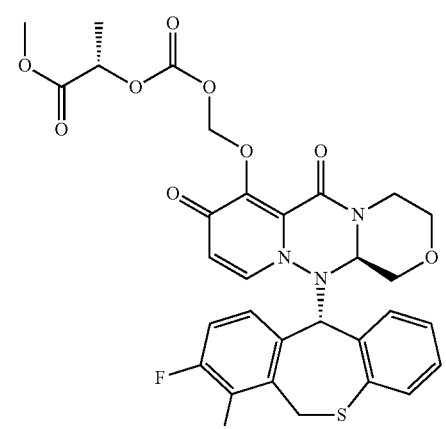 | LC/MS (ESI): m/z = 644 [M + H]+, RT = 2.13 min, method (1) |

TABLE 22-continued
| No. | Structure | NMR or LC/MS |
|---|---|---|
| II-91 | 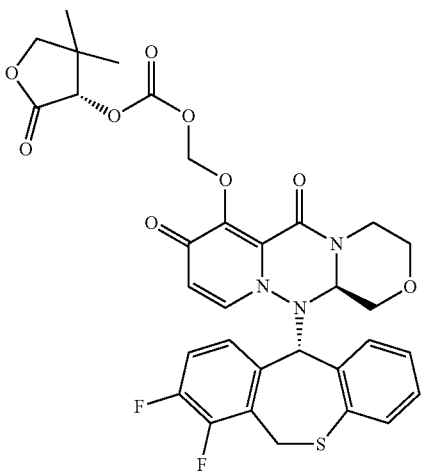 [SMILES: CC1(C)COC(=O)[C@H]1OC(=O)OCOc1c2n(ccc1=O)N([C@@H]1c3ccccc3SCc3c1ccc(F)c3F)[C@@H]1COCCN1C2=O] | LC/MS (ESI): m/z = 670 [M + H]+, RT = 2.16 min, method (1) |
TABLE 23
| No. | Structure | NMR or LC/MS |
|---|---|---|
| II-92 | 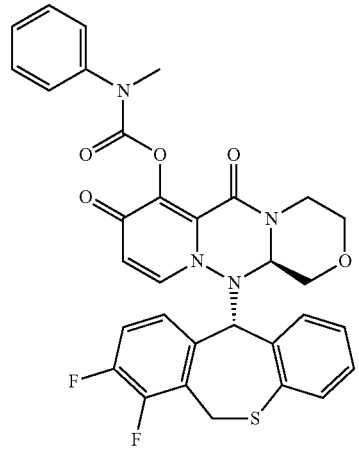 [SMILES: CN(C(=O)Oc1c2n(ccc1=O)N([C@@H]1c3ccccc3SCc3c1ccc(F)c3F)[C@@H]1COCCN1C2=O)c1ccccc1] | LC/MS (ESI): m/z = 617.00 [M + H]+, RT = 2.09 min, method (2) |
| II-93 | 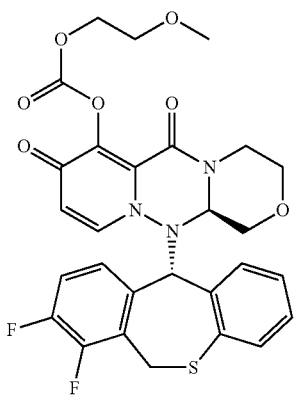 [SMILES: COCCOC(=O)Oc1c2n(ccc1=O)N([C@@H]1c3ccccc3SCc3c1ccc(F)c3F)[C@@H]1COCCN1C2=O] | LC/MS (ESI): m/z = 586.00 [M + H]+, RT = 1.91 min, method (2) |

TABLE 23-continued

| No. | Structure | NMR or LC/MS |
|---|---|---|
| II-94 | 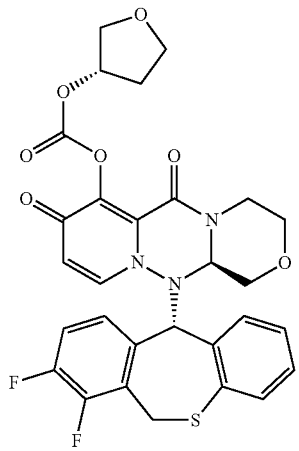 [SMILES: O=C(Oc1c2n(ccc1=O)N([C@@H]1c3ccccc3SCc3c1ccc(F)c3F)[C@@H]1COCCN1C2=O)O[C@H]1CCOC1] | LC/MS (ESI): m/z = 598.00 [M + H]+, RT = 1.89 min, method (2) |
| II-95 | 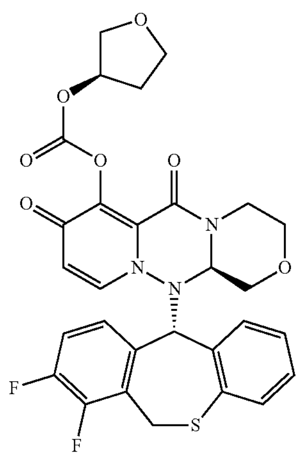 [SMILES: O=C(Oc1c2n(ccc1=O)N([C@@H]1c3ccccc3SCc3c1ccc(F)c3F)[C@@H]1COCCN1C2=O)O[C@@H]1CCOC1] | LC/MS (ESI): m/z = 598.00 [M + H]+, RT = 1.89 min, method (2) |
| II-96 | 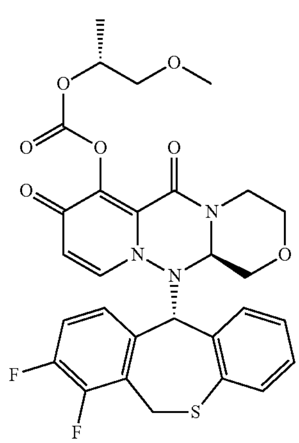 [SMILES: COC[C@@H](C)OC(=O)Oc1c2n(ccc1=O)N([C@@H]1c3ccccc3SCc3c1ccc(F)c3F)[C@@H]1COCCN1C2=O] | LC/MS (ESI): m/z = 600.00 [M + H]+, RT = 2.01 min, method (2) |

TABLE 24
| No. | Structure | NMR or LC/MS |
|---|---|---|
| II-97 | 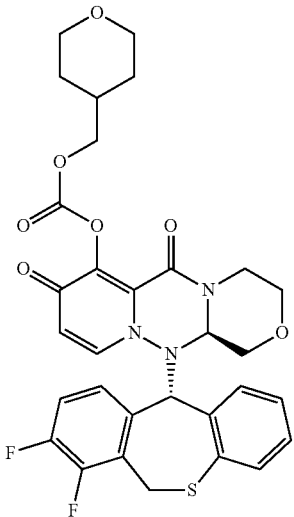 [SMILES: O=C(OCC1CCOCC1)Oc1c2n(ccc1=O)N([C@@H]1c3ccccc3SCc3c1ccc(F)c3F)[C@@H]1COCCN1C2=O] | LC/MS (ESI): m/z = 626.00 [M + H]+, RT = 1.98 min, method (2) |
| II-98 | 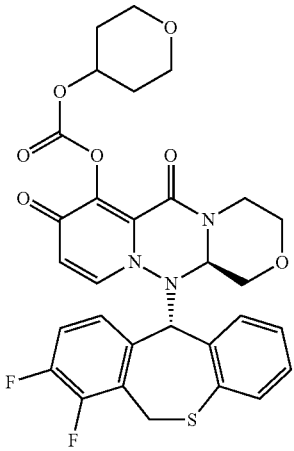 [SMILES: O=C(Oc1c2n(ccc1=O)N([C@@H]1c3ccccc3SCc3c1ccc(F)c3F)[C@@H]1COCCN1C2=O)OC1CCOCC1] | LC/MS (ESI): m/z = 611.95 [M + H]+, RT = 1.93 min, method (2) |
| II-99 | 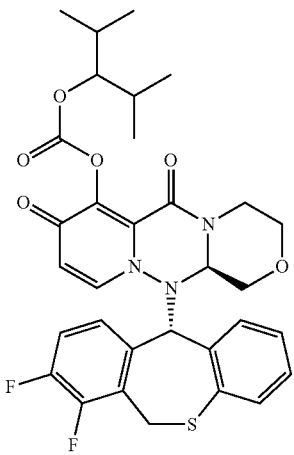 [SMILES: CC(C)C(OC(=O)Oc1c2n(ccc1=O)N([C@@H]1c3ccccc3SCc3c1ccc(F)c3F)[C@@H]1COCCN1C2=O)C(C)C] | LC/MS (ESI): m/z = 626.05 [M + H]+, RT = 2.46 min, method (2) |

TABLE 24-continued
| No. | Structure | NMR or LC/MS |
|---|---|---|
| II-100 | 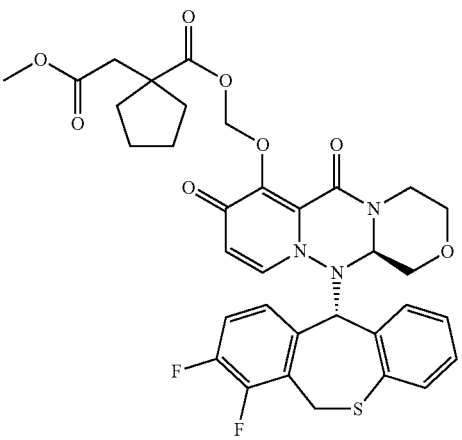 [SMILES: COC(=O)CC1(C(=O)OCOc2c3n(ccc2=O)N([C@@H]2c4ccccc4SCc4c2ccc(F)c4F)[C@@H]2COCCN2C3=O)CCCC1] | LC/MS (ESI): m/z = 682.05 [M + H]+, RT = 2.27 min, method (2) |
TABLE 25
| No. | Structure | NMR or LC/MS |
|---|---|---|
| II-101 | 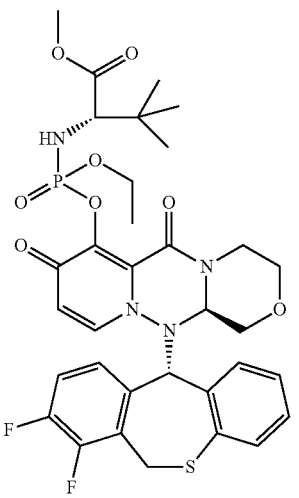 [SMILES: CCOP(=O)(N[C@H](C(=O)OC)C(C)(C)C)Oc1c2n(ccc1=O)N([C@@H]1c3ccccc3SCc3c1ccc(F)c3F)[C@@H]1COCCN1C2=O] | LC/MS (ESI): m/z = 719.05 [M + H]+, RT = 2.26 min, method (2) |
| II-102 | 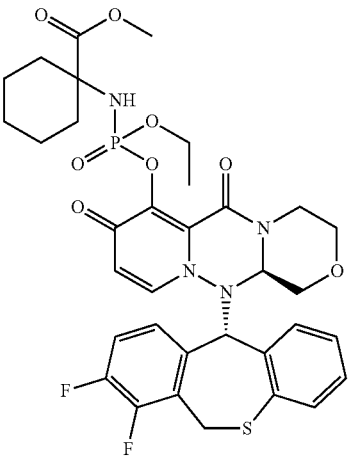 [SMILES: CCOP(=O)(NC1(C(=O)OC)CCCCC1)Oc1c2n(ccc1=O)N([C@@H]1c3ccccc3SCc3c1ccc(F)c3F)[C@@H]1COCCN1C2=O] | LC/MS (ESI): m/z = 731.15 [M + H]+, RT = 2.29 min, method (2) |

TABLE 25-continued
| No. | Structure | NMR or LC/MS |
|---|---|---|
| II-103 | 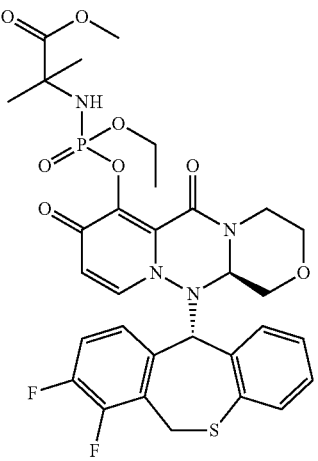 [SMILES: CCOP(=O)(NC(C)(C)C(=O)OC)Oc1c2n(ccc1=O)N([C@@H]1c3ccccc3SCc3c1ccc(F)c3F)[C@@H]1COCCN1C2=O] | LC/MS (ESI): m/z = 691.10 [M + H]+, RT = 2.05 min, method (2) |
| II-104 | 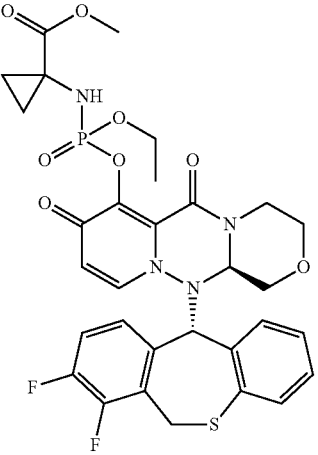 [SMILES: CCOP(=O)(NC1(C(=O)OC)CC1)Oc1c2n(ccc1=O)N([C@@H]1c3ccccc3SCc3c1ccc(F)c3F)[C@@H]1COCCN1C2=O] | LC/MS (ESI): m/z = 688.95 [M + H]+, RT = 1.98 min, method (2) |
TABLE 26
| No. | Structure | NMR or LC/MS |
|---|---|---|
| II-105 | 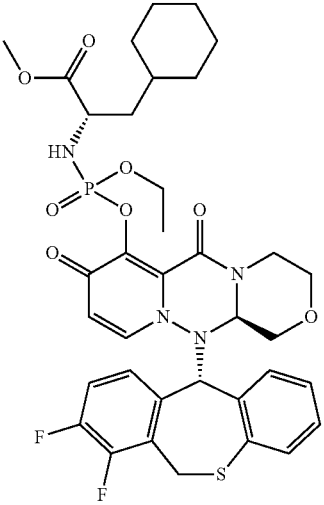 [SMILES: CCOP(=O)(N[C@@H](CC1CCCCC1)C(=O)OC)Oc1c2n(ccc1=O)N([C@@H]1c3ccccc3SCc3c1ccc(F)c3F)[C@@H]1COCCN1C2=O] | LC/MS (ESI): m/z = 759.05 [M + H]+, RT = 2.53 min, method (2) |

TABLE 26-continued
| No. | Structure | NMR or LC/MS |
| --- | --- | --- |
| II-106 | 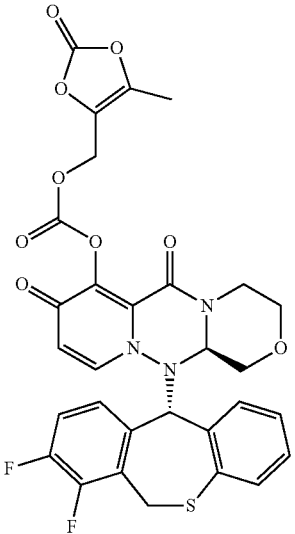 [SMILES: Cc1oc(=O)oc1COC(=O)Oc1c2n(ccc1=O)N([C@@H]1c3ccccc3SCc3c1ccc(F)c3F)[C@@H]1COCCN1C2=O] | LC/MS (ESI): m/z = 639.95 [M + H]+, RT = 2.01 min, method (2) |
| II-107 | 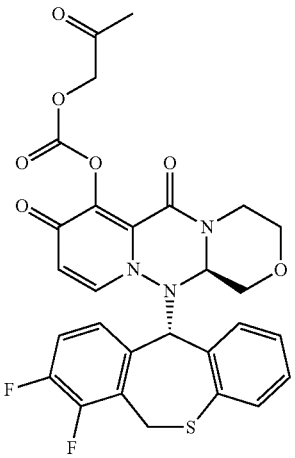 | LC/MS (ESI): m/z = 683.95 [M + H]+, RT = 1.87 min, method (2) |
| II-108 | 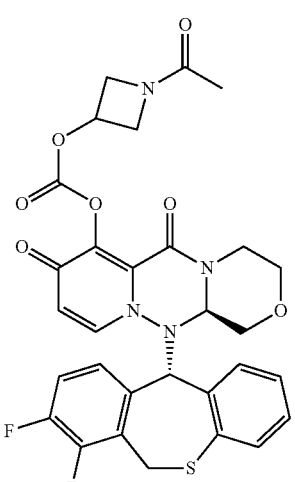 | LC/MS (ESI): m/z = 625.00 [M + H]+, RT = 1.75 min, method (2) |

TABLE 27

| No. | Structure | NMR or LC/MS |
|---|---|---|
| II-109 | 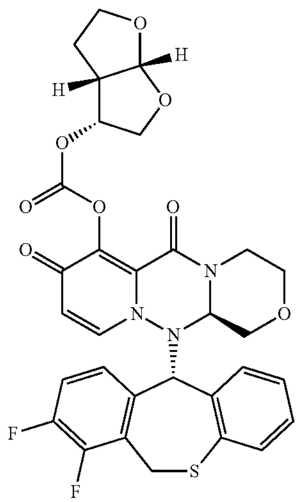 [SMILES: O=C(Oc1c2n(ccc1=O)N([C@@H]1c3ccccc3SCc3c1ccc(F)c3F)[C@@H]1COCCN1C2=O)O[C@H]1CO[C@H]2OCC[C@H]21] | LC/MS (ESI): m/z = 640.00 [M + H]+, RT = 1.90 min, method (2) |
| II-110 | 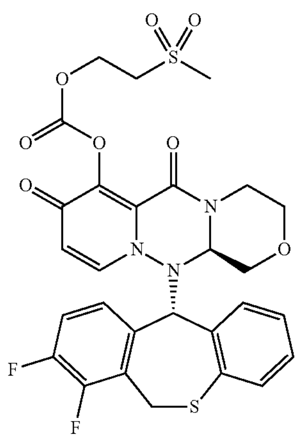 [SMILES: CS(=O)(=O)CCOC(=O)Oc1c2n(ccc1=O)N([C@@H]1c3ccccc3SCc3c1ccc(F)c3F)[C@@H]1COCCN1C2=O] | LC/MS (ESI): m/z = 633.90 [M + H]+, RT = 1.82 min, method (2) |
| II-111 | 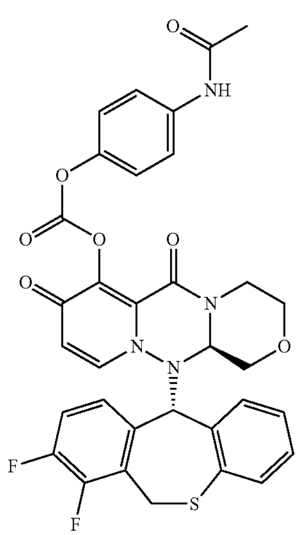 [SMILES: CC(=O)Nc1ccc(OC(=O)Oc2c3n(ccc2=O)N([C@@H]2c4ccccc4SCc4c2ccc(F)c4F)[C@@H]2COCCN2C3=O)cc1] | LC/MS (ESI): m/z = 661.00 [M + H]+, RT = 1.90 min, method (2) |

TABLE 27-continued

| No. | Structure | NMR or LC/MS |
|---|---|---|
| II-112 | 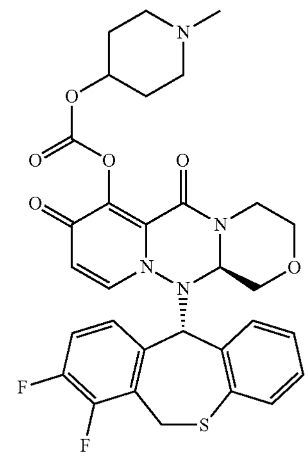 [SMILES: CN1CCC(OC(=O)Oc2c3n(ccc2=O)N([C@@H]2c4ccccc4SCc4c2ccc(F)c4F)[C@@H]2COCCN2C3=O)CC1] | LC/MS (ESI): m/z = 624.95 [M + H]+, RT = 1.38 min, method (2) |

TABLE 28

| No. | Structure | NMR or LC/MS |
|---|---|---|
| II-113 | 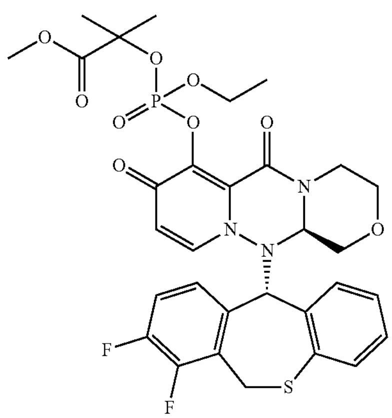 [SMILES: CCOP(=O)(Oc1c2n(ccc1=O)N([C@@H]1c3ccccc3SCc3c1ccc(F)c3F)[C@@H]1COCCN1C2=O)OC(C)(C)C(=O)OC] | LC/MS (ESI): m/z = 691.95 [M + H]+, RT = 2.00 min, method (2) |
| II-114 | 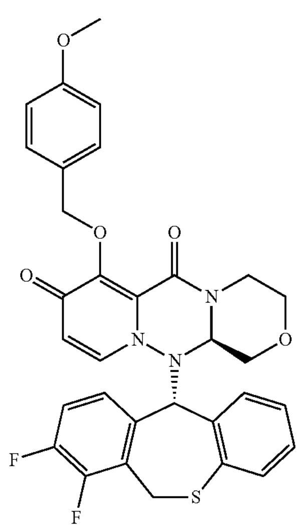 [SMILES: COc1ccc(COc2c3n(ccc2=O)N([C@@H]2c4ccccc4SCc4c2ccc(F)c4F)[C@@H]2COCCN2C3=O)cc1] | LC/MS (ESI): m/z = 604.00 [M + H]+, RT = 2.09 min, method (2) |

TABLE 28-continued
| No. | Structure | NMR or LC/MS |
|---|---|---|
| II-116 | 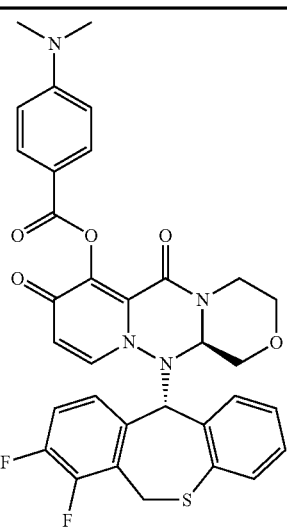 | LC/MS (ESI): m/z = 631.00 [M + H]+, RT = 2.18 min, method (2) |
| II-117 | 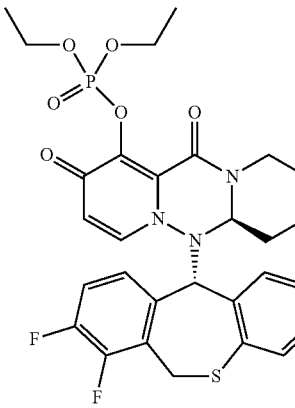 | LC/MS (ESI): m/z = 620.00 [M + H]+, RT = 1.93 min, method (2) |
TABLE 29
| No. | Structure | NMR or LC/MS |
|---|---|---|
| II-118 | 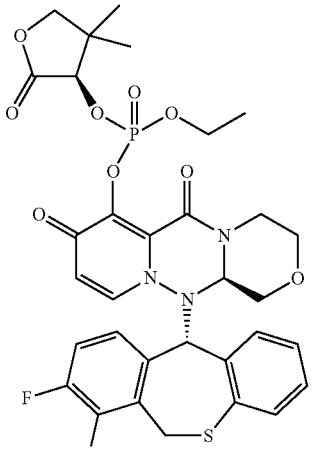 | LC/MS (ESI): m/z = 620.00 [M + H]+, RT = 1.93 min, method (2) |

TABLE 29-continued
| No. | Structure | NMR or LC/MS |
|---|---|---|
| II-119 | 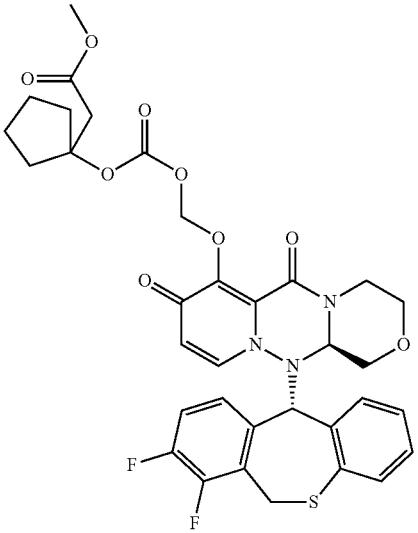 | LC/MS (ESI): m/z = 614 [M + H]+, RT = 2.31 min, method (1) |
| II-120 | 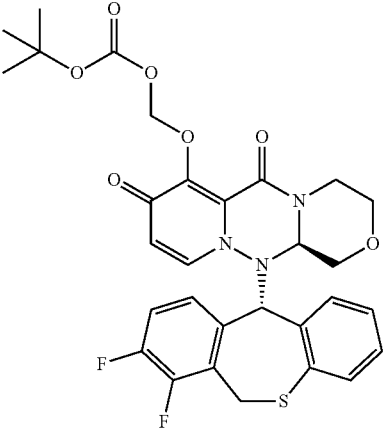 [SMILES: CC(C)(C)OC(=O)OCOc1c2n(ccc1=O)N([C@@H]1c3ccccc3SCc3c1ccc(F)c3F)[C@@H]1COCCN1C2=O] | LC/MS (ESI): m/z = 614 [M + H]+, RT = 2.24 min, method (1) |
| II-121 | 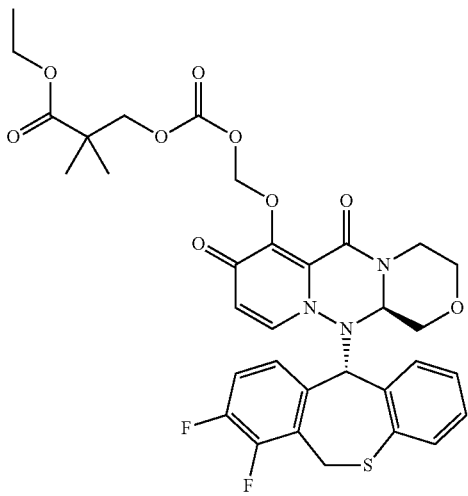 [SMILES: CCOC(=O)C(C)(C)COC(=O)OCOc1c2n(ccc1=O)N([C@@H]1c3ccccc3SCc3c1ccc(F)c3F)[C@@H]1COCCN1C2=O] | LC/MS (ESI): m/z = 686 [M + H]+, RT = 2.27 min, method (1) |

TABLE 30
| No. | Structure | NMR or LC/MS |
|---|---|---|
| II-122 | 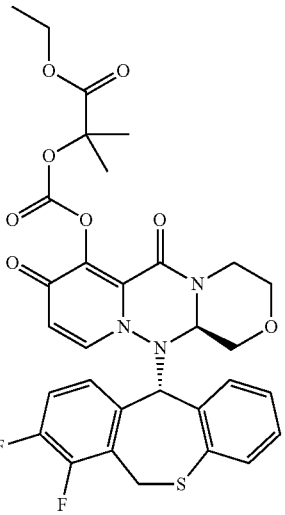 | LC/MS (ESI): m/z = 642 [M + H]+, RT = 2.19 min, method (1) |
| II-123 | 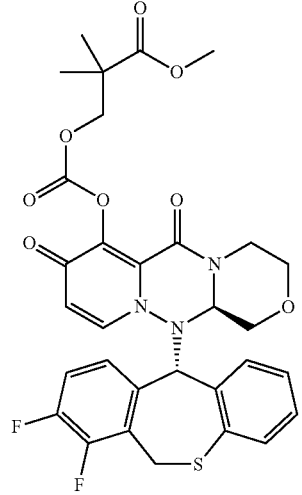 [SMILES: COC(=O)C(C)(C)COC(=O)Oc1c2n(ccc1=O)N([C@@H]1c3ccccc3SCc3c1ccc(F)c3F)[C@@H]1COCCN1C2=O] | LC/MS (ESI): m/z = 642 [M + H]+, RT = 2.17 min, method (1) |
| II-124 | 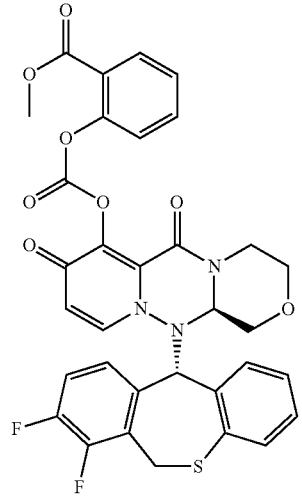 [SMILES: COC(=O)c1ccccc1OC(=O)Oc1c2n(ccc1=O)N([C@@H]1c3ccccc3SCc3c1ccc(F)c3F)[C@@H]1COCCN1C2=O] | LC/MS (ESI): m/z = 662 [M + H]+, RT = 2.22 min, method (1) |

TABLE 30-continued
| No. | Structure | NMR or LC/MS |
|---|---|---|
| II-125 | 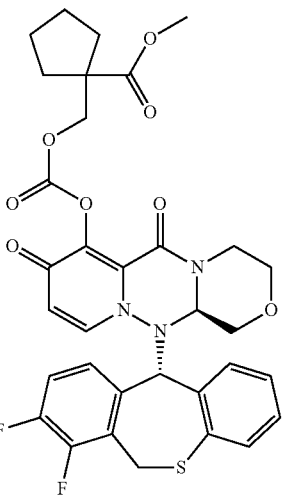 | LC/MS (ESI): m/z = 668 [M + H]+, RT = 2.32 min, method (1) |
TABLE 31
| No. | Structure | NMR or LC/MS |
|---|---|---|
| II-126 | 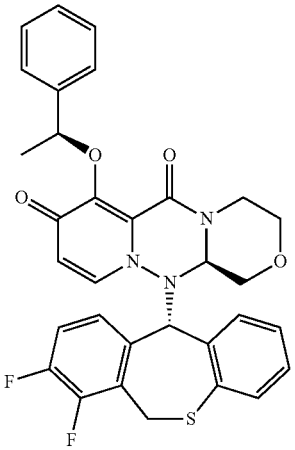 [SMILES: C[C@H](Oc1c2n(ccc1=O)N([C@@H]1c3ccccc3SCc3c1ccc(F)c3F)[C@@H]1COCCN1C2=O)c1ccccc1] | LC/MS (ESI): m/z = 587.95 [M + H]+, RT = 2.24 min, method (2) |
| II-127 | 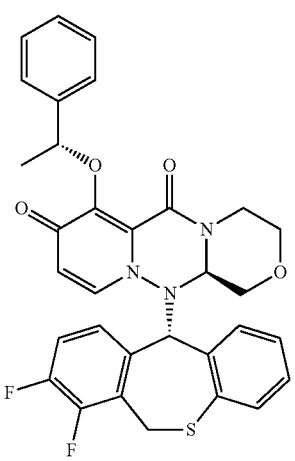 [SMILES: C[C@@H](Oc1c2n(ccc1=O)N([C@@H]1c3ccccc3SCc3c1ccc(F)c3F)[C@@H]1COCCN1C2=O)c1ccccc1] | LC/MS (ESI): m/z = 588.05 [M + H]+, RT = 2.17 min, method (2) |

TABLE 31-continued
| No. | Structure | NMR or LC/MS |
|---|---|---|
| II-128 | 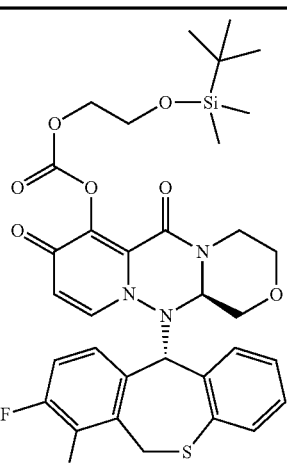 | LC/MS (ESI): m/z = 686.00 [M + H]+, RT = 2.67 min, method (2) |
| II-130 | 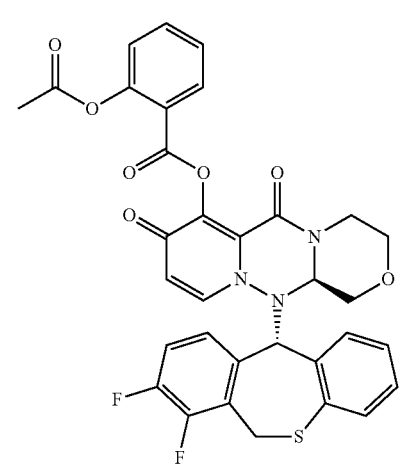 [SMILES: CC(=O)Oc1ccccc1C(=O)Oc1c2n(ccc1=O)N([C@@H]1c3ccccc3SCc3c1ccc(F)c3F)[C@@H]1COCCN1C2=O] | LC/MS (ESI): m/z = 645.95 [M + H]+, RT = 2.12 min, method (2) |
TABLE 32
| No. | Structure | NMR or LC/MS |
|---|---|---|
| II-131 | 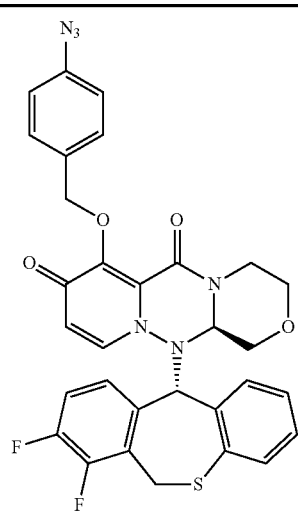 | LC/MS (ESI): m/z = 615.00 [M + H]+, RT = 2.24 min, method (2) |

TABLE 32-continued
| No. | Structure | NMR or LC/MS |
|---|---|---|
| II-132 | 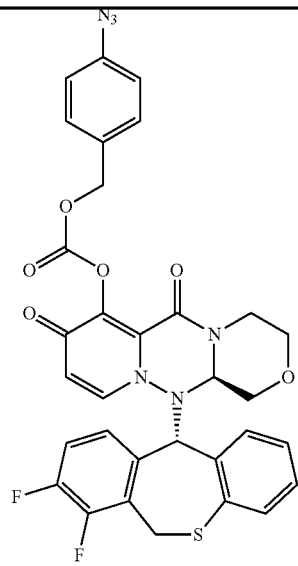 | LC/MS (ESI): m/z = 658.95 [M + H]+, RT = 2.31 min, method (2) |
| II-133 | 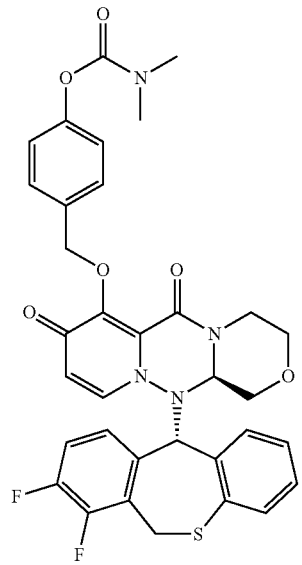 [SMILES: CN(C)C(=O)Oc1ccc(COc2c3n(ccc2=O)N([C@@H]2c4ccccc4SCc4c2ccc(F)c4F)[C@@H]2COCCN2C3=O)cc1] | LC/MS (ESI): m/z = 661.00 [M + H]+, RT = 2.06 min, method (2) |
| II-134 | 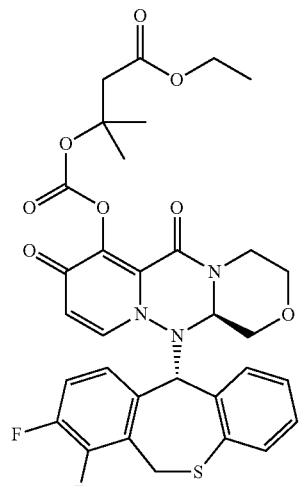 | LC/MS (ESI): m/z = 656 [M + H]+, RT = 2.24 min, method (1) |

TABLE 33
| No. | Structure | NMR or LC/MS |
|---|---|---|
| II-135 | 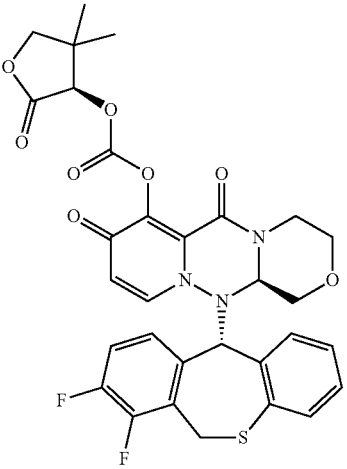 [SMILES: CC1(C)COC(=O)[C@@H]1OC(=O)Oc1c2n(ccc1=O)N([C@@H]1c3ccccc3SCc3c1ccc(F)c3F)[C@@H]1COCCN1C2=O] | 1H-NMR (CDCl3) δ: 1.24 (s, 3H), 1.38 (s, 3H), 2.94 (td, J = 11.8, 3.5 Hz, 1H), 3.44 (dd, J = 12.0, 10.9 Hz, 1H), 3.57 (t, J = 10.9 Hz, 1H), 3.78 (dd, J = 12.0, 3.5 Hz, 1H), 3.96 (dd, J = 10.9, 2.9 Hz, 1H), 4.05-4.12 (m, 3H), 4.58 (dd, J = 10.0, 2.9 Hz, 1H), 4.66 (d, J = 13.5 Hz, 1H), 5.24 (d, J = 13.5 Hz, 1H), 5.32 (s, 1H), 5.58 (s, 1H), 5.91 (d, J = 7.8 Hz, 1H), 6.81 (s, 2H), 7.06-7.20 (m, 5H). |
| II-136 | 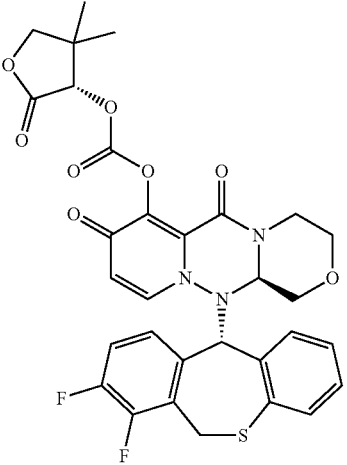 [SMILES: CC1(C)COC(=O)[C@H]1OC(=O)Oc1c2n(ccc1=O)N([C@@H]1c3ccccc3SCc3c1ccc(F)c3F)[C@@H]1COCCN1C2=O] | 1H-NMR (CDCl3) δ: 1.26 (s, 3H), 1.33 (s, 3H), 2.96 (t, J = 11.9 Hz, 1H), 3.46 (t, J = 10.6 Hz, 1H), 3.59 (t, J = 10.6 Hz, 1H), 3.77 (dd, J = 11.9, 2.9 Hz, 1H), 3.95 (dd, J = 11.0, 2.9 Hz, 1H), 4.04-4.13 (m, 3H), 4.56 (dd, J = 10.0, 2.9 Hz, 1H), 4.72 (d, J = 13.4 Hz, 1H), 5.27-5.31 (m, 2H), 5.37 (s, 1H), 5.91 (d, J = 8.0 Hz, 1H), 6.87-6.91 (m, 2H), 7.00-7.05 (m, 1H), 7.07-7.15 (m, 4H). |
| II-137 | 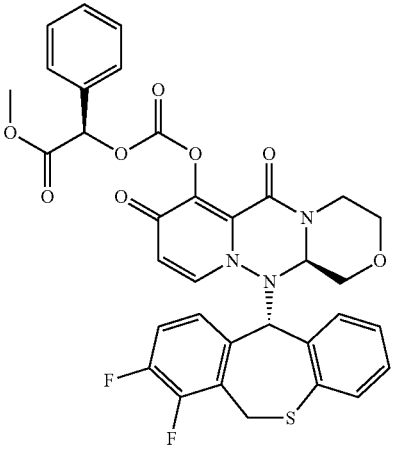 [SMILES: COC(=O)[C@H](OC(=O)Oc1c2n(ccc1=O)N([C@@H]1c3ccccc3SCc3c1ccc(F)c3F)[C@@H]1COCCN1C2=O)c1ccccc1] | 1H-NMR (CDCl3) δ: 2.92 (t, J = 11.0 Hz, 1H), 3.38 (t, J = 11.0 Hz, 1H), 3.56 (t, J = 10.4 Hz, 1H), 3.75 (d, J = 9.3 Hz, 1H), 3.81 (s, 3H), 3.95 (d, J = 9.3 Hz, 1H), 4.06 (d, J = 13.9 Hz, 1H), 4.55 (d, J = 8.1 Hz, 1H), 4.63 (d, J = 13.0 Hz, 1H), 5.27 (d, J = 13.9 Hz, 1H), 5.43 (br s, 1H), 5.91 (d, J = 8.1 Hz, 1H), 6.09 (s, 1H), 6.82-6.86 (m, 1H), 6.93 (d, J = 8.1 Hz, 1H), 7.04-7.13 (m, 5H), 7.39-7.43 (m, 3H), 7.56-7.59 (m, 2H). |

TABLE 33-continued
| No. | Structure | NMR or LC/MS |
|---|---|---|
| II-138 | 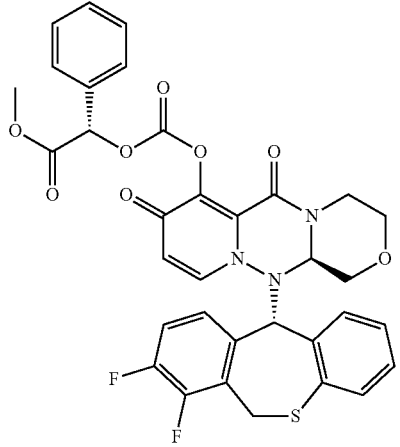 [SMILES: COC(=O)[C@@H](OC(=O)Oc1c2n(ccc1=O)N([C@@H]1c3ccccc3SCc3c1ccc(F)c3F)[C@@H]1COCCN1C2=O)c1ccccc1] | 1H-NMR (CDCl3) δ: 2.94 (t, J = 11.3 Hz, 1H), 3.41 (t, J = 11.3 Hz, 1H), 3.57 (t, J = 10.5 Hz, 1H), 3.76 (d, J = 11.0 Hz, 1H), 3.83 (s, 3H), 3.94 (dd, J = 10.5, 2.7 Hz, 1H), 4.06 (d, J = 14.0 Hz, 1H), 4.55 (dd, J = 9.5, 2.7 Hz, 1H), 4.68 (d, J = 12.6 Hz, 1H), 5.28 (d, J = 14.0 Hz, 1H), 5.35 (s, 1H), 5.90 (d, J = 8.0 Hz, 1H), 6.05 (s, 1H), 6.84-6.90 (m, 2H), 7.00-7.15 (m, 5H), 7.38-7.42 (m, 3H), 7.56-7.60 (m, 2H). |
TABLE 34
| No. | Structure | NMR or LC/MS |
|---|---|---|
| II-139 | 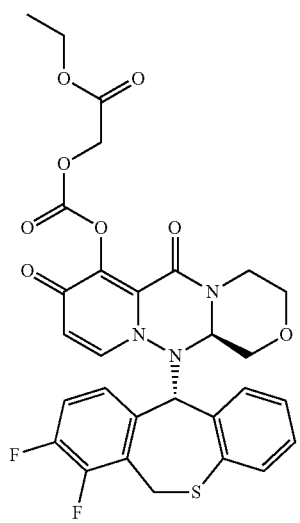 [SMILES: CCOC(=O)COC(=O)Oc1c2n(ccc1=O)N([C@@H]1c3ccccc3SCc3c1ccc(F)c3F)[C@@H]1COCCN1C2=O] | LC/MS (ESI): m/z = 614 [M + H]+, RT = 2.10 min, method (1) |

TABLE 34-continued
| No. | Structure | NMR or LC/MS |
|---|---|---|
| II-140 | 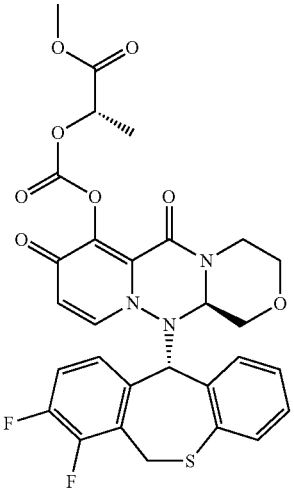 [SMILES: COC(=O)[C@H](C)OC(=O)Oc1c2n(ccc1=O)N([C@@H]1c3ccccc3SCc3c1ccc(F)c3F)[C@@H]1COCCN1C2=O] | LC/MS (ESI): m/z = 614 [M + H]+, RT = 2.04 min, method (1) |
| II-141 | 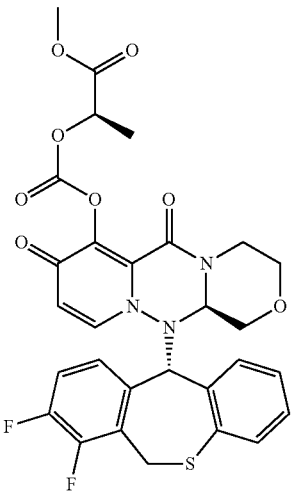 [SMILES: COC(=O)[C@@H](C)OC(=O)Oc1c2n(ccc1=O)N([C@@H]1c3ccccc3SCc3c1ccc(F)c3F)[C@@H]1COCCN1C2=O] | LC/MS (ESI): m/z = 614 [M + H]+, RT = 2.02 min, method (1) |
| II-142 | 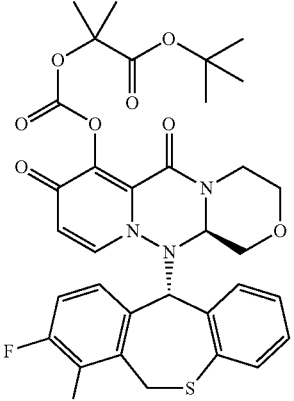 | LC/MS (ESI): m/z = 670 [M + H]+, RT = 2.41 min, method (1) |

TABLE 35
| No. | Structure | NMR or LC/MS |
|---|---|---|
| II-144 | 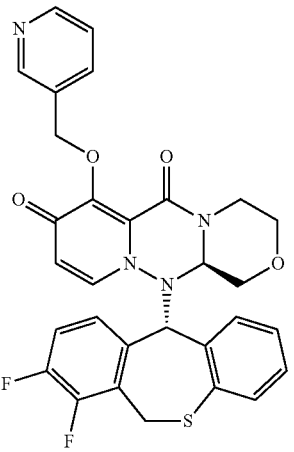 [SMILES: O=C1c2c(OCc3cccnc3)c(=O)ccn2N([C@@H]2c3ccccc3SCc3c2ccc(F)c3F)[C@@H]2COCCN12] | LC/MS (ESI): m/z = 575.20 [M + H]+, RT = 1.49 min, method (2) |
| II-145 | 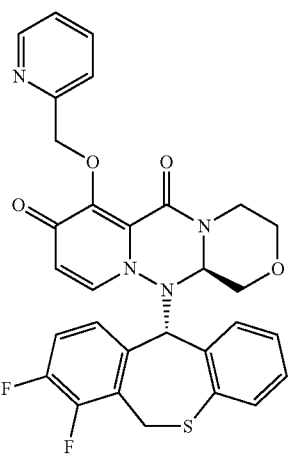 [SMILES: O=C1c2c(OCc3ccccn3)c(=O)ccn2N([C@@H]2c3ccccc3SCc3c2ccc(F)c3F)[C@@H]2COCCN12] | LC/MS (ESI): m/z = 575.00 [M + H]+, RT = 1.52 min, method (2) |
| II-146 | 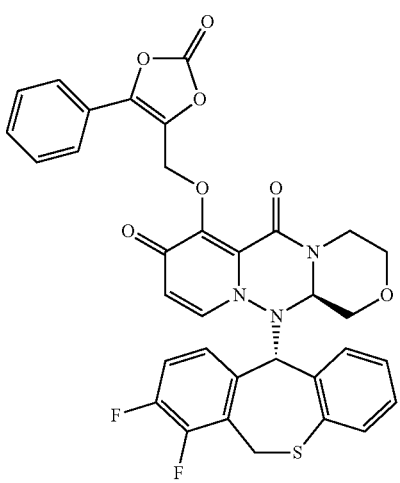 [SMILES: O=C1c2c(OCc3oc(=O)oc3-c3ccccc3)c(=O)ccn2N([C@@H]2c3ccccc3SCc3c2ccc(F)c3F)[C@@H]2COCCN12] | LC/MS (ESI): m/z = 657.90 [M + H]+, RT = 2.23 min, method (2) |

The following compounds can be synthesized by the above methods as well.

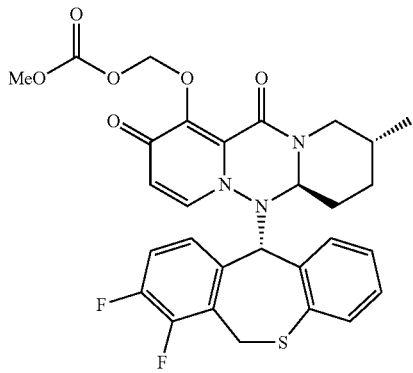

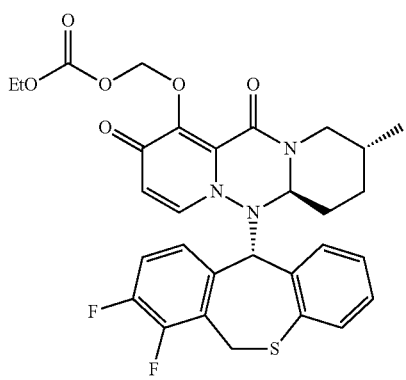

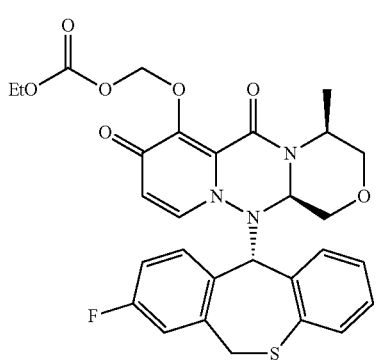

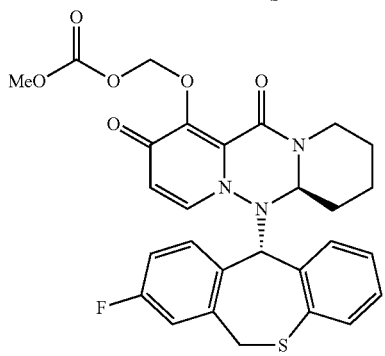

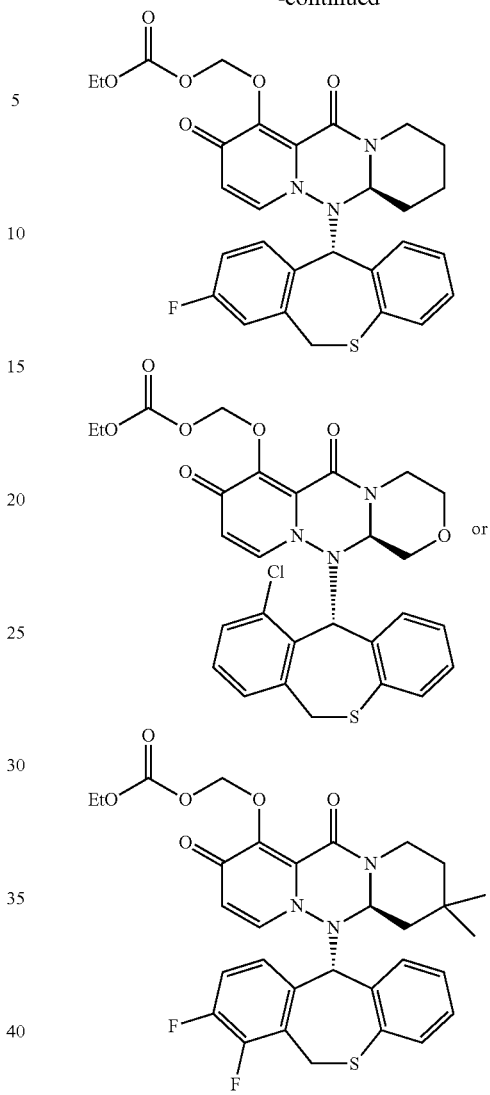

Example 21: Method for Producing II-Form Crystals of Compound II-6

Acetonitrile (50 mL) and water (5 mL) were added to Compound II-6 (10.00 g), the compound was heated to dissolve, and water (95 mL) was added thereto. The solution was stirred for 10 minutes at room temperature, and the precipitated crystals were filtered. The obtained crystals were subjected to through-flow drying to obtain II-form crystals (9.04 g) of Compound II-6.

Figure 4:
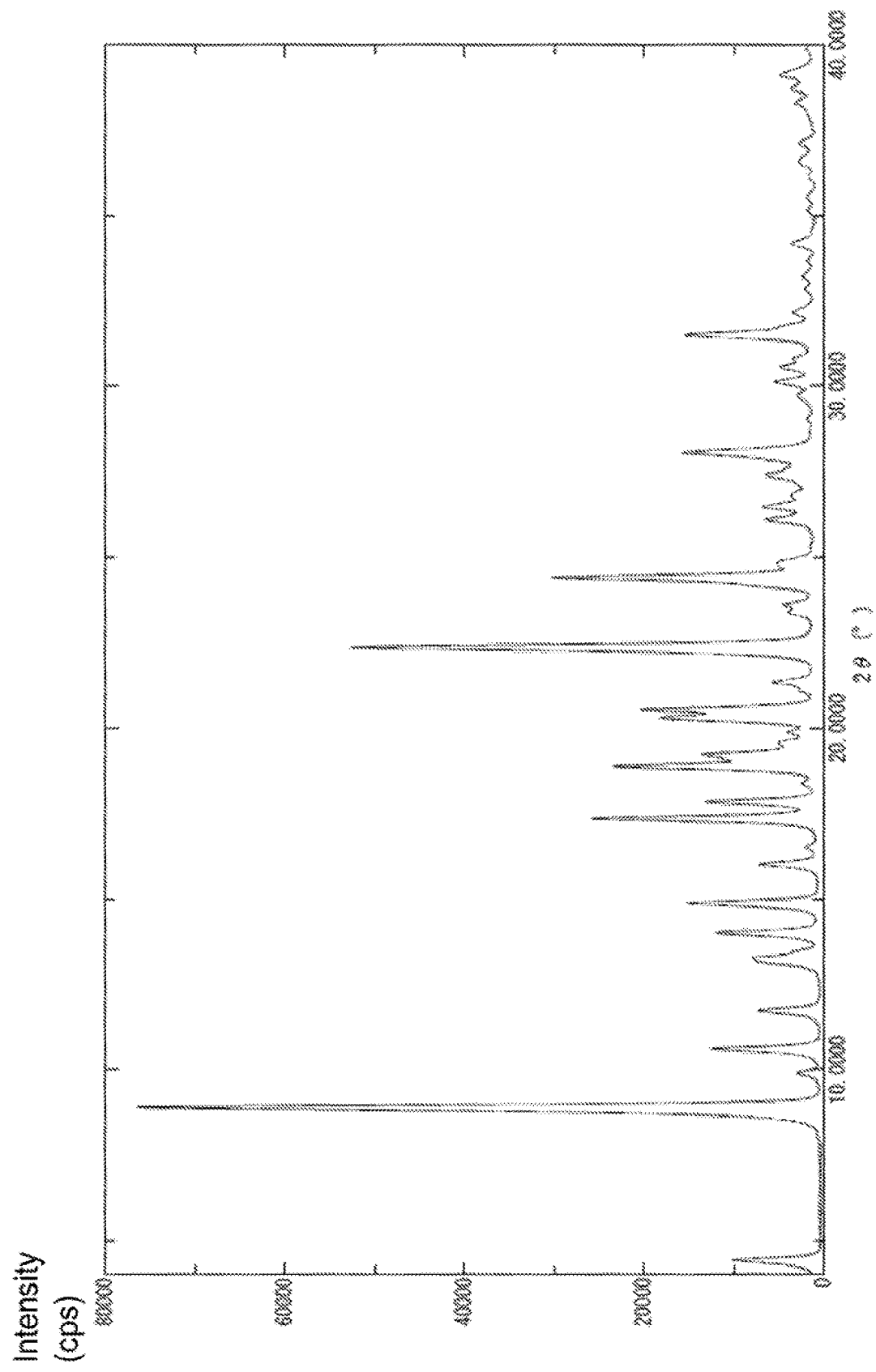
FIG. 4 is powder X-ray diffraction data of II-form crystals of Compound II-6.

FIG. 4 shows powder X-ray diffraction results of II-form crystals of Compound II-6.

Example 22: Method for Producing III-Form Crystals of Compound II-6

Methyl acetate (400 mL) was added to Compound II-6 (10.00 g), and the compound was heated to dissolve. Methyl acetate (about 230 mL) of the solution was concentrated under reduced pressure, the solution was stirred for 70 minutes at room temperature, and the precipitated crystals were filtered. The obtained crystals were subjected to through-flow drying to obtain III-form crystals (7.87 g) of Compound II-6.

Figure 5:
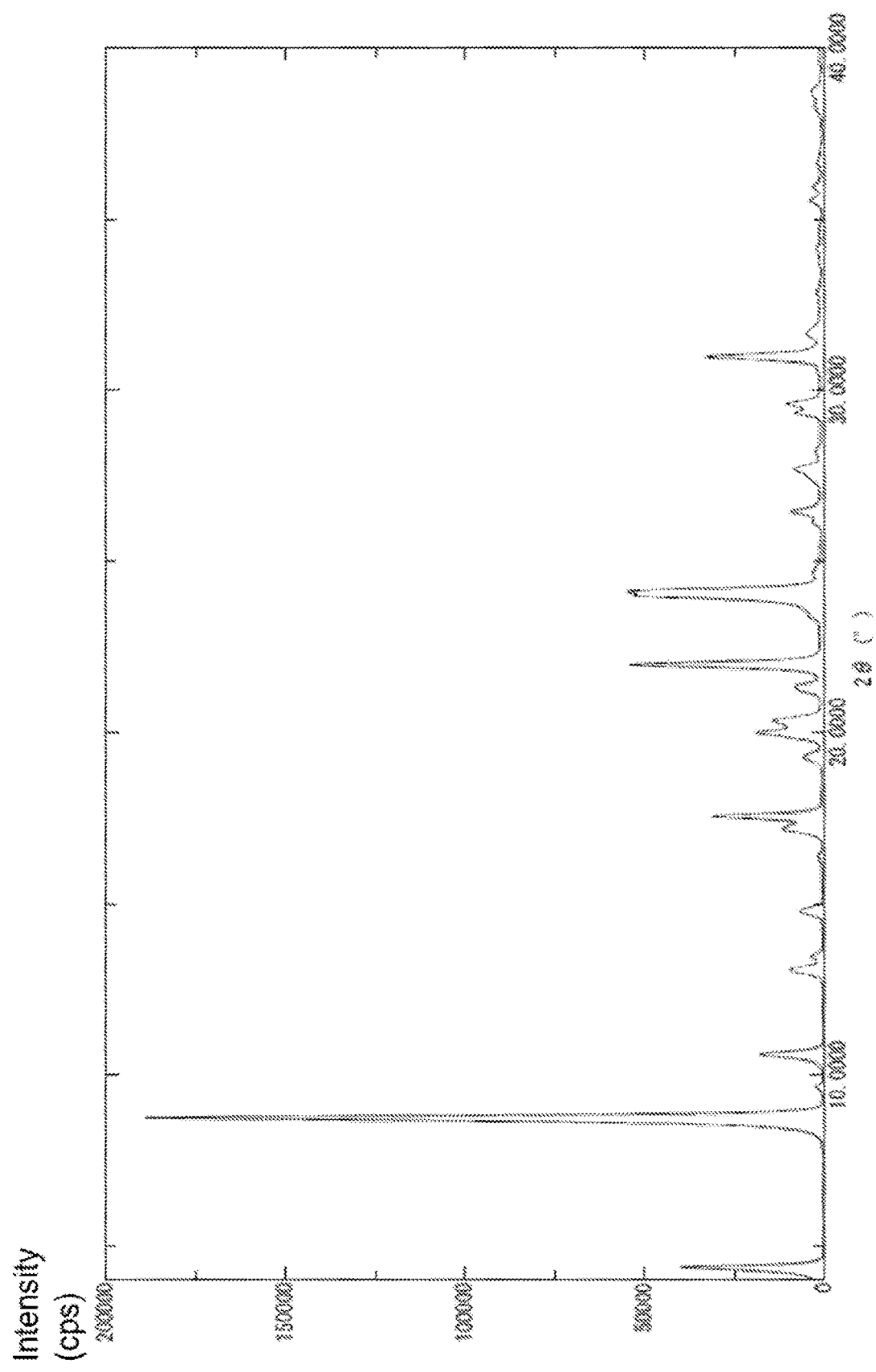
FIG. 5 is powder X-ray diffraction data of III-form crystals of Compound II-6.

FIG. 5 shows powder X-ray diffraction results of III-form crystals of Compound II-6.

Biological test examples for compounds used in the present invention were described below.

Test Example 1: Measurement of Cap-Dependant Endonuclease (CEN) Inhibitory Activity 1) Preparation of Substrate 30merRNA(5'-pp-[m2'-O]GAA UAU(-Cy3) GCA UCA CUA GUA AGC UUU GCU CUA-BHQ2-3': manufactured by Japan Bio Services Co., LTD.) in which G at a 5' end is diphosphate-modified, a hydroxy group at 2' position is methoxylation-modified, U sixth from a 5' end is labelled with Cy3, and a 3' end is labelled with BHQ2 was purchased, and a cap structure was added using ScriptCap system manufactured by EPICENTRE (a product was m7G [5']-ppp-[5'] [m2'-O]GAA UAU(-Cy3) GCA UCA CUA GUA AGC UUU GCU CUA(BHQ2)-3'). This was separated and purified by denatured polyacrylamide gel electrophoresis, and used as a substrate.

2) Preparation of Enzyme

RNP was prepared from a virus particle using standard method (Reference Document: VIROLOGY (1976) 73, p 327-338 OLGA M. ROCHOVANSKY). Specifically, A/WSN/33 virus ($1\times10^3$ PFU/mL, 200 µL) was inoculated in a 10 days old embryonated chicken egg. After incubation at 37° C. for 2 days, the allantoic fluid of the chicken egg was recovered. A virus particle was purified by ultracentrifugation using 20% sucrose, solubilized using TritonX-100 and lysolecithin, and an RNP fraction (50-70% glycerol fraction) was collected by ultracentrifugation using a 30-70% glycerol density gradient, and was used as an enzyme solution (containing approximately 1 nM PB1-PB2-PA complex).

3) Enzymatic Reaction

An enzymatic reaction solution (2.5 µL) (composition: 53 mM Tris-hydrochloride (pH 7.8), 1 mM $MgCl_2$, 1.25 mM dithiothreitol, 80 mM NaCl, 12.5% glycerol, enzyme solution 0.15 µL) was dispensed into a 384-well plate made of polypropylene. Then, 0.5 µL of a test compound solution which had been serially diluted with dimethyl sulfoxide (DMSO) was added to the plate. As a positive control (PC) or a negative control (NC), 0.5 µL of DMSO was added to the plate respectively. Each plate was mixed well. Then, 2 µL of a substrate solution (1.4 nM substrate RNA, 0.05% Tween20) was added to initiate a reaction. After room temperature incubation for 60 minutes, 1 µL of the reaction solution was collected and added to 10 µL of a Hi-Di formamide solution (containing GeneScan 120 Liz Size Standard as a sizing marker: manufactured by Applied Biosystems (ABI)) in order to stop the reaction. For NC, the reaction was stopped in advance by adding EDTA (4.5 mM) before initiation of the reaction (all concentrations described above are final concentrations).

4) Measurement of Inhibition Ratio ($IC_{50}$ Value)

The solution for which the reaction was stopped was heated at 85° C. for 5 minutes, rapidly cooled on ice for 2 minutes, and analyzed with an ABI PRIZM 3730 genetic analyzer. A peak of the cap-dependent endonuclease product was quantitated by analysis software ABI Genemapper, a CEN reaction inhibition ratio (%) of a test compound was obtained by setting fluorescent intensities of PC and NC to be 0% inhibition and 100% inhibition, respectively, an $IC_{50}$ value was obtained using curve fitting software (XLfit2.0: Model 205 (manufactured by I DBS) etc.). The $IC_{50}$ values of test substances being a parent compound, are shown in Table 39.

Test Example 2: CPE Inhibitory Effect Confirming Assay

<Material>

2% FCS E-MEM (prepared by adding kanamycin and FCS to MEM (Minimum Essential Medium) (Invitrogen))

0.5% BSA E-MEM (prepared by adding kanamycin and BSA to MEM (Minimum Essential Medium) (Invitrogen))

HBSS (Hanks' Balanced Salt Solution)

MDBK cell

Cells were adjusted to the appropriate cell number ($3\times10^5$/mL) with 2% FCS E-MEM.

MDCK cell

After washing with HBSS two times, cells were adjusted to the appropriate cell number ($5\times10^5$/mL) with 0.5% BSA E-MEM.

Trypsin solution

Trypsin from porcine pancreas (SIGMA) was dissolved in PBS(-), and filtrated with a 0.45 µm filter.

EnVision (PerkinElmer)

WST-8 Kit (Kishida Chemical Co., Ltd.)

10% SDS solution

<Operation Procedure>

Dilution and Dispensation of Test Sample

As a culture medium, 2% FCS E-MEM was used at the use of MDBK cells, and 0.5% BSA E-MEM was used at the use of MDCK cells. Hereinafter, for diluting virus, cells and a test sample, the same culture medium was used.

A test sample was diluted with a culture medium to an appropriate concentration in advance, and then 2 to 5-fold serial dilution on a 96 well plate (50 µL/well) was prepared. Two plates, one for measuring anti-Flu activity and the another for measuring cytotoxicity, were prepared. Each assay was performed triplicate for each drug.

At the use of MDCK cells, Trypsin was added to the cells to be a final concentration of 3 µg/mL only for measuring anti-Flu activity.

Dilution and Dispensation of Influenza Virus

An influenza virus was diluted with a culture medium to an appropriate concentration in advance, and each 50 µL/well was dispensed on a 96-well plate containing a test substance. Each 50 µL/well of a culture medium was dispensed on a plate containing a test substance for measuring cytotoxity.

Dilution and Dispensation of Cell

Each 100 µL/well of cells which had been adjusted to the appropriate cell number was dispensed on a 96 well plate containing a test sample.

This was mixed with a plate mixer, and incubated in a CO2 incubator for 3 days for measuring anti-Flu activity and measuring cytotoxicity.

Dispensation of WST-8

The cells in the 96-well plate which had been incubated for 3 days was observed visually under a microscope, and appearance of the cells, the presence or absence of a crystal of test substance were checked. The supernatant was removed so that the cells were not absorbed from the plate.

WST-8 Kit was diluted 10-fold with a culture medium, and each 100 µL was dispensed into each well. After mixing with a plate mixer, cells were incubated in a CO2 incubator for 1 to 3 hours.

After incubation, regarding the plate for measuring anti-Flu activity, each 10 μL/well of a 10% SDS solution was dispensed in order to inactivate a virus.

Measurement of Absorbance

After the 96-well plate was mixed, absorbance was measured with EnVision at two wavelengths of 450 nm/620 nm.

<Calculation of Each Measurement Item Value>

The value was calculated using Microsoft Excel or a program having the equivalent calculation and processing ability, based on the following calculation equation.

Calculation of effective inhibition concentration to achieve 50% influenza infected cell death (EC50)

$$EC50 = 10^Z$$

$$Z = (50\% - \text{High }\%)/(\text{High }\% - \text{Low }\%) \times \{\log(\text{High conc.}) - \log(\text{Low conc.})\} + \log(\text{High conc.})$$

For the parent compounds used in the present invention, measurement results of Test Example 1 and Test Example 2 are shown below.

TABLE 36

| No. | CEN_IC50 nM | CPE_EC50 nM |
|---|---|---|
| III-2 | 1.93 | 1.13 |
| III-3 | 2.22 | 3.39 |
| III-9 | 2.17 | 10.90 |
| III-10 | 4.05 | 3.46 |
| III-11 | 13.10 | 9.98 |
| III-12 | 2.18 | 3.38 |
| III-13 | 3.94 | 4.00 |
| III-14 | 15.00 | 15.70 |
| III-19 | 2.37 | 1.43 |
| III-20 | 3.24 | 4.00 |
| III-21 | 4.06 | 2.70 |
| III-22 | 3.46 | 3.07 |
| III-23 | 1.48 | 0.86 |
| III-26 | 1.63 | 3.00 |
| III-28 | 10.70 | 5.67 |
| III-29 | 0.87 | 0.66 |
| III-30 | 5.68 | 3.01 |
| III-31 | 18.50 | 3.17 |
| III-33 | 2.08 | 2.36 |
| III-34 | 4.69 | 2.85 |
| III-35 | 3.86 | 3.00 |
| III-36 | 2.37 | 2.45 |
| III-37 | 4.24 | 3.43 |
| III-38 | 8.26 | 4.04 |
| III-39 | 2.75 | 2.81 |
| III-40 | 2.99 | 2.95 |
| III-41 | 2.10 | 2.17 |
| III-42 | 3.93 | 2.64 |
| III-43 | 3.90 | 3.18 |
| III-44 | 3.81 | 3.68 |
| III-45 | 1.63 | 3.07 |
| III-46 | 2.91 | 3.18 |
| III-47 | 2.25 | 2.53 |
| III-48 | 3.49 | 3.57 |
| III-49 | 6.79 | 4.17 |
| III-50 | 2.55 | 4.36 |
| III-51 | 2.22 | 2.58 |
| III-52 | 3.62 | 3.28 |

TABLE 37

| No. | CEN IC50 nM | CPE IC50 nM |
|---|---|---|
| III-53 | 2.46 | 3 |
| III-54 | 1.27 | 1.18 |
| III-55 | 2.13 | 3.45 |
| III-57 | 4.27 | 3.47 |
| III-58 | 2.65 | 3.13 |
| III-59 | 0.57 | 3.11 |

Based on the above results, the parent compounds used in the present invention exhibit high cap-dependent endonuclease (CEN) inhibitory activity and/or high CPE inhibitory effect and thus can be a useful agent for treatment and/or prevention of symptom and/or disease induced by infection with influenza virus.

Test Example 3: CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a compound used in the present invention was assessed.

The reaction conditions were as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2DG), 1 μmol/L terfenedine (CYP3A4); reaction time, 15 minutes; reaction temperature, 37° C.; enzyme, pooled human hepatic microsome 0.2 mg protein/mL; concentration of a compound used in the present invention, 1, 5, 10, 20 μmol/L (four points).

Each five kinds of substrates, human hepatic microsome, or a compound used in the present invention in 50 mmol/L Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and toltributamide hydroxide (CYP2C9P metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a compound used in the present invention to a reaction system was adopted as a control (100%), remaining activity (%) was calculated at each concentration of a compound used in the present invention added as the solution and IC50 was calculated by reverse presumption by a logistic model using a concentration and an inhibition rate.

(Result)

Compound III-2: five kinds >20 μmol/L

Test Example 4: BA Test

Materials and methods for experiments to evaluate oral absorption (1) Experimental animals: mice or SD rats were used.
(2) Rearing condition: mice or SD rats were allowed free access to solid feed and sterilized tap water.

(3) Setting of dosage and grouping: Oral administration and intravenous administration were performed with the predetermined dosage. Grouping was set as below. (Dosage was changed per compound)
  Oral administration 1 to 30 mg/kg (n=2 to 3)
  Intravenous administration 0.5 to 10 mg/kg (n=2 to 3)
(4) Preparation of administration solutions: Oral administration was performed as solution or suspension. Intravenous administration was performed after solubilization.
(5) Routes of administration: Oral administration was performed mandatory into the stomach by oral sonde. Intravenous administration was performed from caudal vein by syringes with needle.
(6) Evaluation items: Blood was collected serially and concentration of a compound used in the present invention in plasma was measured by LC/MS/MS.
(7) Statistical analysis: About transition of concentration of a compound used in the present invention in plasma, the area under the plasma concentration versus time curve (AUC) was calculated by non-linear least-squares method program, WinNonlin (a registered trademark), and bioavailability (BA) of a compound used in the present invention was calculated from AUCs of the oral administration group and the intravenous administration group.
(Result)
Compound II-6: 14.9%
Compound III-2: 4.2%
  Based on the above results, the prodrug had improved bioavailability other than the parent compound.
  Therefore, the compound used in the present invention has excellent oral absorbability and can be a useful agent for treatment and/or prevention of symptom and/or disease induced by infection with influenza virus.

Test Example 5: Metabolism Stability Test

Using commercially available pooled human hepatic microsomes, a compound used in the present invention was reacted for a constant time, and a remaining rate was calculated by comparing a reacted sample and an unreacted sample, thereby, a degree of metabolism in liver was assessed.
  A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), mixed and centrifuged at 3000 rpm for 15 minutes. The compound used in the present invention in the supernatant was quantified by LC/MS/MS or Solid Phase Extraction (SPE)/MS, and a remaining amount of the compound used in the present invention after the reaction was calculated, letting a compound amount at 0 minute reaction time to be 100%. Hydrolysis reaction was performed in the absence of NADPH and glucuronidation reaction was in the presence of 5 mM UDP-glucuronic acid in place of NADPH, followed by similar operations.
(Result) % inhibition was shown at 2 µmol/L of test compound.
Compound III-2: 90.1%

Test Example 6: CYP3A4 Fluorescent MBI Test

The CYP3A4 fluorescent MBI test is a test of investigating enhancement of CYP3A4 inhibition of a compound used in the present invention by a metabolism reaction, and the test was performed using, as CYP3A4 enzyme expressed in *Escherichia coli* and employing, as an index, a reaction in which 7-benzyloxytrifluoromethylcoumarin (7-BFC) is debenzylated by the CYP3A4 enzyme to produce a metabolite, 7-hydroxytrifluoromethylcoumarin (HFC) emitting fluorescent light.
  The reaction conditions were as follows: substrate, 5.6 µmol/L 7-BFC; pre-reaction time, 0 or 30 minutest reaction time, 15 minutest reaction temperature, 25° C. (room temperature); CYP3A4 content (expressed in *Escherichia coli*), at pre-reaction 62.5 pmol/mL, at reaction 6.25 pmol/mL (at 10-fold dilution); test drug concentration of a compound used in the present invention, 0.625, 1.25, 2.5, 5, 10, 20 µmol/L (six points).
  An enzyme in a K-Pi buffer (pH 7.4) and a solution of a compound used in the present invention as a pre-reaction solution were added to a 96-well plate at the above composition of the pre-reaction, a part of it was transferred to another 96-well plate so that it was $\frac{1}{10}$ diluted with a substrate and a K-Pi buffer, NADPH as a co-factor was added to initiate a reaction as an index (without preincubation) and, after a predetermined time of a reaction, acetonitrile/0.5 mol/L Tris (trishydroxyaminomethane)=4/1 (V/V) was added to stop the reaction. In addition, NADPH was added to a remaining preincubation solution to initiate a preincubation (with preincubation) and, after a predetermined time of a preincubation, a part was transferred to another plate so that it was $\frac{1}{10}$ diluted with a substrate and a K-Pi buffer to initiate a reaction as an index. After a predetermined time of a reaction, acetonitrile/0.5 mol/L Tris (trishydroxyaminomethane)=4/1 (V/V) was added to stop the reaction. For the plate on which each index reaction had been performed, a fluorescent value of 7-HFC which is a metabolite was measured with a fluorescent plate reader. (Ex=420 nm, Em=535 nm).
  Addition of only DMSO which is a solvent dissolving a compound used in the present invention to a reaction system was adopted as a control (100%), remaining activity (%) was calculated at each concentration of a compound used in the present invention added as the solution, and $IC_{50}$ was calculated by reverse-presumption by a logistic model using a concentration and an inhibition rate. When a difference between $IC_{50}$ values is 5 µmol/L or more, this was defined as (+) and, when the difference is 3 µmol/L or less, this was defined as (−).
(Result)
Compound III-2: (−)

Test Example 7: Fluctuation Ames Test

Mutagenicity of compounds used in the present invention was evaluated.
  20 µL of freezing-stored rat typhoid *bacillus* (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution. The bacteria was suspended in 9 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L), the suspension was added to 110 mL of an Exposure medium (Micro F buffer containing Biotin: 8 µg/mL, histidine: 0.2 µg/mL, glucose: 8 mg/mL). The TA100 strain was added to 120 mL of the Exposure medium relative to 3.16 mL of the bacterial solution to prepare a test bacterial solution. Each 12 µL of DMSO solution of a compound used in the present invention (several stage dilution from maximum dose 50 mg/mL at 2 to 3 fold ratio), DMSO as a negative control, and 50 µg/mL of 4-nitroquinoline-1-oxide DMSO solution for the TA98 strain, 0.25 µg/mL of 2-(2-furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/mL of 2-aminoanthracene DMSO solution for the TA100 strain under the metabolism activating condition as a positive control, and 588 µL of the test bacterial solution (a mixed solution of 498 µl of the test bacterial solution and 90 µL of S9 mix under the metabolism activating condition) were mixed, and this was shaking-cultured at 37° C. for 90 minutes. 460 µL of the bacterial solution exposed to a compound used in the present invention was mixed with 2300 µL of an Indicator medium (Micro F buffer containing biotin: 8 µg/mL, histidine: 0.2 µg/mL, glucose: 8 mg/mL, Bromo Cresol Purple: 37.5 µg/mL), each 50 µL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group. (−) means that mutagenicity is negative and (+) is positive.
(Result)
Compound III-2: (−)

Test Example 8: hERG Test

For the purpose of assessing risk of an electrocardiogram QT interval prolongation of the compound used in the present invention, effects of the compound used in the present invention on delayed rectifier K+ current (IKF), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$, induced by depolarization pulse stimulation at +40 mV for 2 seconds and, further, repolarization pulse stimulation at −50 mV for 2 seconds, was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazineethanesulfonic acid): 10 mmol/L, pH=7.4), in which the compound used in the present invention had been dissolved at an objective concentration, was applied to the cell at room temperature for 10 minutes. From the recording $I_{Kr}$, an absolute value of the tail peak current was measured based on the current value at the resting membrane potential using analysis software (DataXpress ver. 1, Molecular Devices Corporation). Further, the % inhibition relative to the tail peak current before application of the compound used in the present invention was calculated, and compared with the vehicle-applied group (0.1% dimethyl sulfoxide solution) to assess influence of the compound used in the present invention on I Hr.

(Result) % inhibition was shown al 0.3 to 10 µM of test compound.
Compound III-2: 7.9%

Test Example 9: Solubility Test

The solubility of the compound used in the present invention was determined under 1% DMSO addition conditions. A 10 mmol/L solution of the compound was prepared with DMSO, and 2 µL of the solution of the compound used in the present invention was added, respectively, to 198 µL of JP-1 solution (water were added to 2.0 g of sodium chloride and 7.0 mL of hydrochloric acid to reach 1000 mL) and JP-2 solution (1 volume of water were added to 1 volume of the solution which 3.40 g of potassium dihydrogen phosphate and 3.55 g of anhydrous disodium hydrogen phosphate to reach 1000 mL). The mixture was shaken for 1 hour at a room temperature, and the mixture was filtered. The filtrate was ten-fold diluted with methanol/water=1/1 (v/v), and the compound concentration in the filtrate was measured with LC/MS or SPE/MS by the absolute calibration method.
(Result)
Compound III-2: 42.2 µmol/L Test Example 10: Powder Solubility Test Appropriate amounts of the compound used in the present invention was put into vials and 200 µL of JP-1st Fluid (water was added to 2.0 g of sodium chloride in 7.0 mL of hydrochloride acid to reach 1000 mL), JP-2nd Fluid (water was added to 500 mL of phosphate buffer solution with a pH of 6.8) and 20 mmol/L sodium taurocholate (TCA)/JP-2nd Fluid (JP-2nd Fluid was added to 1.08 g of TCA in JP-2nd Fluid to reach 100 mL) was added to each vial. When the compound was completely dissolved, appropriate amount of compound was added. After shaken for 1 hour at 37° C., the mixture was filtered and 100 µL of methanol was added to 100 µL of each filtrate (double dilution). Dilution magnification was changed if necessary. After it was confirmed whether there were air bubbles and precipitates in the vials, the vials were shaken with tight stopper. The compound concentration was determined with HPLC by the absolute calibration method.
(Result)
Compound III-2: JP-1 solution; 7.1 µg/mL, JP-2 solution; 4.4 µg/mL, 20 mmol/L TCA/JP-2 solution; 16.1 µg/mL Test Example 11: Ames Test Ames test was performed by using Salmonellas (*Salmonella typhimurium*) TA 98, TA100, TA1535 and TA1537 and *Escherichia coli* WP2uvrA as test strains with or without metabolic activation in the pre-incubation method to check the presence or absence of gene mutagenicity of compounds used in the present invention.
(Result)
Compound III-2: (−)

Test Example 12: Light Hemolysis Test

The compound used in the present invention was dissolved at target concentrations and was mixed with a 2.5 v/v % suspension of red blood cells prepared from a defibrinated blood of sheep on a microplate at concentrations of 0.0008 to 0.1 w/v %. The mixtures were exposed to 10° $J/cm^2$ of UV-irradiation within a range of wavelength 290 to 400 nm, UVA and UVB using ultra violet fluorescent lamps, GL20SE and FL20S-BLB lamps manufactured by Sankyo Denki Co., Ltd. and Panasonic Corporation, respectively. After the completion of the irradiation, the mixtures were centrifuged, and a supernatant of the mixture was collected and was located on a microplate. The phototoxicity was assessed by measuring an absorbance at wavelength of 540 nm and 630 nm in the supernatant. The absorbance data at wavelength of 540 nm and 630 nm were used as indicators of biomembrane damage (photohemolysis %) and hyperoxidation of lipid membrane (methemoglobin formation), respectively. The criteria of phototoxicity was as follows; It was judged to be non-phototoxic (−) when the photohemolysis %<10 and the maximal change in the absorbance at 630 nm ($\Delta OD$)<0.05 were observed. It was judged to be non-phototoxic (+) when the photohemolysis was more than 10% and the maximal change in the absorbance at 630 nm ($\Delta OD$) was more than 0.05.
(Result)
Compound III-2: (−)

Test Example 13: Transition of Plasma Concentration

The plasma concentration of Compound III-2 and Compound II-6 after oral administration of prodrug Compound II-6, the parent compound of which was Compound III-2, to rat under non-fasting conditions was measured. The result is shown in FIGS. 1 and 2.

The concentration of Compound II-6 in all plasma samples was a determination limit or less. Therefore, prodrug Compound II-6, the parent compound of which was Compound III-2 was found to have changed promptly to Compound III-2 in vivo after administration (see FIG. 2).

Based on the above test results, it was revealed that the compound converted into a prodrug was absorbed into the body after oral administration, and rapidly converted into a parent compound in the blood. Therefore, the compounds (parent compounds and/or prodrugs) used in the present invention can be useful agents for treatment and/or prevention of symptoms and/or diseases induced by infection with influenza virus.

Test Example 14: Intravenous Administration Test

Examined experimental materials and method of intravenous administration test
(1) Animals used: SD rats were used.
(2) Rearing conditions: Pellets and sterilized tap water were fed to SD rats ad libitum.
(3) Dosage and grouping: A predetermined dosage was intravenously administered. Groups were set as follows. (Dosage varied for each compound)
Intravenous administration 0.5-1 mg/kg (n=2-3)
(4) Preparation of administration solution: Intravenous administration was performed after solubilization.
(5) Administration method: Intravenous administration was performed with a needle-equipped syringe on the caudal vein.
(6) End point: Blood was collected over time, and the plasma concentration of the compound used in the present invention was measured using LC/MS/MS.
(7) Statistical analysis: As for the transition of the plasma concentration of the compound used in the present invention, the total body clearance (CLtot) and the elimination half-life (t½, z) were calculated using nonlinear least-squares program WinNonlin (Registered trademark).

(Results)
Compound No. III-2:
CLtot: 16.4 mL/min/kg
t½, z: 3.4 hours
From the above results, it was found that Compound III-2 is a compound having a low total body clearance and a long half-life.
Therefore, the compound used in the present invention has excellent persistence and can be a useful agent for treatment and/or prevention of symptom and/or disease induced by infection with influenza virus.

Test Example 15: Clinical Test

The efficacy and safety of a single oral administration of an investigational drug (active ingredient (Compound II-6): 10 mg, 20 mg, 40 mg) to patients infected by influenza virus were evaluated by a randomized, placebo-controlled, double-blind comparative study. As for the primary endpoint, subjects made evaluations by themselves on a 4-point scale [0: none, 1: mild, 2: moderate, 3: severe] concerning the time to alleviation of influenza symptoms (the time from the beginning of administration of the investigational drug until 7 influenza symptoms ("cough", "sore throat", "headache", "nasal congestion", "feverishness or chills", "muscular or joint pain", and "fatigue") were alleviated) to evaluate the efficacy of the investigational drug over the placebo.

Patients who satisfied all of the following criteria were selected as subjects.
(a) Male or female patients at 20 years old or older and younger than 65 years old
(b) Patients satisfying all of the following criteria and diagnosed with influenza virus infectious disease
Positive in influenza rapid diagnosis [Rapid antigen test (RAT)] based on a nasal or throat swab
Body temperature (axillary temperature) of 38.0° C. or higher
Having one or more moderate or severer symptoms among the following systemic symptoms and respiratory symptoms due to influenza virus infectious disease
Systemic symptoms (headache, feverishness or chills, muscular or joint pain, fatigue)
Respiratory symptoms (cough, sore throat, nasal congestion)
(C) Patients within 48 hours from onset (at registration)
The definition of onset is any of the following.
When the body temperature increased for the first time (at least an increase of 1° C. from normal temperature)
When any one or more of the systemic symptoms and respiratory symptoms were developed
Method for Administering Investigational Drug
(i) Test Drug
10 mg Tablet of Compound II-6: White to pale yellowish white, circular, film-coated tablet containing 10 mg of Compound II-6
20 mg Tablet of Compound II-6: White to pale yellowish white, elliptical, film-coated tablet containing 20 mg of Compound II-6
(ii) Placebo or Control Drug
Placebo for 10 mg tablet of Compound II-6: Tablet undistinguishable from 10 mg tablet of Compound II-6
Placebo for 20 mg tablet of Compound II-6: Tablet undistinguishable from 20 mg tablet of Compound II-G
Dosage and Administration Method
Eligible subjects were randomly allocated to a Compound II-6 10 mg group, 20 mg group, 40 mg group, and placebo group in a ratio of 1:1:1:1. Subjects received a single oral administration of total 3 tables of Compound II-6 tablets and/or placebo tablets in a combination indicated in the following table on Day 1.

Investigational Drug for Each Administered Group

TABLE 38

| Treatment Groups | Compound II-6 10 mg tablet | Compound II-6 20 mg tablet | Placebo tablet Matching Compound II-6 10 mg tablet | Placebo tablet Matching Compound II-6 20 mg tablet |
|---|---|---|---|---|
| Compound II-6 10 mg tablet | 1 tablet | — | — | 2 tablets |
| Compound II-6 20 mg tablet | — | 1 tablet | 1 tablet | 1 tablet |
| Compound II-6 40 mg tablet | — | 2 tablets | 1 tablet | — |
| Placebo | — | — | 1 tablet | 2 tablets |

Main Efficacy Endpoint

The main efficacy endpoint is the time to alleviation of influenza symptoms (the time to alleviation of influenza symptoms).

It is the time from the beginning of administration until alleviation of influenza symptoms. Alleviation of influenza symptoms refers to when all 7 influenza symptoms (cough, sore throat, headache, nasal congestion, feverishness or chills, muscular or joint pain, fatigue) become "0: none" or "1: mild" in the patient diary that the subject keeps, and this condition continues at least 21.5 hours (24 hours—10%).

Secondary Efficacy Endpoint

The secondary efficacy endpoint is as follows.

(1) Time to Alleviation of Each Influenza Symptom

It is the time from the beginning of administration until alleviation of each influenza symptom. Alleviation of a symptom refers to when the target item becomes "0: none" or "1: mild", and this condition continues at least 21.5 hours (24 hours—10%).

Analysis of Primary Endpoint

As for the time to alleviation of influenza symptoms, which is the primary endpoint, the primary analysis and the secondary analysis are described. In addition to the ITTI group, the primary analysis was also performed on the PPS group for sensitivity analysis. Other analyses were performed only on the ITTI group.

(1) Primary Analysis

The hazard ratio, 95% confidence interval, and P value of each administered group relative to the placebo group were calculated by a Cox proportional hazard model using the time to alleviation of influenza symptoms as a response, the administered groups as fixed effects, and the current smoking habit and the total score of 7 influenza symptoms al baseline before administration, which are allocation factors, as covariates. In order to prevent an increase of the probability of type I error due to performing the test multiple times, the P value was adjusted by the Hommel's method.

(2) Secondary Analysis

The placebo group and each investigational drug administered group were compared by stratified generalized Wilcoxon test using the time to alleviation of influenza symptoms as a response, the administered groups as explanatory variables, and the category (11 points or less, 12 points or more) of the total score of 7 influenza symptoms before administration and the smoking habit, which are allocation factors, as stratification factors.

Also, a Kaplan-Meier survival curve was drawn for each group to calculate the median time to alleviation of influenza symptoms and the 95% confidence interval thereof. The Greenwood's method was used for calculating the confidence interval.

Analysis of Secondary Endpoint (1) Time Until Each Alleviation of Influenza Symptom The same analysis as in the primary endpoint was performed, with the time until each alleviation of influenza symptom being regarded as a response. At this time, cases where the symptom before administration was "0: none" or "1: mild" were excluded from the analysis target.

(1) Results of Primary Endpoint (Time to Alleviation of Influenza Symptoms)

Out of 400 randomly selected patients, 389 patients (98 patients (98%) in the 10 mg administered group, 95 patients (95%) in the 20 mg administered group, 99 patients (99%) in the 40 mg administered group, and 97 patients (97%) in the placebo group) completed the test. As for the primary endpoint, the ITTI Population (cases where an investigational drug was administered, and influenza virus infection was confirmed) consisted of 400 patients.

The per protocol set cases consisted of 368 patients (89 patients (89%) in the 10 mg administered group, 92 patients (92%) in the 20 mg administered group, 96 patients (96%) in the 40 mg administered group, and 91 patients (91%) in the placebo group). As for the ITTI Population of each group, it was found from the rapid antigen detection test that 75% to 79% of the patients were infected by influenza A virus, and 21% to 25% of the patients were infected by influenza B virus.

Analysis results are shown in the following tables.

TABLE 39

| | Testdrug 10 mg administered group | Testdrug 20 mg administered group | Testdrug 40 mg administered group | Placebo administered group |
|---|---|---|---|---|
| N (human) | 100 | 100 | 100 | 100 |
| Median value (hour) | 54.2 | 51 | 49.5 | 77.7 |

TABLE 39-continued

|  | Testdrug 10 mg administered group | Testdrug 20 mg administered group | Testdrug 40 mg administered group | Placebo administered group |
|---|---|---|---|---|
| 95% Confidence interval (hour) | 47.7, 66.8 | 44.5, 62.4 | 44.5, 64.4 | 67.6, 88.7 |
| Difference from placebo (hour) Generated Wilson test | −23.4 | −26.6 | −28.2 | — |
| P value | 0.0085 | 0.0182 | 0.0046 | — |
| Cox proportional hazard model relative to placebo |  |  |  |  |
| Hazard ratio | 0.758 | 0.81 | 0.817 | — |
| 95% Confdence interval | 0.571, 1.007 | 0.608, 1.078 | 0.614, 1.087 | — |
| P value | 0.0561 | 0.1488 | 0.165 | — |

The primary endpoint of this test, i.e., the median time until the symptoms were alleviated, was 54.2 hours in the 10 mg administered group (95% CI: 47.7, 66.8), 51.0 hours in the 20 mg administered group (95% CI: 47.7, 66.8), 49.5 hours in the 40 mg administered group (95% CI: 44.5, 64.4), and 77.7 hours in the placebo group (95% CI: 67.6, 88.7).

(2) Time Until Each of the Seven Symptoms is Alleviated

The following tables show the results of analyzing the time until each of the 7 influenza symptoms ("cough", "sore throat", "headache", "nasal congestion", "feverishness or chills", "muscular or joint pain", "fatigue") is alleviated.

(i) Time Until "Nasal Congestion" Symptom is Alleviated

TABLE 40

|  | Testdrug 10 mg administered group | Testdrug 20 mg administered group | Testdrug 40 mg administered group | Placebo administered group |
|---|---|---|---|---|
| N (human) | 49 | 38 | 45 | 47 |
| Median value (95% CI) (hour) | 25.2 (19.0, 47.2) | 21.6 (13.4, 30.5) | 21.9 (16.0, 28.7) | 42.8 (22.9, 68.3) |
| Difference from placebo (hour) | −17.6 | −21.3 | −21 | — |
| P value (G. Wilcoxon test)$^a$ | 0.043 | 0.0516 | 0.0003 | — |
| Hazard ratio (95% CI)$^b$ | 0.742 (0.494, 1.114) | 0.59 (0.379, 0.920) | 0.564 (0.369, 0.862) | — |
| P value (Cox model)$^b$ | 0.15 | 0.0199 | 0.0081 | — |

(ii) Time Until "Muscular or Joint Pain" Symptom is Alleviated

TABLE 41

|  | Testdrug 10 mg administered group | Testdrug 20 mg administered group | Testdrug 40 mg administered group | Placebo administered group |
|---|---|---|---|---|
| N (human) | 73 | 77 | 71 | 71 |
| Median value (95% CI) (hour) | 31.2 (24.9, 39.9) | 29.9 (22.8, 37.0) | 25.4 (20.5, 28.9) | 41.9 (28.7, 48.6) |
| Difference from placebo (hour) | −10.7 | −12 | −16.4 | — |
| P value (G. Wilcoxon test)$^a$ | 0.2153 | 0.0346 | 0.0048 | — |
| Hazard ratio (95% CI)$^b$ | 0.77 (0.553, 1.072) | 0.687 (0.494, 0.955) | 0.657 (0.469, 0.920) | — |
| P value (Cox model)$^b$ | 0.1217 | 0.0255 | 0.0145 | — |

(iii) Time Until "Fatigue" Symptom is Alleviated

TABLE 42

|  | Testdrug 10 mg administered group | Testdrug 20 mg administered group | Testdrug 40 mg administered group | Placebo administered group |
|---|---|---|---|---|
| N (human) | 82 | 82 | 77 | 79 |
| Median value | 32 | 31.3 | 31.1 | 42.7 |
| (95% CI) (hour) | (29.2, 39.9) | (26.7, 42.4) | (24.6, 38.6) | (30.3, 53.2) |
| Difference from placebo (hour) | −10.7 | −11.5 | −11.7 | — |
| P value (G. Wilcoxon test)[a] | 0.1221 | 0.0594 | 0.0224 | — |
| Hazard ratio (95% CI)[b] | 0.783 (0.574, 1.069) | 0.876 (0.637, 1.203) | 0.724 (0.527, 0.995) | — |
| P value (Cox model)[b] | 0.1236 | 0.412 | 0.0463 | — |

(iv) Time Until "Feverishness or Chills" Symptom is Alleviated

TABLE 43

|  | Testdrug 10 mg administered group | Testdrug 20 mg administered group | Testdrug 40 mg administered group | Placebo administered group |
|---|---|---|---|---|
| N (human) | 97 | 93 | 94 | 95 |
| Median value | 24.7 | 29.4 | 23 | 28.8 |
| (95% CI) (hour) | (21.3, 28.4) | (22.0, 34.8) | (19.8, 28.6) | (21.1, 33.4) |
| Difference from placebo (hour) | −4.1 | 0.6 | −5.8 | — |
| P value (G. Wilcoxon test)[a] | 0.0602 | 0.3774 | 0.0258 | — |
| Hazard ratio (95% CI)[b] | 0.635 (0.475, 0.850) | 0.848 (0.6347, 1.133) | 0.71 (0.529, 0.951) | — |
| P value (Cox model)[b] | 0.0023 | 0.2642 | 0.0216 | — |

(v) Time Until "Headache" Symptom is Alleviated

TABLE 44

|  | Testdrug 10 mg administered group | Testdrug 20 mg administered group | Testdrug 40 mg administered group | Placebo administered group |
|---|---|---|---|---|
| N (human) | 61 | 58 | 54 | 57 |
| Median value | 42.2 | 37 | 37.9 | 43.7 |
| (95% CI) (hour) | (29.8, 47.3) | (28.5, 43.5) | (28.6, 44.5) | (29.7, 53.6) |
| Difference from placebo (hour) | −1.5 | −6.7 | −5.8 | — |
| P value (G. Wilcoxon test)[a] | 0.6846 | 0.7741 | 0.0904 | — |
| Hazard ratio (95% CI)[b] | 0.803 (0.557, 1.157) | 0.936 (0.635, 1.381) | 0.655 (0.447, 0.961) | — |
| P value (Cox model)[b] | 0.2388 | 0.7404 | 0.0304 | — |

(vi) Time Until "Cough" Symptom is Alleviated

TABLE 45

|  | Testdrug 10 mg administered group | Testdrug 20 mg administered group | Testdrug 40 mg administered group | Placebo administered group |
|---|---|---|---|---|
| N (human) | 74 | 74 | 78 | 75 |
| Median value | 31.1 | 29.8 | 24.6 | 31.2 |
| (95% CI) (hour) | (21.3, 41.5) | (21.9, 32.9) | (16.1, 29.4) | (20.9, 51.4) |
| Difference from placebo (hour) | −0.1 | −1.4 | −6.6 | — |

TABLE 45-continued

|  | Testdrug 10 mg administered group | Testdrug 20 mg administered group | Testdrug 40 mg administered group | Placebo administered group |
|---|---|---|---|---|
| P value (G. Wilcoxon test)[a] | 0.6643 | 0.8536 | 0.1551 | — |
| Hazard ratio (95% CI)[b] | 0.941 (0.675, 1.312) | 0.883 (0.636, 1.226) | 0.865 (0.626, 1.196) | — |
| P value (Cox model)[b] | 0.7188 | 0.4569 | 0.3796 | — |

(vii) Time Until "Sore Throat" Symptom is Alleviated

TABLE 46

|  | Testdrug 10 mg administered group | Testdrug 20 mg administered group | Testdrug 40 mg administered group | Placebo administered group |
|---|---|---|---|---|
| N (human) | 56 | 64 | 55 | 46 |
| Median value (95% CI) (hour) | 35.3 (21.2, 49.8) | 27.8 (19.9, 32.1) | 31.9 (17.3, 43.0) | 26.3 (16.5, 45.2) |
| Difference from placebo (hour) | 9.1 | 1.5 | 5.6 | — |
| P value (G. Wilcoxon test)[a] | 0.2905 | 0.6293 | 0.993 | — |
| Hazard ratio (95% CI)[b] | 1.312 (0.882, 1.951) | 1.05 (0.713, 1.547) | 1.092 (0.738, 1.617) | — |
| P value (Cox model)[b] | 0.18 | 0.8047 | 0.6602 | — | a Stratified generalized Wilson test relative to placebo. Stratification factors: Smoking habit, and composite symptom scores at baseline.
b Cox proportional hazard model relative to placebo. Covariates: Smoking habit, and composite symptom scores at baseline.
Subset of patients whose score of symptoms at baseline was "moderate" or "severe" CI: Confidence interval An analysis using a Cox proportional hazard model revealed that the 40 mg administered group in comparison to the placebo group showed a significant decrease in time until the following 5 symptoms: "nasal congestion", "muscular or joint pain", "fatigue", "feverishness or chills", and "headache" were alleviated. For example, as for 2 symptoms, i.e., "nasal congestion" and "muscular or joint pain", the median times until these symptoms were improved were 21.0 hours and 16.4 hours, respectively, and they were shorter in the 40 mg administered group than the placebo group.

Statistically significant differences were observed also in the 10 mg administered group and the 20 mg administered group with respect to the following symptoms: "muscular or joint pain", "nasal congestion", and "feverishness or chills".

Test Example 16: Clinical Test (Ph3: Adults and Adolescents)

The efficacy and safety of a single oral administration of an investigational drug (active ingredient (Compound II-6): 40 mg, 80 mg) to patients infected by influenza virus were evaluated by a randomized, double-blind comparative study in comparison to 75 mg Oseltamivir administered twice per day for 5 days or a placebo. As for the primary endpoint, subjects made evaluations by themselves on a 4-point scale [0: none, 1: mild, 2: moderate, 3: severe] concerning the time to alleviation of influenza symptoms (the time from the beginning of administration of the investigational drug until 7 influenza symptoms ("cough", "sore throat", "headache", "nasal congestion", "feverishness or chills", "muscular or joint pain", and "fatigue") were alleviated) to evaluate the efficacy of the investigational drug over the placebo.

Moreover, as for the secondary efficacy endpoint, the efficacy and the side effects of the investigational drug were evaluated according to the influenza virus titer using a nasal or throat swab.
Patients who satisfied all of the following criteria were selected as subjects.
(a) Male or female patients at 12 years old or older and younger than 65 years old
(b) Patients satisfying all of the following criteria and diagnosed with influenza virus infectious disease
Body temperature (axillary temperature) of 38.0° C. or higher
Having one or more moderate or severer symptoms among the following systemic symptoms and respiratory symptoms due to influenza virus infectious disease
Systemic symptoms (headache, feverishness or chills, muscular or joint pain, fatigue)
Respiratory symptoms (cough, sore throat, nasal congestion)
(c) Patients within 48 hours from onset (at registration)
The definition of onset is any of the following.
When the body temperature increased for the first, time (at least an increase of 1° C. from normal temperature)
When any one or more of the systemic symptoms and respiratory symptoms were developed
Method for Administering Investigational Drug
(i) Test Drug
20 mg Tablet of Compound II-6
(ii) Placebo or Control Drug
Placebo for 20 mg tablet of Compound II-6
75 mg Capsule of Oseltamivir
Placebo for 75 mg capsule of Oseltamivir: Capsule undistinguishable from 75 mg capsule of Oseltamivir
Dosage and Administration Method Eligible patients at 20 to 64 years old were randomly allocated to a group receiving a single administration of Compound II-6 (40 or 80 mg depending on the body weight), a group receiving 75 mg Oseltamivir twice a day for 5 days, and a placebo group in a ratio of 2:2:1.

Eligible patients at 12 to 19 years old were randomly allocated to a group receiving a single administration of Compound II-6 (40 or 80 mg depending on the body weight) and a placebo administered group in a ratio of 2-1.

The dosage of Compound II-6 was 40 mg for subjects weighing less than 80 kg, and 80 mg for subjects weighing 80 kg or more.

Investigational Drug for Each Administered Group

[Compound II-6 Group]
Day 1:
20 mg Tablets of Compound II-6 were administered orally (2 tablets or 4 tablets depending on the body weight). Placebo capsules for Oseltamivir were administered orally twice a day (morning, evening), one capsule per administration.
Day 2 to Day 5:
Placebo capsules for Oseltamivir were administered orally twice a day (morning, evening), one capsule per administration.

[Oseltamivir Group]
Day 1:
Placebo tablets for Compound II-6 were administered orally (2 tablets or 4 tablets depending on the body weight). 75 mg Capsules of Oseltamivir were administered orally twice a day (morning, evening), one capsule per administration.
Day 2 to Day 5:
75 mg Capsules of Oseltamivir were administered orally twice a day (morning, evening), one capsule per administration.

[Placebo Group]
Day 1:
Placebo tablets for Compound II-6 were administered orally (2 tablets or 4 tablets depending on the body weight). Placebo capsules for Oseltamivir were administered orally twice a day (morning, evening), one capsule per administration.
Day 2 to Day 5:
Placebo capsules for Oseltamivir were administered orally twice a day (morning, evening), one capsule per administration.

"Day 1" indicates the first day of administration, and "Day 2 to Day 5" indicates the second day to the fifth day as counted from the first day of administration.

Main Efficacy Endpoint

The main efficacy endpoint is the time to alleviation of influenza symptoms (the time to alleviation of influenza symptoms).

It is the time from the beginning of administration until alleviation of influenza symptoms. Alleviation of influenza symptoms refers to when all 7 influenza symptoms (cough, sore throat, headache, nasal congestion, feverishness or chills, muscular or joint pain, fatigue) become "0: none" or "1: mild" in the patient diary that the subject keeps, and this condition continues at least 21.5 hours (24 hours—10%).

Secondary Efficacy Endpoint

The secondary efficacy endpoint is as follows.
(1) Proportion of patients having a positive influenza virus titer at each point
(2) Amount of change in virus titer from baseline at each point
(3) Time to termination of viral shedding based on virus titer
(4) Incidence of side effects The virus Liter was measured in the following manner.
(1) MDCK-SIAT1 cells seeded in a flat-bottom 96-well microplate were cultured in a 5% $CO_2$ incubator at 37±1° C. for 1 day.
(2) A standard strain (influenza virus AII3N2, A/Victoria/361/2011, storage condition: −80° C., origin: National Institute of Infectious Diseases), a sample (collected from patients in Phase III clinical test of Compound II-6 and stored in an ultra-low-temperature freezer), and a medium for cell control were diluted 101 to 107 folds by a 10-fold serial dilution method.
(3) After cells present in a sheet form were confirmed under an inverted microscope, the medium was removed, and a new medium was added at 100 µL/well.
(4) The medium was removed.
(5) Each of the samples (100 to 107) prepared at (2) above was inoculated at 100 µL/well, using 4 wells per sample.
(6) Centrifugal adsorption was performed at room temperature at 1000 rpm for 30 minutes.
(7) After centrifugation, the medium was removed, and cells were washed once with a new medium.
(8) A new medium was added at 100 µL/well.
(9) Incubation was performed in a 5% $CO_2$ incubator at 33±1° C. for 3 days.
(10) After incubation, the CytoPathic Effect (CPE) was evaluated under an inverted microscope.

Method for Determining to have a Positive Virus Titer

When the detection limit was exceeded as measured by the above virus titer measurement method, it was determined to be positive.

Analysis of Primary Endpoint

As for the time to alleviation of influenza symptoms, which is the primary endpoint, the primary analysis and the secondary analysis are described. The primary analysis was performed on the ITTI group.

(1) Primary Analysis

For patients at 12 to 64 years old, the placebo group and the investigational drug administered group were compared by stratified generalized Wilcoxon test using the total score of 7 influenza symptoms before administration (11 points or less, 12 points or more) and regions (Japan/Asia, other regions) as stratification factors.

Also, a Kaplan-Meier survival curve was drawn for each group to calculate the median time to alleviation of influenza symptoms and the 95% confidence interval thereof as well as the difference between the groups in the time to alleviation of influenza symptoms and the 95% confidence interval thereof.

(2) Secondary Analysis

For patients at 20 to 64 years old, the time to alleviation of influenza symptoms was compared between the Compound II-6 group and the Oseltamivir group by the same method as the primary analysis.

Analysis of Secondary Endpoint

The following secondary efficacy endpoints were compared between the Compound II-6 group and the placebo group and between the Compound II-6 group and the Oseltamivir group (the age group of 20 to 64 years old).

(1) Proportion of Patients Having a Positive Influenza Virus Titer at Various Time Points Only the patients having a virus titer equal to or greater than the determination limit before the beginning of administration in Visit 1 were included in the analysis. In each Visit, a Mantel-Haenszel test using the total score of 7 influenza symptoms before administration and the regions as stratification factors was applied, and the proportion of patients having a positive virus titer was compared between two groups.

(2) Amount of Change in Virus Titer from Baseline at Various Time Points

Only the patients having a virus titer before the beginning of administration in Visit 1 were included in the analysis. In each Visit, a van Elteren test using the total score of 7 influenza symptoms before administration and the regions as stratification factors was applied, and the amount of change in influenza virus titer from the baseline was compared between two groups.

(3) Time to Termination of Viral Shedding Based on Virus Titer

Only the patients having a virus titer equal to or greater than the determination limit before the beginning of administration in Visit 1 were included in the analysis. A stratified generalized Wilcoxon test using the total score of 7 influenza symptoms before administration and the regions as stratification factors was applied.

(4) Incidence of Side Effects

The number of side-effect episodes and the number of patients with side effect were counted for each administration group.

(1) Results of Primary Endpoint (Time to Alleviation of Influenza Symptoms)

Out of 1436 randomly selected patients, 1366 patients (578 patients in the 40 mg or 80 mg Compound II-6 administered group, 498 patients in the Oseltamivir administered group, and 290 patients in the placebo group) completed the test. As for the primary endpoint, the ITTI cases (cases where GCP was followed, the investigational drug was administered, and influenza virus infection was confirmed) consisted of 1064 patients.

The per protocol set cases consisted of 990 patients (427 patients in the 40 mg or 80 mg Compound II-6 administered group, 351 patients in the Oseltamivir administered group, and 212 patients in the placebo group).

Analysis results are shown in the following table.

TABLE 47

|  | 12 Years old or older and younger than 65 years old | | 20 Years old or older and younger than 65 years old | |
| --- | --- | --- | --- | --- |
|  | Compound II-6 administered group | Placebo administered group | Compound II-6 administered group | Oseltamivir administered group |
| Number of patients | 455 | 230 | 375 | 377 |
| Median (hour) | 53.7 | 80.2 | 53.5 | 53.8 |
| 95% Confidence interval (hour) | 49.5, 58.5 | 72.6, 87.1 | 48.0, 58.5 | 50.2, 56.4 |
| Difference between groups[a] (hour) | −26.5 | — | −0.3 | — |
| 95% Confidence interval of difference between groups (hour)[b] | −35.8, −17.8 | — | −6.6, 6.6 | — |
| Stratified generalized Wilcoxon test[c] p Value[a] | <.0001 | — | 0.7560 | — |

[a] vs Placebo or vs Oseltamivir

[b] Bootstrap estimation

[c] Used the regions and the total score of 7 influenza symptoms before administration as stratification factors, and censored at final evaluation for patients whose symptoms were no alleviated.

In the ITTI group, the time to alleviation of influenza symptoms (median) (95% CI) was 53.7 hours (95% CI: 49.5, 58.5) in the Compound II-6 group while 80.2 hours (95% CI: 72.6, 87.1) in the placebo group, and the difference between the Compound II-6 group and the placebo group was −26.5 hours. The time to alleviation of influenza symptoms of the Compound II-6 group was significantly shorter than that of the placebo group in the primary analysis using a stratified generalized Wilcoxon test (p<0.0001).

In the subgroup of patients at 20 years old or older and younger than 65 years old, the time to alleviation of influenza symptoms was 53.5 hours (95% CI: 48.0, 58.5) in the Compound II-6 group while 53.8 hours (95% CI: 50.2, 56.4) in the Oseltamivir group, and the difference between the Compound II-6 group and the Oseltamivir group was −0.3 hours. There was no significant difference between the times to alleviation of influenza symptoms of the Compound II-6 group and the Oseltamivir group in the stratified generalized Wilcoxon test.

Analysis of Secondary Endpoint (1) Proportion of Patients Having a Positive Influenza Virus Titer at Various Points Analysis results are shown in the following table.

TABLE 48

| Observation time point | | 12 Years old or older and younger than 65 years old | | 20 Years old or older and younger than 65 years old | |
|---|---|---|---|---|---|
| | | Compound II-6 administered group N = 427 | Placebo administered group N = 210 | Compound II-6 administered group N = 352 | Oseltamivir administered group N = 359 |
| Day 2 | Proportion | 47.8% (197/412) | 96.0% (193/201) | 47.6% (161/338) | 91.0% (315/346) |
| | 95% Confidence interval | 42.9, 52.8 | 92.3, 98.3 | 42.2, 53.1 | 87.5, 93.8 |
| | p Value $^a$ | <.0001 | — | <.0001 | — |
| Day 3 | Proportion | 21.5% (87/404) | 70.2% (134/191) | 19.8% (66/333) | 57.3% (197/344) |
| | 95% Confidence Interval | 17.6, 25.9 | 63.1, 76.5 | 15.7, 24.5 | 51.9, 62.6 |
| | p Value $^a$ | <.0001 | — | <.0001 | — |
| Day 4 | Proportion | 16.7% (19/114) | 56.1% (32/57) | 16.1% (14/87) | 27.6% (29/105) |
| | 95% Confidence interval | 10.3, 24.8 | 42.4, 69.3 | 9.1, 25.5 | 19.3, 37.2 |
| | p Value $^a$ | <.0001 | — | 0.0852 | — |
| Day 5 | Proportion | 13.6% (55/403) | 29.7% (57/192) | 13.0% (43/331) | 20.9% (70/335) |
| | 95% Confidence interval | 10.4, 17.4 | 23.3, 36.7 | 9.6, 17.1 | 16.7, 25.6 |
| | p Value $^a$ | <.0001 | — | 0.0066 | — |
| Day 6 | Proportion | 8.2% (8/97) | 12.5% (6/48) | 5.6% (4/71) | 9.0% (7/78) |
| | 95% Confidence interval | 3.6, 15.6 | 4.7, 25.2 | 1.6, 13.8 | 3.7, 17.6 |
| | p Value $^a$ | 0.4767 | — | 0.6187 | — |
| Day 9 | Proportion | 2.9% (12/407) | 4.6% (9/197) | 3.0% (10/335) | 3.2% (11/339) |
| | 95% Confidence interval | 1.5, 5.1 | 2.1, 8.5 | 1.4, 5.4 | 1.6, 5.7 |
| | p Value $^a$ | 0.3379 | — | 0.8618 | — |

Day 2 indicates 24 hours later, as counted from the first day of administration, Day 3 indicates 48 hours later, Day 4 indicates 72 hours later, Day 5 indicates 96 hours later, Day 6 indicates 120 hours later, and Day 9 indicates 192 hours later, a vs Placebo or vs Oseltamivir. Mantel-Haenszel test. Used the regions and the total score of 7 influenza symptoms before administration as stratification factors, and intended for a group having a positive virus Liter before administration.

The proportion of patients having a positive virus titer was significantly lower in the Compound II-6 group than in the placebo group on Day 2 (Mantel-Haenszel test: $p \leq 0.0001$), and likewise, significantly lower in the Compound II-6 group than in the placebo group on Day 3 ($p < 0.0001$). In the subgroup of patients at 20 years old or older and younger than 65 years old, the proportion of patients having a positive virus titer was significantly lower in the Compound II-6 group than in the Oseltamivir group on Day 2 and Day 3 ($p < 0.0001$).

(2) Amount of Change in Virus Titer from Baseline at Various Points

Analysis results are shown in the following table.

TABLE 49

| Observation time point | | 12 Years old or older and younger than 65 years old | | 20 Years old or older and younger than 65 years old | |
|---|---|---|---|---|---|
| | | Compound II-6 administered group N = 427 | Placebo administered group N = 210 | Compound II-6 administered group N = 352 | Oseltamivir administered group N = 359 |
| Day 2 | Number of patients | 412 | 201 | 338 | 346 |
| | Mean | −4.44 | −1.19 | −4.39 | −2.51 |
| | Standard deviation | 2.03 | 2.43 | 2.07 | 2.03 |
| | p Value [a] | <.0001 | — | <.0001 | — |
| Day 3 | Number of patients | 404 | 191 | 333 | 344 |
| | Mean | −4.82 | −2.91 | −4.78 | −4.20 |
| | Standard deviation | 1.99 | 2.85 | 2.03 | 2.02 |
| | p Value [a] | <.0001 | — | <.0001 | — |
| Day 4 | Number of patients | 114 | 57 | 87 | 105 |
| | Mean | −4.50 | −3.31 | −4.46 | −4.63 |
| | Standard deviation | 2.02 | 2.34 | 2.03 | 1.89 |
| | p Value [a] | 0.0008 | — | 0.8010 | — |
| Day 5 | Number of patients | 403 | 192 | 331 | 335 |
| | Mean | −4.95 | −4.47 | −4.95 | −4.98 |
| | Standard deviation | 1.93 | 2.21 | 1.94 | 1.82 |
| | p Value [a] | 0.0132 | — | 0.9425 | — |
| Day 6 | Number of patients | 97 | 48 | 71 | 78 |
| | Mean | −4.58 | −4.68 | −4.56 | −4.85 |
| | Standard deviation | 1.99 | 2.12 | 1.99 | 1.95 |
| | p Value [a] | 0.9307 | — | 0.2256 | — |
| Day 9 | Number of patients | 407 | 197 | 335 | 339 |
| | Mean | −5.06 | −4.87 | −5.03 | −5.22 |
| | Standard deviation | 1.87 | 1.85 | 1.89 | 1.70 |
| | p Value [a] | 0.1684 | — | 0.3267 | — |

Unit: $\log_{10}$ [$TCID_{50}$/mL].

Day 2 indicates 24 hours later, as counted from the first day of administration, Day 3 indicates 48 hours later, Day 4 indicates 72 hours later, Day 5 indicates 96 hours later, Day 6 indicates 120 hours later, and Day 9 indicates 192 hours later, a vs Placebo or vs Oseltamivir, van Elteren test. Used the regions and the total score of 7 influenza symptoms before administration as stratification factors. Intended for a group having a positive virus titer before administration.

The virus titer decreased significantly in the Compound II-6 group as compared to the placebo group on Day 2, and likewise, decreased significantly as compared to the placebo group on Day 3 (van Elteren test: p<0.0001). In the subgroup of patients at 20 years old or older and younger than 65 years old, the virus titer decreased significantly in the Compound II-6 group as compared to the Oseltamivir group on Day 2 and Day 3 (p<0.0001).

(3) Time to Termination of Viral Shedding Based on Virus Titer

Analysis results are shown in the following table.

TABLE 50

| | 12 Years old or older and younger than 65 years old | | 20 Years old or older and younger than 65 years old | |
| --- | --- | --- | --- | --- |
| | Compound II-6 administered group | Placebo administered group | Compound II-6 administered group | Oseltamivir administered group |
| Number of patients | 423 | 207 | 348 | 355 |
| 95% Confidence interval (hour) | 24.0, 48.0 | — | 24.0, 48.0 | 72.0, 96.0 |
| Difference between groups (hour) [a] | −72.0 | — | −48.0 | — |
| Stratified generalized Wilcoxon test [b] p Value | <.0001 | — | <.0001 | — |

[a] vs Placebo or vs Oseltamivir.
[b] Used the regions and the total score of 7 influenza symptoms before administration as stratification factors.

Censored at final evaluation for patients whose virus titer was not eliminated. Intended for analyzing patients who had a positive virus titer on Day 1 and whose data concerning the time to termination of viral shedding was not missing.

The time (median) to termination of viral shedding based on virus titer was 24.0 hours in the Compound II-6 group while 96.0 hours in the placebo group, and was significantly shorter in the Compound II-6 group than in the placebo group (stratified generalized Wilcoxon test: p≤0.0001). The time to termination of viral shedding in the subgroup of patients at 20 years old or older and younger than 65 years old was 24.0 hours in the Compound II-6 group and 72.0 hours in the Oseltamivir group, and was significantly shorter in the Compound II-6 group than in the Oseltamivir group (p<0.0001).

(4) Incidence of Adverse Events

Severe adverse events the causal relationship of which cannot be denied are not reported. Adverse events the causal relationship of which cannot be denied occurred in 27 patients out of 610 patients (4.4%, 37 episodes) in the Compound II-6 group, 12 patients out of 309 patients (3.9%, 19 episodes) in the placebo group, and 43 patients out of 513 patients (8.4%, 53 episodes) in the Oseltamivir group. There was no statistically significant difference between the incidences in the Compound II-6 group and the placebo group (Fisher's exact test, two-sided P value: 0.8627). However, the incidence in the Compound II-6 group was significantly lower than that in the Oseltamivir group (Fisher's exact test, two-sided P value: 0.0088).

Test Example 17: Clinical Test (Ph3: Child)

The efficacy and safety of a single oral administration of an investigational drug (active ingredient (Compound II-6): 5 mg, 10 mg, 20 mg, 40 mg) to patients infected by influenza virus were evaluated. As for the primary endpoint, guardians or subjects by themselves made evaluations and measurements concerning the time to alleviation of influenza symptoms (the time from the beginning of administration of the investigational drug until influenza symptoms ("cough", "runny nose/nasal congestion", and "fever") were alleviated) to evaluate the efficacy of the investigational drug.

"Cough" and "runny nose/nasal congestion" were evaluated on a 4-point scale [0: none, 1: mild, 2: moderate, 3: severe].

Patients who satisfied all of the following criteria were selected as subjects.

(a) Male or female patients at 6 months old or older and younger than 12 years old (b) Patients satisfying all of the following criteria and diagnosed with influenza virus infectious disease Positive in influenza rapid diagnosis [Rapid antigen test (RAT)] based on a nasal or throat swab Body temperature (axillary temperature) of 38.0° C. or higher Having one or more moderate or severer symptoms among the respiratory symptoms due to influenza virus infectious disease for patients at 7 years old or older (c) Patients within 48 hours from onset (at registration). The onset is defined as when the body temperature exceeding 37.5° C. is confirmed for the first time.

(d) Patients having a body weight of 5 kg or more.

Method for Administering Investigational Drug (i) Test Drug 5 mg Tablet of Compound II-6: Half of 10 mg tablet of Compound II-6

10 mg Tablet of Compound II-6

20 mg Tablet of Compound II-6

Dosage and Administration Method

Patients received a single oral administration on Day 1 in a dose calculated based on the body weight (see the table below).

TABLE 51

| Body weight of patient at the time of screening | Dose of Compound II-6 | Compound II-6 tablet |
|---|---|---|
| 5 kg or more and less than 10 kg | 5 mg | Half of 10 mg tablet |
| 10 kg or more and less than 20 kg | 10 mg | One 10 mg tablet |
| 20 kg or more and less than 40 kg | 20 mg | One 20 mg tablet or two 10 mg tablets |
| 40 kg or more | 40 mg | Two 20 mg tablets |

Main Efficacy Endpoint

The main efficacy endpoint is the time to alleviation of influenza symptoms (the time to alleviation of influenza symptoms).

It is the time from the beginning of administration until alleviation of influenza symptoms. Alleviation of an influenza symptom refers to the time when a and b below are satisfied from the beginning of administration, and this clinical condition continues at least 21.5 hours (24 hours—10%).

a. "Cough" and "runny nose/nasal congestion" are both "0: none" or "1: mild" in the patient diary b. Body temperature (axillary temperature) is lower than 37.5° C.

Analysis of Primary Endpoint

As for the time to alleviation of influenza symptoms, which is the primary endpoint, the primary analysis is described. The primary analysis was performed on the ITTI group.

(1) Primary Analysis

A Kaplan-Meier curve of the time to alleviation of influenza symptoms ("cough", "runny nose/nasal congestion", and "fever") (the time to alleviation of influenza symptoms) was drawn to calculate the median time to complete alleviation of influenza symptoms and the 95% confidence interval thereof. Patients whose influenza symptoms were not completely alleviated during the observation period were treated as censored cases.

(1) Results of Primary Endpoint (Time to Alleviation of Influenza Symptoms)

As for the primary endpoint, 103 patients were involved. The time (median) to alleviation of influenza symptoms in the ITTI group was 44.6 hours (95% CI: 38.9, 62.5).

Formulation Example

The following Formulation Examples are only exemplified and not intended to limit the scope of the invention.

Formulation Example 1: Tablets

The compounds used in the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds used in the present invention, lactose and calcium stearate are mixed uniformly to obtain powder medicines in the form of powders or fine granules. The powder medicines are filled into capsule containers to give capsules.

Formulation Example 3: Granules

The compounds used in the present invention, lactose and calcium stearate are mixed uniformly and the mixture is compressed and molded. Then, it is crushed, granulated and sieved to give suitable sizes of granules.

Formulation Example 4: Orally Disintegrated Tablets

The compounds used in the present invention and crystalline cellulose are mixed, granulated and tablets are made to give orally disintegrated tablets.

Formulation Example 5: Dry Syrups

The compounds used in the present invention and lactose are mixed, crushed, granulated and sieved to give suitable sizes of dry syrups.

Formulation Example 6: Injections

The compounds used in the present invention and phosphate buffer are mixed to give injection.

Formulation Example 7: Infusions

The compounds used in the present invention and phosphate buffer are mixed to give injection.

Formulation Example 8: Inhalations

The compound used in the present invention and lactose are mixed and crushed finely to give inhalations.

Formulation Example 9: Ointments

The compounds used in the present invention and petrolatum are mixed to give ointments.

Formulation Example 10: Patches

The compounds used in the present invention and base such as adhesive plaster or the like are mixed to give patches.

INDUSTRIAL APPLICABILITY

The parent compounds used in the present invention have cap-dependent endonuclease (CEN) inhibitory activity after absorption into the body. The compounds (the parent compounds and/or the prodrugs) used in the present invention can be useful agents for treatment and/or prevention of symptom and/or disease induced by infection with influenza virus. The pharmaceutical composition is effective for shortening the time to alleviation of influenza symptoms, and is useful for treating and/or preventing an influenza virus infectious disease.

The invention claimed is:
1. A method for treating a disease caused by a virus having cap-dependent endonuclease comprising administering to a patient in need thereof a crystal of the compound of the following formula:

wherein the crystal is selected from the group consisting of:
(i) crystal Form I having two or more peaks in diffraction angles (2θ) selected from 8.6±0.2°, 14.1±0.2°, 17.4±0.2°, 20.0±0.2°, 24.0±0.2°, 26.3±0.2°, 29.6±0.2° and 35.4±0.2° in an X-ray powder diffraction spectrum,
(ii) crystal Form II having two or more peaks in diffraction angles (2θ) selected from 4.4±0.2°, 8.9±0.2°, 11.7±0.2°, 14.9±0.2°, 22.3±0.2°, 24.4±0.2°, 28.0±0.2° and 31.5±0.2° in an X-ray powder diffraction spectrum, and
(iii) crystal Form III having two or more peaks in diffraction angles (2θ) selected from 4.4±0.2°, 8.7±0.2°, 10.6±0.2°, 17.3±0.2°, 17.5±0.2°, 22.0±0.2°, 24.0±0.2°, 24.1±0.2° and 31.0±0.2° in an X-ray powder diffraction spectrum.

2. The method according to claim 1, wherein the crystal is (i) crystal Form I having peaks in diffraction angles (2θ) of 8.6±0.2°, 14.1±0.2°, 17.4±0.2°, 20.0±0.2°, 24.0±0.2°, 26.3±0.2°, 29.6±0.2° and 35.4±0.2° in an X-ray powder diffraction spectrum.

3. The method according to claim 1, wherein the (i) crystal Form I is administered orally in a single dose.

4. The method according to claim 1, wherein 40 mg or 80 mg of the (i) crystal Form I is administered in a single dose.

5. The method according to claim 1, wherein 5 to 40 mg of the (i) crystal Form I is administered in a single dose depending on the body weight of the patient.

6. The method according to claim 1, wherein 40 mg of the (i) crystal Form I is administered in two tablets of 20 mg per tablet.

7. The method according to claim 1, wherein the (i) crystal Form I is administered and the patient is a human 12 years old or older.

8. The method according to claim 1, wherein the crystal is (ii) crystal Form II having peaks in diffraction angles (2θ) of 4.4±0.2°, 8.9±0.2°, 11.7±0.2°, 14.9±0.2°, 22.3±0.2°, 24.4±0.2°, 28.0±0.2° and 31.5±0.2° in an X-ray powder diffraction spectrum.

9. The method according to claim 1, wherein the (ii) crystal Form II is administered orally in a single dose.

10. The method according to claim 1, wherein 40 mg or 80 mg of the (ii) crystal Form II is administered in a single dose.

11. The method according to claim 1, wherein 5 to 40 mg of the (ii) crystal Form II is administered in a single dose depending on the body weight of the patient.

12. The method according to claim 1, wherein 40 mg of the (ii) crystal Form II is administered in two tablets of 20 mg per tablet.

13. The method according to claim 1, wherein the (ii) crystal Form II is administered and the patient is a human 12 years old or older.

14. The method according to claim 1, wherein the crystal is (iii) crystal Form III having peaks in diffraction angles (2θ) of 4.4±0.2°, 8.7±0.2°, 10.6±0.2°, 17.3±0.2°, 17.5±0.2°, 22.0±0.2°, 24.0±0.2°, 24.1±0.2° and 31.0±0.2° in an X-ray powder diffraction spectrum.

15. The method according to claim 1, wherein the (iii) crystal Form III is administered orally in a single dose.

16. The method according to claim 1, wherein 40 mg or 80 mg of the (iii) crystal Form III is administered in a single dose.

17. The method according to claim 1, wherein 5 to 40 mg of the (iii) crystal Form III is administered in a single dose depending on the body weight of the patient.

18. The method according to claim 1, wherein 40 mg of the (iii) crystal Form III is administered in two tablets of 20 mg per tablet.

19. The method according to claim 1, wherein the (iii) crystal Form III is administered and the patient is a human 12 years old or older.

20. A method for treating influenza comprising administering to a patient in need thereof a crystal of the compound of the following formula:

wherein the crystal is selected from the group consisting of:
(i) crystal Form I having two or more peaks in diffraction angles (2θ) selected from 8.6±0.2°, 14.1±0.2°, 17.4±0.2°, 20.0±0.2°, 24.0±0.2°, 26.3±0.2°, 29.6±0.2° and 35.4±0.2° in an X-ray powder diffraction spectrum,
(ii) crystal Form II having two or more peaks in diffraction angles (2θ) selected from 4.4±0.2°, 8.9±0.2°, 11.7±0.2°, 14.9±0.2°, 22.3±0.2°, 24.4±0.2°, 28.0±0.2° and 31.5±0.2° in an X-ray powder diffraction spectrum, and (iii) crystal Form III having two or more peaks in diffraction angles (2θ) selected from 4.4±0.2°, 8.7±0.2°, 10.6±0.2°, 17.3±0.2°, 17.5±0.2°, 22.0±0.2°, 24.0±0.2°, 24.1±0.2° and 31.0±0.2° in an X-ray powder diffraction spectrum.

21. The method according to claim 20, wherein the crystal is (i) crystal Form I having peaks in diffraction angles (2θ) of 8.6±0.2°, 14.1±0.2°, 17.4±0.2°, 20.0±0.2°, 24.0±0.2°, 26.3±0.2°, 29.6±0.2° and 35.4±0.2° in an X-ray powder diffraction spectrum.

22. The method according to claim 20, wherein the (i) crystal Form I is administered orally in a single dose.

23. The method according to claim 20, wherein 40 mg or 80 mg of the (i) crystal Form I is administered in a single dose.

24. The method according to claim 20, wherein 5 to 40 mg of the (i) crystal Form I is administered in a single dose depending on the body weight of the patient.

25. The method according to claim 20, wherein 40 mg of the (i) crystal Form I is administered in two tablets of 20 mg per tablet.

26. The method according to claim 20, wherein the (i) crystal Form I is administered and the patient is a human 12 years old or older.

27. The method according to claim 20, wherein the crystal is (ii) crystal Form II having peaks in diffraction angles (2θ) of 4.4±0.2°, 8.9±0.2°, 11.7±0.2°, 14.9±0.2°, 22.3±0.2°, 24.4±0.2°, 28.0±0.2° and 31.5±0.2° in an X-ray powder diffraction spectrum.

28. The method according to claim 20, wherein the (ii) crystal Form II is administered orally in a single dose.

29. The method according to claim 20, wherein 40 mg or 80 mg of the (ii) crystal Form II is administered in a single dose.

30. The method according to claim 20, wherein 5 to 40 mg of the (ii) crystal Form II is administered in a single dose depending on the body weight of the patient.

31. The method according to claim 20, wherein 40 mg of the (ii) crystal Form II is administered in two tablets of 20 mg per tablet.

32. The method according to claim 20, wherein the (ii) crystal Form II is administered and the patient is a human 12 years old or older.

33. The method according to claim 20, wherein the crystal is (iii) crystal Form III having peaks in diffraction angles (2θ) of 4.4±0.2°, 8.7±0.2°, 10.6±0.2°, 17.3±0.2°, 17.5±0.2°, 22.0±0.2°, 24.0±0.2°, 24.1±0.2° and 31.0±0.2° in an X-ray powder diffraction spectrum.

34. The method according to claim 20, wherein the (iii) crystal Form III is administered orally in a single dose.

35. The method according to claim 20, wherein 40 mg or 80 mg of the (iii) crystal Form III is administered in a single dose.

36. The method according to claim 20, wherein 5 to 40 mg of the (iii) crystal Form III is administered in a single dose depending on the body weight of the patient.

37. The method according to claim 20, wherein 40 mg of the (iii) crystal Form III is administered in two tablets of 20 mg per tablet.

38. The method according to claim 20, wherein the (iii) crystal Form III is administered and the patient is a human 12 years old or older.

39. A method for preventing influenza comprising administering to a patient in need thereof a crystal of the compound of the following formula:

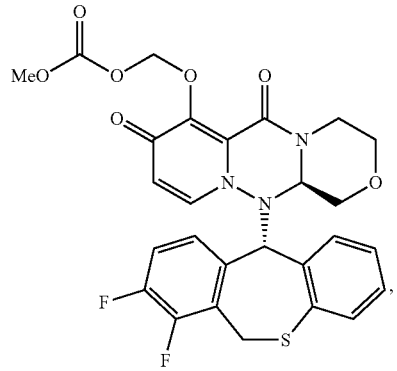 [SMILES: COC(=O)OCOc1c2n(ccc1=O)N([C@@H]1c3ccccc3SCc3c1ccc(F)c3F)[C@@H]1COCCN1C2=O]

wherein the crystal is selected from the group consisting of:
(i) crystal Form I having two or more peaks in diffraction angles (2θ) selected from 8.6±0.2°, 14.1±0.2°, 17.4±0.2°, 20.0±0.2°, 24.0±0.2°, 26.3±0.2°, 29.6±0.2° and 35.4±0.2° in an X-ray powder diffraction spectrum,
(ii) crystal Form II having two or more peaks in diffraction angles (2θ) selected from 4.4±0.2°, 8.9±0.2°, 11.7±0.2°, 14.9±0.2°, 22.3±0.2°, 24.4±0.2°, 28.0±0.2° and 31.5±0.2° in an X-ray powder diffraction spectrum, and
(iii) crystal Form III having two or more peaks in diffraction angles (2θ) selected from 4.4±0.2°, 8.7±0.2°, 10.6±0.2°, 17.3±0.2°, 17.5±0.2°, 22.0±0.2°, 24.0±0.2°, 24.1±0.2° and 31.0±0.2° in an X-ray powder diffraction spectrum.

40. The method according to claim 39, wherein the crystal is (i) crystal Form I having peaks in diffraction angles (2θ) of 8.6±0.2°, 14.1±0.2°, 17.4±0.2°, 20.0±0.2°, 24.0±0.2°, 26.3±0.2°, 29.6±0.2° and 35.4±0.2° in an X-ray powder diffraction spectrum.

41. The method according to claim 39, wherein the (i) crystal Form I is administered orally in a single dose.

42. The method according to claim 39, wherein 40 mg or 80 mg of the (i) crystal Form I is administered in a single dose.

43. The method according to claim 39, wherein 5 to 40 mg of the (i) crystal Form I is administered in a single dose depending on the body weight of the patient.

44. The method according to claim 39, wherein 40 mg of the (i) crystal Form I is administered in two tablets of 20 mg per tablet.

45. The method according to claim 39, wherein the (i) crystal Form I is administered and the patient is a human 12 years old or older.

46. The method according to claim 39, wherein the crystal is (ii) crystal Form II having peaks in diffraction angles (2θ) of 4.4±0.2°, 8.9±0.2°, 11.7±0.2°, 14.9±0.2°, 22.3±0.2°, 24.4±0.2°, 28.0±0.2° and 31.5±0.2° in an X-ray powder diffraction spectrum.

47. The method according to claim 39, wherein the (ii) crystal Form II is administered orally in a single dose.

48. The method according to claim 39, wherein 40 mg or 80 mg of the (ii) crystal Form II is administered in a single dose.

49. The method according to claim 39, wherein 5 to 40 mg of the (ii) crystal Form II is administered in a single dose depending on the body weight of the patient.

50. The method according to claim 39, wherein 40 mg of the (ii) crystal Form II is administered in two tablets of 20 mg per tablet.

51. The method according to claim 39, wherein the (ii) crystal Form II is administered and the patient is a human 12 years old or older.

52. The method according to claim 39, wherein the crystal is (iii) crystal Form III having peaks in diffraction angles (2θ) of 4.4±0.2°, 8.7±0.2°, 10.6±0.2°, 17.3±0.2°, 17.5±0.2°, 22.0±0.2°, 24.0±0.2°, 24.1±0.2° and 31.0±0.2° in an X-ray powder diffraction spectrum.

53. The method according to claim 39, wherein the (iii) crystal Form III is administered orally in a single dose.

54. The method according to claim 39, wherein 40 mg or 80 mg of the (iii) crystal Form III is administered in a single dose.

55. The method according to claim 39, wherein 5 to 40 mg of the (iii) crystal Form III is administered in a single dose depending on the body weight of the patient.

56. The method according to claim 39, wherein 40 mg of the (iii) crystal Form III is administered in two tablets of 20 mg per tablet.

57. The method according to claim 39, wherein the (iii) crystal Form III is administered and the patient is a human 12 years old or older.

\* \* \* \* \*